(12) United States Patent      (10) Patent No.: US 7,601,725 B2
Lew et al.      (45) Date of Patent: Oct. 13, 2009

(54) THIENOPYRIMIDINES USEFUL AS AURORA KINASE INHIBITORS

(75) Inventors: Willard Lew, San Mateo, CA (US); Subramanian Baskaran, Foster City, CA (US); Johan D. Oslob, Sunnyvale, CA (US); Joshua C. Yoburn, San Francisco, CA (US); Min Zhong, Foster City, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 366 days.

(21) Appl. No.: 11/182,215

(22) Filed: Jul. 15, 2005

(65) Prior Publication Data

US 2006/0035908 A1    Feb. 16, 2006

Related U.S. Application Data

(60) Provisional application No. 60/632,568, filed on Dec. 1, 2004, provisional application No. 60/588,718, filed on Jul. 16, 2004.

(51) Int. Cl.
| | | |
|---|---|---|
| A01N 43/90 | (2006.01) | |
| A61K 31/519 | (2006.01) | |
| C07D 491/00 | (2006.01) | |
| C07D 495/00 | (2006.01) | |

(52) U.S. Cl. .................................. 514/260.1; 544/278
(58) Field of Classification Search ........................ None
See application file for complete search history.

(56) References Cited

U.S. PATENT DOCUMENTS

| | | | |
|---|---|---|---|
| 4,146,716 A | 3/1979 | Cox et al. ................... 544/278 |
| 4,196,207 A | 4/1980 | Webber et al. ............... 424/251 |
| 5,073,558 A | 12/1991 | Obata et al. ................. 514/259 |
| 5,124,333 A | 6/1992 | Obata et al. ................. 514/256 |
| 5,141,941 A | 8/1992 | Fujii et al. ................... 514/256 |
| 5,187,168 A | 2/1993 | Primeau et al. ............... 514/259 |
| 5,227,387 A | 7/1993 | Dreikorn et al. ............. 514/312 |
| 5,654,307 A | 8/1997 | Bridges et al. ............... 514/258 |
| 5,859,020 A | 1/1999 | Preuss et al. ................. 514/269 |
| 6,133,271 A | 10/2000 | Pamukcu et al. | |
| 6,166,016 A | 12/2000 | Okamura et al. ............. 514/246 |
| 6,169,091 B1 | 1/2001 | Cockerill et al. ............. 514/258 |
| 6,187,777 B1 | 2/2001 | Norman et al. ............... 514/258 |
| 6,284,764 B1 | 9/2001 | Kath et al. ................... 514/259 |
| 6,288,078 B1 | 9/2001 | Walsh et al. ................. 514/300 |
| 6,407,124 B1 | 6/2002 | Rawlins et al. .............. 514/342 |
| 6,414,156 B2 | 7/2002 | Chen et al. .................. 546/209 |
| 6,465,449 B1 | 10/2002 | Kath et al. ................... 514/183 |
| 6,503,914 B1 | 1/2003 | Benish et al. | |
| 6,515,004 B1 | 2/2003 | Misra et al. .................. 514/369 |
| 6,534,531 B2 | 3/2003 | Kimball et al. .............. 514/369 |
| 6,541,481 B2 | 4/2003 | Kath et al. ............... 514/260.1 |
| 6,596,744 B2 | 7/2003 | Wagle et al. ................. 514/365 |
| 6,596,746 B1 | 7/2003 | Das et al. .................... 514/370 |
| 6,608,053 B2 | 8/2003 | Hayakawa et al. ....... 514/227.8 |
| 6,608,056 B1 | 8/2003 | Hayakawa et al. ....... 514/232.5 |
| 6,627,767 B2 | 9/2003 | Liu et al. ....................... 560/19 |
| 6,660,737 B2 | 12/2003 | Almstead et al. ............. 514/247 |
| 6,706,717 B2 | 3/2004 | Barrish et al. ........... 514/254.02 |
| 6,720,347 B2 | 4/2004 | Rawlins et al. .............. 514/371 |
| 6,770,641 B2 | 8/2004 | Hayakawa et al. ....... 514/228.2 |
| 6,770,663 B2 | 8/2004 | Wagle et al. ................. 514/365 |
| 6,838,547 B2 | 1/2005 | Beria et al. .................. 530/329 |
| 6,903,085 B1 | 6/2005 | Thom et al. .................. 514/183 |
| 2002/0022622 A1 | 2/2002 | Wagle et al. ............. 514/227.8 |
| 2002/0119970 A1 | 8/2002 | Wagle et al. ............. 514/227.8 |
| 2002/0165261 A1 | 11/2002 | Borisy et al. ................. 514/394 |
| 2004/0024208 A1 | 2/2004 | Das et al. ..................... 544/137 |
| 2004/0053897 A1 | 3/2004 | Dalton et al. ................ 514/169 |
| 2004/0054186 A1 | 3/2004 | Das et al. .................. 546/268.1 |
| 2004/0067989 A1 | 4/2004 | Barrish et al. ............... 514/365 |
| 2004/0067990 A1 | 4/2004 | Barrish et al. ............... 514/365 |
| 2004/0073026 A1 | 4/2004 | Das et al. ..................... 544/137 |
| 2004/0077695 A1 | 4/2004 | Barrish et al. ............... 514/367 |
| 2004/0077875 A1 | 4/2004 | Das et al. ..................... 548/192 |
| 2004/0082576 A1 | 4/2004 | Arrhenius et al. ......... 514/227.5 |

(Continued)

FOREIGN PATENT DOCUMENTS

DE      19827611      7/1997

(Continued)

OTHER PUBLICATIONS

Vippagunta, et. al., Advanced Drug Delivery Reviews; 48, (2001) 3-26.*

(Continued)

*Primary Examiner*—James O Wilson
*Assistant Examiner*—Jeffrey H Murray
(74) *Attorney, Agent, or Firm*—Andrea L. C. Robidoux; Choate Hall & Stewart, LLP

(57) ABSTRACT

The present invention provides compounds having the formula:

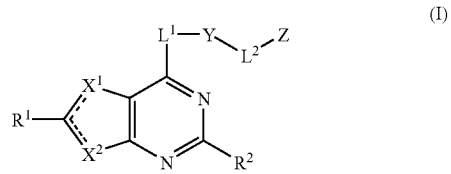

(I)

wherein $R^1$, $R^2$, $X^1$, $X^2$, $L^1$, $L^2$, Y and Z are as defined in classes and subclasses herein, and pharmaceutical compositions thereof, as described generally and in subclasses herein, which compounds are useful as inhibitors of protein kinase (e.g., Aurora), and thus are useful, for example, for the treatment of Aurora mediated diseases.

21 Claims, 5 Drawing Sheets

U.S. PATENT DOCUMENTS

| | | | |
|---|---|---|---|
| 2004/0087557 A1 | 5/2004 | Steiner et al. | 514/114 |
| 2004/0110752 A1 | 6/2004 | Barrish et al. | 514/235.5 |
| 2004/0122235 A1 | 6/2004 | Polisetti et al. | 546/207 |
| 2004/0171075 A1 | 9/2004 | Flynn et al. | 435/7.1 |
| 2004/0180906 A1 | 9/2004 | Flynn et al. | 514/256 |
| 2004/0197928 A1 | 10/2004 | Dalton et al. | 436/173 |
| 2004/0224979 A1 | 11/2004 | Dalton et al. | 514/312 |
| 2005/0014771 A1 | 1/2005 | Hayakawa et al. | 514/266.4 |
| 2005/0032788 A1 | 2/2005 | Wagle et al. | 514/227.5 |
| 2005/0070538 A1 | 3/2005 | Cheng et al. | 514/241 |
| 2005/0080054 A1 | 4/2005 | Dalton et al. | 514/114 |

FOREIGN PATENT DOCUMENTS

| | | |
|---|---|---|
| EP | 356158 | 8/1989 |
| EP | 370704 | 11/1989 |
| EP | 411634 | 8/1990 |
| EP | 424125 | 10/1990 |
| EP | 447891 | 3/1991 |
| EP | 452002 | 3/1991 |
| EP | 0534341 | 9/1992 |
| EP | 1029853 | 12/1999 |
| JP | 3-63266 | 3/1991 |
| JP | 3-063271 | 3/1991 |
| JP | 3-173872 | 7/1991 |
| JP | 4-164072 | 6/1992 |
| JP | 4-235976 | 8/1992 |
| JP | 7-10712 | 1/1995 |
| JP | 11-222435 | 8/1999 |
| JP | 2002-105081 | 4/2002 |
| WO | WO 93/04583 | 3/1993 |
| WO | WO 95/19774 | 7/1995 |
| WO | WO 96/17843 | 6/1996 |
| WO | WO 97/09316 | 3/1997 |
| WO | WO 97/46560 | 11/1997 |
| WO | WO 99/40091 | 8/1999 |
| WO | WO 99/65884 | 12/1999 |
| WO | WO 00/44728 | 8/2000 |
| WO | WO 00/53185 | 9/2000 |
| WO | WO 00/53602 | 9/2000 |
| WO | WO 00/69843 | 11/2000 |
| WO | WO 00/69844 | 11/2000 |
| WO | WO 01/14333 | 3/2001 |
| WO | WO 01/32632 | 5/2001 |
| WO | WO 01/52847 | 7/2001 |
| WO | WO 01/80813 | 11/2001 |
| WO | WO 01/83456 | 11/2001 |
| WO | WO 02/18321 | 3/2002 |
| WO | WO 02/50071 | 6/2002 |
| WO | WO 02/053156 | 7/2002 |
| WO | WO 02/053158 | 7/2002 |
| WO | WO 02/053161 | 7/2002 |
| WO | WO 02/058697 | 8/2002 |
| WO | WO 02/058698 | 8/2002 |
| WO | WO 02/089809 | 11/2002 |
| WO | WO 03/009852 | 2/2003 |
| WO | WO 03/049675 | 6/2003 |
| WO | WO 03/053446 | 7/2003 |
| WO | WO 03/055491 | 7/2003 |
| WO | WO 03/064428 | 8/2003 |
| WO | WO 03/065992 | 8/2003 |
| WO | WO 03/090869 | 11/2003 |
| WO | WO 2004/002481 | 1/2004 |
| WO | WO 2004/006849 | 1/2004 |
| WO | WO 2004/029060 | 4/2004 |
| WO | WO 2004/034978 | 4/2004 |
| WO | WO 2004/035739 | 4/2004 |
| WO | WO 2004/060305 | 7/2004 |
| WO | WO 2004/060306 | 7/2004 |
| WO | WO 2004/085388 | 10/2004 |
| WO | WO 2004/110350 | 12/2004 |

OTHER PUBLICATIONS

Dorwald F. A. Side Reactions in Organic Synthesis, 2005, Wiley: VCH, Weinheim p. IX of Preface.*

Borisy, et. al., Proceedings of the National Academy of Sciences of the United States of America, 100(13) 7977-7982.*

Cecil Textbook of Medicine, 21st Edition (2000), Goldman & Bennett (Editors), W.B. Saunders Company (Publisher), Chapter 198, pp. 1060-1074.*

Internal Medicine, 4th Edition, Editor-in-Chief Jay Stein, Chapters 71-72, pp. 699-715.*

Bischoff et al., "A homologue of *Drosophila aurora* kinase is oncogenic and amplified in human colorectal cancers" *EMBO J.* 1998, 17, 3052-3065.

Garcia-Bustos et al., "PIK1, an essential phosphatidylinositol 4-kinase associated with the yeast nucleus" *EMBO J.* 1994, 13, 2352-2361.

Hanks, S.K., Hunter, T., "Protein kinases 6. The eukaryotic protein kinase superfamily: kinase (catalytic) domain structure and classification" *FASEB J.* 1995, 9, 576-596.

Hiles et al., "Phosphatidylinositol 3-kinase: structure and expression of the 110 kd catalytic subunit" *Cell* 1992, 70, 419-429.

Kimura et al., "Cell Cycle-dependent Expression and Spindle Pole Localization of a Novel Human Protein Kinase, Aik, Related to Aurora of *Drosophila* and Yeast Ipl1" *J. Biol. Chem.* 1997, 272, 13766-13771.

Knighton et al., "Crystal structure of the catalytic subunit of cyclic adenosine monophosphate-dependent protein kinase" *Science* 1991, 253, 407-414.

Kunz et al., "Target of rapamycin in yeast, TOR2, is an essential phosphatidylinositol kinase homolog required for G1 progression" *Cell* 1993, 73, 585-596.

Schumacher et al., "AIR-2: An Aurora/Ipl1-related Protein Kinase Associated with Chromosomes and Midbody Microtubules Is Required for Polar Body Extrusion and Cytokinesis in *Caenorhabditis elegans* Embryos" *J. Cell Biol.* 1998, 143, 1635-1646.

Bohm, et al., "Uber Thieno-Verbindungen," Pharmazie (1986) 41:23-25 (English Abstract).

* cited by examiner

THIENOPYRIMIDINES USEFUL AS AURORA KINASE INHIBITORS

PRIORITY

The present application claims priority under 35 U.S.C. 119(e) to U.S. Provisional Patent Application Nos.: 60/632,568 filed Dec. 1, 2004 and 60/588,718 filed Jul. 16, 2004; The entire contents of each-of these applications are incorporated herein by reference.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor a (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

The Aurora family of serine/threonine kinases plays an important role in cell proliferation. The three known mammalian family members, Aurora-A ("1"), B ("2") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. Elevated levels of all Aurora family members are observed in a wide variety of tumor cell lines. For example, the Aurora-2 protein has been found to be overexpressed in human colon cancer tissue [Bischoff et al., *EMBO J.* 1998, 17, 3052-3065; Schumacher et al., *J. Cell Biol.* 1998, 143, 1635-1646; Kimura et al., *J. Biol. Chem.* 1997, 272, 13766-13771]. Aurora-2 has been implicated in human cancer, such as colon, breast and other solid tumors. This kinase is involved in protein phosphorylation events that regulate the cell cycle. Specifically, Aurora-2 plays a role in controlling the accurate segregation of chromosomes during mitosis. Thus, Aurora inhibitors have an important role in the treatment of Aurora-mediated diseases.

Accordingly, there is a great need to develop compounds useful as inhibitors of protein kinases. In particular, it would be desirable to develop compounds that are useful as inhibitors of Aurora, particularly given the inadequate treatments currently available for the majority of the disorders implicated in their activation.

SUMMARY OF THE INVENTION

As discussed above, there remains a need for the development of novel therapeutic agents and agents useful for treating disorders mediated by Aurora. In certain embodiments, the present invention provides novel compounds having the structure:

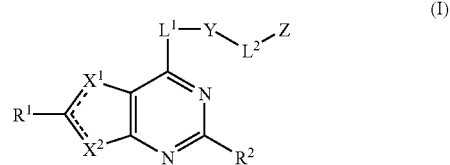

(I)

wherein $R^1$, $R^2$, $X^1$, $X^2$, $L^1$, $L^2$, Y and Z are as defined in classes and subclasses herein, and pharmaceutical compositions thereof, as described generally and in subclasses herein, which compounds are useful as inhibitors of protein kinase (e.g., Aurora), and thus are useful, for example, for the treatment of Aurora mediated diseases.

In certain other embodiments, the invention provides pharmaceutical compositions comprising an inventive compound, wherein the compound is present in an amount effective to inhibit Aurora activity. In certain other embodiments, the invention provides pharmaceutical compositions comprising an inventive compound and optionally further comprising an additional therapeutic agent. In yet other embodiments, the additional therapeutic agent is an agent for the treatment of cancer.

In yet another aspect, the present invention provides methods for inhibiting kinase activity (e.g., Aurora) activity in a patient or a biological sample, comprising administering to said patient, or contacting said biological sample with an effective inhibitory amount of a compound of the invention. In still another aspect, the present invention provides methods for treating any disorder involving Aurora activity, comprising administering to a subject in need thereof a therapeutically effective amount of a compound of the invention.

DEFINITIONS

Figure 1:
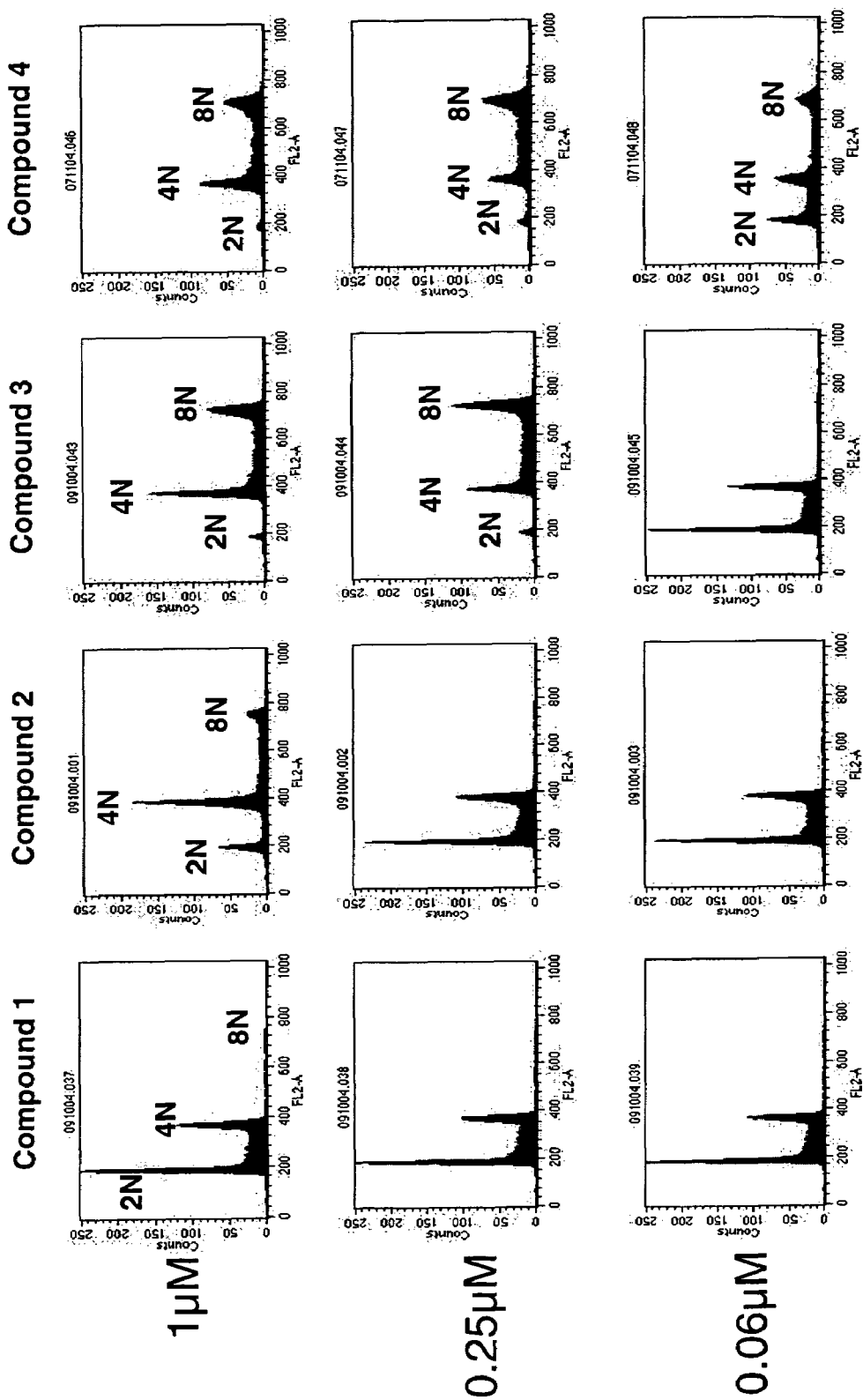
FIG. 1 depicts exemplary histograms of G2/M phase cell growth arrest experiments using four compounds of the invention.
Figure 2:
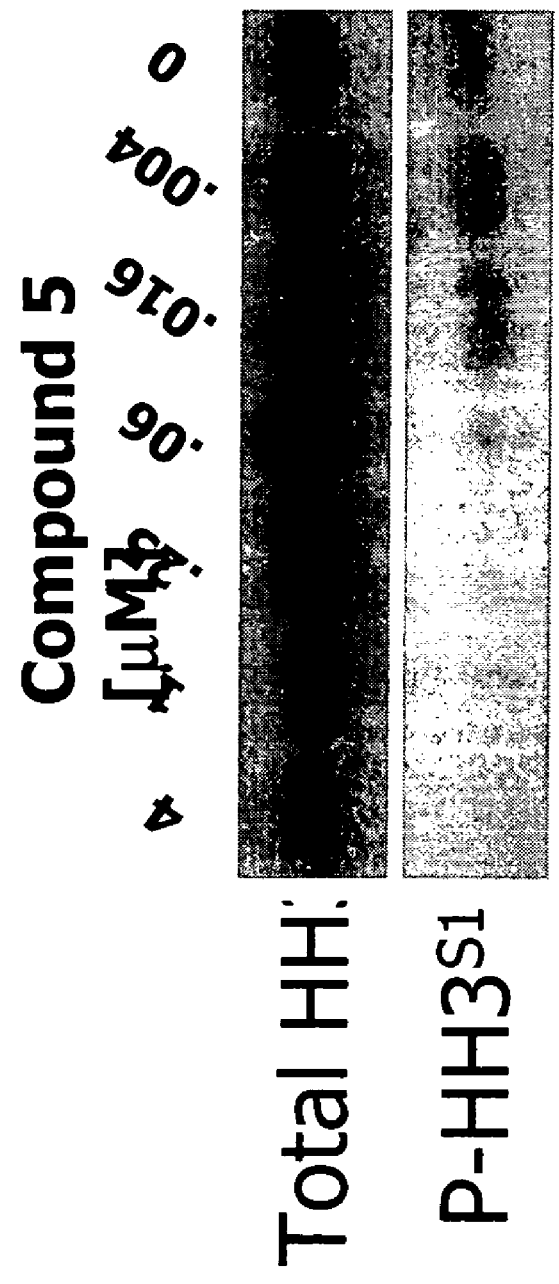
FIG. 2 depicts results of Histone H3 phosphorylation inhibition experiments in HCT-116 cells. A compound of the invention, cultured with HCT-116 cells, exhibits a concentration-related inhibition of histone H3 serine phosphorylation.
Figure 3:
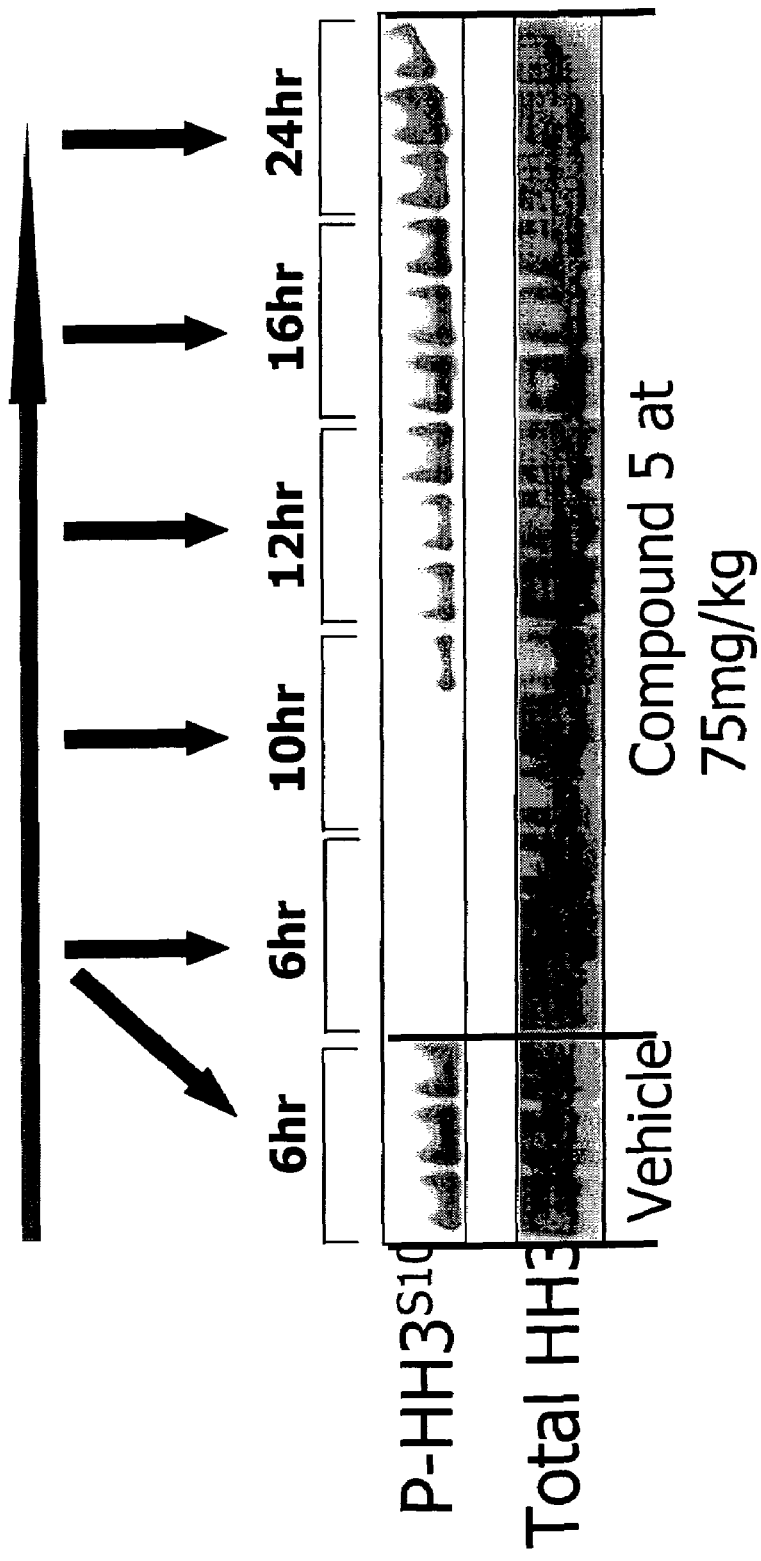
FIG. 3 depicts results of Histone H3 phosphorylation inhibition experiments in a HCT-116 tumor xenograft model. A compound of the invention was administered intra-peritoneally (single dose, 75 mg/kg) to mice implanted with HCt-116 tumors. The compound inhibits histone H3 serine phosphorylation in HCT-116 tumors for up to 10 hours after administration to implanted mice.
Figure 4:
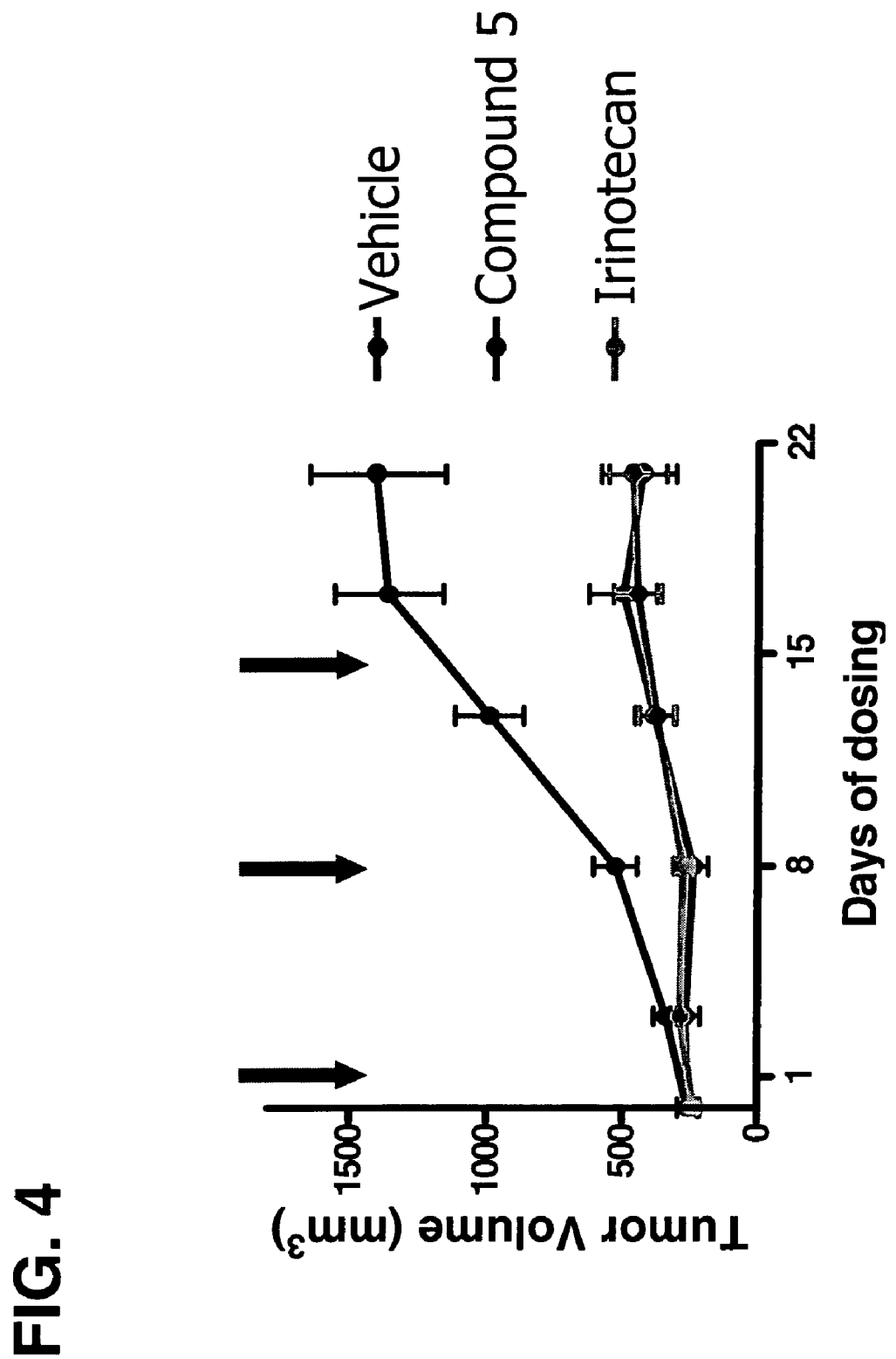
FIG. 4 depicts results of tumor growth inhibition experiments in a HCT-116 tumor xenograft model. A compound of the invention was administered intra-peritoneally (IP) to mice implanted with HCt-116 tumors. The compound inhibits tumor growth following a dosing regimen of 75 mg/kg, once a week, for 3 weeks.
Figure 5:
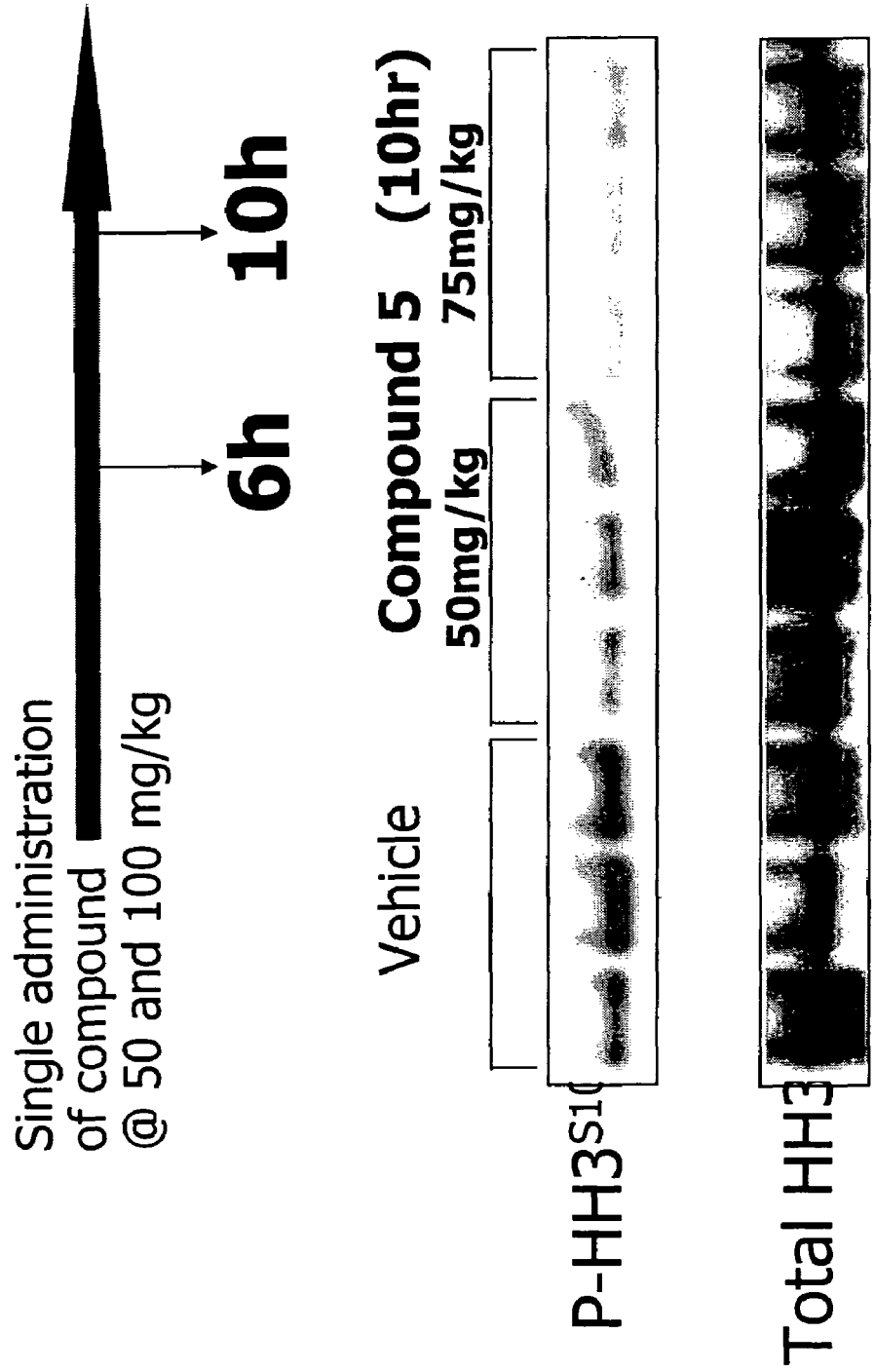
FIG. 5 depicts results of phosphorylated Histone H3 modulation experiments in a HCT-116 tumor xenograft model. A compound of the invention was administered intravenously as a single dose at 6 h (50 mg/kg) and 10 h (75 mg/kg).

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; - or —$GR^{G1}$ wherein G is —O—, —S—, —$NR^{G2}$, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$, —$NR^{G2}$C(=O)O, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —CH$_2$-cyclohexyl, cyclohexenylethyl, cyclohexanylethyl, norborbyl moieties and the like, which again, may bear one or more substituents.

The term "cycloalkyl", as used herein, refers specifically to cyclic alkyl groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, i.e., in place of carbon atoms. Thus, a 1-6 atom heteroaliphatic linker having at least one N atom in the heteroaliphatic main chain, as used herein, refers to a $C_{1-6}$aliphatic chain wherein at least one carbon atom is replaced with a nitrogen atom, and wherein any one or more of the remaining 5 carbon atoms may be replaced by an oxygen, sulfur, nitrogen, phosphorus or silicon atom. As used herein, a 1-atom heteroaliphatic linker having at least one N atom in the heteroaliphatic main chain refers to —NH— or —NR— where R is aliphatic, heteroaliphatic, acyl, aromatic, heteroaromatic or a nitrogen protecting group. Heteroaliphatic moieties may be branched or linear unbranched. In certain embodiments, heteroaliphatic moieties are substituted by independent replacement of one or more of the hydrogen atoms thereon with one or more moieties including, any of the substituents described above.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to stable substituted or unsubstituted unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -aliphatic)aromatic, -(heteroaliphatic)aromatic, -(aliphatic)heteroaromatic, -(heteroaliphatic)heteroaromatic, -(alkyl)aromatic, (heteroalkyl) aromatic, -(alkyl)heteroaromatic, and -heteroalkyl) heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound.

The terms "alkoxy" (or "alkyloxy"), and "thioalkyl" as used herein refers to an alkyl group, as previously defined, attached to the parent molecular moiety through an oxygen atom ("alkoxy") or through a sulfur atom ("thioalkyl"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 14 aliphatic carbon atoms. Examples of alkoxy groups, include but are not limited to, methoxy, ethoxy, propoxy, isopropoxy, n-butoxy, tert-butoxy, neopentoxy and n-hexoxy. Examples of thioalkyl groups include, but are not limited to, methylthio, ethylthio, propylthio, isopropylthio, n-butylthio, and the like.

The term "amine" refers to a group having the structure —N(R)$_2$ wherein each occurrence of R is independently hydrogen, or an aliphatic, heteroaliphatic, aromatic or heteroaromatic moiety, or the R groups, taken together, may form a heterocyclic moiety.

The term "alkylamino" refers to a group having the structure —NHR' wherein R' is alkyl, as defined herein. The term "aminoalkyl" refers to a group having the structure $NH_2R'$—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

The terms "halo" and "halogen" as used herein refer to an atom selected from fluorine, chlorine, bromine and iodine.

The term "halogenated" denotes a moiety having one, two, or three halogen atoms attached thereto.

The term "haloalkyl" denotes an alkyl group, as defined above, having one, two, or three halogen atoms attached thereto and is exemplified by such groups as chloromethyl, bromoethyl, trifluoromethyl, and the like.

The term "acyloxy", as used herein, does not substantially differ from the common meaning of this term in the art, and refers to a moiety of structure —OC(O)$R_X$, wherein $R_X$ is a substituted or unsubstituted aliphatic, alicyclic, heteroaliphatic, heteroalicyclic, aryl or heteroaryl moiety.

The term "acyl", as used herein, does not substantially differ from the common meaning of this term in the art, and refers to a moiety of structure —C(O)$R_X$, wherein $R_X$ is a substituted or unsubstituted, aliphatic, alicyclic, heteroaliphatic, heteroalicyclic, aryl or heteroaryl moiety.

The term "imino", as used herein, does not substantially differ from the common meaning of this term in the art, and refers to a moiety of structure —C(=N$R_X$)$R_Y$, wherein $R_X$ is hydrogen or an optionally substituted aliphatic, alicyclic, heteroaliphatic, heteroalicyclic, aryl or heteroaryl moiety; and $R_Y$ is an optionally substituted aliphatic, alicyclic, heteroaliphatic, heteroalicyclic, aryl or heteroaryl moiety.

The term "$C_{1-6}$alkylene", as used herein, refers to a substituted or unsubstituted, linear or branched saturated divalent radical consisting solely of carbon and hydrogen atoms, having from one to six carbon atoms, having a free valence "-" at both ends of the radical.

The term "$C_{2-6}$alkenylene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like, used alone or as part of a larger moiety, encompass both substituted and unsubstituted groups.

As used herein, the term "isolated", when applied to the compounds of the present invention, refers to such compounds that are (i) separated from at least some components with which they are associated in nature or when they are made and/or (ii) produced, prepared or manufactured by the hand of man.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety that is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "Aurora-mediated disease" or "Aurora-mediated condition", as used herein, means any disease or other deleterious condition in which Aurora is known to play a role. The terms "Aurora-mediated disease" or "Aurora-mediated condition" also mean those diseases or conditions that are alleviated by treatment with an Aurora inhibitor. Such conditions include, without limitation, colon, breast, stomach, and ovarian cancer. The term "Aurora-mediated disease", as used herein, means any disease or other deleterious condition or disease in which Aurora is known to play a role. Such diseases or conditions include, without limitation, cancers such as colon and breast cancer.

The term "treating", as used herein generally means that the compounds of the invention can be used in humans or animals with at least a tentative diagnosis of disease. In certain embodiments, compounds of the invention will delay or slow the progression of the disease thereby giving the individual a longer life span.

The term "preventing" as used herein means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of disease, or prevent the individual from developing the disease at all. Preventing also includes administration of the compounds of the invention to those individuals thought to be predisposed to the disease due to familial history, genetic or chromosomal abnormalities, and/or due to the presence of one or more biological markers for the disease.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF CERTAIN PREFERRED EMBODIMENTS OF THE INVENTION

As noted above, there has been increasing interest in recent years in the development of protein kinase inhibitors, particularly Aurora inhibitors, as therapeutic agents for the treatment of diseases/conditions involving protein kinase-mediated events. In one aspect, the present invention provides Aurora inhibitors.

Compounds of this invention include those generally set forth above and described specifically herein, and are illustrated in part by the various classes, subgenera and species disclosed herein. Additionally, the present invention provides pharmaceutically acceptable derivatives of the inventive compounds, and methods of treating a subject using these compounds, pharmaceutical compositions thereof, or either of these in combination with one or more additional therapeutic agents.

1) General Description of Compounds of the Invention

In certain embodiments, the compounds of the invention include compounds of the general formula (I) as further defined below:

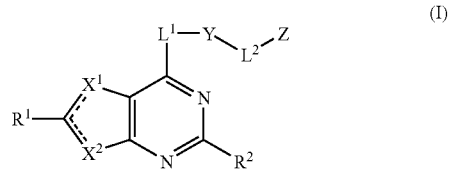

and pharmaceutically acceptable derivatives thereof;

wherein one of - - - - - is a double bond, as valency permits;

$R^1$ and $R^2$ are independently hydrogen, halogen, cyano, nitro, or an aliphatic, heteroaliphatic, alicyclic, heteroalicyclic, aromatic or heteroaromatic moiety;

one of $X^1$ and $X^2$ is S, the other is —C($R^{X1}$)—; wherein $R^{X1}$ is hydrogen, halogen, cyano, nitro, or an aliphatic, heteroaliphatic, alicyclic, heteroalicyclic, aromatic or heteroaromatic moiety;

$L^1$ is a 2-8 atom heteroaliphatic linker having at least one N, O or S atom in the heteroaliphatic main chain;

$L^2$ is a 1-6 atom heteroaliphatic linker having at least one N atom in the heteroaliphatic main chain;

Y is an alicyclic, heteroalicyclic, aromatic or heteroaromatic moiety; and

Z is an aliphatic, heteroaliphatic, alicyclic, heteroalicyclic, aromatic or heteroaromatic moiety.

In certain embodiments, the following groups do not occur simultaneously as defined: $L^1$ is —OCH$_2$—, —CH$_2$O—, —N(R)CH$_2$— or —CH$_2$N(R)—, wherein R is H or $C_{1-8}$alkyl; Y is phenyl; and Z is a 5-10-membered cycloalkyl, heterocyclyl, aryl or heteroaryl.

In certain embodiments, the following groups do not occur simultaneously as defined: $L^1$—Y is —NHCH$_2$CH$_2$-phenyl or —OCH$_2$CH$_2$-phenyl; $L^2$ is —C(R)=N—O—, wherein R is H, $C_{1-4}$alkyl, $C_{1-4}$haloalkyl or $C_{3-6}$cycloalkyl; and $R^1$ and $R^{X1}$ (or $R^1$ and $R^{X2}$, when $X^1$ is S) are independently hydrogen, halogen or $C_{1-4}$alkyl.

In certain embodiments, the following groups do not occur simultaneously as defined: $L^1$ is —OCH(R)—, —OCH(R)—$C_{1-6}$alkylO— or —OCH(R)—$C_{1-6}$alkylC(=NR$_x$)— where R is H, $C_{1-4}$alkyl, $C_{1-4}$haloalkyl or $C_{3-6}$cycloalkyl and R$_x$ is H, aliphatic, heteroaliphatic, alicyclic, heteroalicyclic, aromatic or heteroaromatic; Y and Z are each optionally substituted phenyl; and $L^2$ is —OCH$_2$— or —OSO$_2$—; and $R^1$ and $R^{X1}$ (or $R^1$ and $R^{X2}$, when $X^1$ is S) are independently hydrogen, halogen or alkyl.

In certain embodiments, the following groups do not occur simultaneously as defined: $X^1$ is $CR^{X1}$ wherein $R^{X1}$ is $Q_4$; $X^2$ is S; $R^1$ is $Q_5$; Y and Z are independently optionally substituted aryl, carbocycle or 5-membered monocyclic heterocycle; and $L^1$ is —W—N=CH— wherein W is O or NR, wherein R is H, $C_{1-6}$alk(en/yn)yl, $C_{3-8}$cycloalk(en)yl, aryl, hydroxy$C_{1-6}$alk(en/yn)yl, $C_{3-8}$cycloalk(en)yl-$C_{1-6}$alk(en/yn)yl or acyl; wherein $Q_4$ is hydrogen, halogen, cyano, nitro, $C_{1-6}$alk(en/yn)yl, $C_{1-6}$alk(en/yn)yloxy, $C_{1-6}$alk(en/yn)yloxy-$C_{1-6}$alk(en/yn)yl, $C_{1-6}$alk(en/yn)ylsulfanyl, hydroxy, hydroxy-$C_{1-6}$alk(en/yn)yl, halo-$C_{1-6}$alk(en/yn)yl, halo-$C_{1-6}$alk(en/yn)yloxy, $C_{3-8}$cycloalk(en)yl, $C_{3-8}$cycloalk(en)yl-$C_{1-6}$alk(en/yn)yl, acyl, $C_{1-6}$alk(en/yn)yloxycarbonyl, $C_{1-6}$alk(en/yn)ylsulfonyl, —NR$^{X1A}$R$^{X1B}$ or R$^{X1A}$R$^{X1B}$NC$_{1-6}$alk(en/yn)yl; and Q5 is hydrogen, halogen, $C_{1-6}$alk(en/yn)yl, $C_{1-6}$alk(en/yn)yloxy, $C_{1-6}$alk(en/yn)yloxy-$C_{1-6}$alk(en/yn)yl, $C_{1-6}$alk(en/yn)ylsulfanyl, acyl, hydroxy, hydroxy-$C_{1-6}$alk(en/yn)yl, $C_{3-8}$cycloalk(en/yn)yl, $C_{3-8}$cycloalk(en/yn)yloxy, aryl, heterocyclyl, —NR$^{X1A}$R$^{X1B}$ or R$^{X1A}$R$^{X1B}$NC$_{1-6}$alk(en/yn)yl, where R$^{X1A}$ and R$^{X1B}$ are independently hydrogen or C$_{1-6}$alk(en/yn)yl.

In certain embodiments, neither R$^1$ nor R$^{X1}$ (or neither R$^1$ nor R$^{X2}$, when X$^1$ is S) is Q$^1$, Q$^2$ or Q$^3$, wherein Q$^1$ is —(CR$^{1A}$R$^{1B}$)$_m$C≡C—(CR$^{1A}$R$^{1B}$)$_t$R$^{1C}$, —(CR$^{1A}$R$^{1B}$)$_m$C≡C—(CR$^{1A}$R$^{1B}$)R$^{1C}$, —C=NOR$^{1D}$, or —X$^3$R$^{1D}$ wherein m is an integer from 0 to 3, t is an integer from 0 to 5, and X$^3$ is a divalent group derived from azetidine, oxetane or a C$_{3-4}$carbocyclic group;

Q$^2$ is —(CR$^{1A}$R$^{1B}$)$_m$C≡C—(CR$^{1A}$R$^{1B}$)$_k$R$^{1E}$, —(CR$^{1A}$R$^{1B}$)$_m$C≡C—(CR$^{1A}$R$^{1B}$)$_k$R$^{1E}$ wherein k is an integer from 1 to 3 and m is an integer from 0 to 3; and Q$^3$ is —(CR$^{1A}$R$^{1B}$)R$^{1C}$, wherein t is an integer from 0 to 5 and the attachment point to R$^{1C}$ is through a carbon atom of the R$^{1C}$ group; wherein R$^{1A}$ and R$^{1B}$ are independently H or C$_{1-6}$alkyl; R$^{1C}$ is an optionally substituted non-aromatic monocyclic ring, a fused or bridged bicyclic ring or a spirocyclic ring; R$^{1E}$ is —NR$^{1A}$R$^{1D}$ or —OR$^{1D}$; R$^{1D}$ is R$^{1F}$, —C(=O)R$^{1F}$, —SO$_2$R$^{1F}$, —C(=O)N(R$^{1F}$)$_2$, —SO$_2$N(R$^{1F}$)$_2$, or —CO$_2$R$^{1F}$, wherein R$^{1F}$ is H, C$_{1-6}$alkyl, —(CR$^{1A}$R$^{1B}$)$_t$(C$_{6-10}$aryl) or —(CR$^{1A}$R$^{1B}$)$_t$(4-10 membered heterocyclic).

In certain embodiments, the following groups do not occur simultaneously as defined: one of R$^1$ and R$^{X1}$ (or one of R$^1$ and R$^{X2}$, when X$^1$ is S) is hydrogen, the other is hydrogen, halogen, C$_{1-4}$alkyl or C$_{1-4}$alkoxy; L$^1$ is —NHC$_{1-6}$alkyl, —OC$_{1-6}$alkyl, —NHC$_{1-6}$heteroalkyl or —OC$_{1-6}$heteroalkyl; Y is cycloalkyl, aryl, heteroaryl or heterocyclyl; L$^2$—Z is —X—R$^x$ where X is —NR—, —C(=O)NH—, —NHC(=O)—, —SO$_2$NH— or —NHSO$_2$— and R$^x$ is C$_{3-10}$cycloalkyl, morpholinyl, phenyl, phenylC$_{1-4}$alkyl or phenylC$_{2-3}$alkenyl.

In certain embodiments, the following groups do not occur simultaneously as defined: one of X$^1$ and X$^2$ is CH, the other is S; L$^1$ is —NR(CR$^x$)$_{1-2}$— or —O(CR$^x$)$_{1-2}$— wherein R is hydrogen, C$_{1-4}$alkyl, C$_{1-4}$alkoxy, OH, NH$_2$ or —C$_{1-4}$alkylNH; and R$^x$ is H or C$_{1-4}$alkyl; Y is phenyl, thienyl, furanyl, pyrrolyl, pyridyl, pyrimidyl, imidazolyl, pyrazinyl, oxazolyl, thiazolyl, naphthyl, benzothienyl, benzofuranyl, indolyl, quinolinyl, isoquinolinyl or quinazolinyl; L$^2$—Z is —SO$_2$NHC$_{3-8}$cycloalkyl, —SO$_2$N(C$_{3-8}$cycloalkyl)$_2$, —C(=O)NHC$_{3-8}$cycloalkyl or —C(=O)N(C$_{3-8}$cycloalkyl)$_2$.

In certain embodiments, the following groups do not occur simultaneously as defined: R$^1$ is hydrogen, halogen, nitro or C$_{1-4}$alkyl; one of X$^1$ and X$^2$ is S, the other is CR$^{X4}$ wherein R$^{X4}$ is hydrogen, C$_{1-4}$alkyl or phenyl optionally substituted with halogen, (halo)C$_{1-4}$alkyl or (halo)C$_{1-4}$alkoxy; L$^1$ is —NRC$_{1-6}$alkyl-, —OC$_{1-6}$alkyl- or —SC$_{1-6}$alkyl- wherein R is hydrogen, C$_{1-4}$alkyl, C$_{1-4}$acyl; Y is phenyl; L$^2$—Z is a C$_{1-12}$alkyl saturated or unsaturated hydrocarbon chain including —NR— and optionally substituted with haloC$_{1-4}$alkoxy, C$_{3-8}$cycloalkyl, C$_{3-8}$cycloalkenyl, C$_{1-4}$acyl, phenoxy, phenyl or phenylthio.

In certain embodiments, compounds specifically and/or generically disclosed in Japanese Application Nos.: JP 3-173872 and JP 3-063271 (which are incorporated herein by reference) are excluded.

In certain embodiments, the present invention defines particular classes of compounds which are of special interest. For example, one class of compounds of special interest includes compounds of formula (I$^A$):

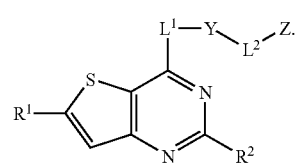

Another class of compounds of special interest includes compounds of formula (I$^B$):

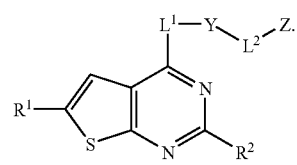

Another class of compounds of special interest includes compounds of formula (I$^C$):

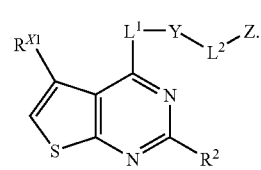

Another class of compounds of special interest includes compounds of formula (I$^D$):

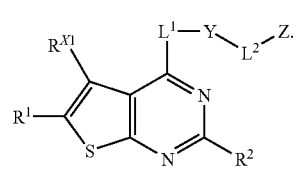

Another class of compounds of special interest includes compounds of formula (I$^E$):

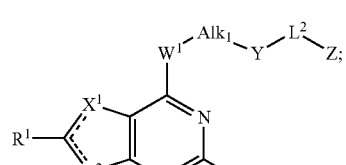

wherein W$^1$ is O or NR$^{W1}$, where R$^{W1}$ is hydrogen, aliphatic, heteroaliphatic, alicyclic, heteroalicyclic, aromatic, heteroaromatic, or acyl; and Alk$_1$ is a C$_{1-6}$alkylene or C$_{2-6}$alkenylene moiety.

Another class of compounds of special interest includes compounds of formula ($I^F$):

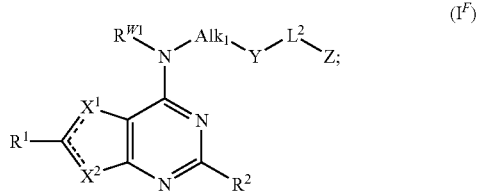

(I$^F$)

wherein $R^{W1}$ is hydrogen, aliphatic, heteroaliphatic, alicyclic, heteroalicyclic, aromatic, heteroaromatic, or acyl; $Alk_1$ is a $C_{1-6}$alkylene or $C_{2-6}$alkenylene moiety; or $R^{W1}$ taken together with a carbon atom present on $Alk_1$ may form a heterocyclic moiety.

Another class of compounds of special interest includes compounds of formula ($I^G$):

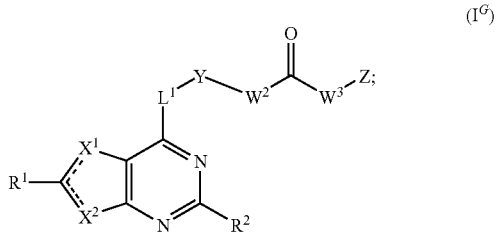

(I$^G$)

wherein $W^2$ and $W^3$ are independently absent, O, $NR^W$, $CR^{W1}R^{W2}$ or $NR^W CR^{W1}R^{W2}$, where $R^W$ is hydrogen, aliphatic, heteroaliphatic, alicyclic, heteroalicyclic, aromatic, heteroaromatic, or acyl; and $R^{W1}$ and $R^{W2}$ are independently hydrogen, aliphatic, heteroaliphatic, alicyclic, heteroalicyclic, aromatic or heteroaromatic; with the proviso that $W^2$ and $W^3$ are not each absent and at least one of $W^2$ and $W^3$ is $NR^W$ or $NR^W CR^{W1}R^{W2}$.

A number of important subclasses of each of the foregoing classes deserve separate mention; these subclasses include subclasses of the foregoing classes in which:

i) neither $R^1$ nor $R^{X1}$ (or neither $R^1$ nor $R^{X2}$, when $X^1$ is S) is —(CR$^{14}$R$^{1B}$)$_m$C≡C—(CR$^{14}$R$^{1B}$)$_t$R$^{1C}$, —(CR$^{14}$R$^{1B}$)$_m$C≡C(CR$^{14}$R$^{1B}$)$_t$R$^{1C}$, —C═NOR$^{1D}$, or —X$^3$R$^{1D}$ wherein m is an integer from 0 to 3, t is an integer from 0 to 5, and $X^3$ is a divalent group derived from azetidine, oxetane or a $C_{3-4}$carbocyclic group; wherein $R^{14}$ and $R^{1B}$ are independently H or $C_{1-6}$alkyl; $R^{1C}$ is an optionally substituted non-aromatic monocyclic ring, a fused or bridged bicyclic ring or a spirocyclic ring; $R^{1E}$ is —NR$^{14}$R$^{1D}$ or —OR$^{1D}$; $R^{1D}$ is $R^{1F}$, —C(═O)R$^{1F}$, —SO$_2$R$^{1F}$, —C(═O)N(R$^{1F}$)$_2$, —SO$_2$N(R$^{1F}$)$_2$, or —CO$_2$R$^{1F}$, wherein $R^{1F}$ is H, $C_{1-6}$alkyl, —(CR$_{14}$R$^{1B}$)$_t$(C$_{6-10}$aryl) or —(CR$^{14}$R$^{1B}$)$_t$(4-10 membered heterocyclic);

ii) neither $R^1$ nor $R^{X1}$ (or neither $R^1$ nor $R^{X2}$, when $X^1$ is S) is —(CR$^{14}$R$^{1B}$)$_m$C≡C—(CR$^{14}$R$^{1B}$)$_k$R$^{1E}$, —(CR$^{14}$R$^{1B}$)$_m$C≡C—(CR$^{14}$R$^{1B}$)$_k$R$^{1E}$ wherein k is an integer from 1 to 3 and m is an integer from 0 to 3;

iii) neither $R^1$ nor $R^{X1}$ (or neither $R^1$ nor $R^{X2}$, when $X^1$ is S) is —(CR$^{14}$R$^{1B}$)$_t$R$^{1C}$, wherein t is an integer from 0 to 5 and the attachment point to $R^{1C}$ is through a carbon atom of the $R^{1C}$ group;

iv) $R^1$ is hydrogen, halogen, —CN, —NO$_2$, —C(═O)R$^{14}$, —C(═O)OR$^{14}$, —C(═O)NR$^{14}$R$^{1B}$, —S(═O)$_2$R$^{1C}$, —P(═O)(R$^{1C}$)$_2$, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; wherein $R^{14}$ and $R^{1B}$ are independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5-6-membered heterocyclic ring; and each occurrence of $R^{1C}$ is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

v) $R^1$ is hydrogen, halogen, —NO$_2$, —CN, —C(═O)OR$^{14}$, —S(═O)$_2$R$^{1C}$, —P(═O)(R$^{1C}$)$_2$, alkyl, alkenyl, alkynyl, heteroalkyl, heteroalkenyl, heteroalkynyl, heterocyclyl, aryl or heteroaryl; wherein $R^{14}$ is hydrogen or $C_{1-6}$alkyl; and each occurrence of $R^{1C}$ is independently $C_{1-6}$alkyl;

vi) $R^1$ is hydrogen, halogen, —NO$_2$, —CN, $C_{1-5}$alkyl or $C_{1-5}$alkoxy;

vii) $R^1$ is hydrogen;

viii) $R^1$ is F, Cl, Br or I;

ix) $R^1$ is alkyl, alkenyl, alkynyl, heteroalkyl, heteroalkenyl or heteroalkynyl;

x) $R^1$ is one of:

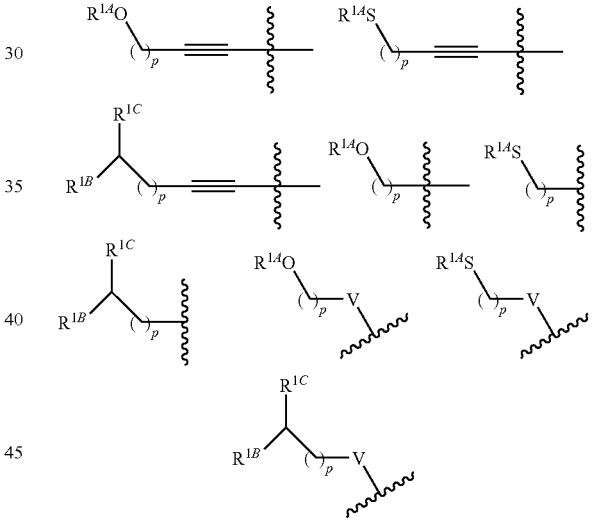

wherein V is O, S or $R^{1B}$; p is an integer from 0 to 6; and $R^{14}$ is hydrogen, alkyl, heteroalkyl, aryl, heteroaryl, -(alkyl)aryl, -(alkyl)heteroaryl, —C(═O)N(R$^{1B}$)$_2$, —C(═O)OR$^{1B}$; wherein each occurrence of $R^{1B}$ and $R^{1C}$ is independently hydrogen, lower alkyl, lower heteroalkyl, aryl, heteroaryl, -(alkyl)aryl, -(alkyl)heteroaryl or acyl; or $R^{1B}$ and $R^{1C}$, taken together with the nitrogen atom to which they are attached, form a substituted or unsubstituted heterocyclic moiety;

xi) $R^1$ is —CN, lower alkyl, lower alkynyl, —CO$_2$R$^{1D}$, or one of:

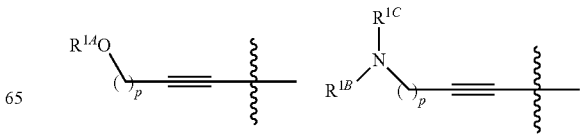

-continued

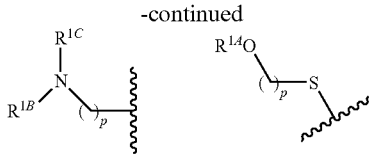

wherein p is an integer from 1 to 4; and $R^{1A}$ is hydrogen, alkyl, heteroalkyl, aryl, heteroaryl, -(alkyl)aryl, -(alkyl)heteroaryl, —C(=O)N($R^{1B}$)$_2$, —C(=O)O$R^{1B}$; wherein each occurrence of $R^{1B}$ and $R^{1C}$ is independently hydrogen, lower alkyl, lower heteroalkyl, aryl, heteroaryl, -(alkyl)aryl, -(alkyl) heteroaryl or acyl; or $R^{1B}$ and $R^{1C}$, taken together with the nitrogen atom to which they are attached, form a substituted or unsubstituted heterocyclic moiety; and $R^{1D}$ is hydrogen or lower alkyl;

xii) $R^1$ is —CN, —C≡CH, methyl, —CO$_2$H, —CO$_2$Me, or one of:

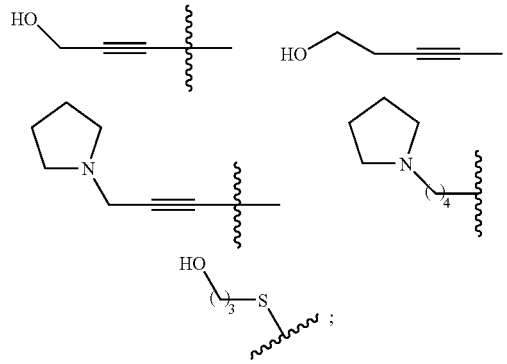

xiii) $R^1$ is aryl, heteroaryl or heterocyclyl;

xiv) $R^1$ is an aryl, heteroaryl or heterocyclyl moiety having one of the structures:

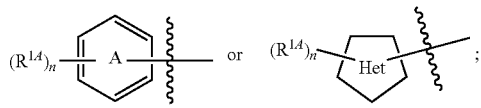

wherein the "A" cyclic moiety is a 6-membered aromatic ring comprising from 0-4 nitrogen atoms; the "Het" moiety represents a fully or partially saturated or unsaturated 5- to 6-membered ring comprising 1-4 heteroatoms selected from N, O and S; n is an integer from 0-6; and each occurrence of $R^{1A}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —O$R^{1B}$, —S$R^{1B}$, —N($R^{1B}$)$_2$, —SO$_2$N($R^{1B}$)$_2$, —SO$_2$$R^{1E}$, —C(=O)N($R^{1B}$)$_2$, halogen, —CN, —NO$_2$, —C(=O)O$R^{1B}$, —N($R^{1B}$)C(=O)$R^{1C}$ or —N($R^{1B}$)SO$_2$$R^{1E}$; wherein each occurrence of $R^{1B}$ and $R^{1C}$ is independently hydrogen, lower alkyl, lower heteroalkyl, aryl, heteroaryl, -(alkyl)aryl, -(alkyl)heteroaryl, acyl; or any two occurrences of $R^{1B}$, taken together with the nitrogen atom to which they are attached (e.g., N($R^{1B}$)$_2$), form a substituted or unsubstituted heterocyclic moiety; $R^{1E}$ is alkyl, heteroalkyl, aryl, heteroaryl, -(alkyl)aryl, or -(alkyl) heteroaryl; and wherein any two adjacent occurrence of $R^{1A}$ may form a fused 5- to 6-membered aryl, heteroaryl or heterocyclic ring;

xv) $R^1$ is one of:

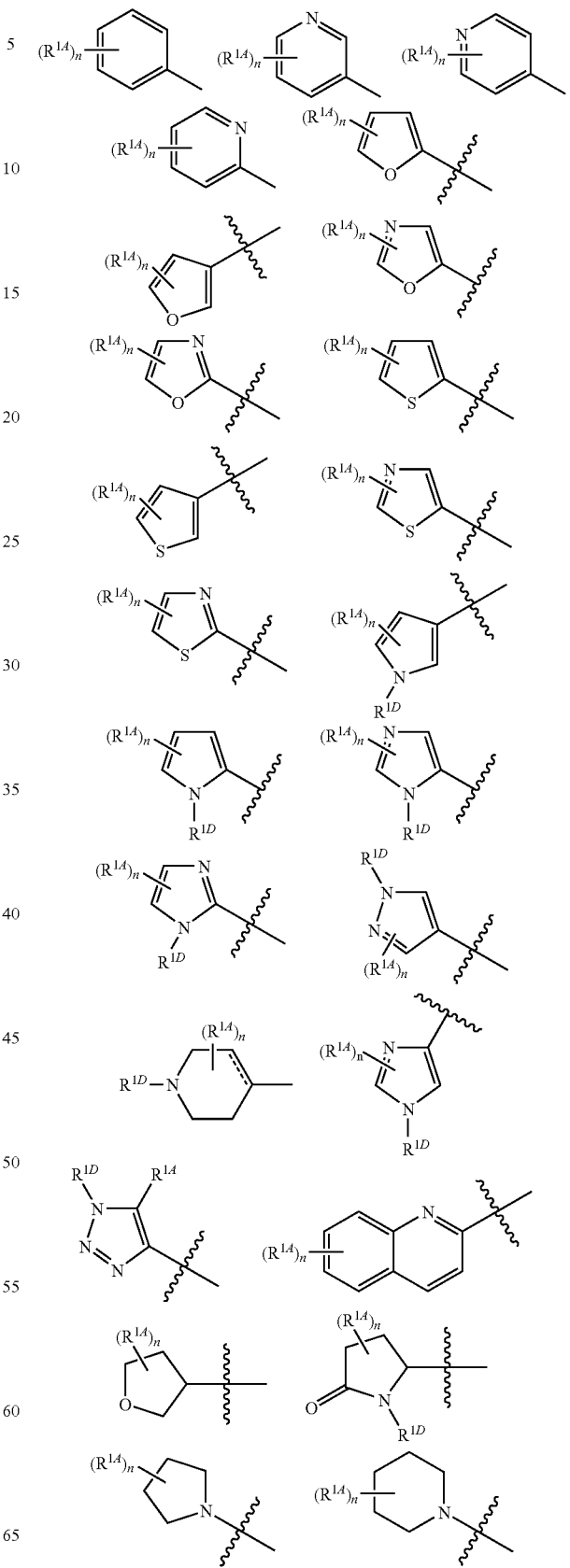

-continued

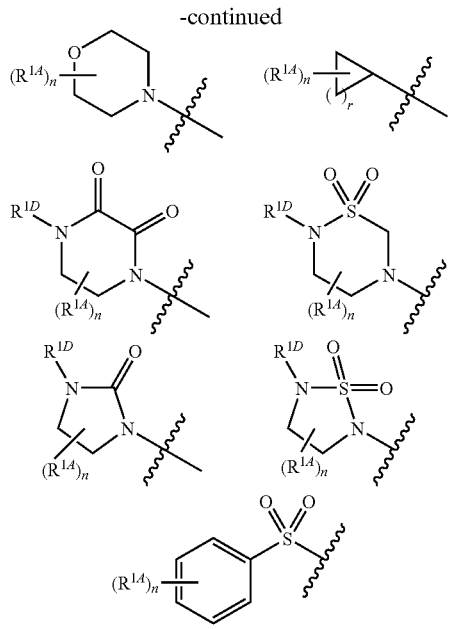

wherein each occurrence of $R^{1A}$ is independently hydrogen, alkyl, cycloalkyl, heteroalkyl, heterocyclyl, aryl, heteroaryl, -(alkyl)heterocyclyl, -(alkyl)heteroaryl, —$OR^{1B}$, —$SR^{1B}$, —$N(R^{1B})_2$, —$SO_2N(R^{1B})_2$, —$SO_2R^{1E}$, —$C(=O)N(R^{1B})_2$, halogen, —CN, —$NO_2$, —$C(=O)OR^{1B}$, —$N(R^{1B})C(=O)R^{1C}$ or —$N(R^{1B})SO_2R^{1E}$; wherein each occurrence of $R^{1B}$ and $R^{1C}$ is independently hydrogen, lower alkyl, lower heteroalkyl, aryl, heterocycyl, -(alkyl)aryl, -(alkyl)heteroaryl, acyl; or $R^{1B}$ and $R^{1C}$, taken together with the atoms to which they are attached, form a substituted or unsubstituted heterocyclic moiety; $R^{1D}$ is hydrogen, alkyl, cycloalkyl, heteroalkyl, heterocyclyl, aryl, heteroaryl, -(alkyl)heterocyclyl, -(alkyl)aryl, -(alkyl)heteroaryl, acyl or a nitrogen protecting group; and $R^{1E}$ is lower alkyl, lower heteroalkyl, aryl, heteroaryl, -(alkyl)aryl, or -(alkyl)heteroaryl; wherein n is an integer from 0 to 3 and r is an integer from 1 to 6;

xvi) $R^1$ is one of:

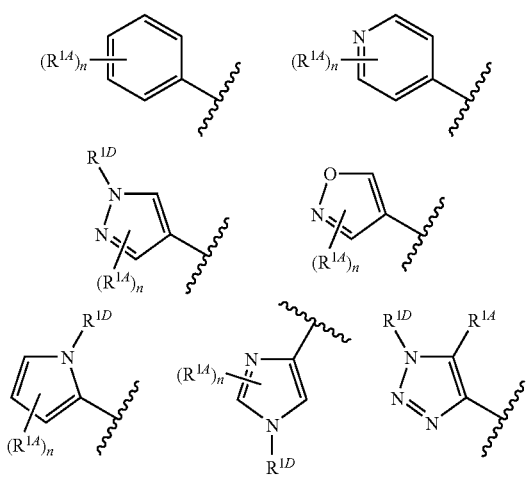

wherein n, $R^{1A}$ and $R^{1D}$ are as defined in xiv) above;

xvii) $R^1$ is one of:

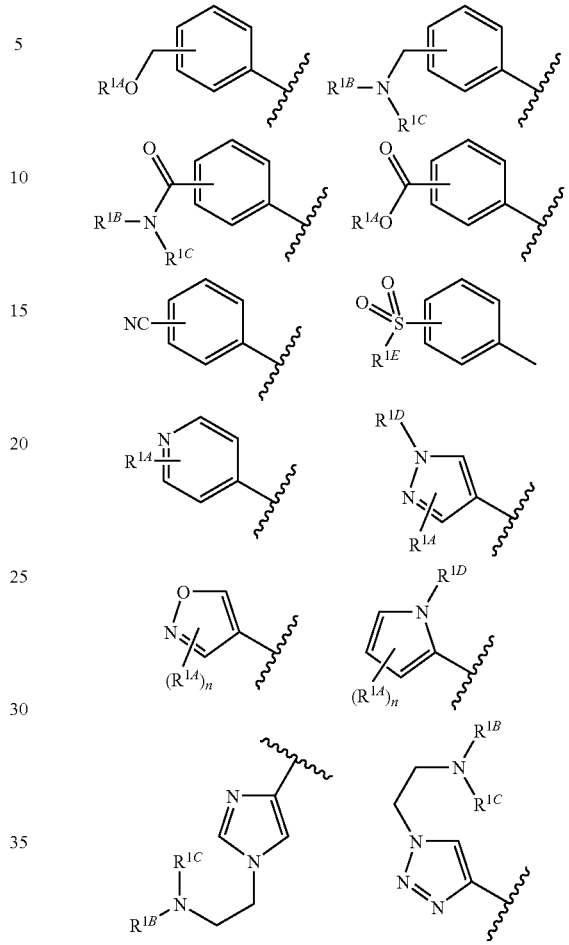

wherein n is 0-2; $R^{1A}$ is hydrogen or lower alkyl; each occurrence of $R^{1B}$ and $R^{1C}$ is independently hydrogen, lower alkyl, or $R^{1B}$ and $R^{1C}$, taken together with the nitrogen atom to which they are attached, form a substituted or unsubstituted 5-6 membered heterocyclic moiety; $R^{1D}$ is hydrogen, or lower alkyl; $R^{1E}$ is hydrogen, or lower alkyl;

xviii) $R^1$ is one of:

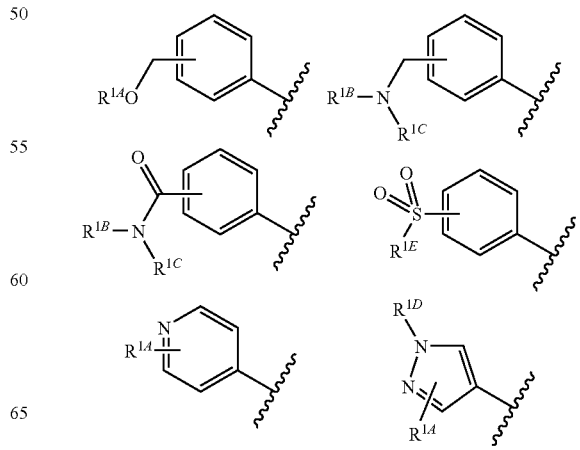

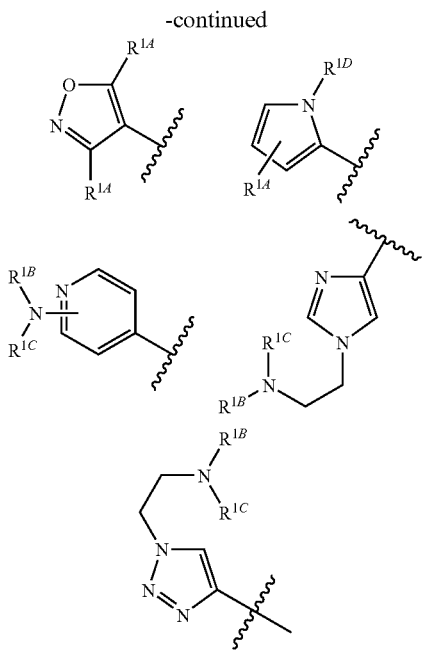

wherein each occurrence of $R^{1A}$ is independently hydrogen or lower alkyl; each occurrence of $R^{1B}$ and $R^{1C}$ is independently hydrogen, lower alkyl, or $R^{1B}$ and $R^{1C}$, taken together with the nitrogen atom to which they are attached, form a substituted or unsubstituted 5-6 membered heterocyclic moiety; $R^{1D}$ is hydrogen, or lower alkyl; $R^{1E}$ is hydrogen, or lower alkyl;

xix) $R^1$ is one of:

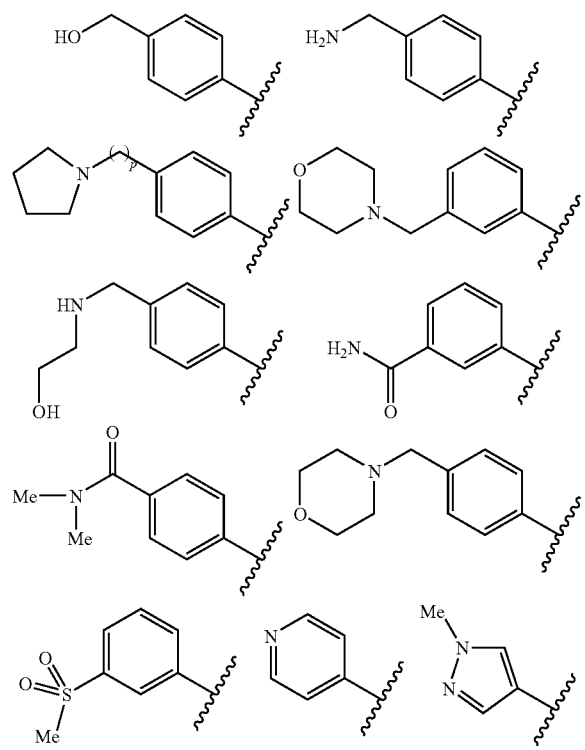

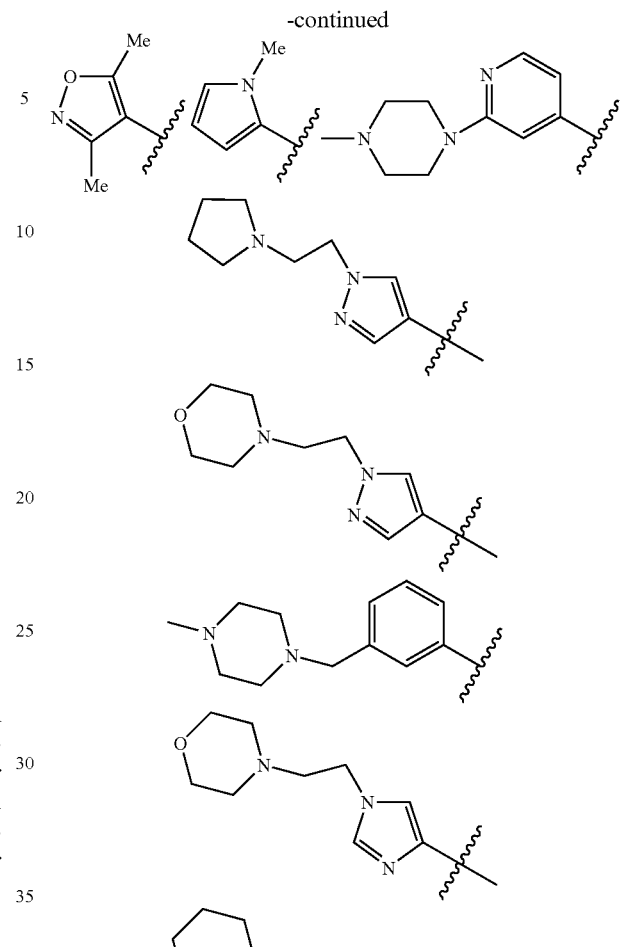

wherein p is 1 or 3;

xx) $R^2$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

xxi) $R^2$ is $C_{1-3}$alkyl or $C_{1-3}$alkoxy;

xxii) $R^2$ is methyl or —$CF_3$;

xxiii) $R^2$ is halogen;

xxiv) $R^2$ is hydrogen;

xxv) one of $X^1$ and $X^2$ is S, the other is —$C(R^{X4})$—; wherein $R^{X4}$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

xxvi) one of $X^1$ and $X^2$ is S, the other is —$C(R^{X4})$—; wherein $R^{X4}$ is hydrogen, halogen, or an alkyl, alkenyl, alkynyl, cycloalkyl, cycloalkenyl, heteroalkyl, heteroalkenyl, heteroalkynyl, heterocyclyl, aryl or heteroaryl moiety;

xxvii) one of $X^1$ and $X^2$ is S, the other is —C($R^{XA}$)—; wherein $R^{XA}$ is hydrogen, halogen, or a lower alkyl, cycloalkyl, cycloalkenyl, lower heteroalkyl, heterocyclyl, aryl or heteroaryl moiety;

xxviii) one of $X^1$ and $X^2$ is S, the other is —C($R^{XA}$)—; wherein $R^{XA}$ is hydrogen, halogen, or a lower alkyl, cycloalkyl, heterocyclyl, aryl or heteroaryl moiety;

xxix) one of $X^1$ and $X^2$ is S, the other is —C($R^{XA}$)—; wherein $R^{XA}$ is hydrogen, halogen, $C_{1-5}$alkyl, $C_{1-5}$alkoxy, —$CO_2H$, —$CO_2C_{1-5}$alkyl, —CN or —$NO_2$;

xxx) $X^1$ is S and $X^2$ is CH;

xxxi) $X^2$ is S and $X^1$ is —C($R^{X1}$)—; wherein $R^{X1}$ is hydrogen, halogen, —CN, —$NO_2$, —C(=O)$R^{1A}$, —C(=O)N$R^{1A}R^{1B}$, —S(=O)$_2R^{1C}$, —P(=O)($R^{1C}$)$_2$, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; wherein $R^{1A}$ and $R^{1B}$ are independently hydrogen, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl; or taken together with the nitrogen atom to which they are attached form a 5-6-membered heterocyclic ring; and each occurrence of $R^{1C}$ is independently alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

xxxii) $X^2$ is S and $X^1$ is —C($R^{X1}$)—; wherein $R^{X1}$ is hydrogen, halogen, —$NO_2$, —CN, —C(=O)O$R^{1A}$, —S(=O)$_2R^{1C}$, —P(=O)($R^{1C}$)$_2$, alkyl, alkenyl, alkynyl, heteroalkyl, heteroalkenyl, heteroalkynyl, heterocyclyl, aryl or heteroaryl; wherein $R^{1A}$ is hydrogen or $C_{1-6}$alkyl; and each occurrence of $R^{1C}$ is independently $C_{1-6}$alkyl;

xxxiii) $X^2$ is S and $X^1$ is —C($R^{X1}$)—; wherein $R^{X1}$ is hydrogen, halogen, —$NO_2$, —CN, $C_{1-5}$alkyl or $C_{1-5}$alkoxy;

xxxiv) $X^2$ is S and $X^1$ is CH;

xxxv) $X^2$ is S and $X^1$ is —C($R^{X1}$)—; wherein $R^{X1}$ is F, Cl, Br or I;

xxxvi) $X^2$ is S and $X^1$ is —C($R^{X1}$)—; wherein $R^{X1}$ is alkyl, alkenyl, alkynyl, heteroalkyl, heteroalkenyl or heteroalkynyl;

xxxvii) $X^2$ is S and $X^1$ is —C($R^{X1}$)—; wherein $R^{X1}$ is one of:

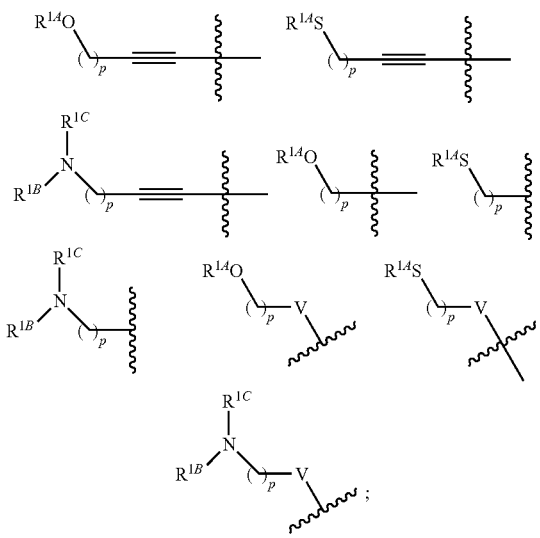

wherein V is O, S or $R^{1B}$; p is an integer from 0 to 6; and $R^{1A}$ is hydrogen, alkyl, heteroalkyl, aryl, heteroaryl, -(alkyl)aryl, -(alkyl)heteroaryl, —C(=O)N($R^{1B}$)$_2$, —C(=O)O$R^{1B}$; wherein each occurrence of $R^{1B}$ and $R^{1C}$ is independently hydrogen, lower alkyl, lower heteroalkyl, aryl, heteroaryl, -(alkyl)aryl, -(alkyl)heteroaryl or acyl; or $R^{1B}$ and $R^{1C}$, taken together with the nitrogen atom to which they are attached, form a substituted or unsubstituted heterocyclic moiety;

xxxviii) $X^2$ is S and $X^1$ is —C($R^{X1}$)—; wherein $R^{X1}$ is —CN, lower alkyl, lower alkynyl, —$CO_2R^{1D}$, or one of:

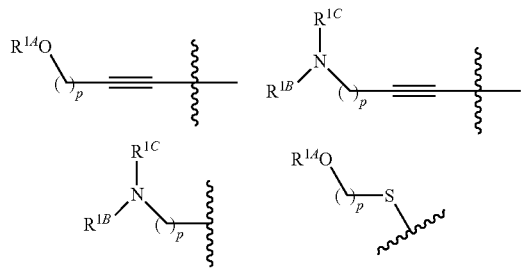

wherein p is an integer from 1 to 4; and $R^{1A}$ is hydrogen, alkyl, heteroalkyl, aryl, heteroaryl, -(alkyl)aryl, -(alkyl)heteroaryl, —C(=O)N($R^{1B}$)$_2$, —C(=O)O$R^{1B}$; wherein each occurrence of $R^{1B}$ and $R^{1C}$ is independently hydrogen, lower alkyl, lower heteroalkyl, aryl, heteroaryl, -(alkyl)aryl, -(alkyl)heteroaryl or acyl; or $R^{1B}$ and $R^{1C}$, taken together with the nitrogen atom to which they are attached, form a substituted or unsubstituted heterocyclic moiety; and $R^{1D}$ is hydrogen or lower alkyl;

xxxix) $X^2$ is S and $X^1$ is —C($R^{X1}$)—; wherein $R^{X1}$ is —CN, —C≡CH, methyl, —$CO_2H$, —$CO_2Me$, or one of:

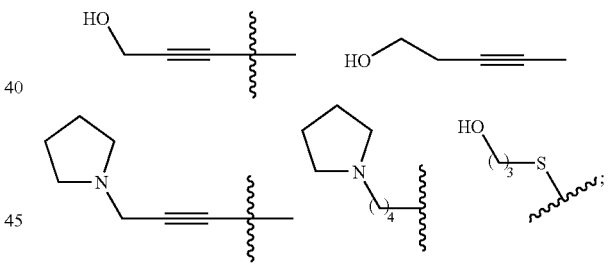

xl) $X^2$ is S and $X^1$ is C($R^{X1}$)—; wherein $R^{X1}$ is aryl, heteroaryl or heterocyclyl;

xli) $X^2$ is S and $X^1$ is —C($R^{X1}$)—; wherein $R^{X1}$ is an aryl, heteroaryl or heterocyclyl moiety having one of the structures:

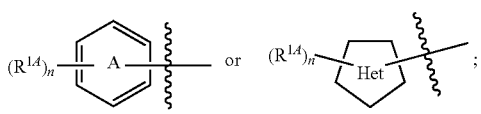

wherein the "A" cyclic moiety is a 6-membered aromatic ring comprising from 0-4 nitrogen atoms; the "Het" moiety represents a fully or partially saturated or unsaturated 5- to 6-membered ring comprising 1-4 heteroatoms selected from N, O and S; n is an integer from 0-6; and each occurrence of $R^{1A}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —OR$^{1B}$, —SR$^{1B}$, —N(R$^{1B}$)$_2$, —SO$_2$N(R$^{1B}$)$_2$, —SO$_2$R$^{1E}$, —C(=O)N(R$^{1B}$)$_2$, halogen, —CN, —NO$_2$, —C(=O)OR$^{1B}$, N(R$^{1B}$)C(=O)R$^{1C}$ or —N(R$^{1B}$)SO$_2$R$^{1E}$; wherein each occurrence of R$^{1B}$ and R$^{1C}$ is independently hydrogen, lower alkyl, lower heteroalkyl, aryl, heteroaryl, -(alkyl)aryl, -(alkyl)heteroaryl, acyl; or any two occurrences of R$^{1B}$, taken together with the nitrogen atom to which they are attached (e.g., N(R$^{1B}$)$_2$), form a substituted or unsubstituted heterocyclic moiety; R$^{1E}$ is alkyl, heteroalkyl, aryl, heteroaryl, -(alkyl)aryl, or -(alkyl)heteroaryl; and wherein any two adjacent occurrence of R$^{1A}$ may form a fused 5- to 6-membered aryl, heteroaryl or heterocyclic ring;

xlii) X$^2$ is S and X$^1$ is —C(R$^{X1}$)—; wherein R$^{X1}$ is one of:

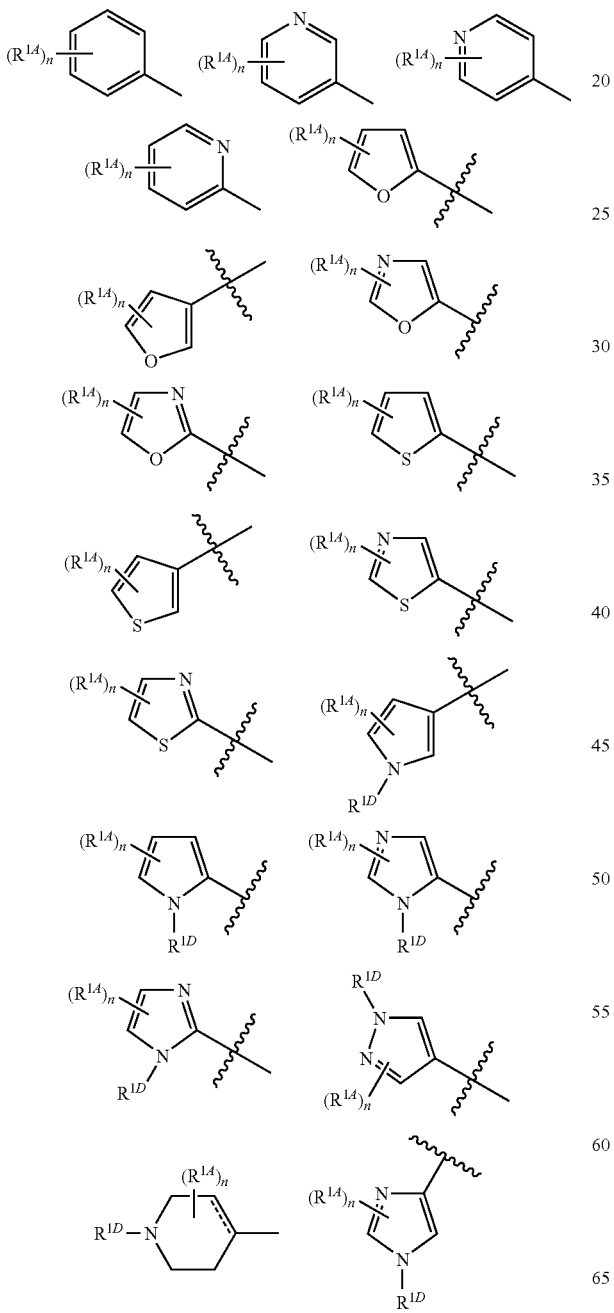
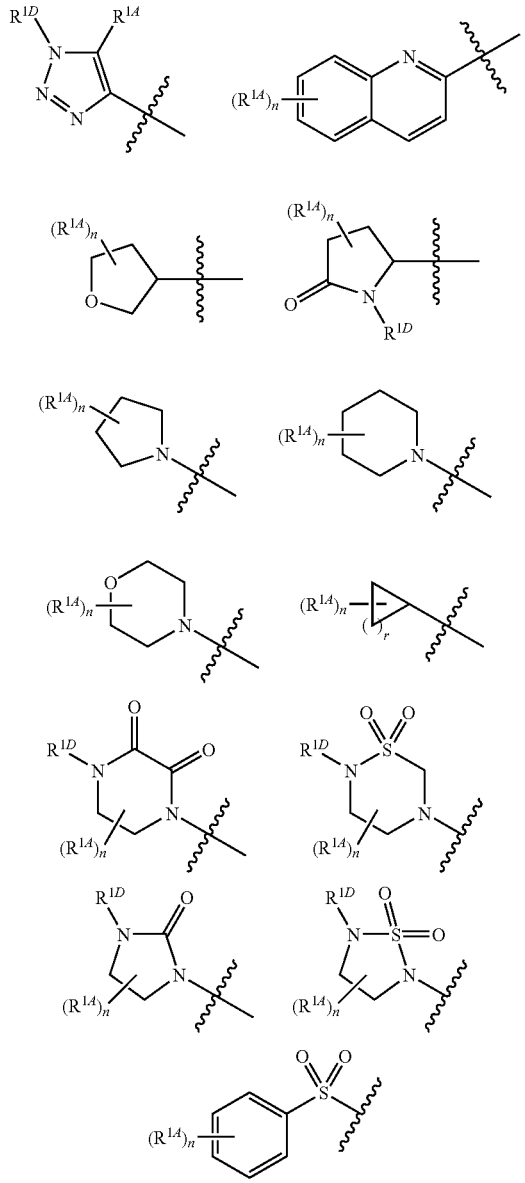

wherein each occurrence of R$^{1A}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —OR$^{1B}$, —SR$^{1B}$, —N(R$^{1B}$)$_2$, —SO$_2$N(R$^{1B}$)$_2$, —SO$_2$R$^{1E}$, C(=O)N(R$^{1B}$)$_2$, halogen, —CN, —NO$_2$, —C(=O)OR$^{1B}$, N(R$^{1B}$)C(=O)R$^{1C}$ or —N(R$^{1B}$)SO$_2$R$^{1E}$; wherein each occurrence of R$^{1B}$ and R$^{1C}$ is independently hydrogen, lower alkyl, lower heteroalkyl, aryl, heteroaryl, -(alkyl)aryl, -(alkyl)heteroaryl, acyl; or R$^{1B}$ and R$^{1C}$, taken together with the atoms to which they are attached, form a substituted or unsubstituted heterocyclic moiety; R$^{1D}$ is hydrogen, alkyl, cycloalkyl, heteroalkyl, heterocyclyl, aryl, heteroaryl, -(alkyl)heterocyclyl, -(alkyl)aryl, -(alkyl)heteroaryl, acyl or a nitrogen protecting group; and R$^{1E}$ is lower alkyl, lower heteroalkyl, aryl, heteroaryl, -(alkyl)aryl, or -(alkyl)heteroaryl; wherein n is an integer from 0 to 3 and r is an integer from 1 to 6;

xliii) $X^2$ is S and $X^1$ is —C($R^{X1}$)—; wherein $R^{X1}$ is one of:

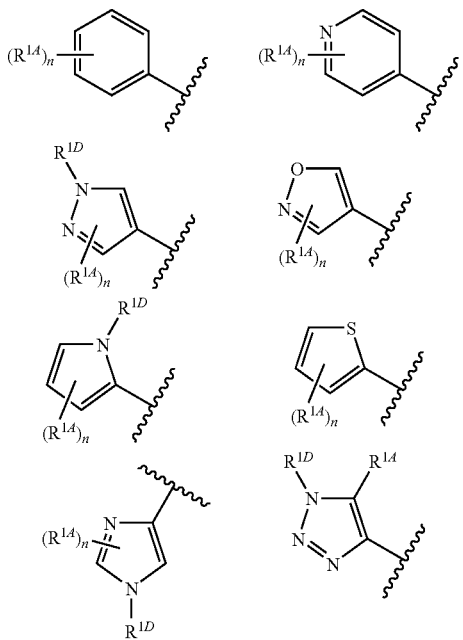

wherein n, $R^{1A}$ and $R^{1D}$ are as defined in xlii) above;

xliv) $X^2$ is S and $X^1$ is —C($R^{X1}$)—; wherein $R^{X1}$ is one of:

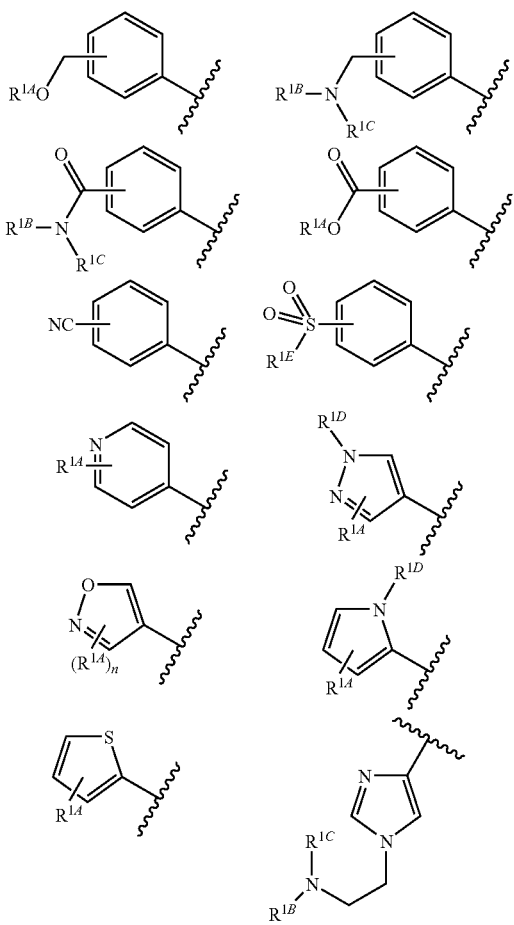

wherein n is 0-2; $R^{1A}$ is hydrogen or lower alkyl; each occurrence of $R^{1B}$ and $R^{1C}$ is independently hydrogen, lower alkyl, or $R^{1B}$ and $R^{1C}$, taken together with the nitrogen atom to which they are attached, form a substituted or unsubstituted 5-6 membered heterocyclic moiety; $R^{1D}$ is hydrogen, or lower alkyl; $R^{1E}$ is hydrogen, or lower alkyl;

xlv) $X^2$ is S and $X^1$ is —($R^{X1}$)—; wherein $R^{X1}$ is one of:

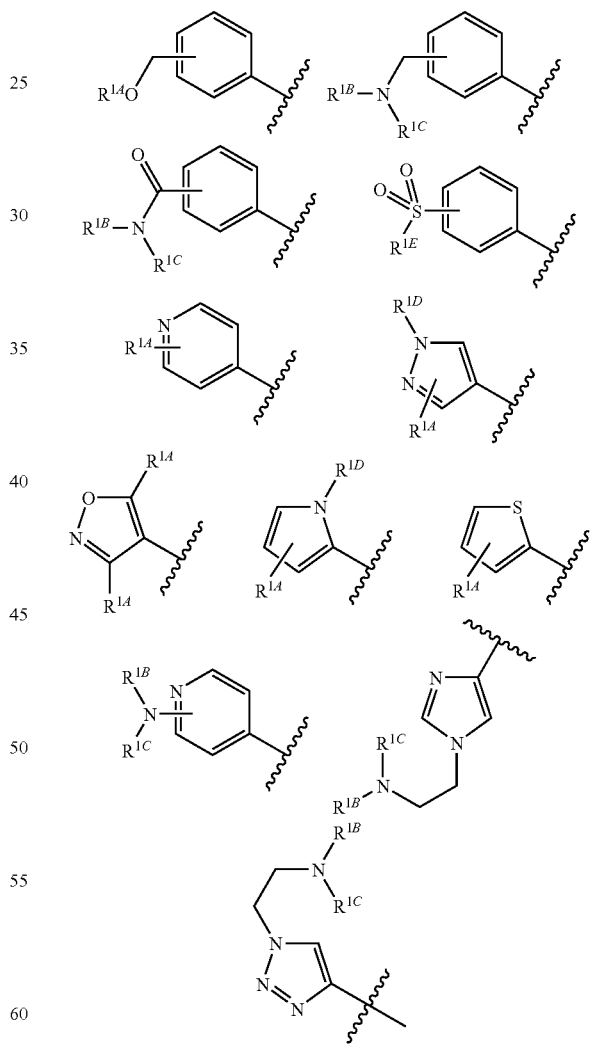

wherein each occurrence of $R^{1A}$ is independently hydrogen or lower alkyl; each occurrence of $R^{1B}$ and $R^{1C}$ is independently hydrogen, lower alkyl, or $R^{1B}$ and $R^{1C}$, taken together with the nitrogen atom to which they are attached, form a substituted or unsubstituted 5-6 membered heterocyclic moiety; $R^{1D}$ is hydrogen, or lower alkyl; $R^{1E}$ is hydrogen, or lower alkyl;

xlvi) $X^2$ is S and $X^1$ is $C(R^{X1})$—; wherein $R^{X1}$ is one of:

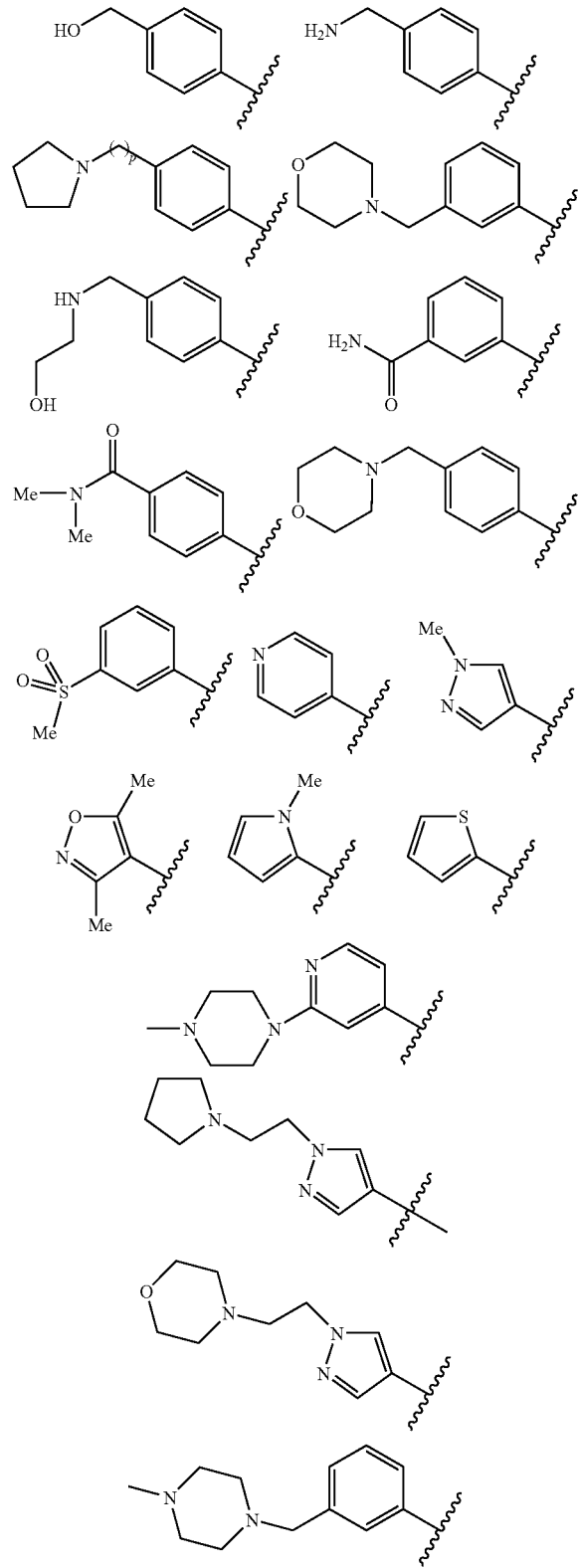

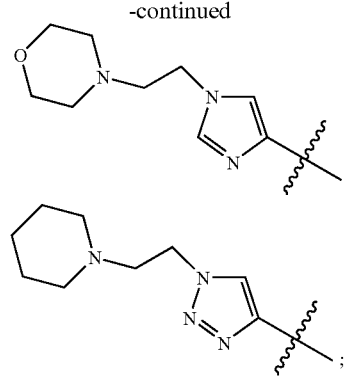

xlvii) $L^1$ is —$W^1$-Alk$_1$-; wherein $W^1$ is O, S, NR$^{W1}$ or —C(=O)NR$^{W1}$ where R$^{W1}$ is hydrogen, alkyl, cycloalkyl, heteroalkyl, heterocyclyl, aryl, heteroaryl, -(alkyl)aryl, -(alkyl)heteroaryl or acyl; and Alk$_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$, —OC(=O)—, —OC(=O)NR$^{L1A}$, —NR$^{L1A}$NR$^{L1B}$—, NR$^{L1A}$NR$^{L1B}$C(=O)—, —NR$^{L1A}$C(=O)—, —NR$^{L1A}$CO$_2$—, NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl;

xlviii) $L^1$ is —$W^1$-Alk$_1$-; wherein $W^1$ is O, S, NR$^{W1}$ or —C(=O)NR$^{W1}$ where R$^{W1}$ is hydrogen, lower alkyl, $C_{3-6}$cycloalkyl, lower heteroalkyl, heterocyclyl, aryl, heteroaryl, -(alkyl)aryl, -(alkyl)heteroaryl or acyl; and Alk$_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl;

xlix) Compounds of subset xlviii) above wherein $W^1$ is S;

l) Compounds of subset xlviii) above wherein $W^1$ is O or NR$^{W1}$;

li) $L^1$ is —O-Alk$_1$-; wherein Alk$_1$ is a substituted or unsubstituted $C_2$alkylene chain;

lii) $L^1$ is —O-cyclopropyl-;

liii) $L^1$ is —O—CH$_2$CH$_2$—;

liv) $L^1$ is —NR$^{W1}$-Alk$_1$-; wherein R$^{W1}$ is hydrogen, lower alkyl, $C_{3-6}$cycloalkyl, lower heteroalkyl, aryl, heteroaryl, -(alkyl)aryl, -(alkyl)heteroaryl or acyl; and Alk$_1$ is a substituted or unsubstituted $C_{2-6}$alkylene chain wherein up to two non-adjacent methylene units are independently optionally replaced by —C(=O)—, —S(=O)—, —SO$_2$—, —O—, —S—, or —NR$^{L1A}$—; wherein R$^{L1A}$ is hydrogen or lower alkyl;

lv) $L^1$ is —NR$^{W1}$-Alk$_1$-; wherein R$^{W1}$ is hydrogen, lower alkyl or lower heteroalkyl; and Alk$_1$ is a substituted or unsubstituted $C_2$alkylene chain;

lvi) $L^1$ is —NH-cyclopropyl-;

lvii) $L^1$ is —NH—CH$_2$CH$_2$—;

lviii) $L^1$ is —NH—CH$_2$CF$_2$—;
lix) $L^1$ is —NH—CH$_2$CH[(CH$_2$)$_p$OR$^{W2}$]—; wherein p is 1 or 2 and $R^{W2}$ is hydrogen or lower alkyl;
lx) $L^1$ is —NH—CH$_2$CH(CH$_2$OH)—;
lxi) $L^1$ is —NH—CH$_2$CH(CH$_2$CH$_2$OH)—;
lxii) $L^1$ is —NR$^{W1}$-Alk$_1$-; wherein $R^{W1}$ is lower heteroalkyl; and Alk$_1$ is a substituted or unsubstituted C$_2$alkylene chain;
lxiii) $L^1$ is —NR$^{W1}$-Alk$_1$-; wherein $R^{W1}$ is —(CH$_2$)$_2$NR$^{W2}$R$^{W3}$; Alk$_1$ is a substituted or unsubstituted C$_2$alkylene chain; and $R^{W2}$ and $R^{W3}$ are independently hydrogen or lower alkyl;
lxiv) $L^1$ is —NR$^{W1}$—(CH$_2$)$_2$—; wherein $R^{W1}$ is —(CH$_2$)$_2$NR$^{W2}$R$^{W3}$; and $R^{W2}$ and $R^{W3}$ are independently hydrogen or lower alkyl;
lxv) $L^1$ is —NR$^{W1}$—(CH$_2$)$_2$—; wherein $R^{W1}$ is —CH$_2$)$_2$NMe$_2$;
lxvi) $L^1$ is —NR$^{W1}$-Alk$_1$-; wherein $R^{W1}$ together with a carbon atom present on Alk$_1$ forms an optionally substituted 5- to 6-membered heterocyclic moiety;
lxvii) $L^1$ has the structure:

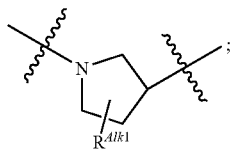

wherein $R^{Alk1}$ is hydrogen, halogen, hydroxy, CN, nitro, lower alkyl, lower alkoxy, aryl, or heteroaryl;
lxviii) $L^1$ has the structure:

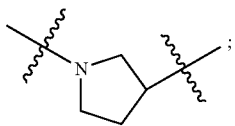

lxix) $L^1$ has the structure:

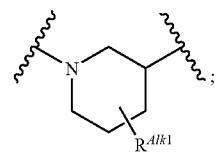

wherein $R^{Alk1}$ is hydrogen, halogen, hydroxy, CN, nitro, lower alkyl, lower alkoxy, aryl, or heteroaryl;
lxx) $L^1$ has the structure:

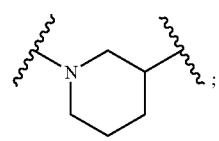

lxxi) $L^1$ is —C(=O)NR$^{W1}$-Alk$_1$-; wherein $R^{W1}$ is hydrogen or lower alkyl; and Alk$_1$ is a substituted or unsubstituted C$_1$alkylene moiety;
lxxii) $L^1$ is —C(=O)NH—CH$_2$—;

lxxiii) Y is a saturated or unsaturated cyclic ring system optionally comprising one or more heteroatoms selected from S, N and O;
lxxiv) Y is a saturated or unsaturated monocyclic cyclic ring system optionally comprising one or more heteroatoms selected from S, N and O;
lxxv) Y is a cycloalkyl, cycloalkenyl, heterocylic, aryl or heteroaryl moiety;
lxxvi) Y is a 5-6 membered cycloalkyl, 5-6 membered cycloalkenyl, 5-6 membered heterocyclic, 6-membered aryl or 6-membered heteroaryl moiety;
lxxvii) Y is one of:

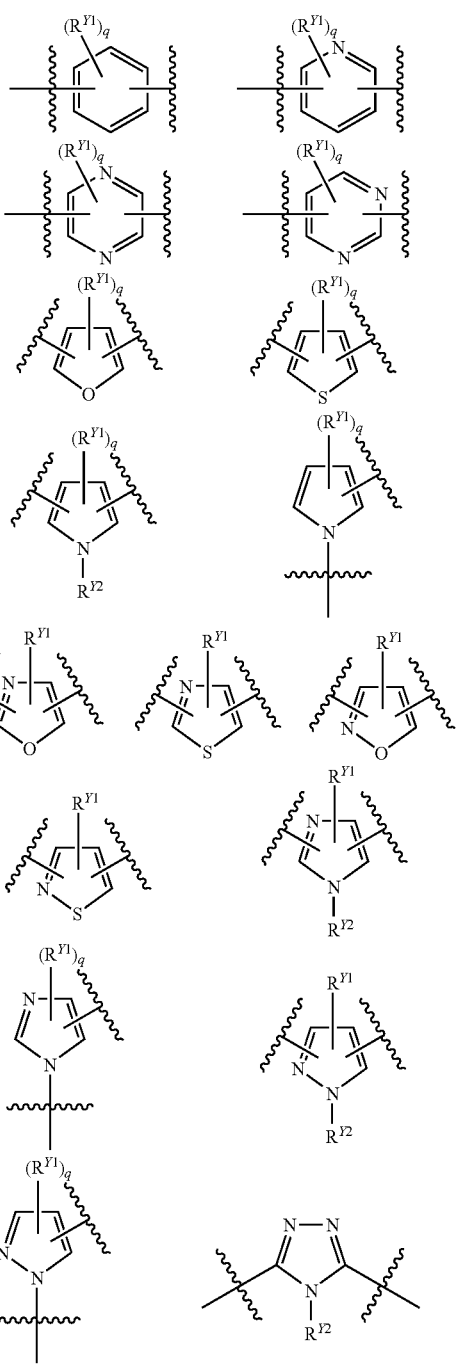

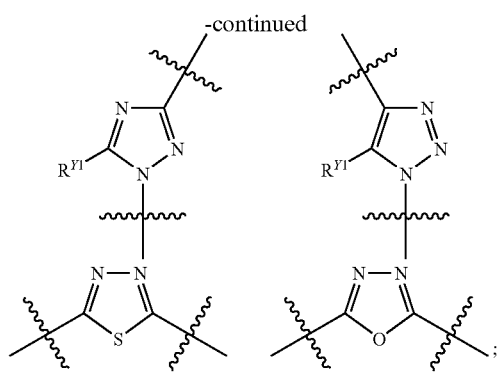

wherein q is an integer from 0 to 3; each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —$C(=O)NR^{Y2}R^{Y3}$, halogen, —CN, —$NO_2$, —$C(=O)OR^{Y3}$, —$N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring;

lxxviii) Y is one of:

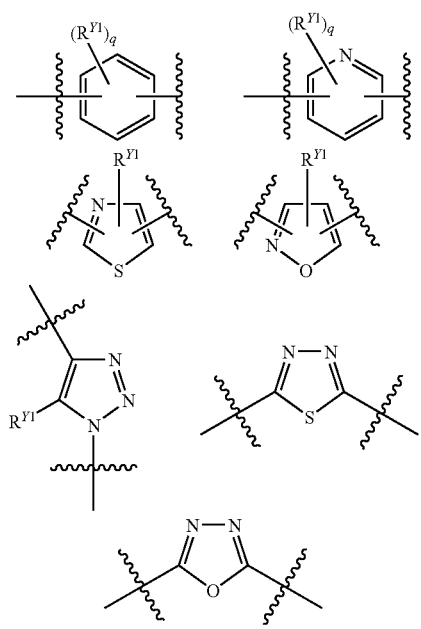

wherein q and $R^{Y1}$ are as defined directly above;

lxxix) Y is one of:

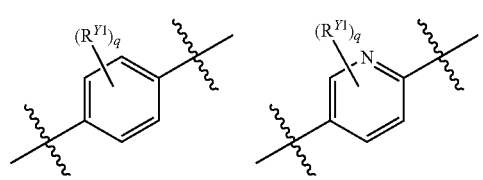

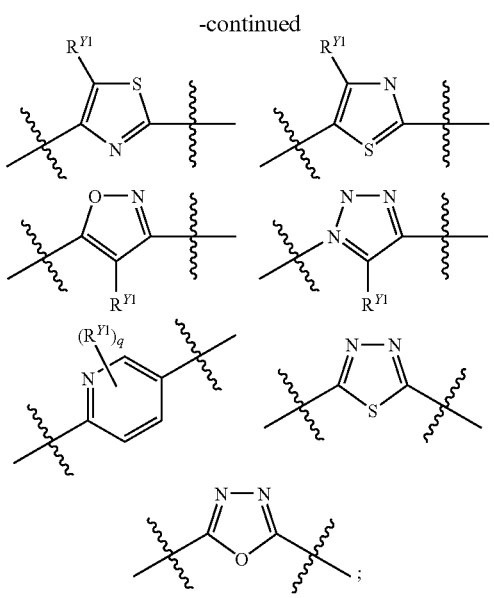

wherein q is 0-3; and $R^{Y1}$ is hydrogen, halogen or lower alkyl;

lxxx) Y is one of:

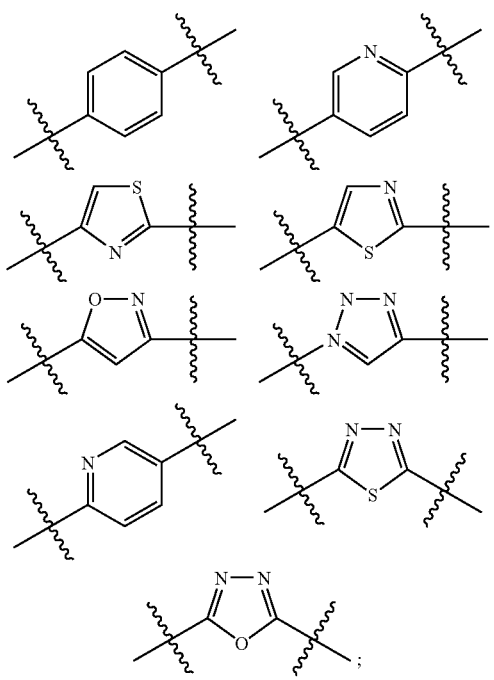

lxxxi) Y is one of:

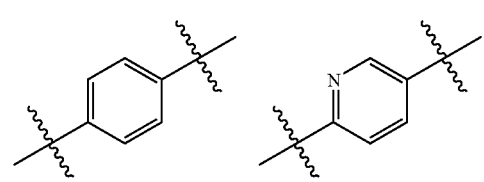

-continued

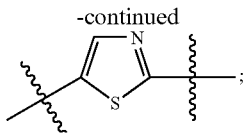

lxxxii) Y is:

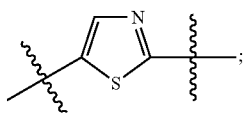

lxxxii) Y is:

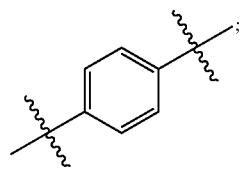

lxxxiii) Y is:

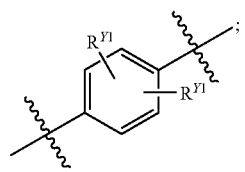

wherein at least one $R^{Y1}$ is halogen, the other is hydrogen or halogen;

lxxxiv) Y is:

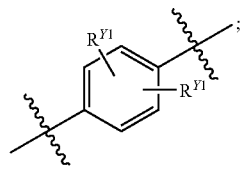

wherein at least one $R^{Y1}$ is fluoro, the other is hydrogen or fluoro;

lxxxv) $L^2$ is —$NR^{L2A}$— or a substituted or unsubstituted $C_{1-6}$alkylene or $C_{2-6}$alkenylene chain interrupted with at least one nitrogen atom wherein up to two non-adjacent methylene units are independently optionally replaced by —C(=O)—, —$CO_2$—, —C(=O)C(=O)—, —C(=O)$NR^{L2A}$—, —OC(=O)—, —OC(=O)$NR^{L2A}$—, $NR^{L2A}NR^{L2B}$—, —$NR^{L2A}NR^{L2B}$C(=O)—, —$NR^{L2A}$C(=O)—, —$NR^{L2A}CO_2$—, —$NR^{L2A}$C(=O)$NR^{L2B}$—, —S(=O)—, —$SO_2$—, —$NR^{L2A}SO_2$—, —$SO_2NR^{L2A}$, —$NR^{L2A}SO_2NR^{L2B}$—, —O—, —S—, or —$NR^{L2A}$—; wherein each occurrence of $R^{L2A}$, $R^{L2B}$, $R^{L2C}$ and $R^{L2D}$ is independently hydrogen, alkyl, heteroalkyl, heterocyclyl, aromatic, heteroaromatic or acyl;

lxxxvi) $L^2$ is —$NR^{L2A}$— or a substituted or unsubstituted $C_{1-6}$alkylene or $C_{2-6}$alkenylene chain interrupted with at least one nitrogen atom wherein up to two non-adjacent methylene units are independently optionally replaced by —C(=O)—, —$CO_2$—, —C(=O)C(=O)—, —C(=O)$NR^{L2A}$—, —OC(=O)—, —OC(=O)$NR^{L2A}$, —$NR^{L2A}NR^{L2B}$—, $NR^{L2A}NR^{L2B}$C(=O)—, —$NR^{L1A}$C(=O)—, —$NR^{L2A}CO_2$—, —$NR^{L2A}$C(=O)$NR^{L2B}$—, —S(=O)—, —$SO_2$—, —$NR^{L2A}SO_2$—, —$SO_2NR^{L2A}$—, —$NR^{L2A}SO_2NR^{L2B}$—, —O, S, or —$NR^{L2A}$—; wherein each occurrence of $R^{L2A}$, $R^{L2B}$, $R^{L2C}$ and $R^{1D}$ is independently hydrogen, lower alkyl, lower heteroalkyl, heterocyclyl, aryl, heteroaryl or acyl;

lxxxvii) $L^2$ is —$(CH_2)_mNR^{L2A}(CH_2)_m$—, —$(CH_2)_mC(=O)NR^{L2A}(CH_2)_m$—, —$(CH_2)_mOC(=O)NR^{L2A}(CH_2)_m$—, —$(CH_2)_mNR^{L2A}NR^{L2B}(CH_2)_m$—, —$(CH_2)_mNR^{L2A}NR^{L2B}C(=O)(CH_2)_m$—, —$(CH_2)_mNR^{L2A}C(=O)(CH_2)_m$—, —$(CH_2)_mNR^{L2A}C(=O)O(CH_2)_m$—, —$(CH_2)_mNR^{L2A}C(=O)NR^{L2B}(CH_2)_m$—, —$(CH_2)_mNR^{L2A}C(=O)NR^{L2B}CR^{L2C}R^{L2D}(CH_2)_m$—, —$(CH_2)_mCR^{L2C}R^{L2D}C(=O)NR^{L2B}(CH_2)_m$—, —$(CH_2)_mNR^{L2A}SO_2(CH_2)_m$—, —$(CH_2)_mSO_2NR^{L2A}(CH_2)_m$—, —$(CH_2)_mNR^{L2A}SO_2NR^{L2B}(CH_2)_m$—; wherein each occurrence of m is independently 0-4; and each occurrence of $R^{L2A}$, $R^{L2B}$, $R^{L2C}$ and $R^{L2D}$ is independently hydrogen, lower alkyl, lower heteroalkyl, heterocyclyl, aryl, heteroaryl or acyl;

lxxxviii) $L^2$ is —$NR^{L2A}$, C(=O)$NR^{L2A}$, —OC(=O)$NR^{L2A}$, —$NR^{L2A}NR^{L2B}$—, —$NR^{L2A}NR^{L2B}$C(=O)—, —$NR^{L2A}$C(=O)—, —$NR^{L2A}CO_2$—, —$NR^{L1A}$C(=O)$NR^{L2B}$—, —$NR^{L2A}$C(=O)$NR^{L2B}CR^{L2C}R^{L2D}$, —$CR^{L2C}R^{L2D}$C(=O)$NR^{L2B}$, $NR^{L2A}SO_2$, —$S_2NR^{L2A}$, —$NR^{L2A}SO_2NR^{L2B}$—, wherein each occurrence of $R^{L2A}$, $R^{L2B}$, $R^{L2C}$ and $R^{L2D}$ is independently hydrogen, lower alkyl, lower heteroalkyl, heterocyclyl, aryl, heteroaryl or acyl;

lxxxix) $L^2$ is —$NR^{L2A}$C(=O)$NR^{L2A}$, —$NR^{L2A}$C(=O)—, —OC(=O)$NR^{L2A}$—, —$NR^{L2A}CO_2$—, —$NR^{L2A}$C(=O)$NR^{L2B}$—, —$NR^{L2A}$C(=O)$NR^{L2B}CR^{L2C}R^{L2D}$ or —$CR^{L2C}R^{L2D}$C(=O)$NR^{L2B}$, wherein each occurrence of $R^{L2A}$, $R^{L2B}$, $R^{L2C}$ and $R^{L2D}$ is independently hydrogen, lower alkyl, lower heteroalkyl, heterocyclyl, aryl, heteroaryl or acyl;

xc) $L^2$ is —$NR^{L2A}$—, —$NR^{L2A}$C(=O)—, —$NR^{L2A}$C(=O)$NR^{L2B}$, $NR^{L2A}$C(=O)$NR^{L2B}CR^{L2C}R^{L2D}$ or —$CR^{L2C}R^{L2D}$C(=O)$NR^{L2B}$, wherein each occurrence of $R^{L2A}$, $R^{L2B}$, $R^{L2C}$ and $R^{L2D}$ is independently hydrogen, lower alkyl, lower heteroalkyl, heterocyclyl, aryl, heteroaryl or acyl;

xci) $L^2$ is —NH—, —NHC(=O)—, —NHC(=O)O—, —NHC(=O)NH—, —$CH_2$—C(=O)NH— or —NHC(=O)NH$CH_2$—;

xcii) $L^2$ is —NH—;

xciii) $L^2$ is —NHC(=O)NH—;

xciv) 12 is —$CH_2$—C(=O)NH—;

xcv) L is —NHC(=O)NH$CH_2$—;

xcvi) Z is an alkyl, alkenyl, alkynyl, cycloalkyl, cycloalkenyl, heteroalkyl, heteroalkenyl, heteroalkynyl, heterocyclyl, aryl or heteroaryl moiety;

xcvii) Z is a branched alkyl, alkenyl, alkynyl, heteroalkyl or heteroalkenyl moiety;

xcviii) Z is one of:

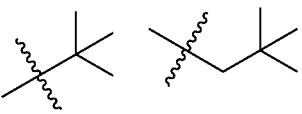

-continued

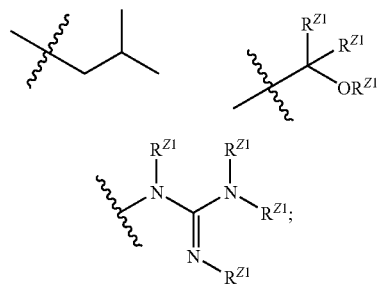

wherein each occurrence of $R^{Z1}$ is independently hydrogen, lower alkyl, lower alkenyl, aryl, heteroaryl or acyl;

xcix) Z is a cycloalkyl, cycloalkenyl, heterocyclyl, aryl or heteroaryl moiety;

c) Z is cycloalkyl, cycloalkenyl, or a heterocyclyl, aryl or heteroaryl moiety having one of the structures:

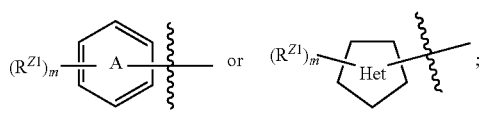

wherein the "A" cyclic moiety is a 6- to 10-membered mono- or fused bicyclic aromatic ring comprising from 0-4 nitrogen atoms; the "Het" moiety represents a fully or partially saturated or unsaturated 5- to 8-membered mono- or fused bicyclic ring comprising 1-4 heteroatoms selected from N, O and S; m is an integer from 0-6; and each occurrence of $R^{Z1}$ is independently hydrogen, alkyl, cycloalkyl, heteroalkyl, heterocyclyl, aryl, heteroaryl, -(alkyl)heterocyclyl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —C(=O)$N(R^{Z2})_2$, halogen, —CN, —$NO_2$, —C(=O)$OR^{Z2}$, —$N(R^{Z2})C(=O)R^{Z3}$ or —$N(R^{Z2})SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl, acyl; or any two occurrences of $R^{Z2}$, taken together with the nitrogen atom to which they are attached (e.g., $N(R^{Z2})_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring;

ci) Z is one of:

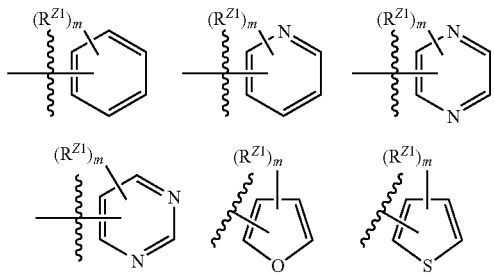

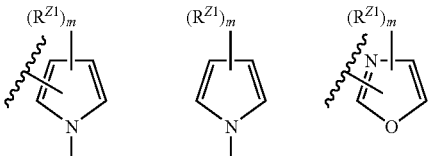
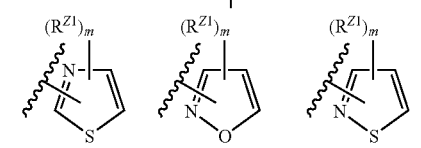
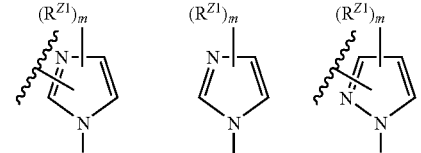
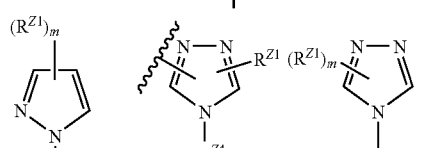

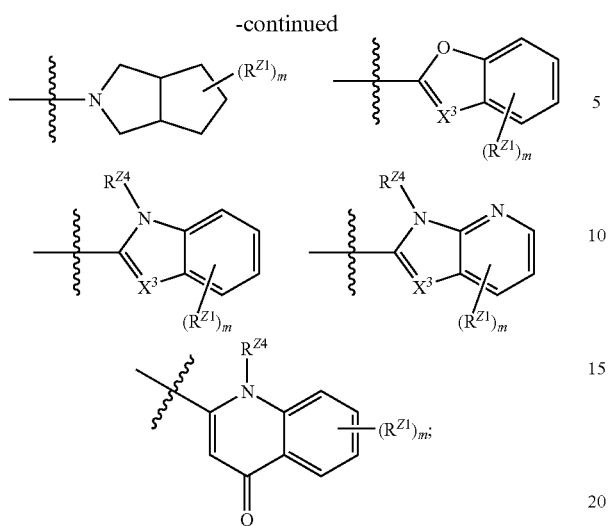

wherein m is an integer from 0 to 3; r is an integer from 1 to 4; $X^3$ is N or $CR^{Z1}$; each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, —$SO_2NR^{Z3}R^{Z3}$, —$SO_2R^{Z1}$, —$C(=O)NR^{Z2}R^{Z3}$, halogen, —CN, —$NO_2$, —$C(=O)OR^{Z3}$, —$N(R^{Z2})C(=O)R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is hydrogen, lower alkyl, lower heteroalkyl, aryl, heteroaryl, -(alkyl)aryl, -(alkyl)heteroaryl or acyl;

cii) Z is one of:

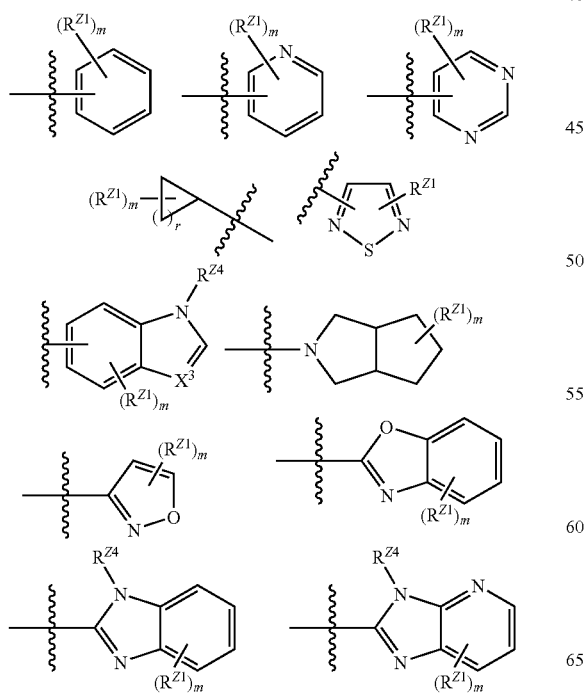

ciii) Z is one of:

wherein $X^3$ is N or $CR^{Z1}$; $R^{Z1}$ is hydrogen, halogen, lower alkyl, lower hydroxyalkyl or lower haloalkyl; $R^{Z2}$ and $R^{Z3}$ are independently hydrogen, lower alkyl, lower heteroalkyl, acyl, or $R^{Z2}$ and $R^{Z3}$ taken together with the nitrogen atom to which they are attached form a 5-6 membered heterocyclic ring; and $R^{Z4}$ is hydrogen or lower alkyl;

civ) Z is one of:

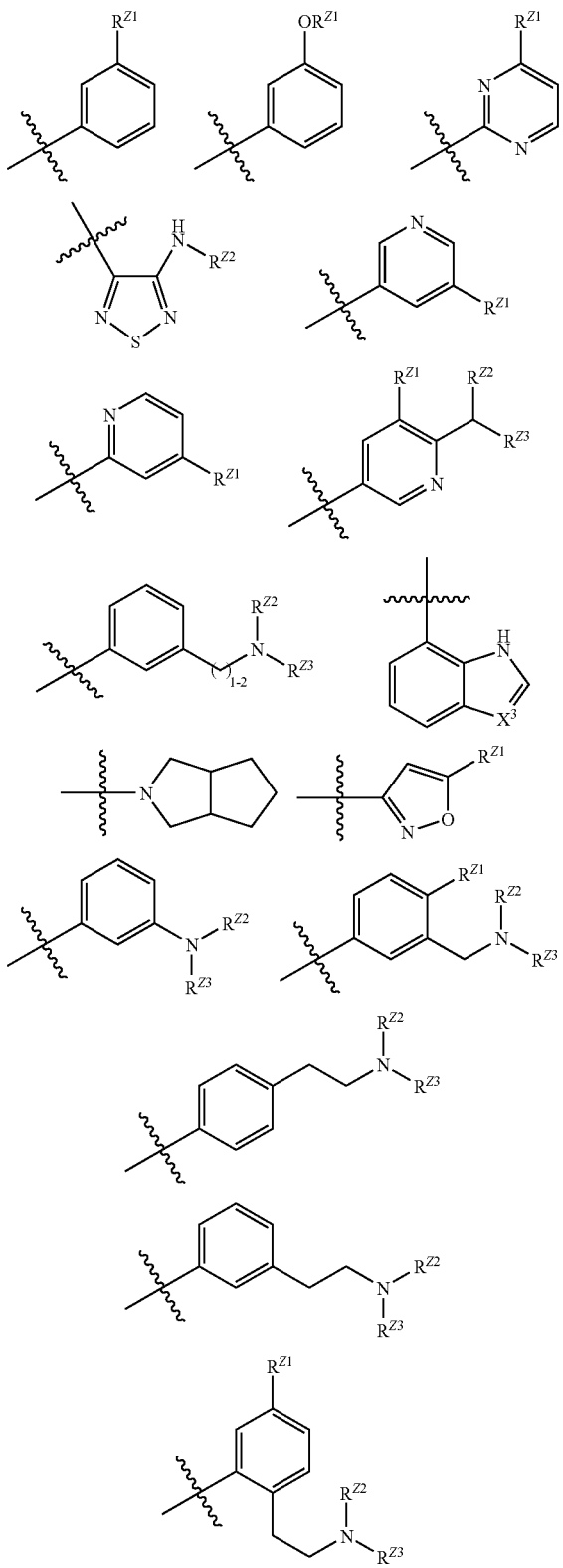

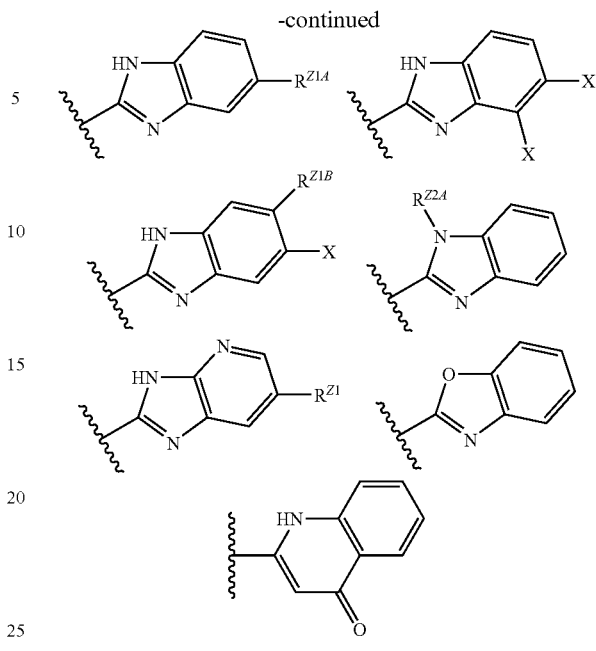

wherein $X^3$ is N or $CR^{Z1}$; $R^{Z1}$ is hydrogen, halogen, lower alkyl or lower haloalkyl; and $R^{Z2}$ and $R^{Z3}$ are independently hydrogen, lower alkyl, lower heteroalkyl, acyl, or $R^{Z2}$ and $R^{Z3}$ taken together with the nitrogen atom to which they are attached form a 5-6 membered heterocyclic ring; X is halogen, $R^{Z1A}$ is hydrogen, halogen, —CN, lower alkyl, lower alkoxy, lower haloalkyl or —SO$_2$R$^{Z4}$; wherein $R^{Z4}$ is lower alkyl; $R^{Z1B}$ is hydrogen or halogen; and $R^{Z2A}$ is hydrogen or lower alkyl;

cv) Z is one of:

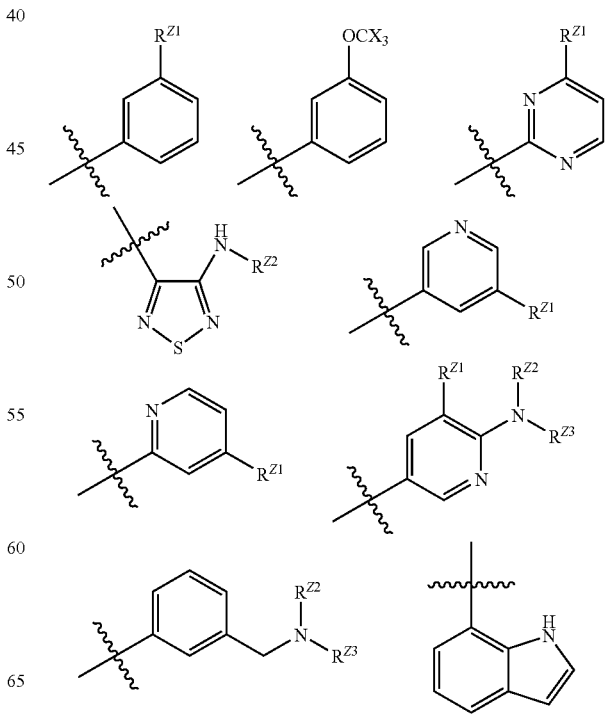

-continued

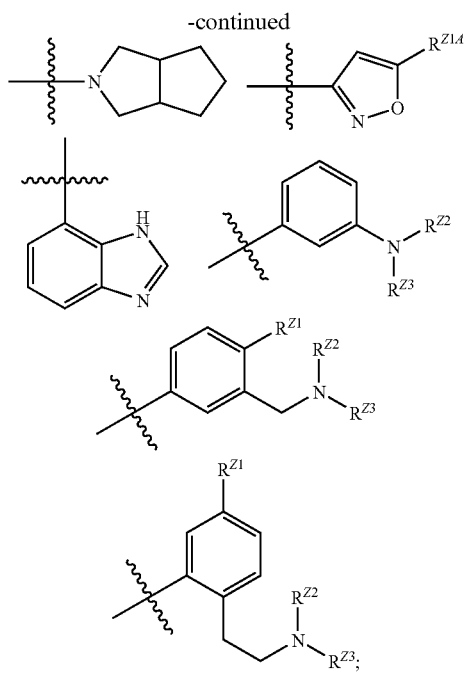

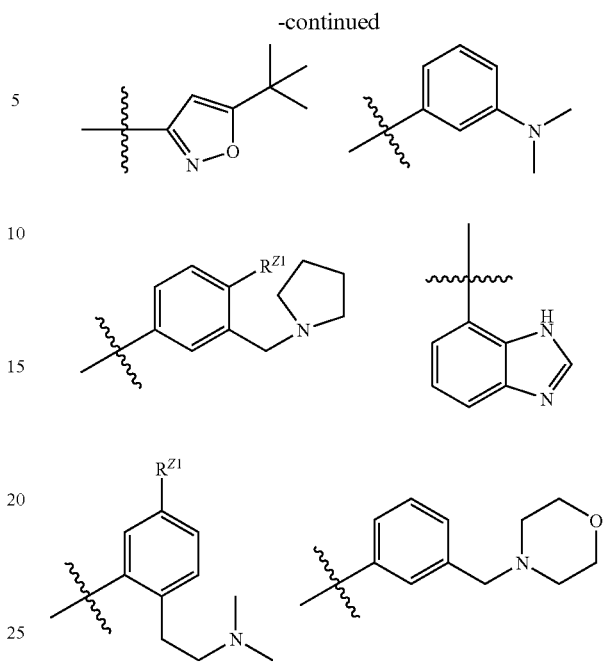

wherein X is halogen; $R^{Z1A}$ is lower alkyl; $R^{Z1}$ is halogen, lower alkyl or lower haloalkyl; and $R^{Z2}$ and $R^{Z3}$ are independently lower alkyl, or $R^{Z2}$ and $R^{Z3}$ taken together with the nitrogen atom to which they are attached form a 5-6 membered heterocyclic ring;

cvi) Z is one of:

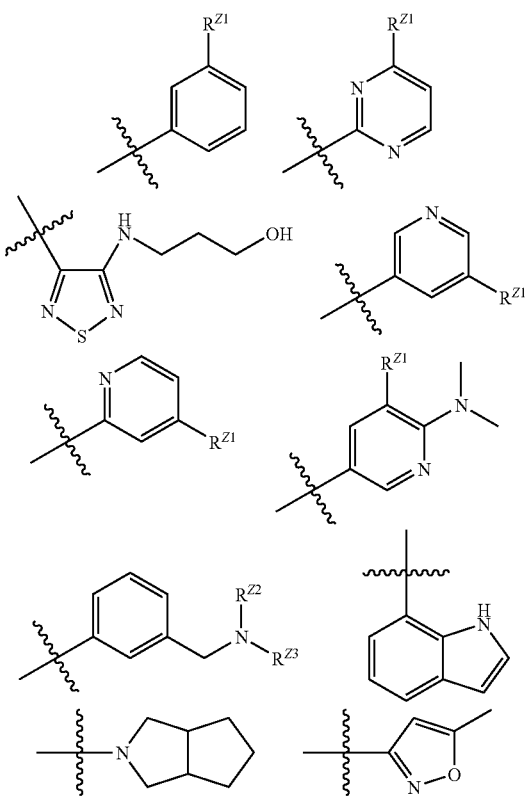

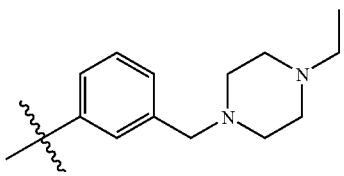

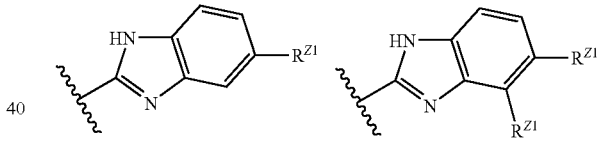

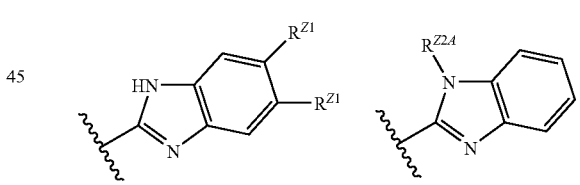

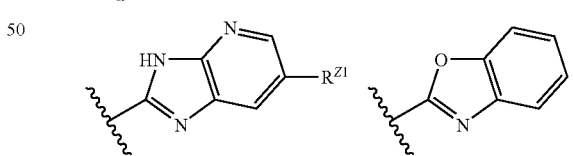

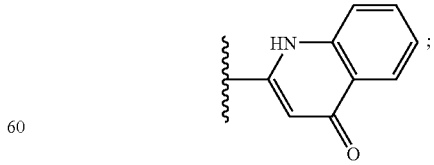

wherein $R^{Z1}$ is Cl, F, methyl or $CF_3$; $R^{Z2}$ and $R^{Z3}$ are each methyl or ethyl, or taken together with the nitrogen atom to which they are attached form a saturated or unsaturated pyrrolidinyl ring; and $R^{Z2A}$ is hydrogen or methyl;

cvii) Z is one of:

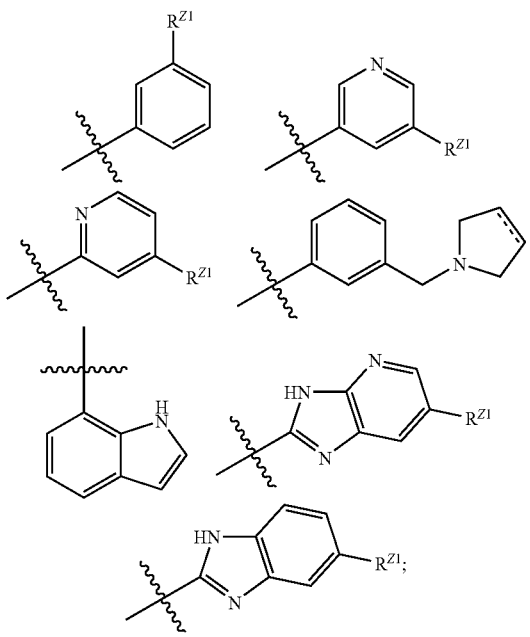

wherein $R^{Z1}$ is Cl, F, methyl or $CF_3$;

cviii) —$L^2$—Z together represent a moiety having one of the following structures:

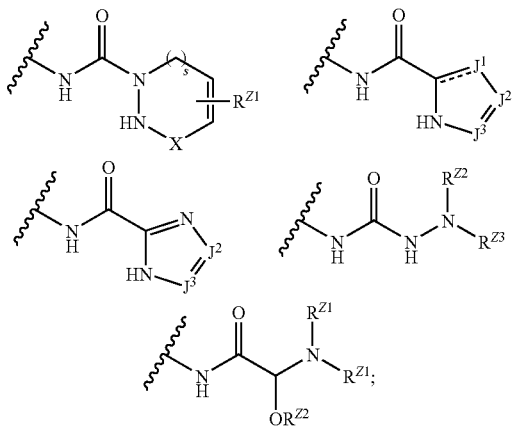

wherein s is 0 or 1; X is —C($R^{Z1}$)$_2$, —C(=O)— or —SO$_2$—; $J^1$, $J^2$ and $J^3$ are independently N, S, O, $NR^{Z1}$ or $CR^{Z1}$; each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{12}$, —$NR^{Z2}R^{Z3}$, —$SO_2NR^{Z2}R^{Z1}$, —$SO_2R^{Z1}$, —C(=O)$NR^{Z2}R^{Z3}$, halogen, —CN, —$NO_2$, —C(=O)$OR^{Z3}$, —N($R^{Z2}$)C(=O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring;

cix) —$L^2$—Z together represent —$CH_2$—Cy or —NH—Cy where Cy is an optionally substituted bicyclic heterocycle;

cx) —$L^2$—Z together represent a moiety having one of the following structures:

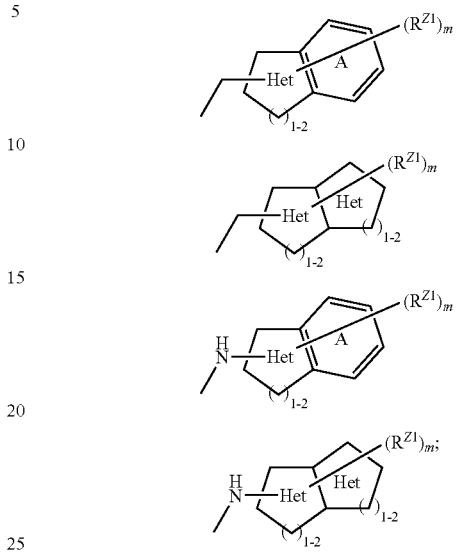

wherein the "A" cyclic moiety is a 6-membered aromatic ring comprising from 0-4 nitrogen atoms; each "Het" moiety independently represents a fully or partially saturated or unsaturated 5- to 6-membered ring comprising 1-4 heteroatoms selected from N, O and S; m is an integer from 0-6; and each occurrence of $R^{Z1}$ is independently hydrogen, alkyl, heteroalkyl, aryl, heteroaryl, -(alkyl)aryl, -(alkyl)heteroaryl, —$OR^{Z2}$, —$SR^{Z2}$, —N($R^{Z2}$)$_2$, —$SO_2N(R^{Z2})_2$, —$SO_2R^{Z4}$, C(=O)N($R^{Z2}$)$_2$, halogen, —CN, —$NO_2$, —C(=O)$OR^{12}$, —N($R^{Z2}$)C(=O)$R^{Z3}$ or —N($R^{Z2}$)$SO_2R^{Z4}$; wherein each occurrence of $R^{Z2}$ and $R^{Z3}$ is independently hydrogen, lower alkyl, lower heteroalkyl, aryl, heteroaryl, -(alkyl)aryl, -(alkyl) heteroaryl, acyl; or any two occurrences of $R^{Z2}$, taken together with the nitrogen atom to which they are attached (e.g., N($R^{Z2}$)$_2$), form a substituted or unsubstituted heterocyclic moiety; and $R^{Z4}$ is alkyl, heteroalkyl, aryl, heteroaryl, -(alkyl)aryl, or -(alkyl)heteroaryl; and wherein any two adjacent occurrence of $R^{Z1}$ may form a fused 5- to 6-membered aryl, heteroaryl or heterocyclic ring;

cxi) —$L^2$—Z together represent a moiety having one of the following structures:

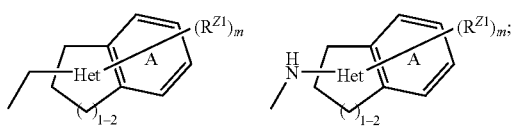

wherein the "A" cyclic moiety is a 6-membered aromatic ring comprising from 0-4 nitrogen atoms; each "Het" moiety independently represents a fully or partially saturated or unsaturated 5- to 6-membered ring comprising 1-4 heteroatoms selected from N, O and S; m is an integer from 0-6; and each occurrence of $R^{Z1}$ is independently hydrogen, lower alkyl, lower alkoxy, —$SO_2R^{Z4}$, halogen or —CN; wherein $R^{Z4}$ is lower alkyl;

cxii) —L²—Z together represent a moiety having one of the following structures:

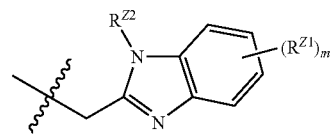
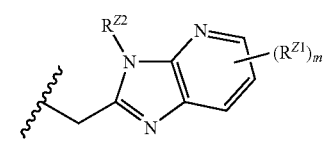
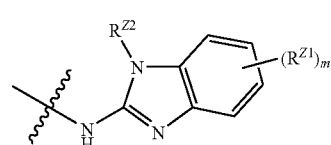
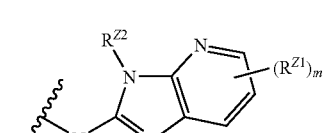

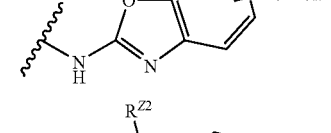
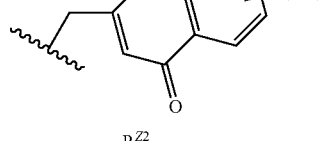
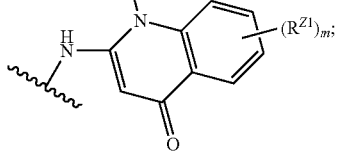
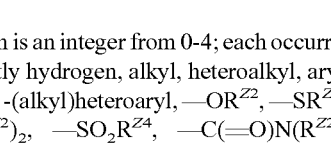

wherein m is an integer from 0-4; each occurrence of $R^{Z1}$ is independently hydrogen, alkyl, heteroalkyl, aryl, heteroaryl, -(alkyl)aryl, -(alkyl)heteroaryl, —$OR^{Z2}$, —$SR^{Z2}$, —$N(R^{Z2})_2$, —$SO_2N(R^{Z2})_2$, —$SO_2R^{Z4}$, —$C(=O)N(R^{Z2})_2$, halogen, —CN, —$NO_2$, —$C(=O)OR^{Z2}$, —$N(R^{Z2})C(=O)R^{Z3}$ or —$N(R^{Z2})SO_2R^{Z4}$; wherein each occurrence of $R^{Z2}$ is hydrogen, lower alkyl, lower heteroalkyl, aryl, heteroaryl, -(alkyl)aryl, -(alkyl)heteroaryl or acyl; and wherein any two adjacent occurrence of $R^{Z1}$ may form a fused 5- to 6-membered aryl, heteroaryl or heterocyclic ring;

cxiii) —L²—Z together represent a moiety having one of the following structures:

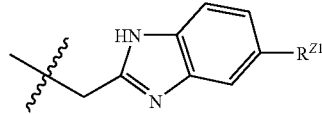
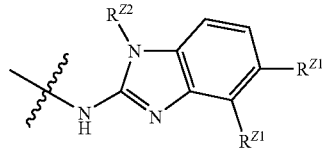
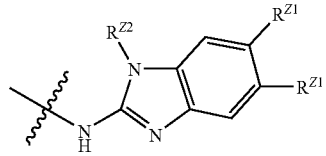
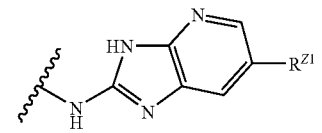
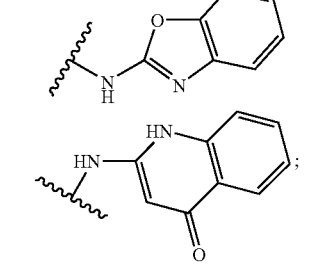

wherein $R^{Z2}$ is hydrogen or lower alkyl; each occurrence of $R^{Z1}$ is independently hydrogen, halogen, —CN, lower alkyl, lower alkoxy, lower haloalkyl or —$SO_2R^{Z4}$; wherein $R^{Z4}$ is lower alkyl;

cxiv) —L²—Z together represent a moiety having one of the following structures:

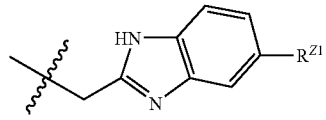
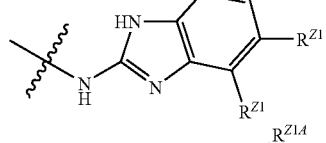
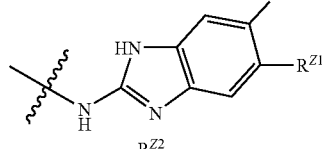
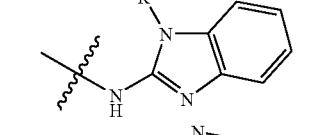
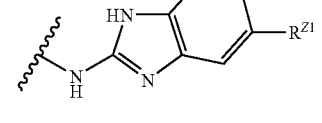

-continued

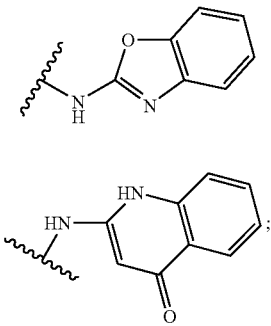

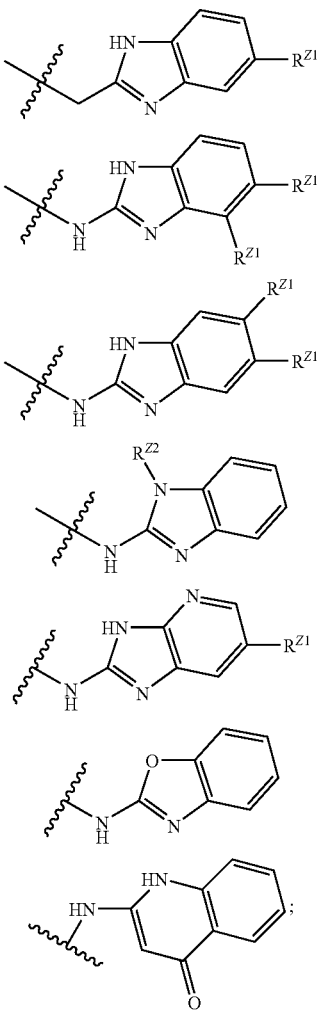

wherein X is halogen, $R^{Z1A}$ is hydrogen, halogen, —CN, lower alkyl, lower alkoxy, lower haloalkyl or —SO$_2$R$^{Z4}$; wherein R$^{Z4}$ is lower alkyl; and R$^{Z2}$ is hydrogen or lower alkyl;

cxv) —L$^2$—Z together represent a moiety having one of the following structures:

wherein R$^{Z1}$ is Cl, F, methyl or CF$_3$; and R$^{Z2}$ is hydrogen or methyl; and/or cxvi) —L$^2$—Z together represent a moiety having one of the following structures:

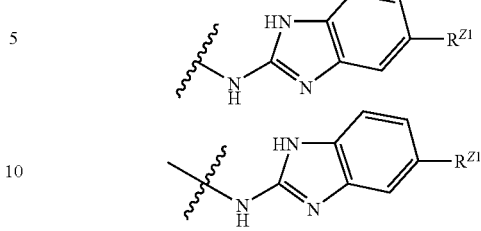

wherein R$^{Z1}$ is Cl, F, methyl or CF$_3$.

It will be appreciated that for each of the classes and subclasses described above and herein, any one or more occurrences of aliphatic or heteroaliphatic may independently be substituted or unsubstituted, cyclic or acyclic, linear or branched, saturated or unsaturated and any one or more occurrences of aryl, heteroaryl, cycloaliphatic, cycloheteroaliphatic may be substituted or unsubstituted.

The reader will also appreciate that any and all possible combinations of the variables described in i)-through cxvi) above (e.g., R$^1$, R$^2$, L$^1$, L$^2$, X$^1$, X$^2$, Y and Z, among others) are considered part of the invention. Thus, the invention encompasses any and all compounds of formula I generated by taking any possible permutation of variables R$^1$, R$^2$, L$^1$, L$^2$, X$^1$, X$^2$, Y and Z, and other variables/substituents (e.g., R$^{X1}$, R$^{X2}$, R$^{Y1}$, R$^{Z1}$ etc.) as further defined for R$^1$, R$^2$, L$^1$, L$^2$, X$^1$, X$^2$, Y and Z, described in i)-through lii) above.

For example, an exemplary combination of variables described in i)-through cxvi) above includes those compounds of Formula I wherein:

R$^1$ is H, halogen, cyano, nitro, alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl;

R$^2$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

X$^1$ is S;

X$^2$ is —C(R$^{X2}$)—; wherein R$^{X2A}$ is hydrogen, halogen, cyano, nitro, or an alkyl, alkenyl, alkynyl, cycloalkyl, cycloalkenyl, heteroalkyl, heteroalkenyl, heteroalkynyl, heterocyclyl, aryl, heteroaryl, -(alkyl)aryl, -(alkyl)heteroaryl, -(heteroalkyl)aryl or -(heteroalkyl)heteroaryl moiety;

L$^1$ is —W$^1$-Alk$_1$-; wherein W$^1$ is O or NR$^{W1}$, where R$^{W1}$ is hydrogen, alkyl, heteroalkyl, aryl, heteroaryl, -(alkyl)aryl, -(alkyl)heteroaryl or acyl; and Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, alkyl, heteroalkyl, heterocyclyl, aromatic, heteroaromatic or acyl;

L$^2$ is —C(=O)NR$^{L2A}$—, —OC(=O)NR$^{L2A}$—, —NR$^{L2A}$NR$^{L2B}$—, —NR$^{L2A}$NR$^{L2B}$C(=O), NR$^{L2A}$C(=O), —NR$^{L2A}$CO$_2$—, —NR$^{L2A}$C(=O)NR$^{L2B}$—, —NR$^{L2A}$SO$_2$—, —SO$_2$NR$^{L2A}$—, —NR$^{L2A}$SO$_2$NR$^{L2B}$—, or a substituted or unsubstituted $C_{1-6}$alkylene or $C_{2-6}$alkenylene chain interrupted with at least one nitrogen atom wherein up to two non-adjacent methylene units are independently optionally replaced by —C(=O)—, —CO$_2$—, —C(=O)C(=O)—, —C(=O)NR$^{L2A}$—, —OC(=O)—, —OC(=O)NR$^{L2A}$—, —NR$^{L2A}$NR$^{L2B}$—, —NR$^{L2A}$NR$^{L2B}$C(=O)—, —NR$^{L2A}$C(=O)—, NR$^{L2A}$CO$_2$—, —NR$^{L2A}$C(=O)NR$^{L2B}$—, —S(=O)—, SO$_2$—, —NR$^{L2A}$SO$_2$—, —SO$_2$NR$^{L2A}$—, —NR$^{L2A}$SO$_2$NR$^{L2B}$—, —O—, —S—, or —NR$^{L2A}$—; wherein each occurrence of R$^{L2A}$ and R$^{L2B}$ is independently hydrogen, alkyl, heteroalkyl, heterocyclyl, aromatic, heteroaromatic or acyl;

Y is a saturated or unsaturated cyclic ring system optionally comprising one or more heteroatoms selected from S, N and O;

Z is an alkyl, alkenyl, alkynyl, cycloalkyl, cycloalkenyl, heteroalkyl, heteroalkenyl, heteroalkynyl, heterocyclyl, aryl or heteroaryl moiety.

Other exemplary combinations are illustrated by compounds of the following subgroups I through XVI:

I. Compounds Having the Structure (and Pharmaceutically Acceptable Derivatives Thereof):

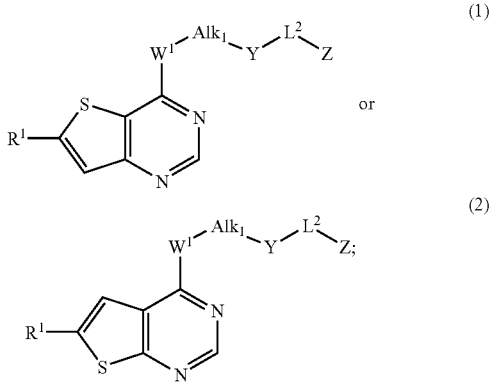

wherein R$^1$, L$^2$, Y and Z are as defined generally and in classes and subclasses herein; W$^1$ is O or NR$^{W1}$, where R$^{W1}$ is hydrogen, lower alkyl, lower heteroalkyl, aryl, heteroaryl, -(alkyl)aryl, -(alkyl)heteroaryl or acyl; and Alk$_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, NR$^{L1A}$NR$^{L1B}$—, —NR$^{L1A}$NR$^{L1B}$C(=O)—, —NR$^{L1A}$C(=O), —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl. In certain embodiments, the invention encompasses the compounds described directly above with the proviso that:

(i) R$^1$ is not Q$^1$, Q$^2$ or Q$^3$;

(ii) for compounds of formula (2), the following groups do not occur simultaneously as defined: R$^1$ is Q$_5$; Y and Z are independently optionally substituted aryl, carbocycle or 5-membered monocyclic heterocycle; Alk$_1$ is —N=CH—.

(iii) the following groups do not occur simultaneously as defined: Y and Z are each optionally substituted phenyl; L$^2$ is —OCH$_2$— or —OSO$_2$—; W$^1$Alk$_1$ is —OCH(R)—, —OCH(R)—$C_{1-6}$alkylO— or —OCH(R)—$C_{1-6}$alkylC(=NR$_x$)— where R is H, $C_{1-4}$alkyl, $C_{1-4}$haloalkyl or $C_{3-6}$cycloalkyl and R$^x$, is H, aliphatic, heteroaliphatic, alicyclic, heteroalicyclic, aromatic or heteroaromatic; and R$^1$ is hydrogen, halogen or alkyl;

(iv) the following groups do not occur simultaneously as defined: W$^1$Alk$_1$ is —NHCH$_2$CH$_2$— or —OCH$_2$CH$_2$—; Y is phenyl or L is —C(R)=N—O—, wherein R is H, $C_{1-4}$alkyl, $C_{1-4}$haloalkyl or $C_{3-6}$cycloalkyl; and R$^1$ is hydrogen, halogen or $C_{1-4}$alkyl;

(v) the following groups do not occur simultaneously as defined: W$^1$Alk$_1$ is —OCH$_2$—, or —N(R)CH$_2$—, wherein R is H or $C_{1-8}$alkyl; Y is phenyl, or Z is a 5-10-membered cycloalkyl, heterocyclyl, aryl or heteroaryl;

(vi) R$^1$ is hydrogen, halogen, $C_{1-4}$alkyl or $C_{1-4}$alkoxy; L$^1$ is —NHC$_{1-6}$alkyl, —OC$_{1-6}$alkyl, —NHC$_{1-6}$heteroalkyl or —OC$_{1-6}$heteroalkyl; Y is cycloalkyl, aryl, heteroaryl or heterocyclyl; L$^2$—Z is —X—R$^x$ where X is —NR—, —C(=O)NH—, —NHC(=O)—, —SO$_2$NH— or —NHSO$_2$— and R$^x$ is $C_{3-10}$cycloalkyl, morpholinyl, phenyl, phenylC$_{1-4}$alkyl or phenylC$_{2-3}$alkenyl;

(vii) the following groups do not occur simultaneously as defined: L$^1$ is —NR(CR$^x$)$_{1-2}$— or —O(CR$^x$)$_{1-2}$— wherein R is hydrogen, $C_{1-4}$alkyl, $C_{1-4}$alkoxy, OH, NH$_2$ or —$C_{1-4}$alkylNH; and R$^x$ is H or $C_{1-4}$alkyl; Y is phenyl, thienyl, furanyl, pyrrolyl, pyridyl, pyrimidyl, imidazolyl, pyrazinyl, oxazolyl, thiazolyl, naphthyl, benzothienyl, benzofuranyl, indolyl, quinolinyl, isoquinolinyl or quinazolinyl; L$^2$—Z is —SO$_2$NHC$_{3-8}$cycloalkyl, —SO$_2$N(C$_{3-8}$cycloalkyl)$_2$, —C(=O)NHC$_{3-8}$cycloalkyl or —C(=O)N(C$_{3-8}$cycloalkyl)$_2$; and (viii) the following groups do not occur simultaneously as defined: R$^1$ is hydrogen, halogen, nitro or $C_{1-4}$alkyl; L$^1$ is —NRC$_{1-6}$alkyl- or —OC$_{1-6}$alkyl- wherein R is hydrogen, $C_{1-4}$alkyl, $C_{1-4}$acyl; Y is phenyl; L$^2$—Z is a $C_{1-12}$alkyl saturated or unsaturated hydrocarbon chain optionally including —NR— and optionally substituted with haloC$_{1-4}$alkoxy, $C_{3-8}$cycloalkyl, $C_{3-8}$cycloalkenyl, $C_{1-4}$acyl, phenoxy, phenyl or phenylthio.

In certain embodiments, compounds of the invention have the structure (1$^A$) or (2$^A$) below:

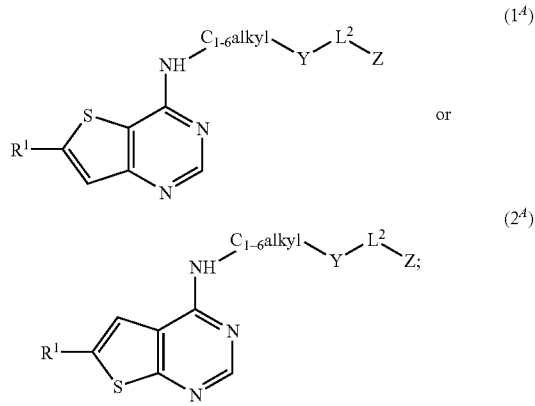

wherein the $C_{1-6}$alkyl moiety may be substituted or unsubstituted.

In certain embodiments, compounds of the invention have the structure (1$^B$) or (2$^B$) below:

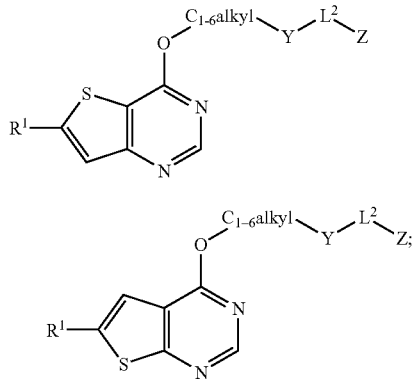

(1<sup>B</sup>)

(2<sup>B</sup>)

wherein the $C_{1-6}$alkyl moiety may be substituted or unsubstituted.

In certain embodiments, for compounds of formulae ($1^A$), ($1^B$), ($2^A$) and ($2^B$), the $C_{1-6}$alkyl moiety is a substituted or unsubstituted $C_2$alkyl moiety. In certain exemplary embodiments, the $C_{1-6}$alkyl moiety is —CH$_2$CH$_2$—.

II. Compounds Having the Structure (and Pharmaceutically Acceptable Derivatives Thereof):

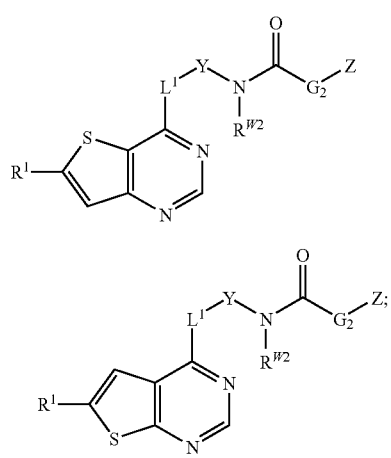

(3)

(4)

wherein $R^1$, $L^2$, Y and Z are as defined generally and in classes and subclasses herein; $G_2$ is absent, O or $NR^{G2}$; and $R^{W2}$ and $R^{G2}$ are independently hydrogen, lower alkyl, lower heteroalkyl, aryl, heteroaryl, -(alkyl)aryl, -(alkyl)heteroaryl or acyl. In certain embodiments, the invention encompasses the compounds described directly above with the proviso that:

(i) $R^1$ is not $Q^1$, $Q^2$ or $Q^3$;

(ii) the following groups do not occur simultaneously as defined: $G^2$ is absent; $L^1$ is —OCH$_2$—, —CH$_2$O—, —N(R)CH$_2$— or —CH$_2$N(R)—, wherein R is H or $C_{1-8}$alkyl; Y is phenyl; and Z is a 5-10-membered cycloalkyl, heterocyclyl, aryl or heteroaryl; and (iii) the following groups do not occur simultaneously as defined: $R^1$ is hydrogen, halogen, $C_{1-4}$alkyl or $C_{1-4}$alkoxy; $L^1$ is —NHC$_{1-6}$alkyl, —OC$_{1-6}$alkyl, —NHC$_{1-6}$heteroalkyl or —OC$_{1-6}$heteroalkyl; Y is cycloalkyl, aryl, heteroaryl or heterocyclyl; $G^2$ is absent and Z is $C_{3-10}$cycloalkyl, morpholinyl, phenyl, phenyl$C_{1-4}$alkyl or phenyl$C_{2-3}$alkenyl.

In certain embodiments, —N($R^{W2}$)C(=O)$G_2$— is —NHC(=O)—, —NHC(=O)O—, or —NHC(=O)NH—. In certain embodiments, compounds of the invention have the structure ($3^A$) or ($4^A$) below:

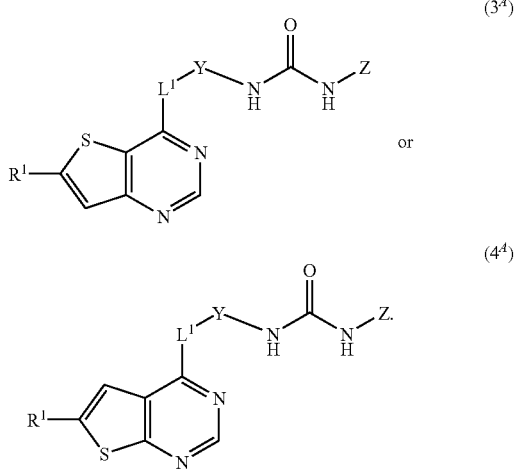

($3^A$)

($4^A$)

III. Compounds Having the Structure (and Pharmaceutically Acceptable Derivatives Thereof):

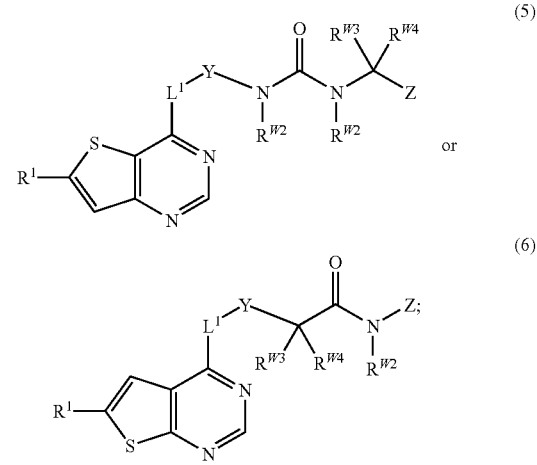

(5)

(6)

wherein $R^1$, $L^1$, Y and Z are as defined generally and in classes and subclasses herein; and $R^{W2}$, $R^{W1}$ and $R^{W4}$ are independently hydrogen, lower alkyl, lower heteroalkyl, heterocyclyl, aryl, heteroaryl, -(alkyl)aryl, -(alkyl)heteroaryl or acyl. In certain embodiments, the invention encompasses the compounds described directly above with the proviso that:

(i) $R^1$ is not $Q^1$, $Q^2$ or $Q^3$; and (ii) the following groups do not occur simultaneously as defined: ($R^{W3}$, $R^{W4}$) is (H,H), (F,F) or (H, $C_{1-4}$alkyl); $L^1$ is —OCH$_2$—, —CH$_2$O—, —N(R)CH$_2$— or —CH$_2$N(R)—, wherein R is H or $C_{1-8}$alkyl; Y is phenyl; and Z is a 5-10-membered cycloalkyl, heterocyclyl, aryl or heteroaryl.

In certain embodiments, compounds of the invention have the structure ($5^A$) or ($6^A$) below:

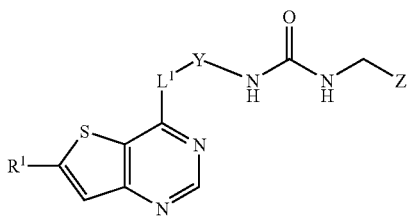
(5<sup>A</sup>)

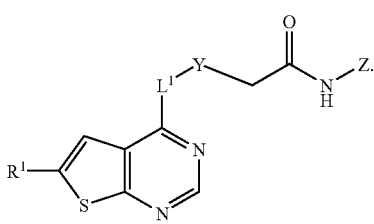
(6<sup>A</sup>)

IV. Compounds Having the Structure (and Pharmaceutically Acceptable Derivatives Thereof):

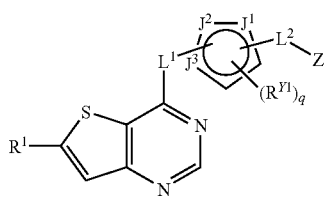
(7)

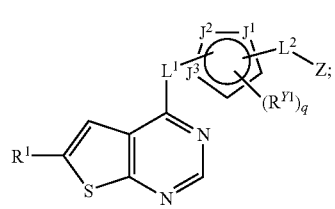
(8)

wherein q is an integer from 0-2; $R^1$, $L^1$, $L^2$ and Z are as defined generally and in classes and subclasses herein; and $J^1$, $J^2$ and $J^3$ are independently O, S, N, $NR^{Y1}$ or $CR^{Y1}$; wherein each occurrence of $R^{Y1}$ is independently hydrogen, alkyl, heteroalkyl, aryl, heteroaryl, -(alkyl)aryl or -(alkyl)heteroaryl, $-OR^{Y3}$, $-SR^{Y3}$, $-NR^{Y2}R^{Y3}$, $-SO_2NR^{Y2}R^{Y3}$, $-C(=O)NR^{Y2}R^{Y3}$, halogen, $-CN$, $-NO_2$, $-C(=O)OR^{Y3}$, $-N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring. In certain embodiments, the invention encompasses the compounds described directly above with the proviso that:

(i) $R^1$ is not $Q^1$, $Q^2$ or $Q^3$;

(ii) for compounds of formula (8), the following groups do not occur simultaneously as defined: $R^1$ is $Q_5$; Z is optionally substituted aryl, carbocycle or 5-membered monocyclic heterocycle; $L^1$ is $-W-N=CH-$, where W is O or NR, wherein R is H, $C_{1-6}$alk(en/yn)yl, $C_{3-8}$cycloalk(en/yn)yl, aryl, hydroxyC$_{1-6}$alk(en/yn)yl, $C_{3-8}$cycloalk(en/yn)yl-C$_{1-6}$alk(en/yn)yl or acyl.

(iii) the following groups do not occur simultaneously as defined: $L^1$ is $-NR(CR^x)_{1-2}-$ or $-O(CR^x)_{1-2}-$ wherein R is hydrogen, $C_{1-4}$alkyl, $C_{1-4}$alkoxy, OH, $NH_2$ or $-C_{1-4}$alkylNH; and $R^x$ is H or $C_{1-4}$alkyl;

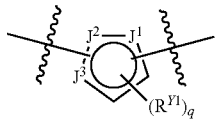

is thienyl, furanyl, pyrrolyl, imidazolyl, oxazolyl or thiazolyl; $L^2-Z$ is $-SO_2NHC_{3-8}$cycloalkyl, $-SO_2N(C_{3-8}$cycloalkyl)$_2$, $-C(=O)NHC_{3-8}$cycloalkyl or $-C(=O)N(C_{3-8}$cycloalkyl)$_2$.

In certain embodiments, compounds of the invention have the structure (7<sup>A</sup>) or (8<sup>A</sup>) below:

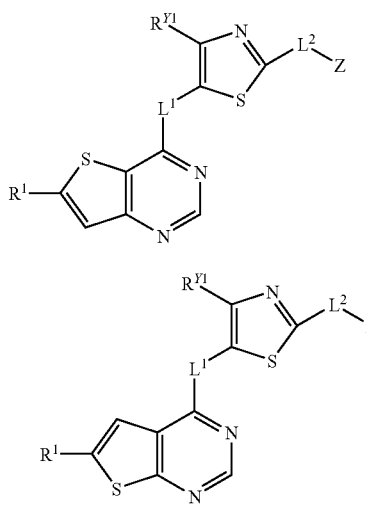
(7<sup>A</sup>)

(8<sup>A</sup>)

V. Compounds Having the Structure (and Pharmaceutically Acceptable Derivatives Thereof):

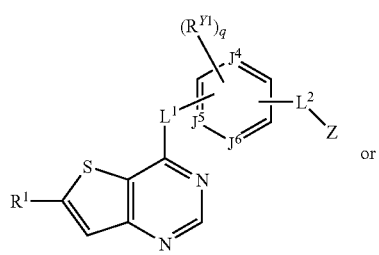
(9)

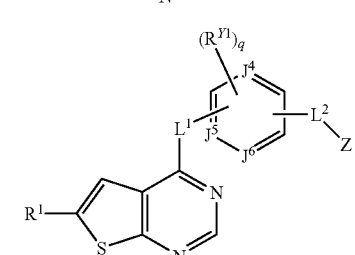
(10)

wherein q is an integer from 0-3; $R^1$, $L^1$, $L^2$ and Z are as defined generally and in classes and subclasses herein; and $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —$C(=O)NR^{Y2}R^{Y3}$, halogen, —CN, —$NO_2$, —$C(=O)OR^{Y3}$, —$N(R^{Y2})C(=O)R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring. In certain embodiments, the invention encompasses the compounds described directly above with the proviso that:

(i) $R^1$ is not $Q^1$, $Q^2$ or $Q^3$;

(ii) the following groups do not occur simultaneously as defined: $L^1$ is —$OCH_2$—, —$CH_2O$—, —$N(R)CH_2$— or —$CH_2N(R)$—, wherein R is H or $C_{1-8}$alkyl; $J^4$, $J^5$ and $J^6$ are each $CR^{Y1}$; and Z is a 5-10-membered cycloalkyl, heterocyclyl, aryl or heteroaryl;

(iii) the following groups do not occur simultaneously as defined: $J^4$, $J^5$ and $J^6$ are each CH; $L^1$ is —$NHCH_2CH_2$— or —$OCH_2CH_2$—; and $L^2$ is —C(R)=N—O—, wherein R is H, $C_{1-4}$alkyl, $C_{1-4}$haloalkyl or $C_{3-6}$cycloalkyl; and $R^1$ is hydrogen, halogen or $C_{1-4}$alkyl.

(iv) the following groups do not occur simultaneously as defined: $J^4$, $J^5$ and $J^6$ are each CH; $L^1$ is —OCH(R)—, —OCH(R)—$C_{1-6}$alkylO— or —OCH(R)—$C_{1-6}$alkylC(=$NR_x$)— where R is H, $C_{1-4}$alkyl, $C_{1-4}$haloalkyl or $C_{3-6}$cycloalkyl and $R_x$ is H, aliphatic, heteroaliphatic, alicyclic, heteroalicyclic, aromatic or heteroaromatic; Z is optionally substituted phenyl; $L^2$ is —$OCH_2$— or —$OSO_2$—; and $R^1$ is hydrogen, halogen or alkyl;

(v) for compounds of formula (10), the following groups do not occur simultaneously as defined: $R^1$ is $Q_5$; $J^4$, $J^5$ and $J^6$ are each $CR^{Y1}$; Z is optionally substituted aryl, carbocycle or 5-membered monocyclic heterocycle; and $L^1$ is —W—N=CH— wherein W is O or NR, wherein R is H, $C_{1-6}$alk(en/yn)yl, $C_{3-8}$cycloalk(en)yl, aryl, hydroxy$C_{1-6}$alk(en/yn)yl, $C_{3-8}$cycloalk(en)yl-$C_{1-6}$alk(en/yn)yl or acyl;

(vi) the following groups do not occur simultaneously as defined: $R^1$ is hydrogen, halogen, $C_{1-4}$alkyl or $C_{1-4}$alkoxy; $L^1$ is —$NHC_{1-6}$alkyl, —$OC_{1-6}$alkyl, —$NHC_{1-6}$heteroalkyl or —$OC_{1-6}$heteroalkyl; $L^2$—Z is —X—$R^x$ where X is —NR—, —C(=O)NH—, —NHC(=O)—, —$SO_2NH$— or —$NHSO_2$— and $R^x$ is $C_{3-10}$cycloalkyl, morpholinyl, phenyl, phenyl$C_{1-4}$alkyl or phenyl$C_{2-3}$alkenyl;

(vii) the following groups do not occur simultaneously as defined: $L^1$ is —$NR(CR^x)_{1-2}$— or —$O(CR^x)_{1-2}$— wherein R is hydrogen, $C_{1-4}$alkyl, $C_{1-4}$alkoxy, OH, $NH_2$ or —$C_{1-4}$alkylNH; and $R^x$ is H or $C_{1-4}$alkyl;

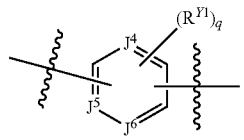

is phenyl, pyridyl, pyrimidyl or pyrazinyl; $L^2$—Z is —$SO_2NHC_{3-8}$cycloalkyl, —$SO_2N(C_{3-8}$cycloalkyl$)_2$, —C(=O)$NHC_{3-8}$cycloalkyl or —C(=O)N($C_{3-8}$cycloalkyl$)_2$; and/or (ix) the following groups do not occur simultaneously as defined: $R^1$ is hydrogen, halogen, nitro or $C_{1-4}$alkyl; $L^1$ is —$NRC_{1-6}$alkyl- or —$OC_{1-6}$alkyl- wherein R is hydrogen, $C_{1-4}$alkyl, $C_{1-4}$acyl; $J^4$, $J^5$ and $J^6$ are each CH; $L^1$—Z is a $C_{1-12}$alkyl saturated or unsaturated hydrocarbon chain optionally including —NR— and optionally substituted with halo$C_{1-4}$alkoxy, $C_{3-8}$cycloalkyl, $C_{3-8}$cycloalkenyl, $C_{1-4}$acyl, phenoxy, phenyl or phenylthio.

In certain embodiments, compounds of the invention have the structure ($9^A$) or ($10^A$) below:

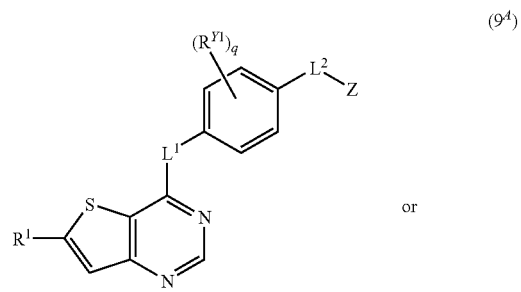

(9$^A$)

or (10$^A$)

In certain embodiments, compounds of the invention have the structure ($9^B$) or ($10^B$) below:

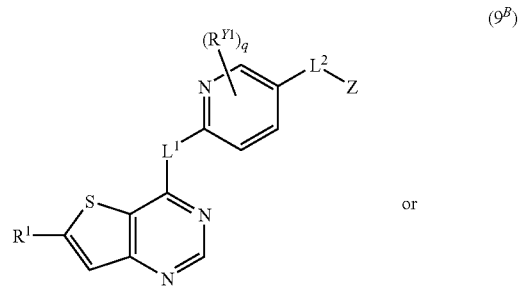

(9$^B$)

or

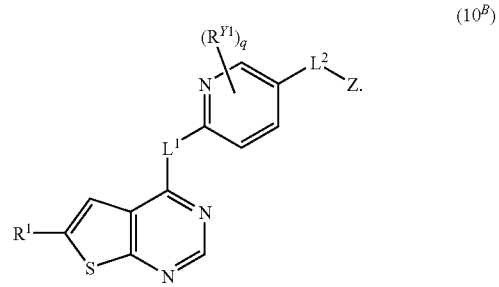

(10$^B$)

VI. Compounds Having the Structure (and Pharmaceutically Acceptable Derivatives Thereof):

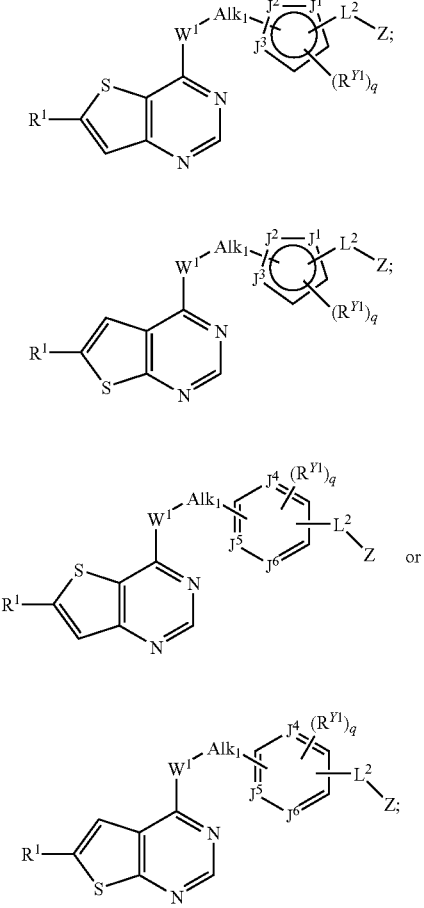

(11)

(12)

(13)

(14)

wherein $R^1$, $L^2$ and Z are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^1$, $J^2$ and $J^3$ are independently O, S, N, $NR^{Y1}$ or $CR^{Y1}$; $J^4$, $J^5$ and $J^6$ are independently N or $CR^{Y1}$; wherein each occurrence of $R^{Y1}$ is independently, hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring. In certain embodiments, the invention encompasses the compounds described directly above with the proviso that:

(i) $R^1$ is not $Q^1$, $Q^2$ or $Q^3$;

(ii) for compounds of formula (12), the following groups do not occur simultaneously as defined: $R^1$ is $Q_5$; Z is optionally substituted aryl, carbocycle or 5-membered monocyclic heterocycle; $Alk_1$ is —N=CH—.

(iii) for compounds of formula (14), the following groups do not occur simultaneously as defined: $R^1$ is $Q_5$; $J^4$, $J^5$ and $J^6$ are each $CR^{Y1}$; Z is optionally substituted aryl, carbocycle or 5-membered monocyclic heterocycle; $Alk_1$ is —N=CH—.

(iv) for compounds of formula (13) and (14), the following groups do not occur simultaneously as defined: Z is optionally substituted phenyl; $L^2$ is —OCH$_2$— or —OSO$_2$—; $W^1Alk_1$ is —OCH(R)—, —OCH(R)—C$_{1-6}$alkylO— or —OCH(R)—C$_{1-6}$alkylC(=NR$_x$)— where R is H, C$_{1-4}$alkyl, C$_{1-4}$haloalkyl or C$_{3-6}$cycloalkyl and $R_x$ is H, aliphatic, heteroaliphatic, alicyclic, heteroalicyclic, aromatic or heteroaromatic; and $R^1$ is hydrogen, halogen or alkyl;

(v) for compounds of formula (13) and (14), the following groups do not occur simultaneously as defined: $W^1Alk_1$ is —NHCH$_2$CH$_2$— or —OCH$_2$CH$_2$—; and $L^2$ is —C(R)=N—O—, wherein R is H, C$_{1-4}$alkyl, C$_{1-4}$haloalkyl or C$_{3-6}$cycloalkyl; and $R^1$ is hydrogen, halogen or C$_{1-4}$alkyl;

(vi) for compounds of formula (13) and (14), the following groups do not occur simultaneously as defined: $W^1Alk_1$ is —OCH$_2$—, or —N(R)CH$_2$—, wherein R is H or C$_{1-8}$alkyl; and Z is not a 5-10-membered cycloalkyl, heterocyclyl, aryl or heteroaryl;

(vii) the following groups do not occur simultaneously as defined: $R^1$ is hydrogen, halogen, C$_{1-4}$alkyl or C$_{1-4}$alkoxy; $W^1Alk_1$ is —NHC$_{1-6}$alkyl, —OC$_{1-6}$alkyl, —NHC$_{1-6}$heteroalkyl or —OC$_{1-6}$heteroalkyl; $L^2$—Z is —X—R$^x$ where X is —NR—, —C(=O)NH—, —NHC(=O)—, —SO$_2$NH— or —NHSO$_2$— and $R^x$ is C$_{3-10}$cycloalkyl, morpholinyl, phenyl, phenylC$_{1-4}$alkyl or phenylC$_{2-3}$alkenyl.

(viii) the following groups do not occur simultaneously as defined: $W^1Alk_1$ is —NR(CR$^x$)$_{1-2}$— or —O(CR$^x$)$_{1-2}$— wherein R is hydrogen, C$_{1-4}$alkyl, C$_{1-4}$alkoxy, OH, NH$_2$ or —C$_{1-4}$alkylNH; and $R^x$ is H or C$_{1-4}$alkyl;

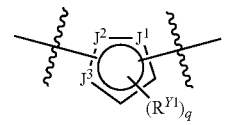

is thienyl, furanyl, pyrrolyl, imidazolyl, oxazolyl or thiazolyl;

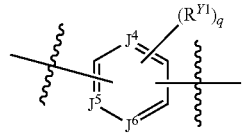

is phenyl, pyridyl, pyrimidyl or pyrazinyl; $L^2$—Z is —SO$_2$NHC$_{3-8}$cycloalkyl, —SO$_2$N(C$_{3-8}$cycloalkyl)$_2$, —C(=O)NHC$_{3-8}$cycloalkyl or —C(=O)N(C$_{3-8}$cycloalkyl)$_2$; and/or (ix) the following groups do not occur simultaneously as defined: $R^1$ is hydrogen, halogen, nitro or C$_{1-4}$alkyl; $W^1Alk_1$ is —NRC$_{1-6}$alkyl- or —OC$_{1-6}$alkyl- wherein R is hydrogen, C$_{1-4}$alkyl, C$_{1-4}$acyl;

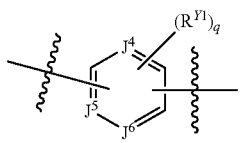

is phenyl; L²—Z is a $C_{1-12}$alkyl saturated or unsaturated hydrocarbon chain optionally including —NR— and optionally substituted with halo$C_{1-4}$alkoxy, $C_{3-8}$cycloalkyl, $C_{3-8}$cycloalkenyl, $C_{1-4}$acyl, phenoxy, phenyl or phenylthio.

In certain embodiments, in compounds of the formulae (11) and (12) the 5-membered ring having the structure:

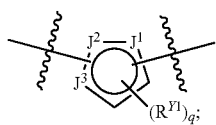

has the structure:

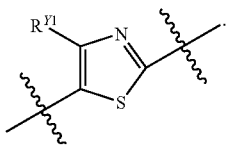

In certain embodiments, in compounds of the formulae (13) and (14) the 6-membered ring having the structure:

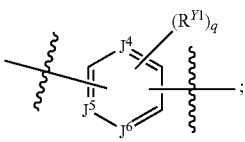

has one of the following structures:

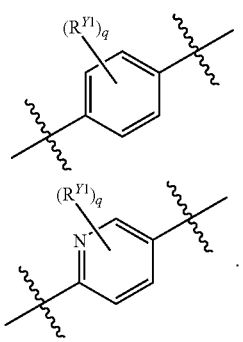

In certain embodiments, —W¹-Alk₁- is —NHC$_{1-6}$alkyl- or —OC$_{1-6}$alkyl-. In certain embodiments, —W¹-Alk₁- is —NHC$_2$alkyl- or —OC$_2$alkyl-. In certain embodiments, —W¹-Alk₁- is —NHCH$_2$CH$_2$—, —OCH$_2$CH$_2$— or —NH—CH$_2$CH(CH$_2$OH)—.

VII. Compounds Having the Structure (and Pharmaceutically Acceptable Derivatives Thereof):

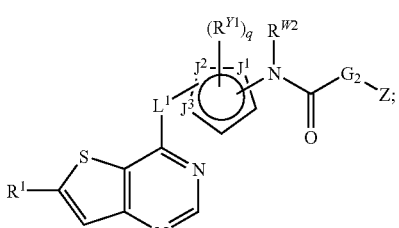
(15)

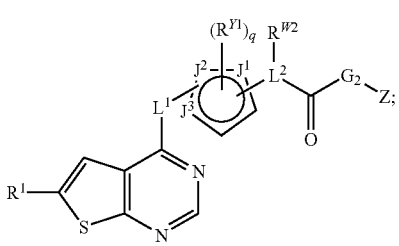
(16)

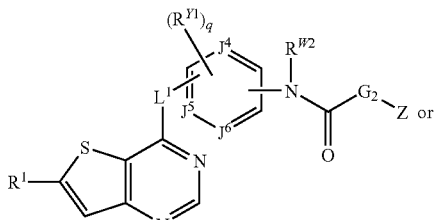
(17)

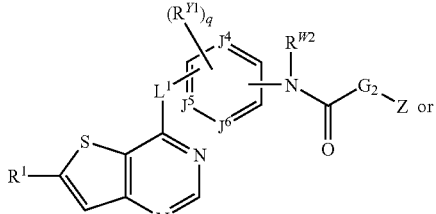
(18)

wherein R¹, L¹ and Z are as defined generally and in classes and subclasses herein; q is an integer from 0-3; J¹, J² and J³ are independently O, S, N, NR$^{Y1}$ or CR$^{Y1}$; J⁴, J⁵ and J⁶ are independently N or CR$^{Y1}$; wherein each occurrence of R$^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of R$^{Y2}$ and R$^{Y3}$ is independently hydrogen, lower alkyl, lower heteroalkyl, aryl, heteroaryl, -(alkyl)aryl, -(alkyl)heteroaryl or acyl, or R$^{Y2}$ and R$^{Y3}$ taken together with the nitrogen atom to which they are attached form a 5-6 membered heterocyclic ring; G2 is absent, O or NR$^{G2}$; and R$^{W2}$ and R$^{G2}$ are independently hydrogen, lower alkyl, lower heteroalkyl, heterocyclyl, aryl, heteroaryl, -(alkyl)aryl, -(alkyl)heteroaryl or acyl. In certain embodiments, the invention encompasses the compounds described directly above with the proviso that:

(i) R¹ is not Q¹, Q² or Q³;

(ii) for compounds of formula (16) and (18), the following groups do not occur simultaneously as defined: G$_2$ is absent; L¹ is —OCH$_2$—, CH$_2$O—, —N(R)CH$_2$— or —CH$_2$N(R)—, wherein R is H or C$_{1-8}$alkyl; and Z is a 5-10-membered cycloalkyl, heterocyclyl, aryl or heteroaryl;

(iii) the following groups do not occur simultaneously as defined: $G^2$ is absent; $R^1$ is hydrogen, halogen, $C_{1-4}$alkyl or $C_{1-4}$alkoxy; $L^1$ is —NH$C_{1-6}$alkyl, —O$C_{1-6}$alkyl, —NH$C_{1-6}$heteroalkyl or —O$C_{1-6}$heteroalkyl; and Z is $C_{3-10}$cycloalkyl, morpholinyl, phenyl, phenyl$C_{1-4}$alkyl or phenyl$C_{2-3}$alkenyl; and/or (iv) the following groups do not occur simultaneously as defined: $G^2$ is absent; $L^1$ is —NR(CR$^x$)$_{1-2}$— or —O(CR$^x$)$_{1-2}$— wherein R is hydrogen, $C_{1-4}$alkyl, $C_{1-4}$alkoxy, OH, NH$_2$ or —$C_{1-4}$alkylNH; and R$^x$ is H or $C_{1-4}$alkyl;

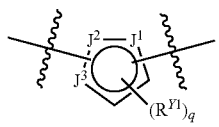

is thienyl, furanyl, pyrrolyl, imidazolyl, oxazolyl or thiazolyl;

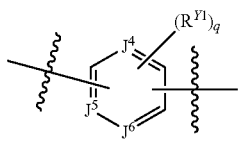

is phenyl, pyridyl, pyrimidyl or pyrazinyl; R$^{W2}$ is H or $C_{3-8}$cycloalkyl; and Z is $C_{3-8}$cycloalkyl.

In certain embodiments, in compounds of the formulae (15) and (16) the 5-membered ring having the structure:

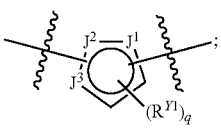

has the structure:

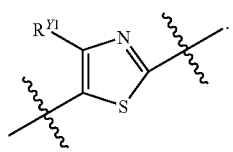

In certain embodiments, in compounds of the formulae (17) and (18) the 6-membered ring having the structure:

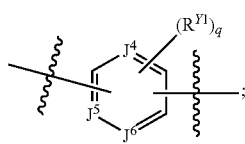

has one of the following structures:

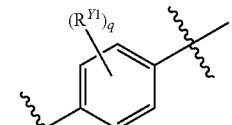

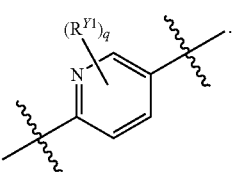

In certain embodiments, —N(R$^{W2}$)C(=O)G$_2$— is —NHC(=O)—, —NHC(=O)O—, or —NHC(=O)NH—.

VIII. Compounds Having the Structure (and Pharmaceutically Acceptable Derivatives Thereof):

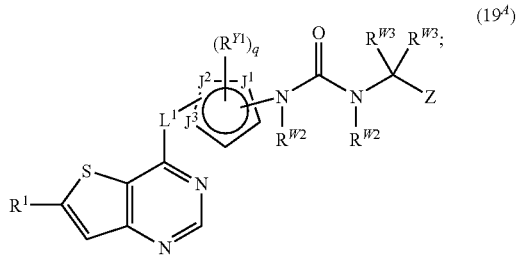

(19$^A$)

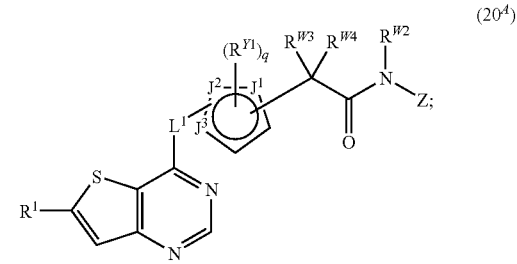

(20$^A$)

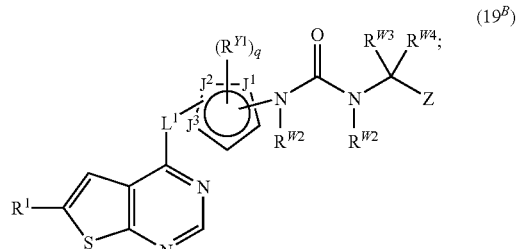

(19$^B$)

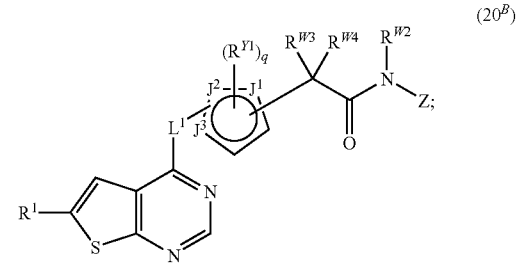

(20$^B$)

-continued

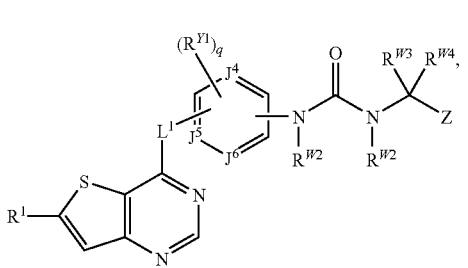
(21^A)

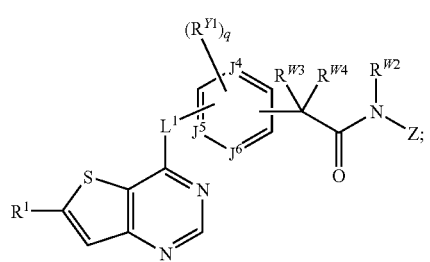
(22^A)

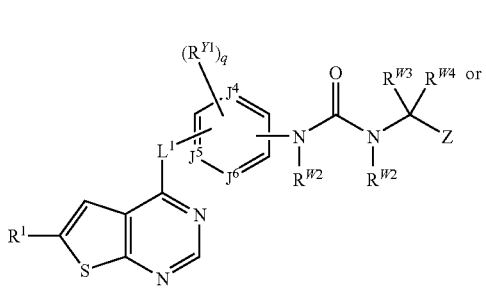
(21^B)

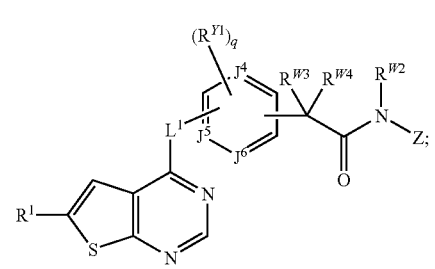
(22^B)

wherein $R^1$, $L^1$ and Z are as defined generally and in classes and subclasses herein; q is an integer from 0-3; $J^1$, $J^2$ and $J^3$ are independently O, S, N, $NR^{Y1}$ or $CR^{Y1}$; $J^4$, $J^5$ and $J^6$ are independently N or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$, —C(=O)$NR^{Y2}R^{Y3}$, halogen, —CN, —$NO_2$, —C(=O)$OR^{Y3}$, —N($R^{Y2}$)C(=O)$R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $R^{W3}$ and $R^{W4}$ are independently hydrogen, lower alkyl, lower heteroalkyl, heterocyclyl, aryl, heteroaryl or acyl; and $R^{W2}$ is hydrogen, lower alkyl, lower heteroalkyl, heterocyclyl, aryl, heteroaryl, -(alkyl)aryl, -(alkyl)heteroaryl or acyl. In certain embodiments, the invention encompasses the compounds described directly above with the proviso that:

(i) $R^1$ is not $Q^1$, $Q^2$ or $Q^3$; and (ii) for compounds of formula $20^{A-B}$ and $22^{A-B}$, if ($R^{W3}$, $R^{W4}$) is (H,H), (F,F) or (H, $C_{1-4}$alkyl), then —$W^1$-$Alk_1$- is not —$OCH_2$— or —N(R)$CH_2$—, wherein R is H or $C_{1-8}$alkyl.

In certain embodiments, in compounds of the formulae (19) and (20) the 5-membered ring having the structure:

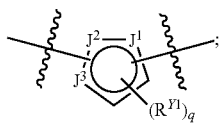

has the structure:

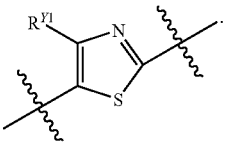

In certain embodiments, in compounds of the formulae (21) and (22) the 6-membered ring having the structure:

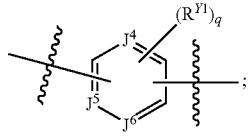

has one of the following structures:

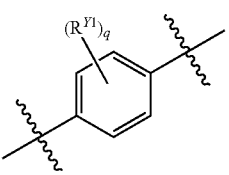

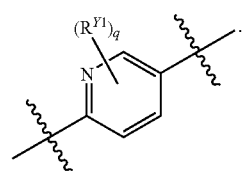

In certain embodiments, —N($R^{W2}$)C(=O)N($R^{W2}$)$CR^{W3}R^{W4}$— is —NHC(=O)$NHCH_2$—, and $CR^{W3}R^{W4}$C(=O)N($R^{W2}$)— is —$CH_2$C(=O)NH—.

IX. Compounds Having the Structure (and Pharmaceutically Acceptable Derivatives Thereof):

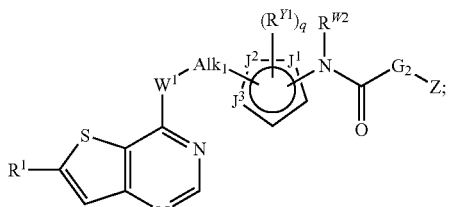

(23)

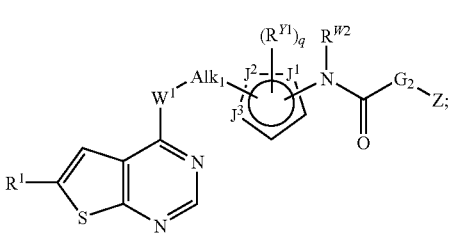

(24)

wherein $R^1$ and Z are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, SO$_2$NR$^{L1A}$—, —NR$^{L1A}$SO$_2$NR$^{L1B}$—, —O—, —S—, or —NR$^{L1A}$—; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^1$, $J^2$ and $J^3$ are independently O, S, N, $NR^{Y1}$ or $CR^{Y1}$; wherein each occurrence of $R^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}R^{Y3}$, —SO$_2$NR$^{Y2}R^{Y3}$, —C(=O)NR$^{Y2}$ $R^{Y3}$, halogen, —CN, —NO$_2$, —C(=O)OR$^{Y3}$, —N(R$^{Y2}$)C(=O)R$^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $G_2$ is absent, O or $NR^{G2}$; and $R^{W2}$ and $R^{G2}$ are independently hydrogen, lower alkyl, lower heteroalkyl, heterocyclyl, aryl, heteroaryl, -(alkyl)aryl, -(alkyl)heteroaryl or acyl. In certain embodiments, the invention encompasses the compounds described directly above with the proviso that:

(i) $R^1$ is not $Q^1$, $Q^2$ or $Q^3$;

(ii) for compounds of formula (23) and (24), the following groups do not occur simultaneously as defined: $G_2$ is absent; $L^1$ is —OCH$_2$—, —CH$_2$O—, —N(R)CH$_2$— or —CH$_2$N(R)—, wherein R is H or $C_{1-8}$alkyl; and Z is not a 5-10-membered cycloalkyl, heterocyclyl, aryl or heteroaryl;

(iii) the following groups do not occur simultaneously as defined: $G_2$ is absent; $R^1$ is hydrogen, halogen, $C_{1-4}$alkyl or $C_{1-4}$alkoxy; $W^1Alk_1$ is —NHC$_{1-6}$alkyl, —OC$_{1-6}$alkyl, —NHC$_{1-6}$heteroalkyl or —OC$_{1-6}$heteroalkyl; and Z is $C_{3-10}$cycloalkyl, morpholinyl, phenyl, phenylC$_{1-4}$alkyl or phenylC$_{2-3}$alkenyl; and/or (iv) the following groups do not occur simultaneously as defined: $G^2$ is absent; $W^1Alk_1$ is —NR(CR$^x$)$_{1-2}$— or —O(CR$^x$)$_{1-2}$— wherein R is hydrogen, $C_{1-4}$alkyl, $C_{1-4}$alkoxy, OH, NH$_2$ or —$C_{1-4}$alkylNH; and $R^x$ is H or $C_{1-4}$alkyl;

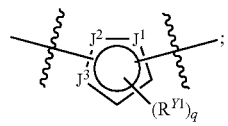

is thienyl, furanyl, pyrrolyl, imidazolyl, oxazolyl or thiazolyl; $R^{W2}$ is H or $C_{3-8}$cycloalkyl; and Z is $C_{3-8}$cycloalkyl.

In certain embodiments, compounds of this class have the structure ($23^A$), ($23^B$), ($24^A$) or ($24^B$) below:

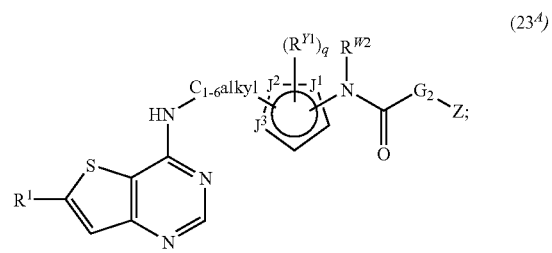

($23^A$)

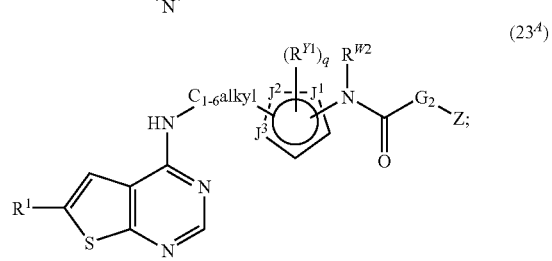

($23^A$)

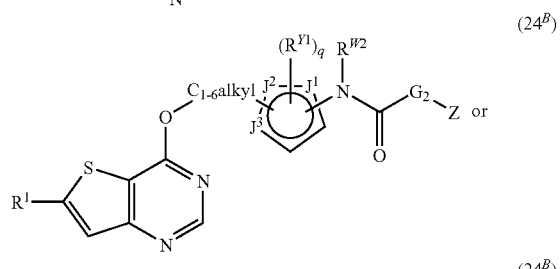

($24^B$)

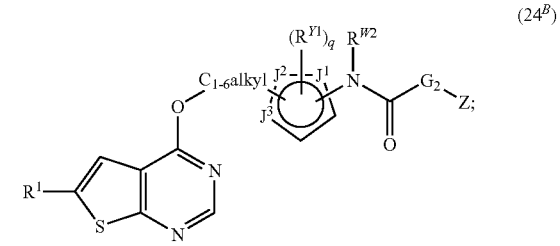

($24^B$)

wherein the $C_{1-6}$alkyl moiety may be substituted or unsubstituted.

In certain embodiments, for compounds of formulae (23) and (24), —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, for compounds of formulae (23), (24), ($23^A$), ($23^B$), ($24^A$) and ($24^B$) the $C_{1-6}$alkyl moiety is a substituted or unsubstituted $C_2$alkyl moiety. In certain exemplary embodiments, the $C_{1-6}$alkyl moiety is —CH$_2$CH$_2$—.

In certain embodiments, in compounds of the formulae (23), (24), (23$^A$), (23$^B$), (24$^A$) and (24$^B$) the 5-membered ring having the structure:

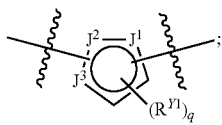

has the structure:

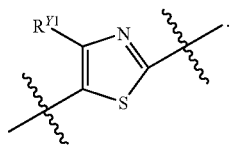

In certain embodiments, —N(R$^{W2}$)C(=O)G$_2$— is —NHC(=O)—, —NHC(=O)O—, or —NHC(=O)NH—.

X. Compounds Having the Structure (and Pharmaceutically Acceptable Derivatives Thereof):

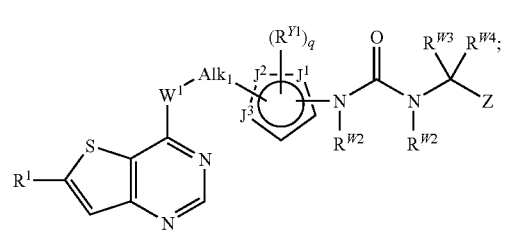
(25)

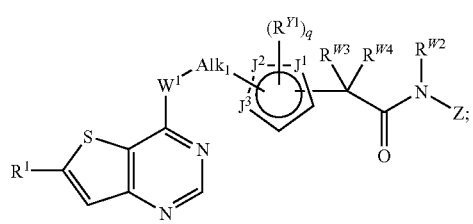
(26)

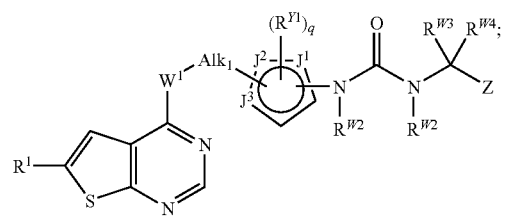
(27)

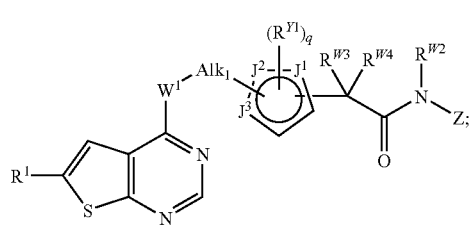
(28)

wherein R$^1$ and Z are as defined generally and in classes and subclasses herein; W$^1$ is O or NR$^{W1}$, where R$^{W1}$ is hydrogen, lower alkyl, lower heteroalkyl, aryl, heteroaryl, -(alkyl)aryl, -(alkyl)heteroaryl or acyl; Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1B}$—, —NR$^{L1A}$NR$^{L1B}$—, —NR$^{L1A}$NR$^{L1B}$C(=O)—, —NR$^{L1A}$C(=O)—, NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl; q is an integer from 0-3; J$^1$, J$^2$ and J$^3$ are independently O, S, N, NR$^{Y1}$ or CR$^{Y1}$; wherein each occurrence of R$^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of R$^{Y2}$ and R$^{Y3}$ is independently hydrogen, lower alkyl, lower heteroalkyl, aryl, heteroaryl, -(alkyl)aryl, -(alkyl)heteroaryl or acyl, or R$^{Y2}$ and R$^{Y3}$ taken together with the nitrogen atom to which they are attached form a 5-6 membered heterocyclic ring; R$^{W3}$ and R$^{W4}$ are independently hydrogen, lower alkyl, lower heteroalkyl, heterocyclyl, aryl, heteroaryl or acyl; and R$^{W2}$ is hydrogen, lower alkyl, lower heteroalkyl, heterocyclyl, aryl, heteroaryl, -(alkyl)aryl, -(alkyl)heteroaryl or acyl. In certain embodiments, the invention encompasses the compounds described directly above with the proviso that:

(i) R$^1$ is not Q$^1$, Q$^2$ or Q$^3$.

In certain embodiments, —W$^1$-Alk$_1$- is —NHC$_{1-6}$alkyl- or —OC$_{1-6}$alkyl-. In certain embodiments, —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, in compounds of the formulae (25), (26), (27) and (28), the 5-membered ring having the structure:

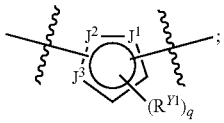

has the structure:

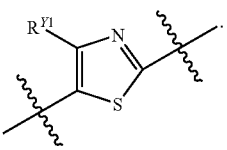

In certain embodiments, —N(R$^{W2}$)C(=O)N(R$^{W2}$)CR$^{W3}$R$^{W4}$ is —NHC(=O)NHCH$_2$—, and —CR$^{W3}$R$^{W4}$C(=O)N(R$^{W2}$)— is —CH$_2$C(=O)NH—.

XI. Compounds Having the Structure (and Pharmaceutically Acceptable Derivatives Thereof):

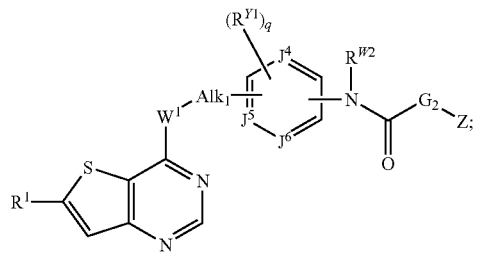
(29)

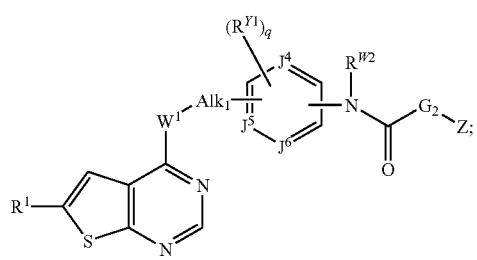
(30)

wherein $R^1$ and Z are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; $Alk_1$ is a substituted or unsubstituted $C_{1-6}$alkylene or $C_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$, —SO$_2$NR$^{L1A}$, —NR$^{L1A}$SO$_2$NR$^{L1B}$, —O—, —S—, or —NR$^{L1A}$; wherein each occurrence of $R^{L1A}$ and $R^{L1B}$ is independently hydrogen, lower alkyl, lower heteroalkyl, heterocyclyl, aryl, heteroaryl or acyl; q is an integer from 0-3; $J^4$, $J^5$ and $J^6$ are independently N or $CR^{Y1}$; wherein each occurrence of $R^{Y1}$ is independently hydrogen, alkyl, heteroalkyl, aryl, heteroaryl, —(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring; $G_2$ is absent, O or $NR^{G2}$; and $R^{W2}$ and $R^{G2}$ are independently hydrogen, lower alkyl, lower heteroalkyl, heterocyclyl, aryl, heteroaryl, -(alkyl)aryl, -(alkyl)heteroaryl or acyl. In certain embodiments, the invention encompasses the compounds described directly above with the proviso that:

(i) $R^1$ is not $Q^1$, $Q^2$ or $Q^3$;

(ii) the following groups do not occur simultaneously as defined: $G_2$ is absent; $W^1Alk_1$ is —OCH$_2$— or —N(R)CH$_2$—, wherein R is H or $C_{1-8}$alkyl; and Z is a 5-10-membered cycloalkyl, heterocyclyl, aryl or heteroaryl;

(iii) the following groups do not occur simultaneously as defined: $G^2$ is absent; $R^1$ is hydrogen, halogen, $C_{1-4}$alkyl or $C_{1-4}$alkoxy; $W^1Alk_1$ is —NHC$_{1-6}$alkyl, —OC$_{1-6}$alkyl, —NHC$_{1-6}$heteroalkyl or —OC$_{1-6}$heteroalkyl; and Z is $C_{3-10}$cycloalkyl, morpholinyl, phenyl, phenylC$_{1-4}$alkyl or phenylC$_{2-3}$alkenyl; and/or (iv) the following groups do not occur simultaneously as defined: $G^2$ is absent; $W^1Alk_1$ is —NR(CR$^x$)$_{1-2}$— or —O(CR$^x$)$_{1-2}$— wherein R is hydrogen, $C_{1-4}$alkyl, $C_{1-4}$alkoxy, OH, NH$_2$ or —C$_{1-4}$alkylNH; and $R^x$ is H or $C_{1-4}$alkyl;

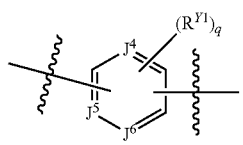

is phenyl, pyridyl, pyrimidyl or pyrazinyl; $R^{W2}$ is H or $C_{3-8}$cycloalkyl; and Z is $C_{3-8}$cycloalkyl.

In certain embodiments, the compounds have the following structures:

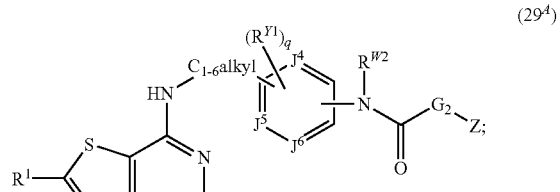
(29$^A$)

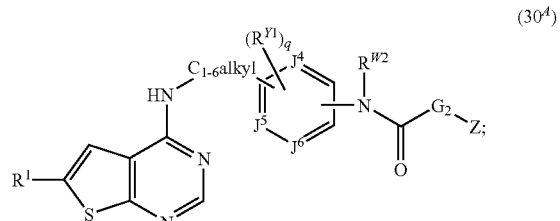
(30$^A$)

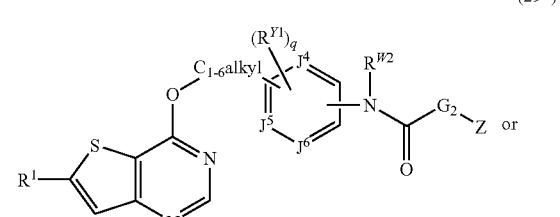
(29$^B$)

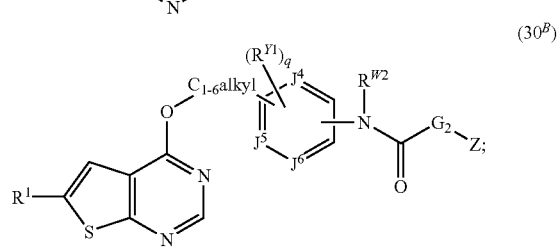
(30$^B$)

wherein the $C_{1-6}$alkyl moiety may be substituted or unsubstituted.

In certain embodiments, for compounds of formulae (XX) and (XXI), —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, for compounds of formulae (29), (30), (29$^A$), (29$^B$), (30$^A$) and (30$^B$) the $C_{1-6}$alkyl moiety is a substituted or unsubstituted C$_2$alkyl moiety. In certain exemplary embodiments, the $C_{1-6}$alkyl moiety is —CH$_2$CH$_2$—.

In certain embodiments, in compounds of the formulae (29) and (30) the 6-membered ring having the structure:

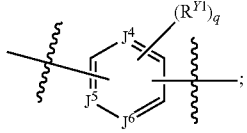

has one of the following structures:

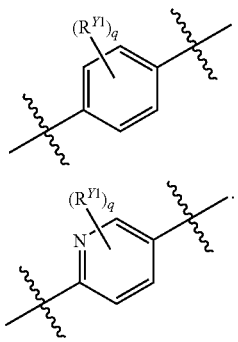

In certain embodiments, —N(R$^{W2}$)C(=O)G$_2$— is —NHC(=O)—, —NHC(=O)O—, or —NHC(=O)NH—.

XII. Compounds Having the Structure (and Pharmaceutically Acceptable Derivatives Thereof):

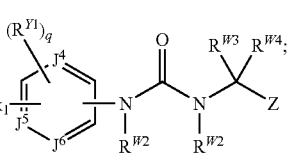
(31)

(32)

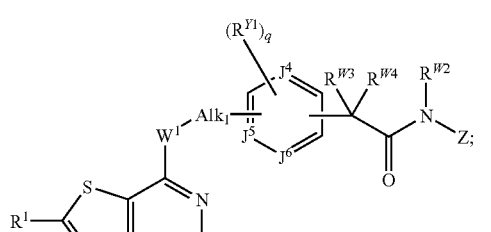
(33)

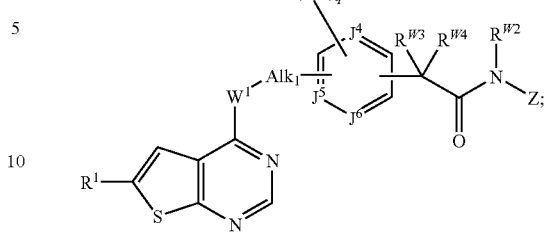
(34)

wherein R$^1$ and Z are as defined generally and in classes and subclasses herein; W$^1$ is O or NR$^{W1}$, where R$^{W1}$ is hydrogen, lower alkyl, lower heteroalkyl, aryl, heteroaryl, -(alkyl)aryl, (alkyl)heteroaryl or acyl; Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl; q is an integer from 0-3; J$^4$, J$^5$ and J$^6$ are independently N or CR$^{Y1}$; wherein each occurrence of R$^{Y1}$ is independently hydrogen, alkyl, heteroalkyl, aryl, heteroaryl, -(alkyl)aryl or -(alkyl)heteroaryl, —OR$^{Y3}$, —SR$^{Y3}$, —NR$^{Y2}$R$^{Y3}$, —SO$_2$NR$^{Y2}$R$^{Y3}$, —C(=O)NR$^{Y2}$R$^{Y3}$, halogen, —CN, —NO$_2$, —C(=O)OR$^{Y3}$, —N(R$^{Y2}$)C(=O)R$^{Y3}$, wherein each occurrence of R$^{Y2}$ and R$^{Y3}$ is independently hydrogen, lower alkyl, lower heteroalkyl, aryl, heteroaryl, -(alkyl)aryl, -(alkyl)heteroaryl or acyl, or R$^{Y2}$ and R$^{Y3}$ taken together with the nitrogen atom to which they are attached form a 5-6 membered heterocyclic ring; R$^{W3}$ and R$^{W4}$ are independently hydrogen, lower alkyl, lower heteroalkyl, heterocyclyl, aryl, heteroaryl or acyl; and R$^{W2}$ is hydrogen, lower alkyl, lower heteroalkyl, heterocyclyl, aryl, heteroaryl, -(alkyl)aryl, -(alkyl)heteroaryl or acyl. In certain embodiments, the invention encompasses the compounds described directly above with the proviso that:

(i) R$^1$ is not Q$^1$, Q$^2$ or Q$^3$; and (ii) for compounds of structure (32) or (34), if (R$^{W3}$, R$^{W4}$) is (H,H), (F,F) or (H, C$_{1-4}$alkyl), then —W$^1$-Alk$_1$- is not —OCH$_2$— or —N(R)CH$_2$—, wherein R is H or C$_{1-8}$alkyl.

In certain embodiments, —W$^1$-Alk$_1$- is —NHC$_{1-6}$alkyl- or —OC$_{1-6}$alkyl-. In certain embodiments, —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

In certain embodiments, in compounds of the formulae (31)-(34) the 6-membered ring having the structure:

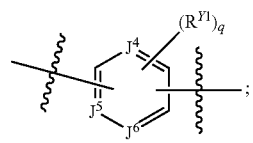

has one of the following structures:

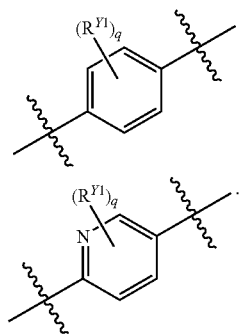

In certain embodiments, —N(R$^{W2}$)C(=O)G$_2$— is —NHC(=O)—, —NHC(=O)O—, or —NHC(=O)NH—.

In certain embodiments, —N(R$^{W2}$)C(=O)N(R$^{W2}$)CR$^{W3}$R$^{W4}$— is —NHC(=O)NHCH$_2$—, and —CR$^{W3}$R$^{W4}$C(=O)N(R$^{W2}$)— is —CH$_2$C(=O)NH—.

XIII. Compounds Having the Structure (and Pharmaceutically Acceptable Derivatives Thereof):

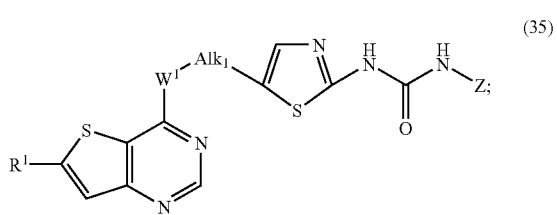

(35)

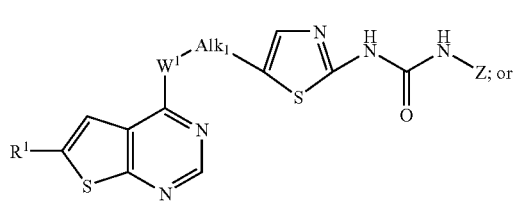

(36)

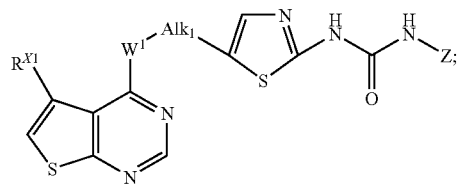

(37)

wherein R$^1$ and R$^{X1}$ are as defined generally and in classes and subclasses herein; Z is an aryl, heteroaryl or heterocyclic moiety; W$^1$ is O or NR$^{W1}$, where R$^{W1}$ is hydrogen, lower alkyl, lower heteroalkyl, aryl, heteroaryl, -(alkyl)aryl, -(alkyl)heteroaryl or acyl; Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C(=O)—, —C(=O)NR$^{L1A}$—, —OC(=O)—, —OC(=O)NR$^{L1A}$, NR$^{L1A}$NR$^{L1B}$—, —NR$^{L1A}$NR$^{L1A}$C(=O)—, —NR$^{L1A}$C(=O)—, —NR$^{L1A}$CO$_2$—, —NR$^{L1A}$C(=O)NR$^{L1B}$—, —S(=O)—, —SO$_2$—, —NR$^{L1A}$SO$_2$—, —SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl; m is an integer from 0 to 3; r is an integer from 1 to 4; each occurrence of R$^{Z1}$ is independently hydrogen, alkyl, heteroalkyl, aryl, heteroaryl, -(alkyl)aryl or -(alkyl)heteroaryl, —OR$^{Z2}$, —SR$^{Z2}$, NR$^{Z2}$R$^{Z3}$, —SO$_2$NR$^{Z2}$R$^{Z3}$ SO$_2$R$^{Z1}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl or acyl, or R$^{Z2}$ and R$^{Z3}$ taken together with the nitrogen or carbon atom to which they are attached form a 5-6 membered heterocyclic, aryl or heteroaryl ring; and R$^{Z4}$ is hydrogen, lower alkyl, lower heteroalkyl, aryl, heteroaryl, -(alkyl)aryl, -(alkyl)heteroaryl or acyl. In certain embodiments, the invention encompasses the compounds described directly above with the proviso that:

(i) neither R$^1$ nor R$^{X1}$ is Q$^1$, Q$^2$ or Q$^3$.

In certain embodiments, —W$^1$-Alk$_1$- is —NH—C$_{1-6}$alkyl- or —O—C$_{1-6}$alkyl-; wherein the C$_{1-6}$alkyl moiety may be substituted or unsubstituted. In certain embodiments, —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH(CH$_2$OH)—.

XIV. Compounds Having the Structure (and Pharmaceutically Acceptable Derivatives Thereof):

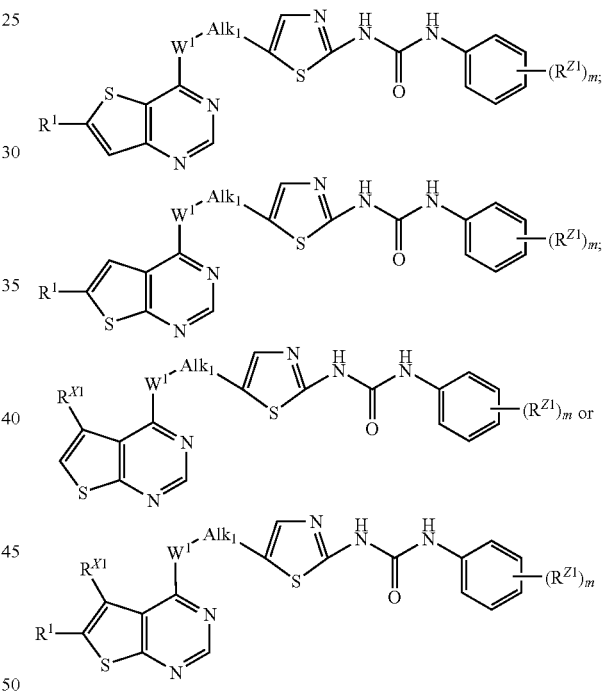

wherein R$^1$ and R$^{X1}$ are as defined generally and in classes and subclasses herein; W$^1$ is O or NR$^{W1}$, where R$^{W1}$ is hydrogen, lower alkyl, lower heteroalkyl, aryl, heteroaryl, -(alkyl)aryl, -(alkyl)heteroaryl or acyl; Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —CN(=O)C(=O)—, —C(=O)NR$^{L1A}$—, —OC(=O)—, —OC(=O)NR$^{L1A}$—, —NR$^{L1A}$NR$_{L1B}$—, —NR$^{L1A}$NR$^{L1B}$C(=O)—, —NR$^{L1A}$C(=O), —NR$^{L1A}$CO$_2$—, —NR$^{L1A}$C(=O)NR$^{L1B}$—, —S(=O)—, —SO$_2$—, —NR$^{L1A}$SO$_2$—, SO$_2$NR$^{L1A}$, —NR$^{L1B}$SO$_2$NR$^{L1B}$, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl; m is an integer from 0 to 3; r is an integer from 1 to 4; each occurrence of R$^{Z1}$ is independently hydrogen, alkyl, heteroalkyl, aryl, heteroaryl, -(alkyl) aryl or -(alkyl)heteroaryl, —OR$^{Z2}$, —SR$^{Z2}$, —NR$^{Z2}$R$^{Z3}$, —SO$_2$NR$^{Z2}$R$^{Z3}$, —SO$_2$R$^{Z1}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl or acyl, or R$^{Z2}$ and R$^{Z3}$ taken together with the nitrogen or carbon atom to which they are attached form a 5-6 membered heterocyclic, aryl or heteroaryl ring; and R$^{Z4}$ is hydrogen, lower alkyl, lower heteroalkyl, aryl, heteroaryl, -(alkyl)aryl, -(alkyl)heteroaryl or acyl. In certain embodiments, the invention encompasses the compounds described directly above with the proviso that:

(i) neither R$^1$ nor R$^{X1}$ is Q$^1$, Q$^2$ or Q$^3$.

In certain embodiments, for compounds of groups XIII and XIV, —W$^1$-Alk$_1$- is —NHC$_{1-6}$alkyl- or —OC$_{1-6}$alkyl-. In certain embodiments, —W$^1$-Alk$_1$- is —NHC$_2$alkyl- or —OC$_2$alkyl-. In certain embodiments, —W$^1$-Alk$_1$- is —NHCH$_2$CH$_2$—, —OCH$_2$CH$_2$— or —NH—CH$_2$CH (CH$_2$OH)—.

In certain embodiments, for compounds of groups XIII and XIV, R$^1$ is hydrogen, halogen, heterocyclyl, aryl or heteroaryl. In certain exemplary embodiments, R$^1$ is hydrogen.

In certain embodiments, for compounds of group XIV, R$^{Z1}$ is hydrogen, halogen, lower alkyl or lower haloalkyl. In certain embodiments, m is 1 and R$^{Z1}$ is halogen, lower alkyl or lower haloalkyl.

In certain embodiments, compounds of group XIV have the structure:

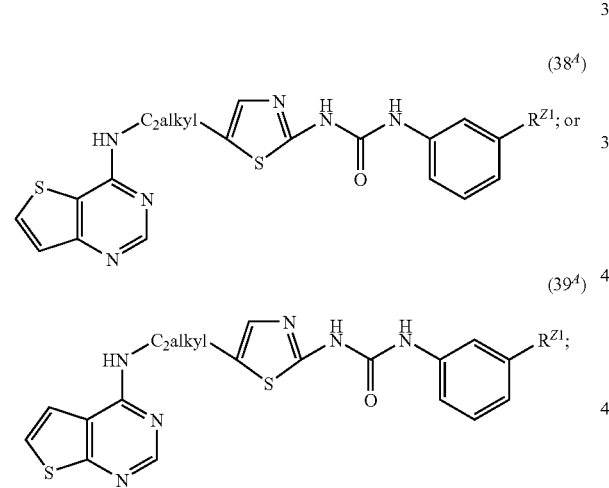

(38$^A$)

(39$^A$)

wherein R$^{Z1}$ is halogen, lower alkyl or lower haloalkyl. In certain exemplary embodiments, R$^{Z1}$ is Cl, F, methyl or —CF$_3$. In certain exemplary embodiments, R$^{Z1}$ is Cl or —CF$_3$.

In certain embodiments, compounds of group XIV have the structure:

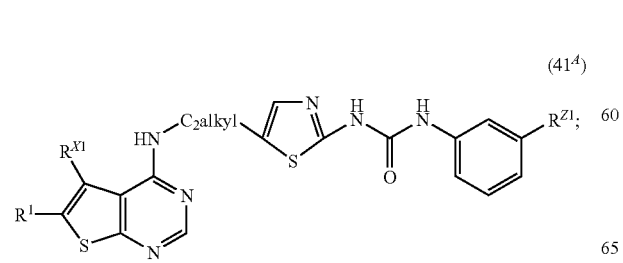

(41$^A$)

wherein R$^1$ is hydrogen, lower alkyl or —CO$_2$R$^{1A}$ where R$^{1A}$ is hydrogen or lower alkyl; R$^{X1}$ is hydrogen, lower alkyl or heterocyclyl; and R$^{Z1}$ is halogen, lower alkyl or lower haloalkyl. In certain exemplary embodiments, R$^1$ is hydrogen, methyl, —CO$_2$H or —CO$_2$Me; R$^{X1}$ is hydrogen, methyl or thienyl; and R$^{Z1}$ is Cl, F, methyl or —CF$_3$.

XV. Compounds Having the Structure (and Pharmaceutically Acceptable Derivatives Thereof):

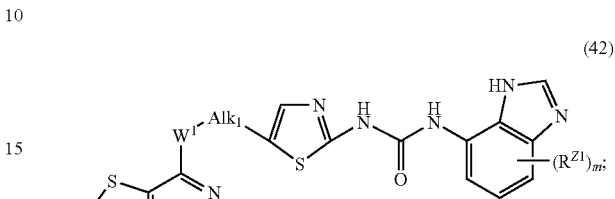

(42)

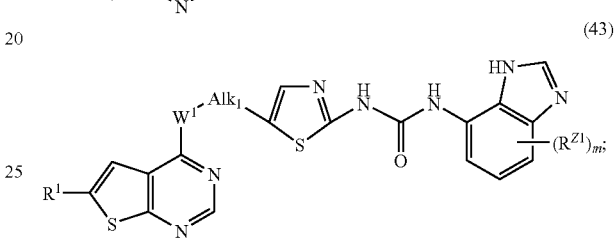

(43)

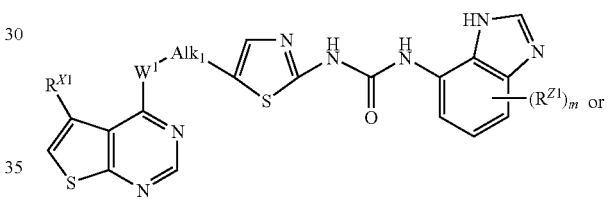

(44)

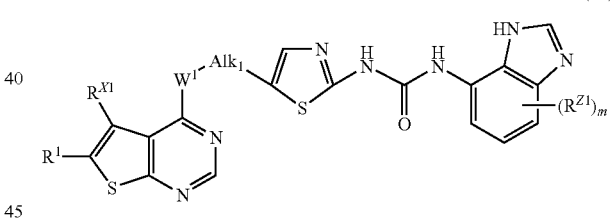

(45)

wherein R$^1$ and R$^{X1}$ are as defined generally and in classes and subclasses herein; W$^1$ is O or NR$^{W1}$, where R$^{W1}$ is hydrogen, lower alkyl, lower heteroalkyl, aryl, heteroaryl, -(alkyl) aryl, -(alkyl)heteroaryl or acyl; Alk$_1$ is a substituted or unsubstituted C$_{1-6}$alkylene or C$_{2-6}$alkenylene chain wherein up to two non-adjacent methylene units are independently optionally replaced by —C(=O)—, —CO$_2$—, —C(=O)C (=O)—, —C(=O)NR$^{L1A}$—, —OC(=O)—, —OC(=O) NR$^{L1A}$—, —NR$^{L1A}$NR$^{L1B}$—, —NR$^{L1A}$NR$^{L1B}$C(=O)—, —NR$^{L1A}$C(=O)—, —NR$^{L1A}$CO$_2$—, —NR$^{L1A}$C(=O) NR$^{L1B}$—, —S(=O)—, —SO$_2$—, —NR$^{L1A}$SO$_2$, SO$_2$NR$^{L1A}$—, —NR$^{L1A}$SO$_2$NR$^{L1B}$—, —O—, —S—, or —NR$^{L1A}$—; wherein each occurrence of R$^{L1A}$ and R$^{L1B}$ is independently hydrogen, lower alkyl, lower heteroalkyl, heterocyclyl, aryl, heteroaryl or acyl; m is an integer from 0 to 3; r is an integer from 1 to 4; each occurrence of R$^{Z1}$ is independently hydrogen, alkyl, heteroalkyl, aryl, heteroaryl, -(alkyl) aryl or -(alkyl)heteroaryl, —OR$^{Z2}$, —SR$^{Z2}$, —NR$^{Z2}$R$^{Z3}$, —SO$_2$NR$^{Z2}$R$^{Z3}$, —SO$_2$R$^{Z1}$, —C(=O)NR$^{Z2}$R$^{Z3}$, halogen, —CN, —NO$_2$, —C(=O)OR$^{Z3}$, —N(R$^{Z2}$)C(=O)R$^{Z3}$, wherein each occurrence of R$^{Z2}$ and R$^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is hydrogen, lower alkyl, lower heteroalkyl, aryl, heteroaryl, -(alkyl)aryl, -(alkyl)heteroaryl or acyl. In certain embodiments, the invention encompasses the compounds described directly above with the proviso that:

(i) neither $R^1$ nor $R^{X1}$ is $Q^1$, $Q^2$ or $Q^3$.

In certain embodiments, for compounds of group XV, —$W^1$-$Alk_1$- is —$NHC_{1-6}$alkyl- or —$OC_{1-6}$alkyl-. In certain embodiments, —$W^1$-$Alk_1$- is —$NHC_2$alkyl- or —$OC_2$alkyl-. In certain embodiments, —$W^1$-$Alk_1$- is —$NHCH_2CH_2$—, —$OCH_2CH_2$— or —NH—$CH_2CH(CH_2OH)$—.

In certain embodiments, for compounds of group XV, $R^1$ is hydrogen, halogen, heterocyclyl, aryl or heteroaryl. In certain exemplary embodiments, $R^1$ is hydrogen.

In certain embodiments, for compounds of group XV, $R^{Z1}$ is hydrogen, halogen, lower alkyl or lower haloalkyl. In certain embodiments, m is 0.

In certain embodiments, compounds of group XV have the structure:

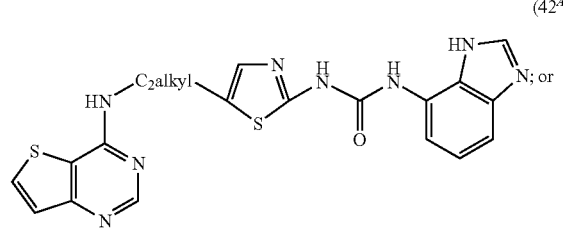

(42$^A$)

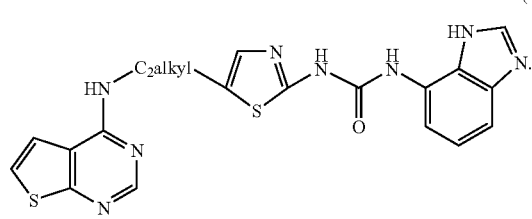

(43$^A$)

In certain embodiments, compounds of group XV have the structure:

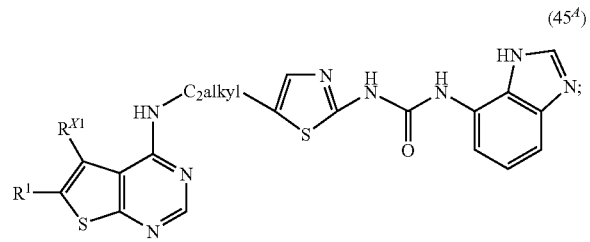

(45$^A$)

wherein $R^1$ is hydrogen, lower alkyl or —$CO_2R^{1A}$ where $R^{1A}$ is hydrogen or lower alkyl; and $R^{X1}$ is hydrogen, lower alkyl or heterocyclyl. In certain exemplary embodiments, $R^1$ is hydrogen, methyl, —$CO_2H$ or —$CO_2Me$; $R^{X1}$ is hydrogen, methyl or thienyl.

XVI. Compounds Having the Structure (and Pharmaceutically Acceptable Derivatives Thereof):

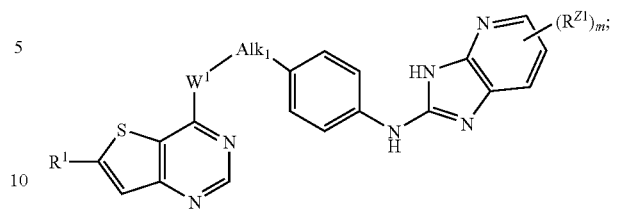

(46)

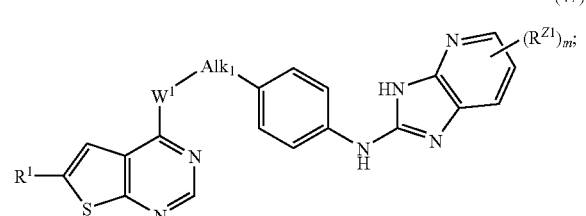

(47)

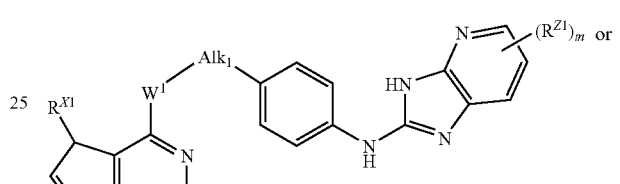

(48)

(49)

wherein $R^1$ and $R^{X1}$ are as defined generally and in classes and subclasses herein; $W^1$ is O or $NR^{W1}$, where $R^{W1}$ is hydrogen, lower alkyl, lower heteroalkyl, aryl, heteroaryl, -(alkyl)aryl, -(alkyl)heteroaryl or acyl; Alk is a substituted or unsubstituted $C_{1-6}$alkylene or $C_{2-6}$alkenylene chain wherein up to two non-adjacent methylene units are independently optionally replaced by —C(=O)— —$CO_2$—, —C(=O)C(=O)—, C(=O)$NR^{L1A}$—, —OC(=O)—, —OC(=O)$NR^{L1A}$—, —$NR^{L1A}NR^{L1B}$—, —$NR^{L1A}NR^{L1B}$C(=O)—, $NR^{L1A}$C(=O)$NR^{L1A}CO_2$—$NR^{L1A}$C(=O)$NR^{L1B}$—, —S(=O)— —$SO_2$—, —$NR^{L1A}SO_2$—, —$SO_2NR^{L1A}$—, —$NR^{L1A}SO_2NR^{L1B}$—, —O—, —S—, or —$NR^{L1A}$—; wherein each occurrence of $R^{L1A}$ and $R^{L1B}$ is independently hydrogen, lower alkyl, lower heteroalkyl, heterocyclyl, aryl, heteroaryl or acyl; m is an integer from 0 to 3; r is an integer from 1 to 4; each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, —$SO_2NR^{Z2}R^{Z3}$, —$SO_2R^{Z1}$, —C(=O)$NR^{Z2}R^{Z3}$, halogen, —CN, —$NO_2$, —C(=O)$OR^{Z3}$, —N($R^{Z2}$)C(=O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, or $R^{Z2}$ and $R^{Z3}$ taken together with the nitrogen or carbon atom to which they are attached form a 5-6 membered heterocyclic, aryl or heteroaryl ring; and $R^{Z4}$ is hydrogen, lower alkyl, lower heteroalkyl, aryl, heteroaryl, -(alkyl)aryl, -(alkyl)heteroaryl or acyl. In certain embodiments, the invention encompasses the compounds described directly above with the proviso that:

(i) neither $R^1$ nor $R^{X1}$ is $Q_1$, $Q_2$ or $Q_3$; and
(ii) —$W^1$-$Alk_1$- is not —$OCH_2$— or —$N(R)CH_2$—, wherein R is H or $C_{1-8}$alkyl.

In certain embodiments, for compounds of group XVI, —$W^1$-$Alk_1$- is —$NHC_{1-6}$alkyl- or —$OC_{1-6}$alkyl-. In certain embodiments, —$W^1$-$Alk_1$- is —$NHC_2$alkyl- or —$OC_2$alkyl-. In certain embodiments, —$W^1$-$Alk_1$- is —$NHCH_2CH_2$—, —$OCH_2CH_2$— or —NH—$CH_2CH(CH_2OH)$—.

In certain embodiments, for compounds of group XVI, $R^1$ is hydrogen, halogen, heterocyclyl, aryl or heteroaryl. In certain exemplary embodiments, $R^1$ is hydrogen.

In certain embodiments, for compounds of group XVI, $R^{Z1}$ is hydrogen, halogen, lower alkyl or lower haloalkyl. In certain embodiments, m is 1 and $R^{Z1}$ is Cl, F, methyl or —$CF_3$. In certain embodiments, m is 1 and $R^{Z1}$ is lower haloalkyl. In certain embodiments, m is 1 and $R^{Z1}$ is —$CF_3$.

In certain embodiments, compounds of group XVI have the structure:

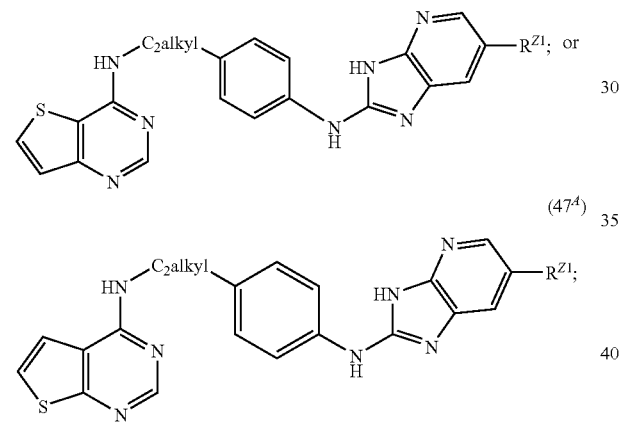

wherein $R^{Z1}$ is halogen, lower alkyl or lower haloalkyl. In certain exemplary embodiments, $R^{Z1}$ is Cl, F, methyl or —$CF_3$.

In certain embodiments, compounds of group XVI have the structure:

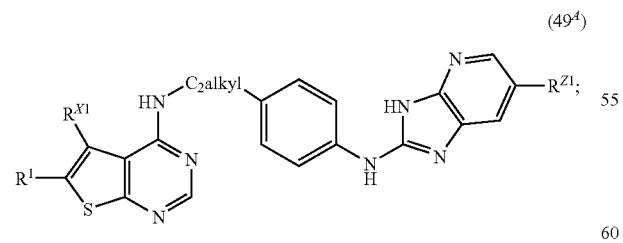

wherein $R^1$ is hydrogen, lower alkyl or —$CO_2R^{1A}$ where $R^{1A}$ is hydrogen or lower alkyl; $R^{X1}$ is hydrogen, lower alkyl or heterocyclyl; and $R^{Z1}$ is halogen, lower alkyl or lower haloalkyl. In certain exemplary embodiments, $R^1$ is hydrogen, methyl, —$CO_2H$ or —$CO_2Me$; $R^{X1}$ is hydrogen, methyl or thienyl; and $R^{Z1}$ is Cl, F, methyl or —$CF_3$.

XVII. Compounds Having the Structure (and Pharmaceutically Acceptable Derivatives Thereof):

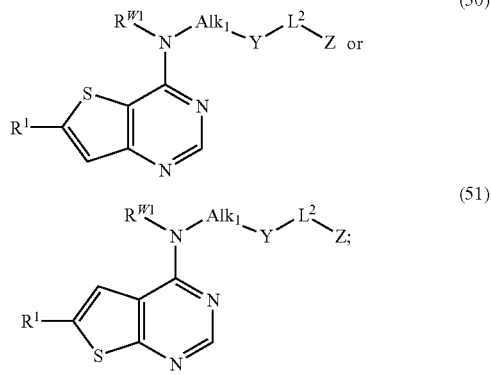

wherein $R^1$, $L^1$, Y and Z are as defined generally and in classes and subclasses herein; and $R^{W1}$ together with a carbon atom present on $Alk_1$ forms an optionally substituted 5- to 6-membered heterocyclic ring.

In certain embodiments, compounds of the invention have the structure ($1^A$) or ($2^A$) below:

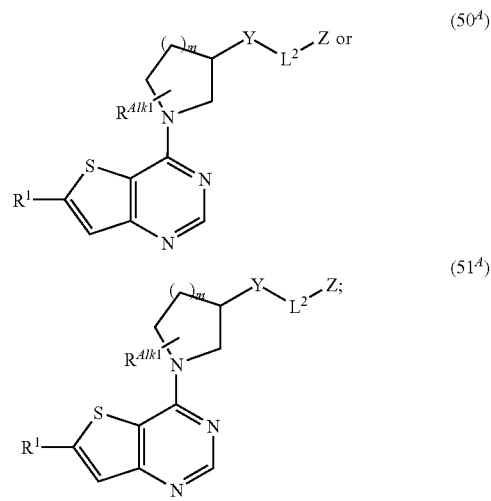

wherein m is 1 or 2 and $R^{Alk1}$ is hydrogen, halogen, hydroxy, CN, nitro, lower alkyl, lower alkoxy, aryl, or heteroaryl. In certain embodiments, $R^{Alk1}$ is hydrogen.

XVIII. Compounds Having the Structure (and Pharmaceutically Acceptable Derivatives Thereof):

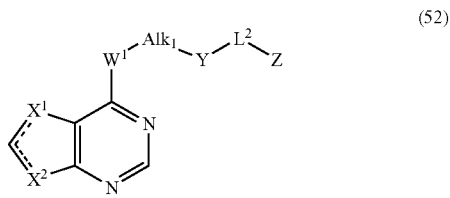

wherein one of - - - - - is a double bond, as valency permits;
one of $X^1$ and $X^2$ is S, the other is —$C(R^{X1})$—; wherein $R^{X1}$ is hydrogen, halogen, cyano, nitro, or an aliphatic, heteroaliphatic, alicyclic, heteroalicyclic, aromatic or heteroaromatic moiety;

$W^1$ is O, S, $NR^{W1}$ or —C(=O)$NR^{W1}$ where $R^{W1}$ is hydrogen, lower alkyl, $C_{3-6}$cycloalkyl, lower heteroalkyl, heterocyclyl, aryl, heteroaryl, -(alkyl)aryl, -(alkyl)heteroaryl or acyl; or $R^{W1}$ together with a carbon atom present on $Alk_1$ forms an optionally substituted 5- to 6-membered heterocyclic ring;

$Alk_1$ is a substituted or unsubstituted $C_{1-6}$alkylene or $C_2$ alkenylene chain wherein up to two non-adjacent methylene units are independently optionally replaced by —C(=O)—, —$CO_2$—, —C(=O)C(=O)—, C(=O)$NR^{L1A}$, —OC(=O)—, —OC(=O)$NR^{L1A}$—, —$NR^{L1A}NR^{L1B}$—, —$NR^{L1A}NR^{L1B}$C(=O)—, —$NR^{L1A}$C(=O), —$NR^{L1A}CO_2$—, —$NR^{L1A}$C(=O)$NR^{L1B}$—, —S(=O)—, —$SO_2$—, —$NR^{L1A}SO_2$—, —$SO_2NR^{L1A}$, —$NR^{L1A}SO_2NR^{L1B}$—, —O—, —S—, or —$NR^{L1A}$—; wherein each occurrence of $R^{L1A}$ and $R^{L1B}$ is independently hydrogen, lower alkyl, lower heteroalkyl, heterocyclyl, aryl, heteroaryl or acyl;

$L^2$ is —$NR^{W2}$—, —N($R^{W2}$)C(=O)$G_2$—, —N($R^{W2}$)C(=O)N($R^{W2}$)$CR^{W3}R^{W4}$— or —$CR^{W3}R^{W4}$C(=O)N($R^{W2}$)—; wherein $G_2$ is absent, O or $NR^{G2}$; and $R^{W2}$, $R^{W3}$, $R^{W4}$ and $R^{G2}$ are independently hydrogen, lower alkyl, lower heteroalkyl, heterocyclyl, aryl, heteroaryl, -(alkyl)aryl, -(alkyl)heteroaryl or acyl;

Y is an optionally substituted phenyl or thiazolyl ring;

Z is an aliphatic, heteroaliphatic, alicyclic, heteroalicyclic, aromatic or heteroaromatic moiety;

with the proviso that (a) $R^{X1}$ is not $Q^1$, $Q^2$ or $Q^3$, wherein $Q^1$ is —($CR^{1A}R^{1B}$)$_m$C≡C—($CR^{1A}R^{1B}$)$_t$$R^{1C}$, —($CR^{1A}R^{1B}$)$_m$C≡C—($CR^{1A}R^{1B}$)$_t$$R^{1C}$, —C=$NOR^{1D}$, or —$X^3R^{1D}$ wherein m is an integer from 0 to 3, t is an integer from 0 to 5, and $X^3$ is a divalent group derived from azetidine, oxetane or a $C_{3-4}$carbocyclic group;

$Q^2$ is —($CR^{1A}R^{1B}$)$_m$C($CR^{1A}R^{1B}$)$_k$$R^{1E}$, —($CR^{1A}R^{1B}$)$_m$C≡C—($CR^{1A}R^{1B}$)$_k$$R^{1E}$ wherein k is an integer from 1 to 3 and m is an integer from 0 to 3; and $Q^3$ is —($CR^{1A}R^{1B}$)$_t$$R^{1C}$, wherein t is an integer from 0 to 5 and the attachment point to $R^{1C}$ is through a carbon atom of the $R^{1C}$ group; wherein $R^{1A}$ and $R^{1B}$ are independently H or $C_{1-6}$alkyl; $R^{1C}$ is an optionally substituted non-aromatic monocyclic ring, a fused or bridged bycyclic ring or a spirocyclic ring; $R^{1E}$ is —$NR^{1A}R^{1D}$ or —$OR^{1D}$; $R^{1D}$ is $R^{1F}$, —C(=O)$R^{1F}$, —$SO_2R^{1F}$, —C(=O)N($R^{1F}$)$_2$, —$SO_2$N($R^{1F}$)$_2$, or —$CO_2R^{1F}$, wherein $R^{1F}$ is H, $C_{1-6}$alkyl, —($CR^{1A}R^{1B}$)($C_{6-10}$aryl) or —($CR^{1A}R^{1B}$)(4-10 membered heterocyclic); and (b) in any one or more of the following groups, the recited variables do not occur simultaneously as defined:

(i) —$W^1$-$Alk_1$- is —$OCH_2$— or —N(R)$CH_2$—, wherein R is H or $C_{1-8}$alkyl; Y is phenyl; and Z is a 5-10-membered cycloalkyl, heterocyclyl, aryl or heteroaryl;

(ii) $R^{X1}$ is hydrogen, halogen, $C_{1-4}$alkyl or $C_{1-4}$alkoxy; —$W^1$-$Alk_1$- is —$NHC_{1-6}$alkyl, —$OC_{1-6}$alkyl, —$NHC_{1-6}$heteroalkyl or —$OC_{1-6}$heteroalkyl; $L^2$—Z is —X—$R^x$ where X is —NR— or —NHC(=O)—, and $R^x$ is $C_{3-10}$cycloalkyl, morpholinyl, phenyl, phenyl$C_{1-4}$alkyl or phenyl$C_{2-3}$alkenyl; and (iii) one of $X^1$ and $X^2$ is S, the other is $CR^{XA}$ wherein $R^{XA}$ is hydrogen, $C_{1-4}$alkyl or phenyl optionally substituted with halogen, (halo)$C_{1-4}$alkyl or (halo)$C_{1-4}$alkoxy; —$W^1$-$Alk_1$- is —$NRC_{1-6}$alkyl-, —$OC_{1-6}$alkyl- or —$SC_{1-6}$alkyl- wherein R is hydrogen, $C_{1-4}$alkyl, $C_{1-4}$acyl; Y is phenyl; $L^2$—Z is a $C_{1-2}$alkyl saturated or unsaturated hydrocarbon chain including —NR— and optionally substituted with halo$C_{1-4}$alkoxy, $C_{3-8}$cycloalkyl, $C_{3-8}$cycloalkenyl, $C_{1-4}$acyl, phenoxy, phenyl or phenylthio.

In certain embodiments, $X^1$ is S and $X^2$ is CH. In certain embodiments, $X^1$ is CH and $X^2$ is S. In certain embodiments, $L^2$ is NH, —NHC(=O)—, —NHC(=O)O—, —NHC(=O)NH—, —NHC(=O)$NHCH_2$—, or —$CH_2$C(=O)NH—.

In certain embodiments, compounds of subgroup XVIII have the following structure:

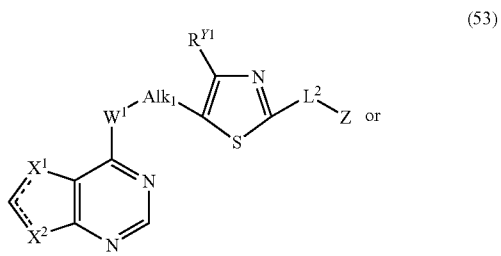

(53)

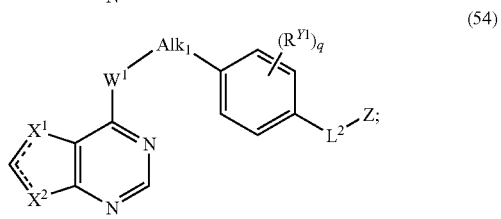

(54)

wherein q is 1-4; one of $X^1$ and $X^2$ is S and the other is —CH—; and each occurrence of $R^{Y1}$ is independently hydrogen, alkyl, heteroalkyl, aryl, heteroaryl, -(alkyl)aryl or -(alkyl)heteroaryl, —$OR^{Y3}$, —$SR^{Y3}$, —$NR^{Y2}R^{Y3}$, —$SO_2NR^{Y2}R^{Y3}$—C(=O)$NR^{Y2}R^{Y3}$, halogen, —CN, —$NO_2$, —C(=O)$OR^{Y3}$, N($R^{Y2}$)C(=O)$R^{Y3}$, wherein each occurrence of $R^{Y2}$ and $R^{Y3}$ is independently hydrogen, lower alkyl, lower heteroalkyl, aryl, heteroaryl, -(alkyl)aryl, -(alkyl)heteroaryl or acyl, or $R^{Y2}$ and $R^{Y3}$ taken together with the nitrogen atom to which they are attached form a 5-6 membered heterocyclic ring.

In certain embodiments, compounds of subgroup XVIII have the following structure:

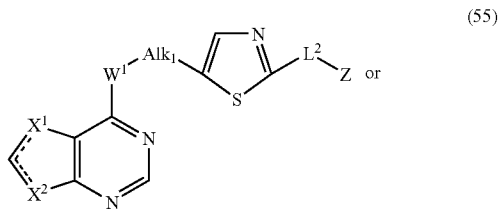

(55)

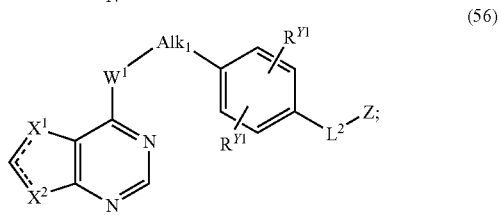

(56)

wherein $W^1$ is O or $NR^{W1}$, where $R^{W1}$ is hydrogen, lower alkyl, $C_{3-6}$cycloalkyl, lower heteroalkyl, heterocyclyl, aryl, heteroaryl, -(alkyl)aryl, -(alkyl)heteroaryl or acyl; and $Alk_1$ is a $C_{1-6}$alkylene or $C_{2-6}$alkenylene moiety; and each occurrence of $R^{Y1}$ is independently hydrogen, halogen or lower alkyl.

In certain embodiments, compounds of subgroup XVIII have the following structure:

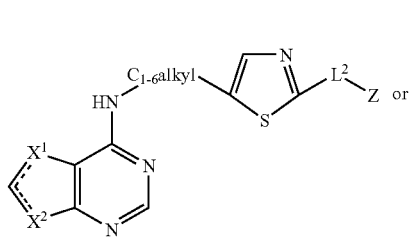 (57)

or

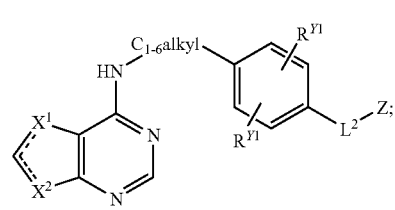 (58)

wherein L² is NH, —NHC(=O)—, —NHC(=O)O—, —NHC(=O)NH—, —NHC(=O)NHCH₂—, or —CH₂C(=O)NH—.

In certain embodiments for compounds as described in subgroups I-XVII above, R¹ is hydrogen.

In certain embodiments, for compounds as described in subgroups I-XVIII above, $R^{W1}$ together with a carbon atom present on $Alk_1$ forms an optionally substituted 5- to 6-membered heterocyclic ring.

In certain embodiments, for compounds as described in subgroups I-XIII and XVII-XVIII above, Z is a branched alkyl, alkenyl, alkynyl, heteroalkyl or heteroalkenyl moiety. In certain exemplary embodiments, Z has one of the following structures:

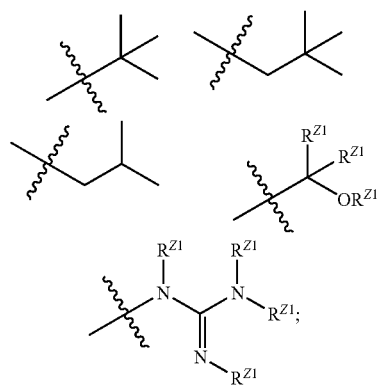

wherein each occurrence of $R^{Z1}$ is independently hydrogen, lower alkyl, lower alkenyl, aryl, heteroaryl or acyl. In certain embodiments, Z has one of the following structures:

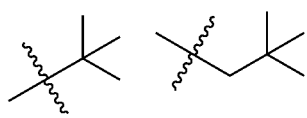

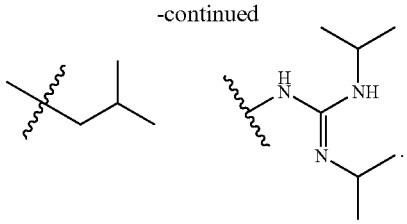

In certain embodiments, for compounds as described in subgroups I-XIII and XVII-XVIII above, Z is a cycloalkyl, cycloalkenyl, heterocyclyl, aryl or heteroaryl moiety. In certain exemplary embodiments, Z has one of the following structures:

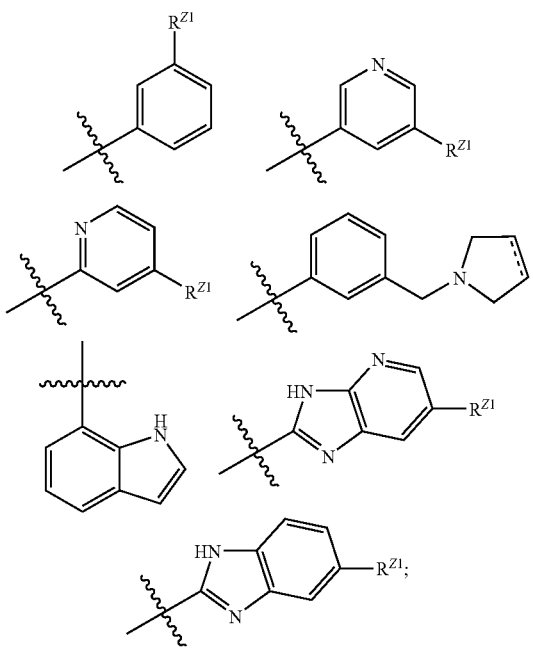

wherein $R^{Z1}$ is Cl, F, methyl or CF₃.

In certain embodiments, for compounds as described in subgroups I, IV-VI and XVII-XVIII above, -L²—Z together represent a moiety having one of the following structures:

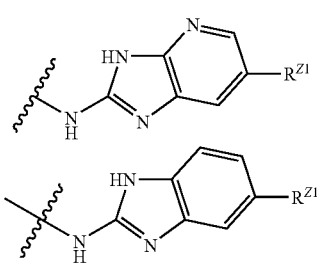

wherein $R^{Z1}$ is Cl, F, methyl or CF₃.

It will also be appreciated that for each of the subgroups I-XVIII described above, a variety of other subclasses are of special interest, including, but not limited to those classes described above i)- cxvi) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Synthetic Overview:

The practitioner has a well-established literature of thienopyrimidine chemistry to draw upon, in combination with the information contained herein, for guidance on synthetic strategies, protecting groups, and other materials and methods useful for the synthesis of the compounds of this invention, including compounds containing the various $R^1$ and $R^2$ substituents and $L^1$, $L^2$, Y and Z moieties.

The various patent documents and other references cited herein provide helpful background information on preparing compounds similar to the inventive compounds described herein or relevant intermediates. Certain cited patent documents also contain information on formulation, uses, and administration of such compounds which may be of interest. For example, guidance may be found in U.S. Pat. Nos. 6,169,091; 5,227,387; 5,654,307 and 5,859,020; European Patent Application No.: EP 452002 and International Application Nos.: WO 97/09316, WO 01/32632 and WO 03/64428. Although U.S. Pat. No. 6,541,481 does not specifically disclose thienopyrimidines, the synthetic guidance provided therein may be adapted to generate compounds of the invention.

Moreover, the practitioner is directed to the specific guidance and examples provided in this document relating to various exemplary compounds and intermediates thereof.

As described above, the present invention provides novel compounds, specifically compounds having the following general structure:

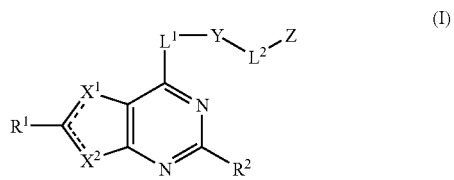

and pharmaceutically acceptable derivatives thereof;

wherein $R^1$, $R^2$, $X^1$, $X^2$, $L^1$, $L^2$, Y and Z are as defined in classes and subclasses herein.

It will be appreciated that for compounds as generally described above, certain classes of compounds are of special interest. For example, one class of compounds of special interest includes thieno[3,2d]pyrimidines having the Formula ($I^A$):

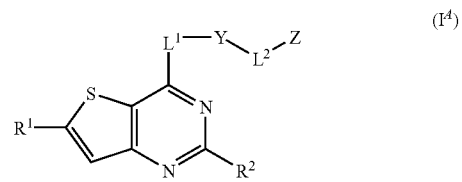

In yet another aspect of the invention, methods for producing intermediates useful for the preparation of compounds of formulae (I) and ($I^A$) are provided, embodiments of said methods being depicted generally in Scheme A:

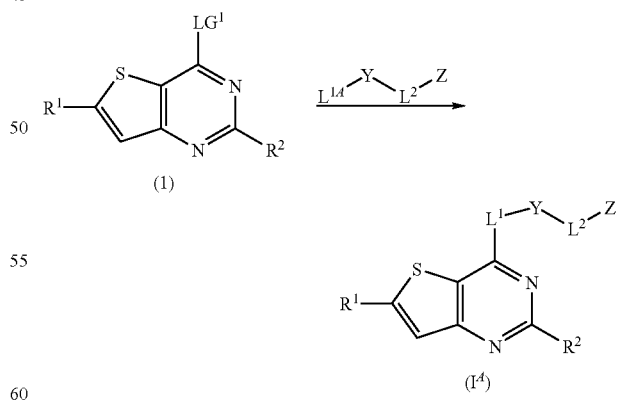

where $LG^1$ is a suitable leaving group and $L^{1A}$ is adapted to displace $LG^1$ upon reaction with thieno[3,2d]pyrimidine (1).

In other embodiments, one class of compounds of special interest includes thieno[2,3d]pyrimidines having the Formula ($I^B$):

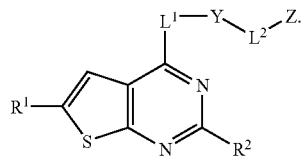

(I^B)

In yet another aspect of the invention, methods for producing intermediates useful for the preparation of compounds of formulae (I) and (I^B) are provided, embodiments of said methods being depicted generally in Scheme B:

Scheme B

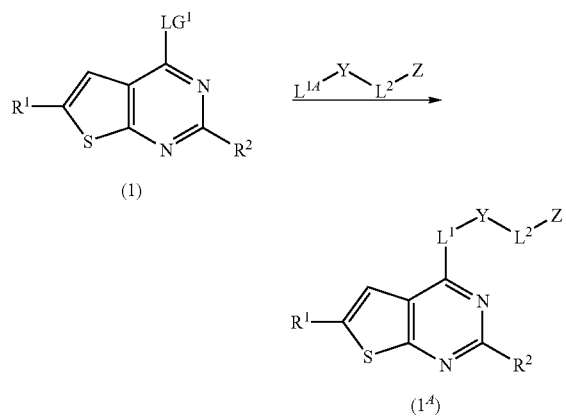

where $LG^1$ is a suitable leaving group and $L^{1A}$ is adapted to displace $LG^1$ upon reaction with thieno[2,3d]pyrimidine (2).

Numerous suitable prodrug moieties, and information concerning their selection, synthesis and use are well known in the art. Examples of prodrug moieties of interest include, among others, prodrug moieties that can be attached to primary or secondary amine-containing functionalities. For instance, prodrug moieties of interest include those that can be attached to group —NH$_2$. Examples of such prodrug moieties include the following:

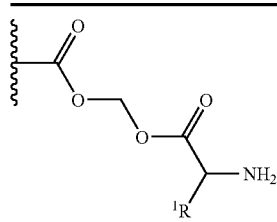

$R^1$ = all natural, unnatural amino acids

For the synthesis of the prodrug groups, see Borchardt, R. T. et. al., J. Org. Chem. 1997, 43, 3641-3652.

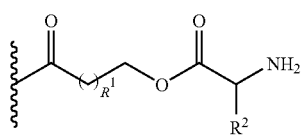

$R^1$ =C1-C4 alkyl, cycloalkyl, oxyalkyl, aminoalkyl, etc.
$R^2$ = all natural, unnatural amino acids For the synthesis of the prodrug groups, see Zhou, X-X. et. al., PCT WO 99/51613.

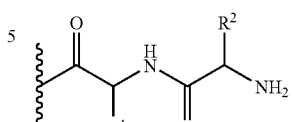

$R^1$, $R^2$ = all natural, unnatural amino acids

For the synthesis of the prodrug groups, see Ezra, A. et. al., J. Med. Chem. 2000, 43, 3641-3652.

The present invention encompasses any prodrug form of the compounds described herein. Although certain other exemplary prodrug moieties generated from the inventive compounds amino group are detailed herein, it will be appreciated that the present invention is not intended to be limited to these prodrug moieties; rather, a variety of additional prodrug moieties can be readily identified by a person skilled in the relevant art.

3) Pharmaceutical Compositions

As discussed above, the present invention provides compounds that are inhibitors of protein kinases (e.g., Aurora kinase), and thus the present compounds are useful for the treatment of diseases, disorders, and conditions including, but not limited to melanoma, leukemia, or cancers such as colon, breast, gastric, ovarian, cervical, renal, prostate, lymphoma, neuroblastoma, pancreatic and bladder cancer. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a Aurora kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

Research Uses

According to the present invention, the inventive compounds may be assayed in any of the available assays known in the art for identifying compounds having protease inhibitory activity. For example, the assay may be cellular or non-cellular, in vivo or in vitro, high- or low-throughput format, etc.

In certain exemplary embodiments, compounds of this invention were assayed for their ability to inhibit protein kinases, more specifically Aurora.

Thus, in one aspect, compounds of this invention which are of particular interest include those which:

are inhibitors of protein kinases;

exhibit the ability to inhibit Aurora kinase;

are useful for treating mammals (e.g., humans) or animals suffering from an Aurora-mediated disease or condition, and for helping to prevent or delay the onset of such a disease/condition;

exhibit a favorable therapeutic profile (e.g., safety, efficacy, and stability).

In certain embodiments, compounds of the invention are Aurora kinase inhibitors. In certain exemplary embodiments, inventive compounds are Aurora-A inhibitors. In certain exemplary embodiments, inventive compounds have $^{Cell}IC_{50}$ values $\leq 100$ μM. In certain other embodiments, inventive compounds have $^{Cell}IC_{50}$ values $\leq 75$ μM. In certain other embodiments, inventive compounds have $^{Cell}IC_{50}$ values $\leq 50$ μM. In certain other embodiments, inventive compounds have $^{Cell}IC_{50}$ values $\leq 25$ μM. In certain other embodiments, inventive compounds have $^{Cell}IC_{50}$ values $\leq 10$ μM. In certain other embodiments, inventive compounds have $^{Cell}IC_{50}$ values $\leq 7.5$ μM. In certain other embodiments, inventive compounds have $^{Cell}IC_{50}$ values $\leq 5$ μM. In certain other embodiments, inventive compounds have $^{Cell}IC_{50}$ values $\leq 2.5$ μM. In certain other embodiments, inventive compounds have $^{Cell}IC_{50}$ values $\leq 1$ μM. In certain other embodiments, inventive compounds have $^{Cell}IC_{50}$ values $\leq 800$ nM. In certain other embodiments, inventive compounds have $^{Cell}IC_{50}$ values $\leq 600$ nM. In certain other embodiments, inventive compounds have Cell $IC_{50}$ values $\leq 500$ nM. In certain other embodiments, inventive compounds have $^{Cell}IC_{50}$ values $\leq 300$ nM. In certain other embodiments, inventive compounds have $^{Cell}IC_{50}$ values $\leq 200$ nM. In certain other embodiments, inventive compounds have $^{Cell}IC_{50}$ values $\leq 100$ nM.

In yet another aspect, a method for the treatment or lessening the severity of an Aurora-mediated disease or condition is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of an Aurora-mediated disease or condition. The compounds and compositions, according to the method of the present invention, may be administered using any amount and any route of administration effective for treating or lessening the severity of an Aurora-mediated disease or condition. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are Aurora kinase inhibitors, and thus, without wishing to be bound by any particular theory, the compounds and compositions are particularly useful for treating or lessening the severity of a disease, condition, or disorder where activation of Aurora kinase is implicated in the disease, condition, or disorder. When activation of Aurora kinase is implicated in a particular disease, condition, or disorder, the disease, condition, or disorder may also be referred to as "Aurora-mediated disease" or disease symptom. Accordingly, in another aspect, the present invention provides a method for treating or lessening the severity of a disease, condition, or disorder where activation of Aurora kinase is implicated in the disease state.

The activity of a compound utilized in this invention as an Aurora kinase inhibitor, may be assayed in vitro, in vivo or in a cell line. In vitro assays include assays that determine inhibition of either the phosphorylation activity or ATPase activity of activated Aurora A, B and/or C. Alternate in vitro assays quantitate the ability of the inhibitor to bind to Aurora A, B and/or C. Inhibitor binding may be measured by radiolabelling the inhibitor prior to binding, isolating the inhibitor/Aurora A, B and/or C, complex and determining the amount of radiolabel bound. Alternatively, inhibitor binding may be determined by running a competition experiment where new inhibitors are incubated with Aurora A, B and/or C bound to known radioligands.

The term "measurably inhibit", as used herein means a measurable change in Aurora A, B and/or C activity between a sample comprising said composition and a Aurora A, B and/or C kinase and an equivalent sample comprising Aurora A, B and/or C kinase in the absence of said composition.

The term "Aurora-mediated disease" or "Aurora-mediated condition", as used herein, means any disease or other deleterious condition in which Aurora is known to play a role. The terms "Aurora-mediated disease" or "Aurora-mediated condition" also mean those diseases or conditions that are alleviated by treatment with an Aurora inhibitor. Such conditions include, without limitation, colon, breast, stomach, and ovarian cancer. The term "Aurora-mediated disease", as used herein, means any disease or other deleterious condition or disease in which Aurora is known to play a role. Such diseases or conditions include, without limitation, cancers such as colon and breast cancer.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, other therapies, chemotherapeutic agents or other anti-proliferative agents may be combined with the compounds of this invention to treat proliferative diseases and cancer. Examples of therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe—See Appendix).

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting Aurora A, B and/or C activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Aurora A, B and/or C kinase activity in a biological sample is useful for a variety of purposes that are known to one of skill in the art. Examples of such purposes include, but are not limited to, blood transfusion, organ-transplantation, biological specimen storage, and biological assays.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

Example 1

This example describes the synthesis of

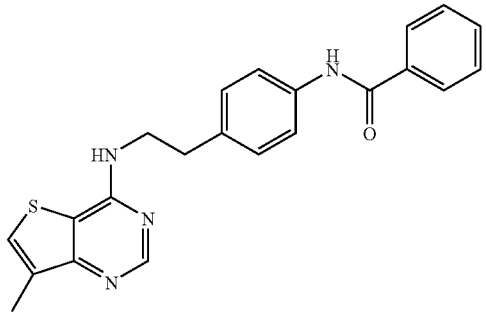

Step 1: A solution of [2-(4-amino-phenyl)-ethyl]-carbamic acid tert-butyl ester (compound 1.1; 1.0 mmol, prepared according to the procedure of Hah, J. M. et. al *J. Med. Chem* 46, 2003, 1661) and triethylamine ("TEA"; 3.0 equivalents) in anhydrous tetrahydrofuran ("THF"; 5.0 mL) is treated with the dropwise addition of benzoyl chloride (1.1 equivalents) at 0° C. After completion of the reaction, the mixture is partitioned between water and diethyl ether. The organic layer is separated, washed with 1.0 N HCl, saturated sodium bicarbonate, brine and dried. Purification by flash column chromatography on silica gel provides [2-(4-benzoylamino-phenyl)-ethyl]-carbamic acid tert-butyl ester (compound 1.2).

Step 2: Compound 1.2 (1.0 mmol), is treated with anhydrous 4.0 N HCl in dioxane (25 mL) at 0° C., stirred at room temperature for 2 hours and concentrated to dryness under reduced pressure. The crude amine salt, 4-chloro-7-methylthieno[3,2-d]pyrimidine (1.0 equiv.) and N,N-diisopropylethylamine. ("DIEA"; 2.5 equivalents) is then heated in n-butanol (10 mL) at 135° C. for 2 hours. The reaction mixture is cooled and then partitioned between dichloromethane and water. The organic layer is separated, washed with brine, dried and concentrated under reduced pressure. The titled compound is precipitated from ethyl acetate ("EtOAc") and methanol ("MeOH") with hexanes.

Example 2

This example describes the synthesis of

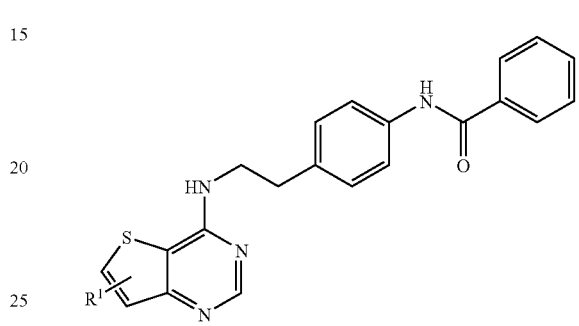

where $R^1$ is as described previously. These compounds are made according to the procedures of Example 1 except that

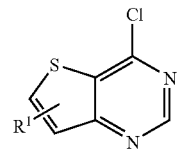

is used instead of 4-chloro-7-methylthieno[3,2-d]pyrimidine in step 2. Illustrative examples of $R^1$'s are found throughout this disclosure as well as in Table 1.

TABLE 1

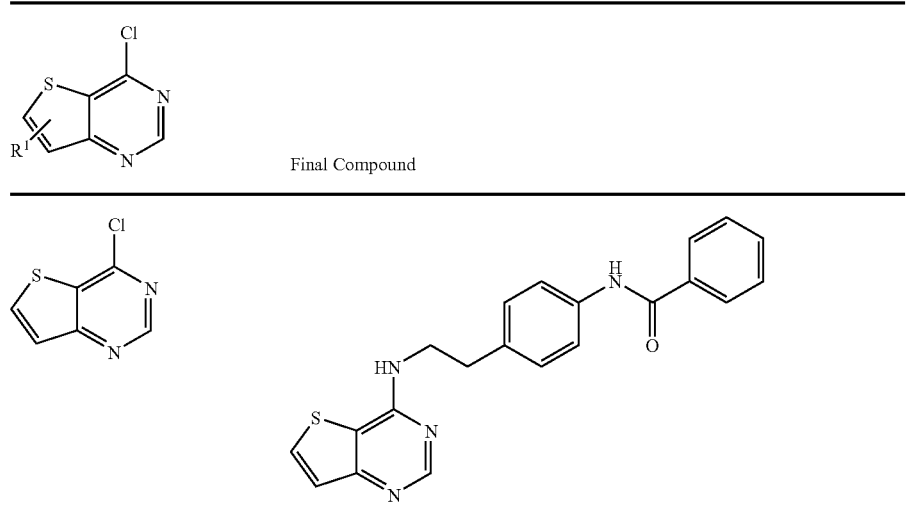

Final Compound

TABLE 1-continued
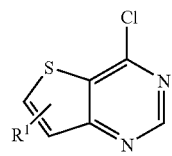
Final Compound
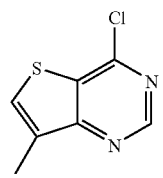 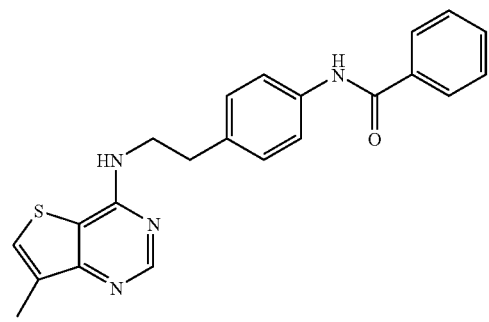
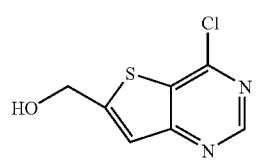 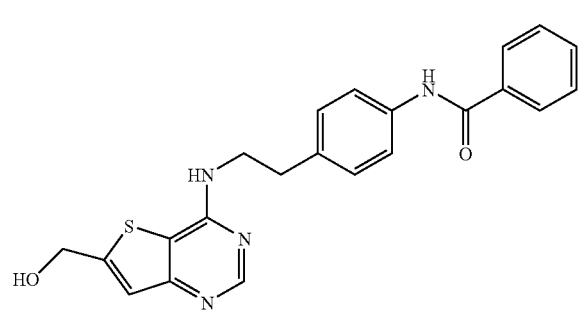
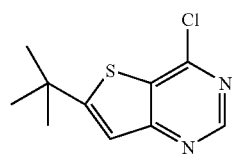 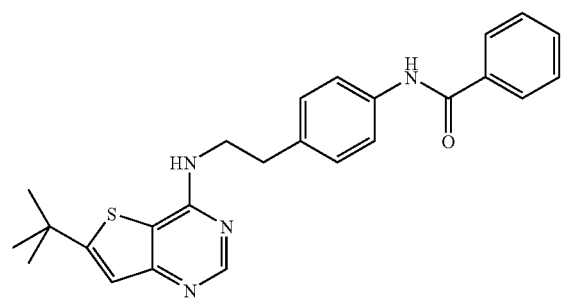
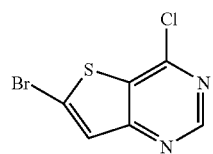 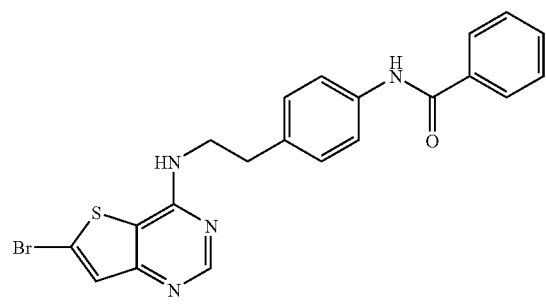

TABLE 1-continued

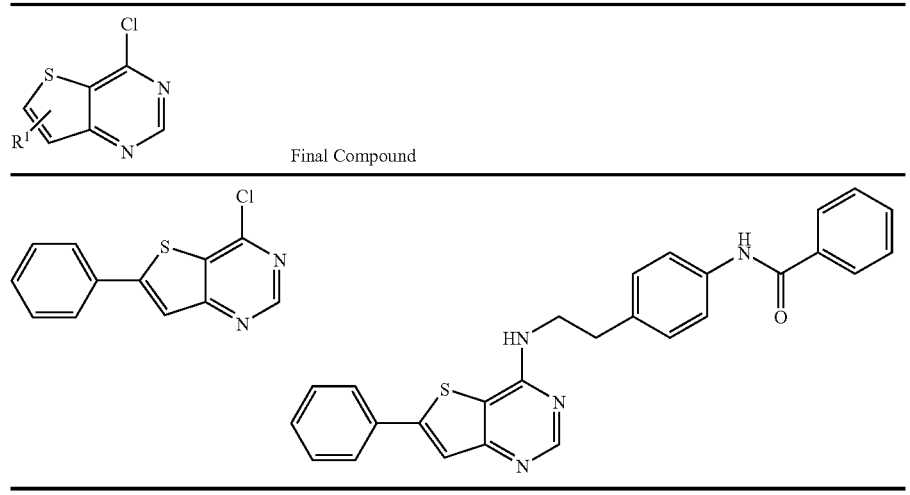

Final Compound

Example 3

This example describes the synthesis of

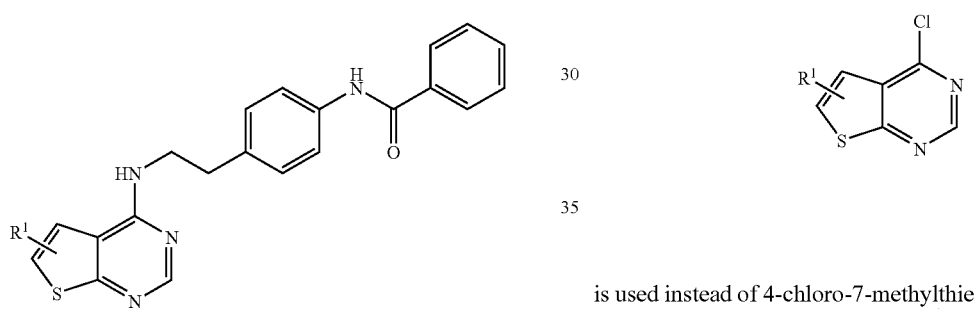

where R[1] is as described previously. These compounds are made according to the procedures of Example 1 except that is used instead of 4-chloro-7-methylthieno[3,2-d]pyrimidine in step 2. Illustrative examples of R[1]'s are found throughout this disclosure as well as in Table 2.

TABLE 2

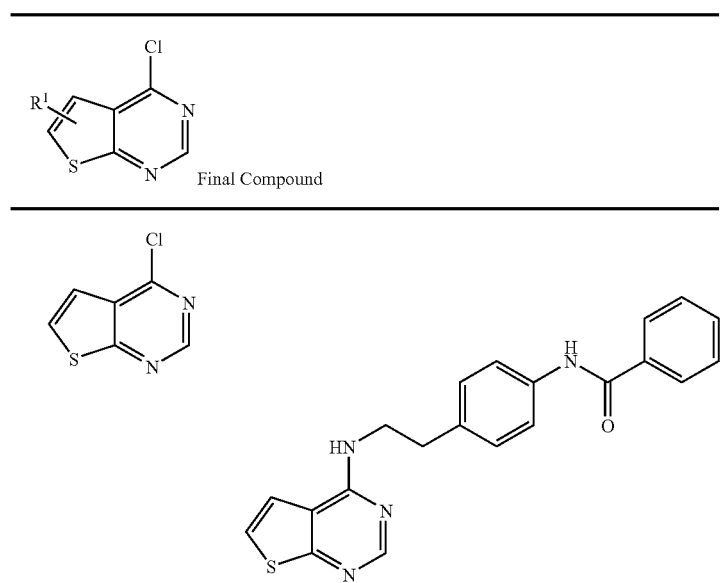

Final Compound

TABLE 2-continued

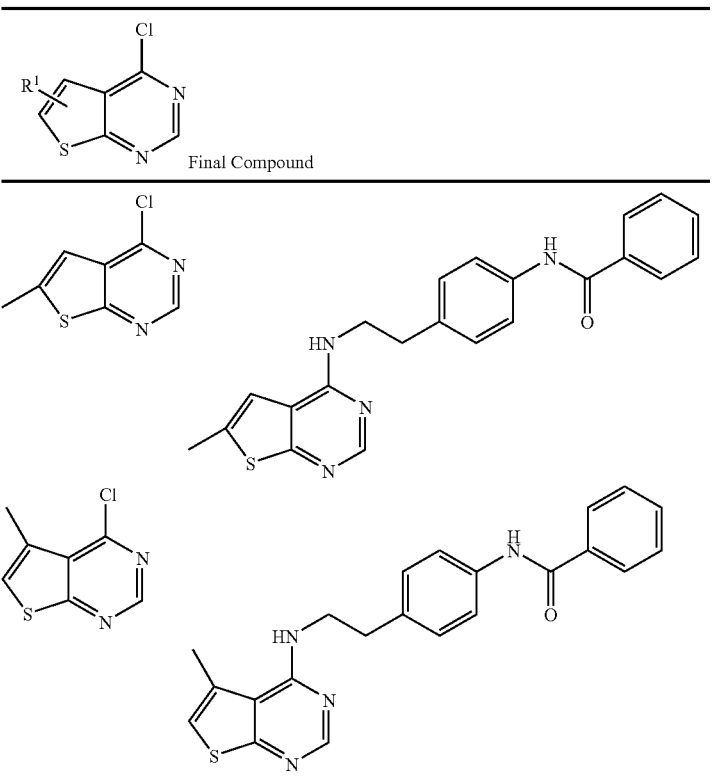

Final Compound

Example 4
This example describes the synthesis of

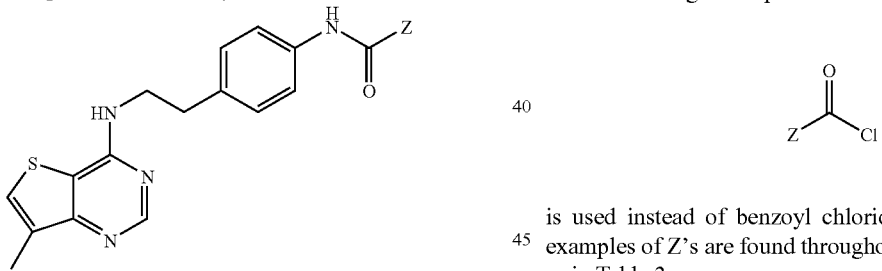

where Z is as described previously. These compounds are made according to the procedures of Example 1 except that $$Z-\overset{O}{\underset{}{C}}-Cl$$

is used instead of benzoyl chloride in step 1. Illustrative examples of Z's are found throughout this disclosure as well as in Table 3.

TABLE 3

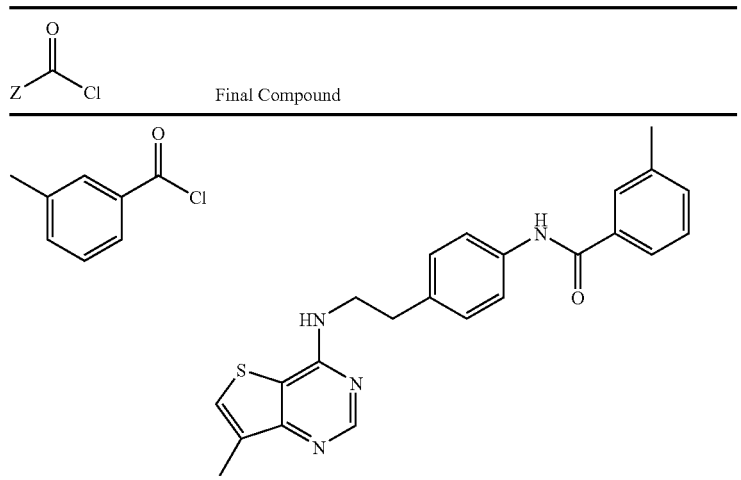

Final Compound

TABLE 3-continued
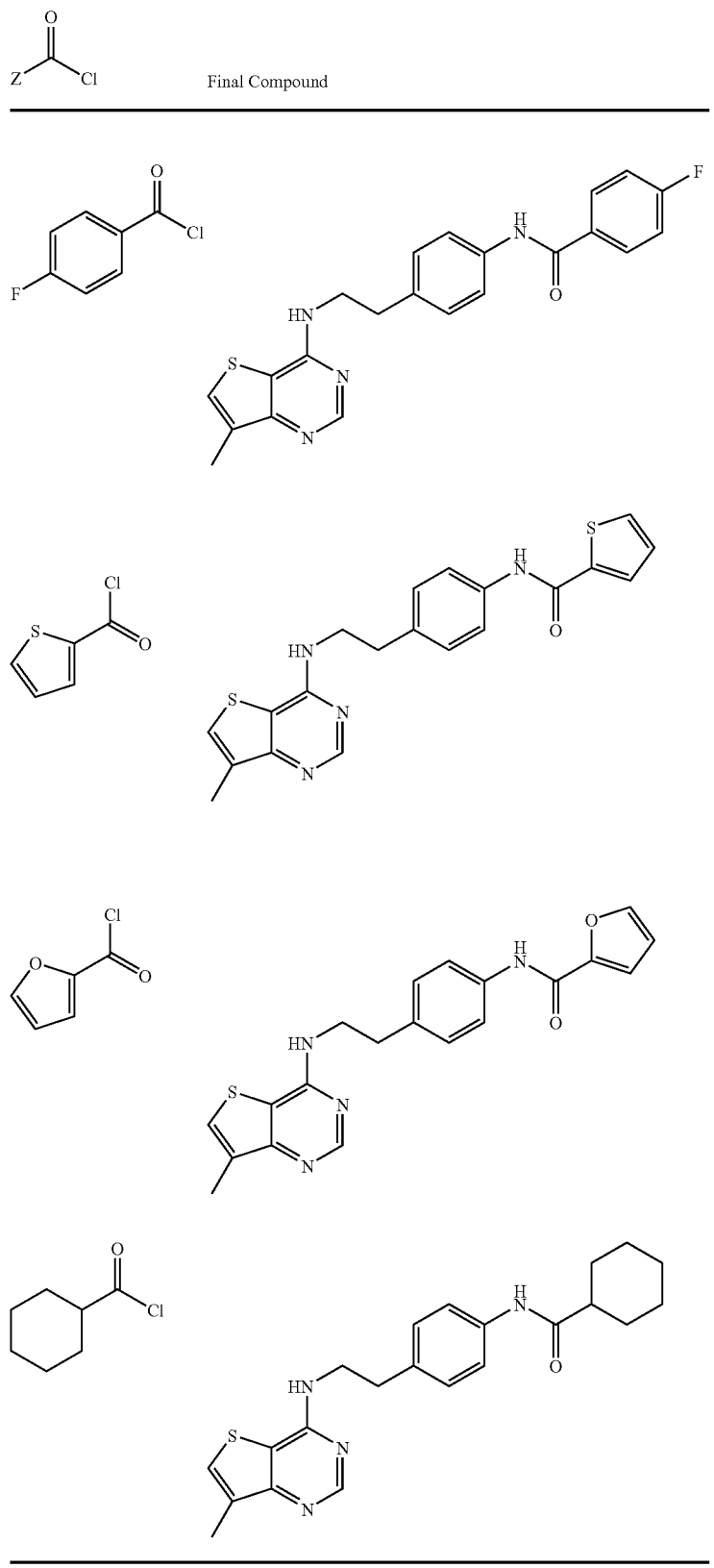

Example 5

This example describes the synthesis of

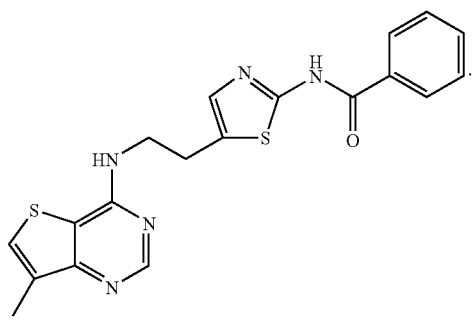

A solution of di-tert-butyl dicarbonate (0.5 equivalents) in anhydrous dioxane (3.0 mL) is added dropwise to a solution of 5-(2-amino-ethyl)-thiazol-2-ylamine (1.0 mmol, prepared according to the procedure of Eriks, J. C. et. al. *J. Med. Chem.* 35, 1992, 3239) in anhydrous dioxane (3.0 mL) at room temperature. After completion of the reaction, the solvents are removed under reduced pressure and the desired product, [2-(2-amino-thiazol-5-yl)-ethyl]-carbamic acid tert-butyl ester (compound 5.1), is purified by flash column chromatography on silica gel.

The titled compound is made according to the procedures of Example 1 except that compound 5.1 is used in step 1 instead of compound 1.1.

Example 6

This example describes the synthesis of

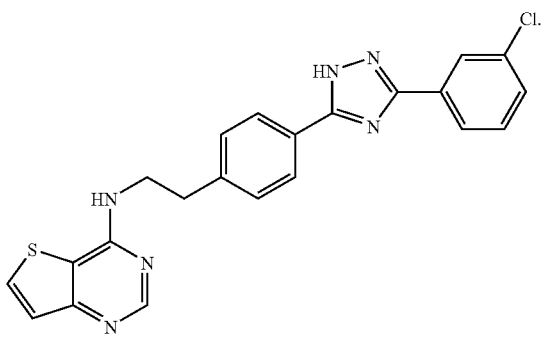

Step 1: 4-(2-Amino-ethyl)-benzonitrile (compound 6.1 (1.0 mmol), 4-chloro-thieno[3,2-d]pyrimidine (compound 6.2; 1.0 equiv.) and DIEA (2.5 equivalents) is heated in n-butanol (10 mL) at 135° C. for 2 hours. The reaction mixture is cooled and then partitioned between dichloromethane and water. The organic layer is separated, washed with brine, dried and concentrated under reduced pressure. The desired product, 4-[2-(thieno[3,2-d]pyrimidin-4-ylamino)-ethyl]-benzonitrile (compound 5.3), is precipitated from EtOAc with hexanes.

Step 2: Compound 6.3 is treated with sodium methoxide ("NaOMe") in MeOH according to a procedure found in Lipinski, C. A. et. al. *J. Med. Chem.* 28, 1985, 1628 to yield 4-[2-(thieno[3,2-d]pyrimidin-4-ylamino)-ethyl]-benzimidic acid methyl ester (compound 6.4).

Step 3: The titled compound is obtained by the reaction of compound 6.4 and 3-chloro-benzoic acid hydrazide by heating in MeOH.

Example 7

This example describes the synthesis of

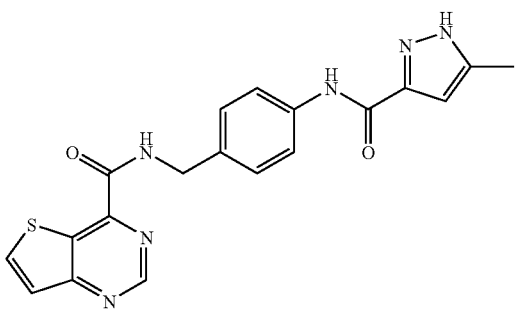

Step 1: Compound 6.2 is reacted with potassium cyanide according to a procedure in Miyashita, A. et. al. (*Heterocycles* 39, 1994, 345) to yield thieno[3,2-d]pyrimidine-4-carbonitrile (compound 7.1).

Step 2: A solution of compound 7.1 (1.0 mmol) in concentrated HCl (20 mL) is stirred at 80° C. overnight. The reaction mixture is then cooled and evaporated to dryness under reduced pressure. The residue is dissolved in a saturated lithium hydroxide ("LiOH"_ solution (pH 9) and evaporated to dryness under reduced pressure. The residue is then dissolved in 10% aqueous HCl (pH 2), evaporated and dried under vacuum to provide thieno[3,2-d]pyrimidine-4-carboxylic acid (compound 7.2).

Step 3: To a solution of compound 7.2 (1.0 mmol) and 4-nitrobenzyl amine (1.0 mmol) in dichloromethane (5.0 mL) is added TEA (3.0 equivalents) and O-(7-azabenzotriazol-1-yl)-N,N,N',N'-tetramethyluronium hexafluorophosphate ("HATU"; 1.1 equivalents). After completion of the reaction, the reaction is partitioned between EtOAc and water. The organic layer is separated, washed with 0.5 N HCl, saturated sodium bicarbonate, brine and dried. Purification by flash column chromatography on silica gel provides thieno[3,2-d]pyrimidine-4-carboxylic acid 4-nitro-benzylamide (compound 7.3).

Step 4: Compound 7.3 (1.0 mmol) and Pd/C (10 w/w %, 60 mg) in MeOH—H$_2$O (12 mL) is stirred under a hydrogen atmosphere at room temperature until the reaction is complete. The catalyst is removed by filtration and the filtrate is evaporated to dryness under reduced pressure to provide thieno[3,2-d]pyrimidine-4-carboxylic acid 4-amino-benzylamide (compound 7.4).

Step 5: To a solution of compound 7.4 (1.0 mmol) and 5-methyl-2H-pyrazole-3-carboxylic acid (1.0 mmol) in dichloromethane (5.0 mL) is added TEA (3.0 equiv.) and HATU (1.1 equiv.). After completion of the reaction, the reaction is partitioned between EtOAc and water. The organic layer is separated, washed with 0.5 N HCl, saturated sodium bicarbonate, brine and dried. Purification by flash column chromatography on silica gel provides the titled compound.

Example 8

This example describes the synthesis of

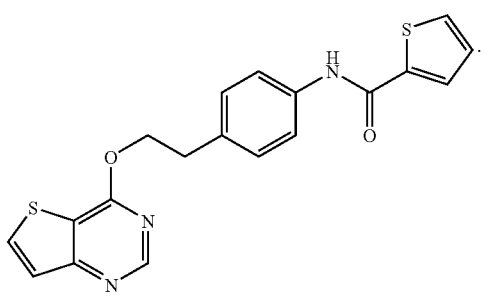

Step 1: 2-Thiophenecarbonyl chloride (1.1 equiv) is added dropwise to a solution of 2-(4-amino-phenyl)-ethanol (1.0 mmol) and TEA (3.0 equiv) in anhydrous THF (5.0 mL) at 0° C. After completion of the reaction, the reaction mixture is poured into water and extracted with dichloromethane. The organic layer is separated, washed with saturated sodium bicarbonate, brine and dried. The desired product, thiophene-2-carboxylic acid [4-(2-hydroxy-ethyl)-phenyl]-amide (compound 8.1) is purified by flash column chromatography on silica gel.

Step 2: To a solution of compound 8.1 (1.0 mmol) and compound 6.2 (1.0 equiv.) in anhydrous THF (8.0 mL) is added NaH (2.3 equiv.) at 0° C. The reaction is warmed to room temperature and stirred overnight. Saturated ammonium chloride is added and the reaction mixture is extracted with EtOAc. The organic layer is separated, washed with brine, dried and concentrated under reduced pressure. The titled compound is precipitated from EtOAc with hexanes.

Example 9

This example describes the synthesis of

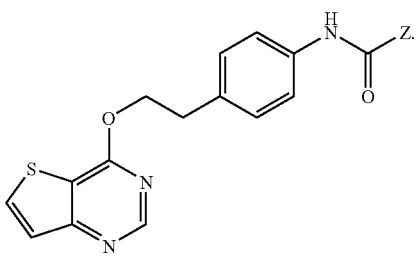

where Z is as described previously. These compounds are made according to the procedures of Example 8 except that

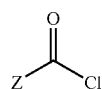

is used instead of 2-thiophenecarbonyl chloride in step 1. Illustrative examples of suitable Z are found throughout this disclosure as well as in Table 3.

Example 10

This example describes the synthesis of

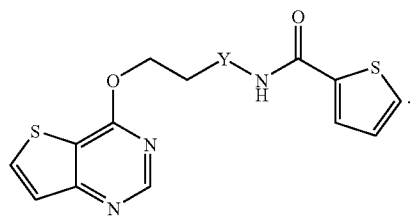

where Z is as described previously. These compounds are made according to the procedures of Example 8 except that HO—(CH$_2$)$_2$—Y—NH$_2$ is used instead of 2-(4-amino-phenyl)-ethanol in step 1. Illustrative examples of suitable Y's are found throughout this disclosure as well as in Table 4.

TABLE 4

| HO—(CH$_2$)$_2$—Y—NH$_2$ | Final Compound |
|---|---|
| ![oxazole aminoethanol] | ![oxazole thiophene amide product] |
| ![thiazole aminoethanol] | ![thiazole thiophene amide product] |
| ![aminopyridine ethanol] | ![pyridine thiophene amide product] |

Example 11

This example describes the synthesis of

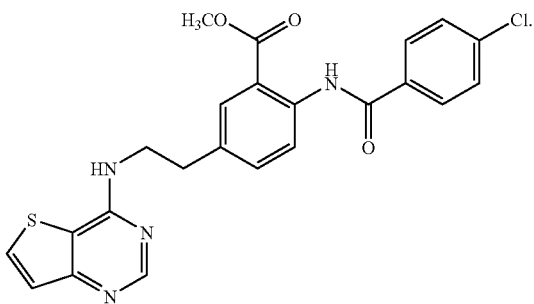

Step 1: To a solution of 2-amino-5-methyl benzoic acid (1.0 mmol) dissolved in 10% MeOH in toluene (2.5 mL) is added dropwise trimethylsilyl-diazomethane (2.0 M in hexanes, 0.75 mL). The reaction mixture is stirred at room temperature for 1 hour and the solvent is removed under reduced pressure. The resulting methyl ester is dissolved in dichloromethane (3.0 mL) and then 4-chlorobenzoyl chloride (1.0 equivalent) and DIEA (1.0 equivalent) is added sequentially. The reaction mixture is stirred for 3 hours and the solvent is evaporated. The yellow residue is diluted with EtOAc, washed with 1 M NaHSO$_4$, brine, dried, filtered and concentrated under reduced pressure to provide 2-(4-chloro-benzoylamino)-5-methyl-benzoic acid methyl ester (compound 11.1) which is used without purification in the next step.

Step 2: To a solution of compound 11.1 (1.0 mmol) in benzene (2.0 mL) is added N-bromosuccinimide (1 equivalent) and benzoyl peroxide (0.33 equivalent). The reaction mixture is refluxed overnight under N$_2$. After cooling to room temperature, the solution is diluted with EtOAc, washed with H$_2$O, brine, dried, filtered and concentrated under reduced pressure. The crude product is purified by flash column chromatography on silica gel to provide 5-bromomethyl-2-(4-chloro-benzoylamino)-benzoic acid methyl ester (compound 11.2).

Step 3: Potassium cyanide (1.0 equivalent) is added to a solution of compound 11.2 (1.0 mmol) in methyl sulfoxide ("DMSO"; 24 mL) and stirred for 2 hours at room temperature. The reaction mixture is diluted with EtOAc, washed with 1 M NaHSO$_4$, brine, filtered and evaporated under reduced pressure. The residue is purified by flash column chromatography on silica gel to provide the nitrile. To a solution of the nitrile (1.0 mmol) dissolved in ethanol (5.0 mL) is added 4.0 N HCl in dioxane (0.25 mL) and catalytic Pd/C. The reaction mixture is subjected to hydrogenolysis at 50 psi for 12 hours. The solution is filtered over a pad of celite followed by careful rinsing with ethanol. The combined organic solution is concentrated under reduced pressure to provide 5-(2-amino-ethyl)-2-(4-chloro-benzoylamino)-benzoic acid methyl ester (compound 11.3).

Step 4: Compound 11.3 (1.0 mmol), compound 6.2 (1.0 equivalent) and DIEA (2.5 equivalents) is heated in n-butanol (10 mL) at 135° C. for 2 hours. The reaction mixture is cooled and then partitioned between dichloromethane and water. The organic layer is separated, washed with brine, dried and concentrated under reduced pressure. The titled compound is precipitated from EtOAc with hexanes.

Example 12

This example describes the synthesis of

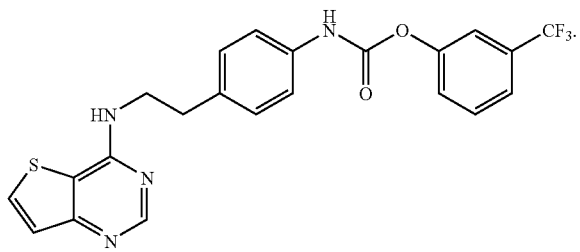

Step 1: A solution of 4-(2-amino-ethyl)-phenylamine (compound 12.1; 0.1 mmol.), compound 6.2 (1.0 equivalent) and DIEA (2.5 equivalents) was heated in n-butanol (2 mL) at 135° C. for 2 hours. The reaction mixture was cooled and partitioned between dichloromethane and water. The organic layer was separated, washed with brine, dried and concentrated under reduced pressure to give crude [2-(4-amino-phenyl)-ethyl]-thieno[3,2-d]pyrimidin-4-yl-amine (compound 12.2) which was used without purification for the next step.

Step 2: To a suspension of compound 12.2 (0.46 mmol) and TEA (2.5 equivalents) in anhydrous THF (3.0 mL) cooled to 0° C. was added 3-(trifluoromethyl)phenyl chloroformate (1.1 equivalents). The reaction was warmed to room temperature and after 45 minutes, water was added and the reaction extracted with EtOAc. The organic layer was separated, washed with brine, dried and concentrated under reduced pressure. Purification by reverse-phase HPLC (aqueous 0.1% trifluoroacetic acid ("TFA")/CH$_3$CN) provided the titled compound.

Example 13

This example describes the synthesis of

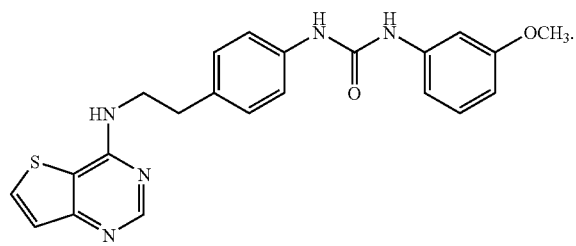

Step 1: 3-Methoxyphenyl isocyanate and compound 1.1 are reacted according to a procedure in Dhar, T. G. et. al. (*Bioorg. Med. Chem. Lett.* 13, 2003, 3557) to yield (2-{4-[3-(3-Methoxy-phenyl)-ureido]-phenyl}-ethyl)-carbamic acid tert-butyl ester (compound 13.1).

Step 2: Compound 13.1 (1.0 mmol) is treated with anhydrous 4.0 N HCl in dioxane (25 mL) at 0° C., stirred at room temperature for 2 hours and concentrated to dryness under reduced pressure. The crude amine salt, compound 6.2 (1.0 equivalent) and DIEA (2.5 equivalents) is then heated in n-butanol (10 mL) at 135° C. for 2 hours. The reaction mixture is cooled and then partitioned between dichloromethane and water. The organic layer is separated, washed with brine, dried and concentrated under reduced pressure. The titled compound is precipitated from EtOAc with hexanes.

Example 14

This example describes the synthesis of

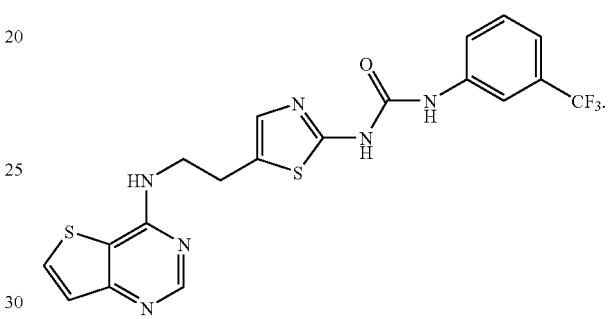

Step 1: [5-(2-Amino-ethyl)-thiazol-2-yl]-carbamic acid tert-butyl ester (compound 14.1; 20.5 mmol), compound 6.2 (0.94 equivalent) and DIEA (1.0 equivalent) was heated in N,N-dimethylformamide ("DMF"; 75 mL) at 90° C. for 1.5 hours. The reaction mixture was cooled and diluted with EtOAc and water. The organic layer was separated, washed with brine, dried, concentrated and purified by flash column chromatography on silica gel to provide {5-[2-(thieno[3,2-d]pyrimidin-4-ylamino)-ethyl]-thiazol-2-yl}-carbamic acid tert-butyl ester (compound 14.2) in 75% yield.

Step 2: To a solution of compound 14.2 (14.5 mmol) in 1,4-dioxane (30 mL) was added anhydrous HCl (20 mL of a 4 N solution in 1,4-dioxane) after stirring at room temperature for 2 hours the reaction was concentrated to dryness, diluted with water and the solution adjusted to pH 8 with saturated sodium bicarbonate. The slurry was extracted several times with EtOAc and the organic layers were combined, dried and concentrated to provide [2-(2-amino-thiazol-5-yl)-ethyl]-thieno[3,2-d]pyrimidin-4-yl-amine (compound 14.3) in 88% yield.

Step 3: To a suspension of compound 14.3 (10.8 mmol) in anhydrous benzene (75 mL) was added 3-trifluoromethylphenyl isocyanate (1.0 equivalent). The reaction mixture was heated at 90° C. for 1 hour, cooled and concentrated to give a solid that was washed with a mixture of dichloromethane and hexanes. The solid was treated with MeOH followed by the addition of 1 N HCl and water. The solution was then sonicated and lyophilized to give a solid that was washed with ethanol and dried under vacuum to provide the HCl salt of the titled compound in 86% yield. Anal. Calcd for $C_{19}H_{16}N_6OS_2F_3Cl$: C, 45.55; H, 3.22; N, 16.78. Found: C, 45.56; H, 3.27; N, 16.75.

Example 15

This example describes the synthesis of

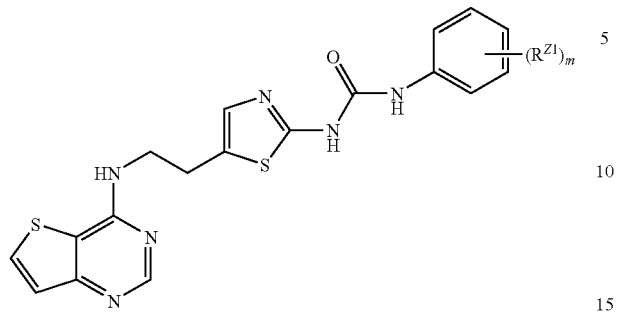

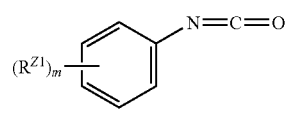

where $R^{Z1}$ and m are as described previously. These compounds are made according to the procedures of Example 14 except that ![structure]

is used instead of 3-trifluromethylphenyl isocyanate in step 3. Illustrative examples of suitable $R^{Z1}$'s are found throughout this disclosure as well as in Table 5.

TABLE 5

| (R^{Z1})_m—[phenyl]—N=C=O | Final Compound |
|---|---|
| 3-Cl-C6H4-N=C=O | thieno[3,2-d]pyrimidin-4-ylamino-ethyl-thiazol-2-yl urea with 3-chlorophenyl |
| C6H5-N=C=O | thieno[3,2-d]pyrimidin-4-ylamino-ethyl-thiazol-2-yl urea with phenyl |
| 3-CF3-4-F-C6H3-N=C=O | thieno[3,2-d]pyrimidin-4-ylamino-ethyl-thiazol-2-yl urea with 3-CF3-4-F-phenyl |
| 3-CF3-4-Cl-C6H3-N=C=O | thieno[3,2-d]pyrimidin-4-ylamino-ethyl-thiazol-2-yl urea with 3-CF3-4-Cl-phenyl |

TABLE 5-continued

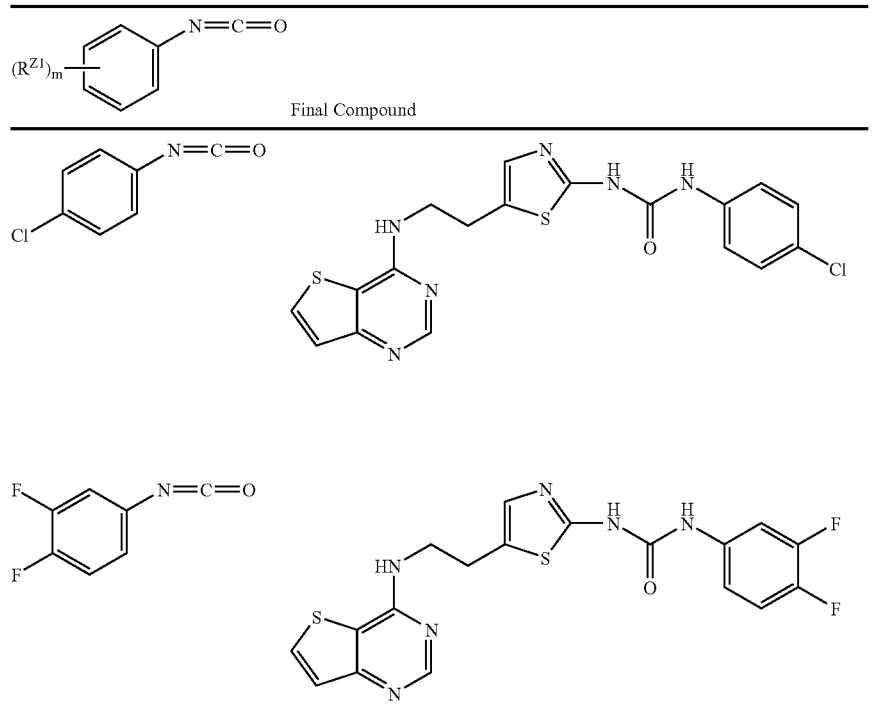

Example 16

This example describes an alternate synthesis of

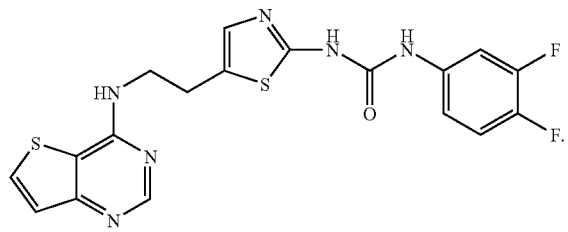

Step 1: To a suspension of compound 14.2 (23.7 mmol) in 1,4-dioxane (100 mL) was added HCl (70 mL of a 4.0 M in 1,4-dioxane) at 0° C. The reaction was allowed to warm to room temperature, stirred for 2 hours and concentrated to dryness to give a tan solid. The crude solid was suspended in THF (200 mL) and cooled to 0° C. Triethylamine (33 mL) was added followed by phenyl chloroformate (26.1 mmol). The reaction mixture was allowed to slowly warm to room temperature and stirred for 2 hours. Volatiles were removed under reduced pressure at room temperature, water was added and the solid collected by vacuum filtration. The solid was washed with ethyl ether and dried under vacuum to give {5-[2-(thieno[3,2-d]pyrimidin-4-ylamino)-ethyl]-thiazol-2-yl}-carbamic acid phenyl ester (compound 16.1) in 80% yield as a tan solid.

Step 2: To a suspension of compound 16.1 (0.63 mmol) in DMSO (3.5 mL) was added 3,4-difluoroaniline (0.63 mmol) and 4-dimethylamino)pyridine ("DMAP"; catalytic amount or 1.0 equivalent). The reaction was heated in an 80° C. oil bath for 30 minutes, diluted with EtOAc and washed with water, 2.0 N NaOH, water, brine, dried and concentrated to give a solid. The solid was dissolved in hot EtOAc/MeOH and then hexanes/ethyl ether was added to precipitate the titled compound as a tan powder in 81% yield.

Example 17

This example describes the synthesis of

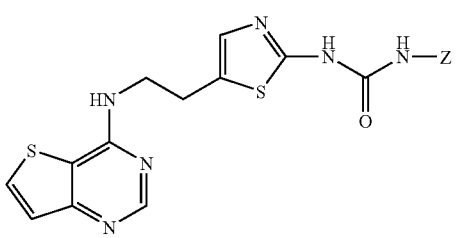

where Z is as described previously. These compounds are made according to Example 16 except that H₂NZ is used instead of 3,4-difluoroaniline in step 2. Illustrative examples of suitable Z's are found throughout this disclosure as well as in Table 6.

TABLE 6
| H$_2$NR | 1. Final Compound |
|---|---|
| 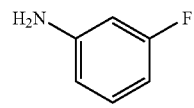 | 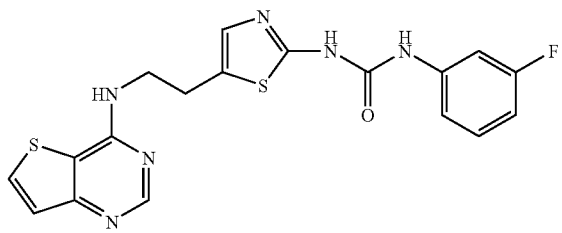 |
| 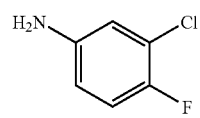 | 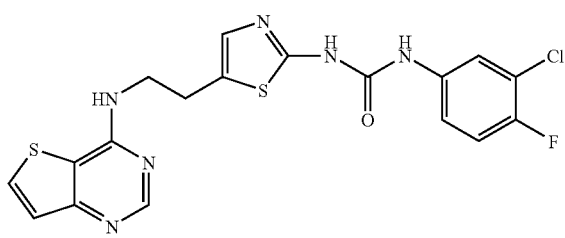 |
| 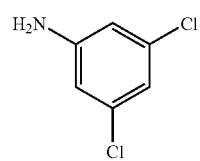 | 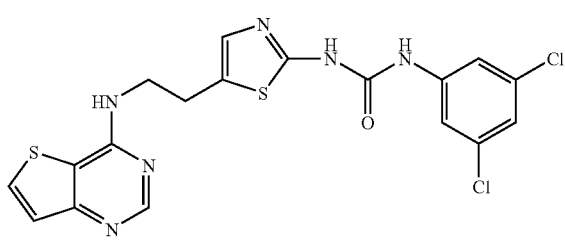 |
| 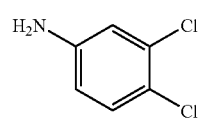 | 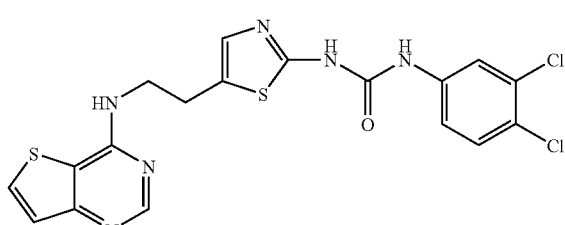 |
| 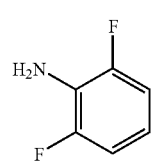 | 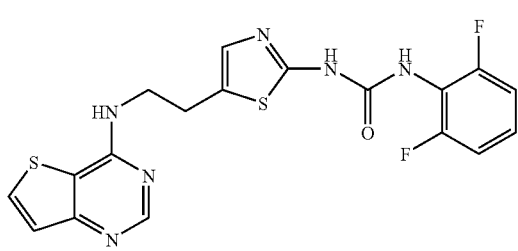 |
| 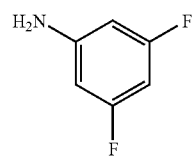 | 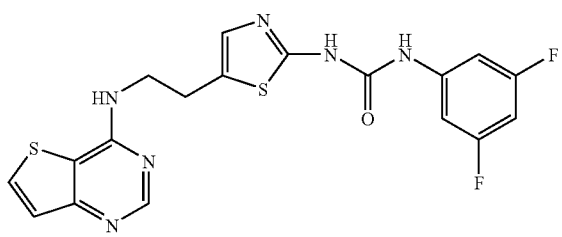 |

TABLE 6-continued
| H₂NR | 1. Final Compound |
|---|---|
| 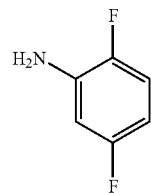 | 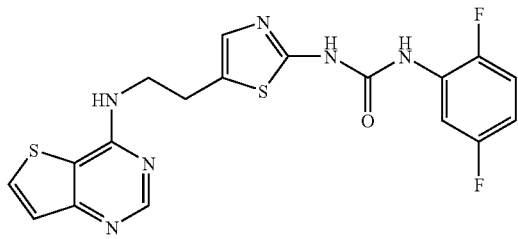 |
| 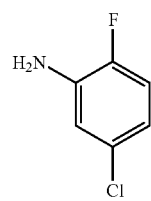 | 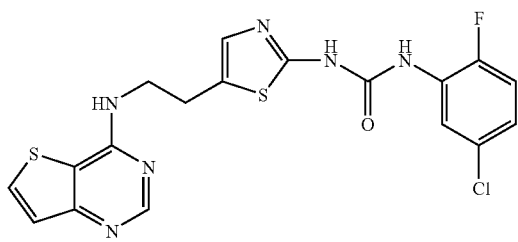 |
| 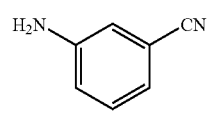 | 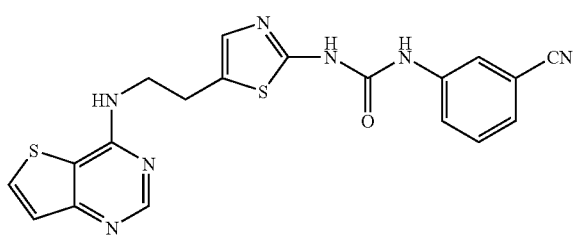 |
| 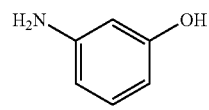 | 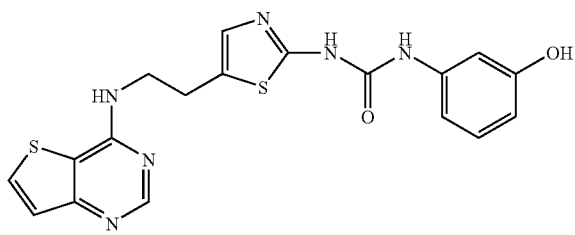 |
| 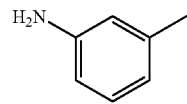 | 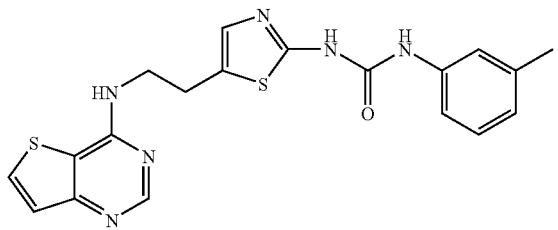 |
| 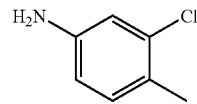 | 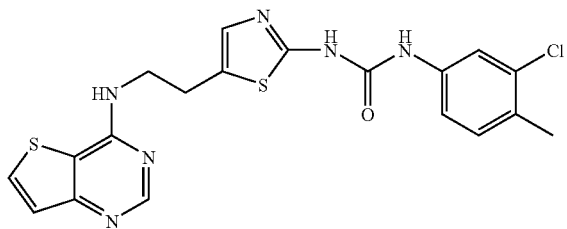 |

TABLE 6-continued
| H₂NR | 1. Final Compound |
|---|---|
| 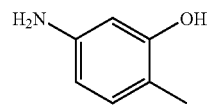 | 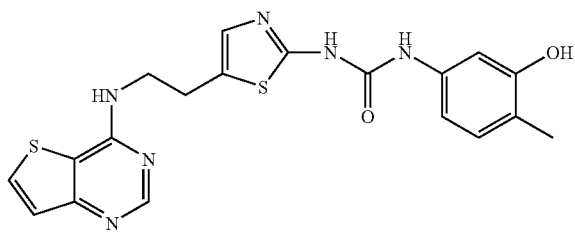 |
| 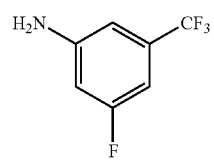 | 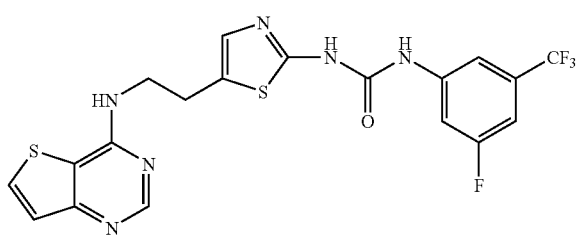 |
| 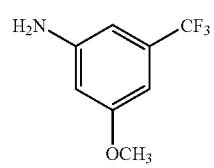 | 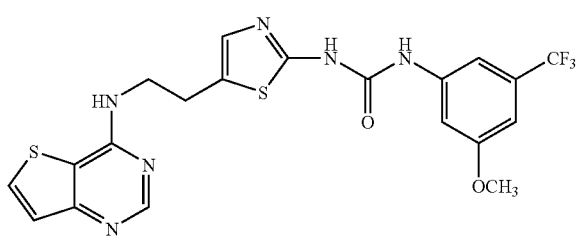 |
| 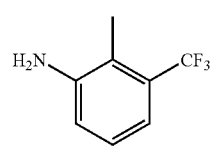 | 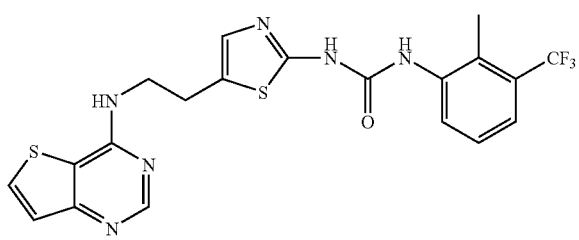 |
| 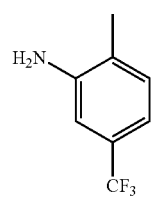 | 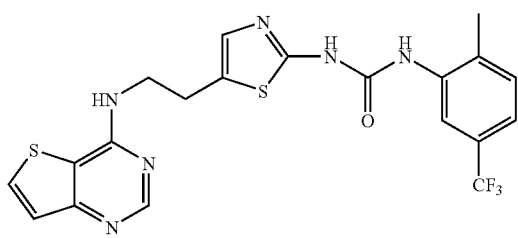 |
| 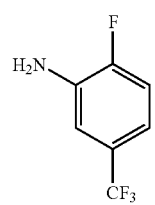 | 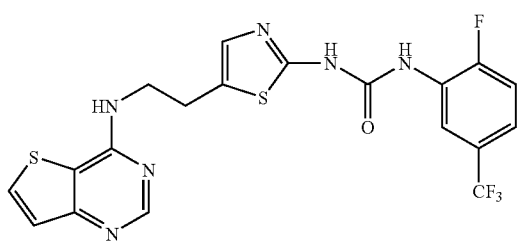 |

TABLE 6-continued
| H₂NR | 1. Final Compound |
|---|---|
| 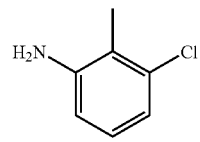 | 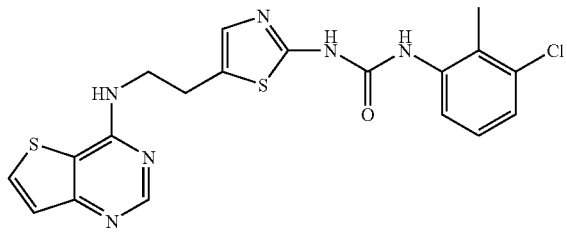 |
| 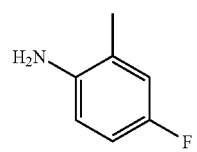 | 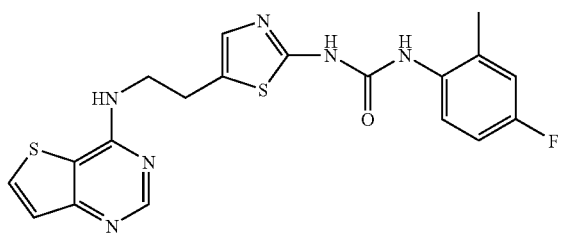 |
| 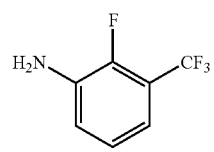 | 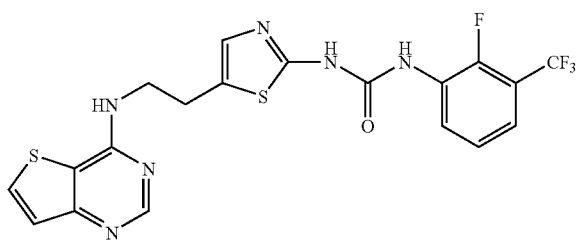 |
| 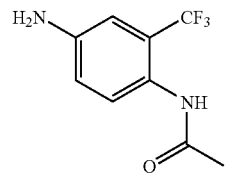 | 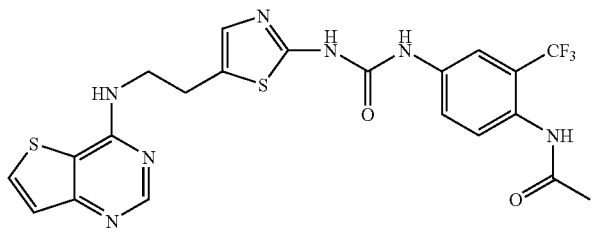 |
| 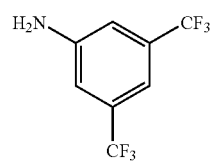 | 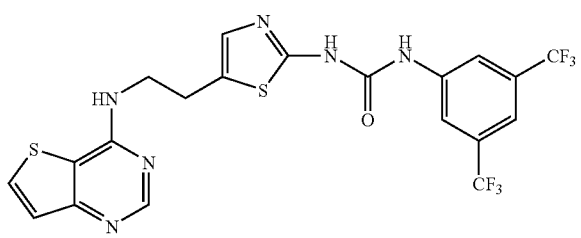 |
| 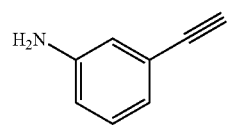 | 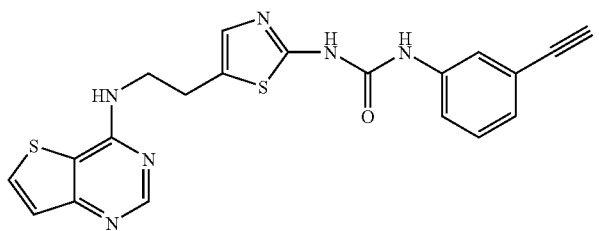 |

TABLE 6-continued
| H$_2$NR | 1. Final Compound |
|---|---|
| 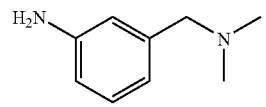 | 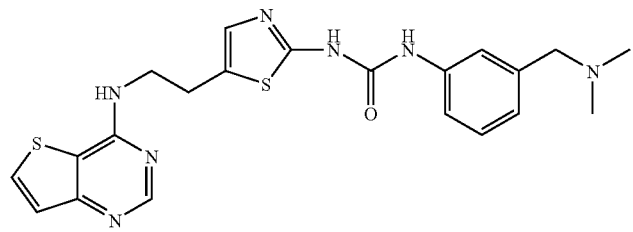 |
| 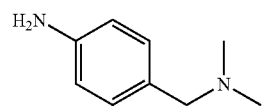 | 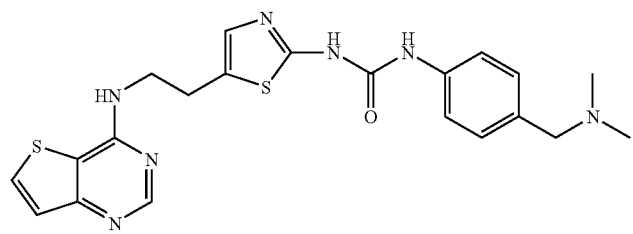 |
| 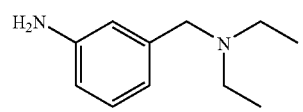 | 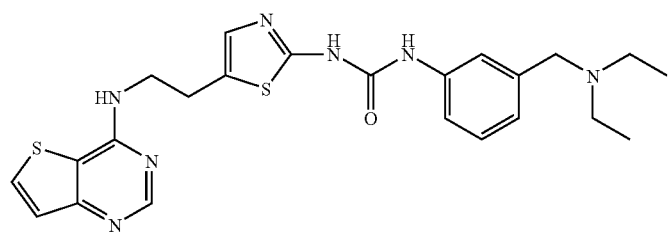 |
| 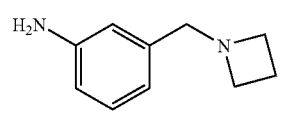 | 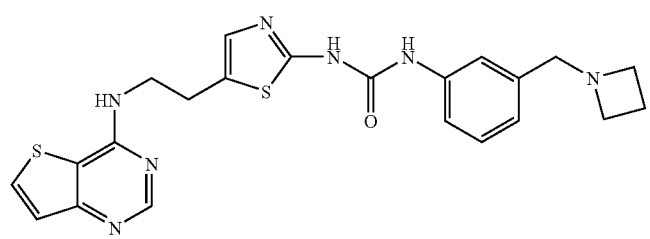 |
| 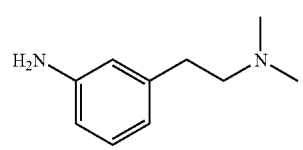 | 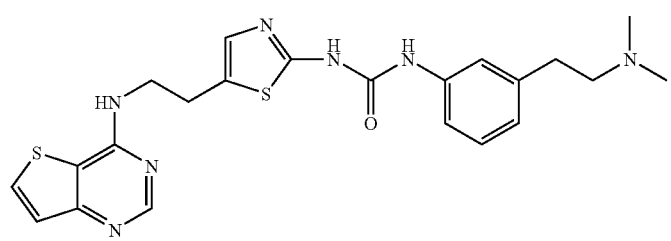 |
| 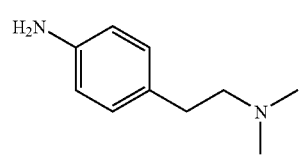 | 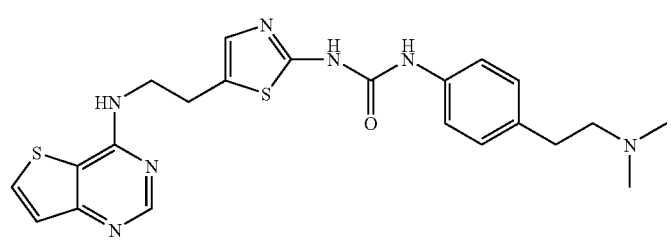 |

TABLE 6-continued
| H₂NR | 1. Final Compound |
|---|---|
| 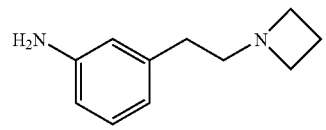 | 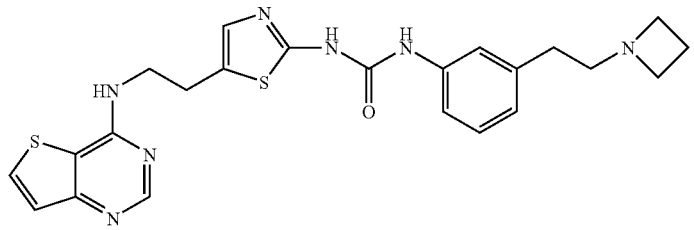 |
| 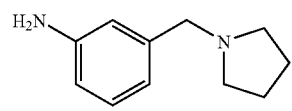 | 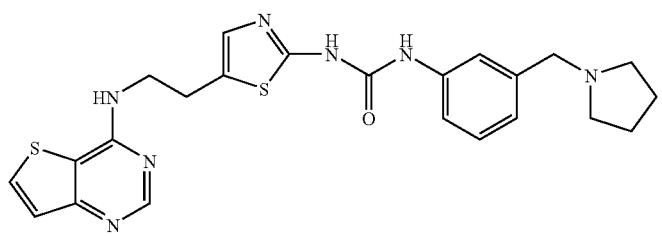 |
| 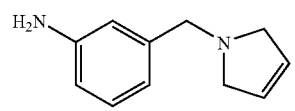 | 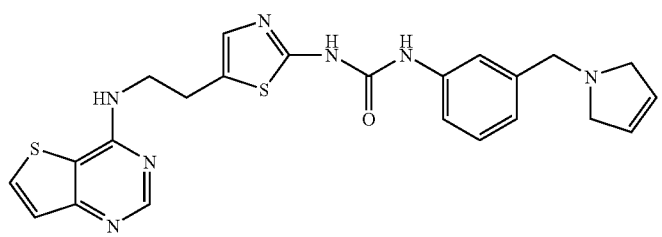 |
| 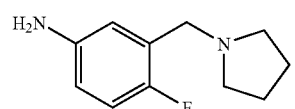 | 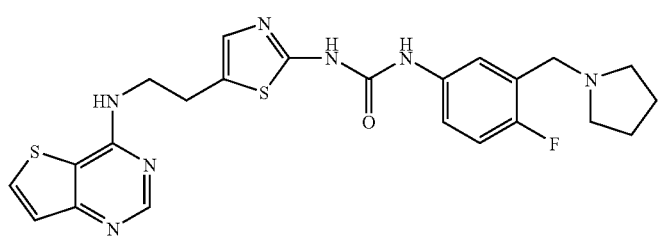 |
| 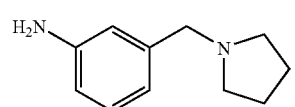 | 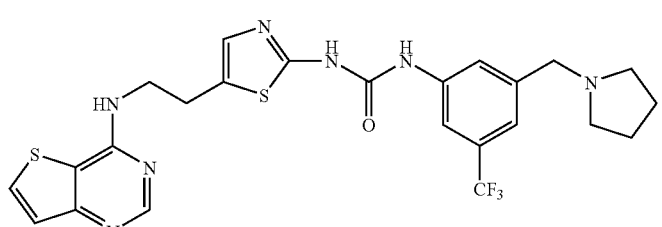 |
| 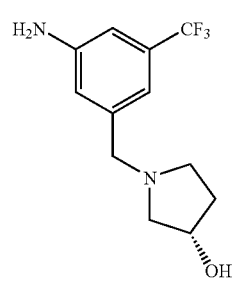 | 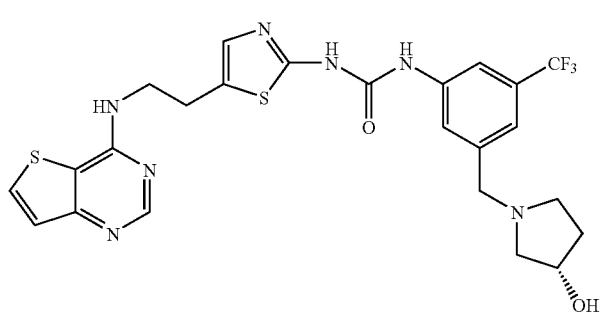 |

TABLE 6-continued

| H₂NR | 1. Final Compound |
|---|---|

TABLE 6-continued
| H$_2$NR | 1. Final Compound |
|---|---|
| 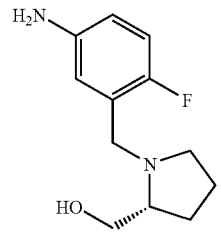 | 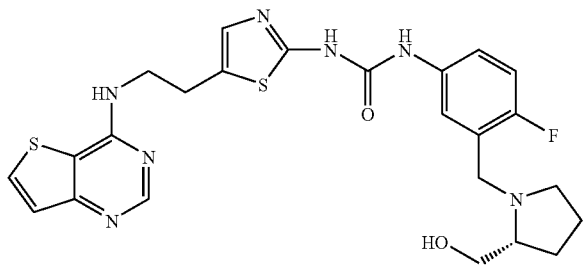 |
| 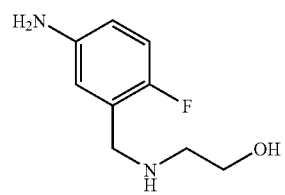 | 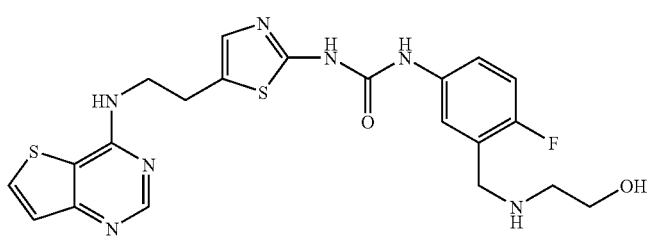 |
| 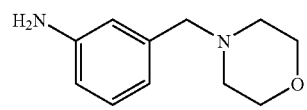 | 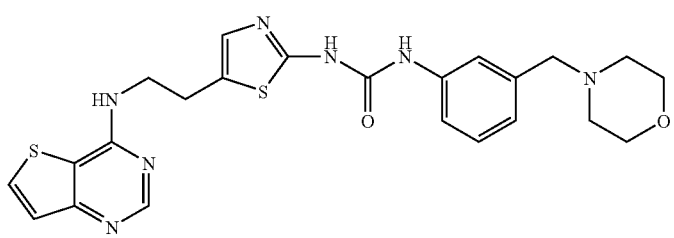 |
| 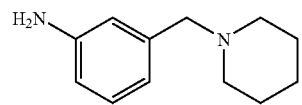 | 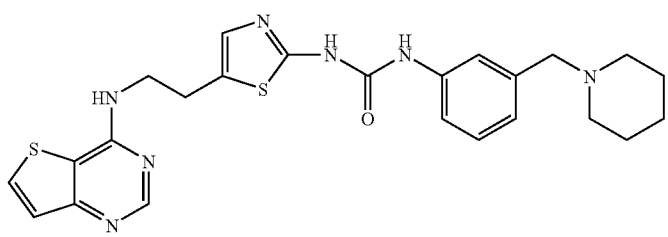 |
| 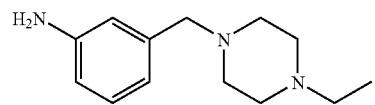 | 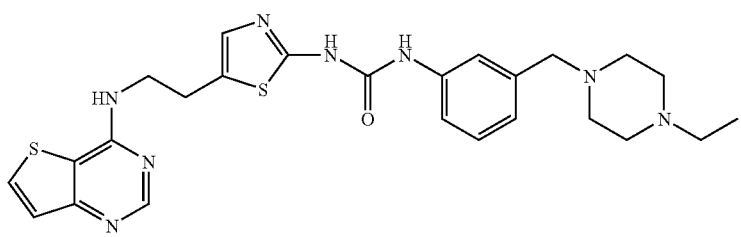 |
| 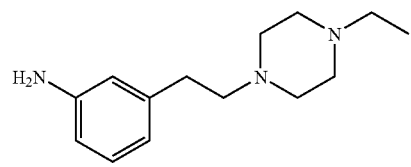 | 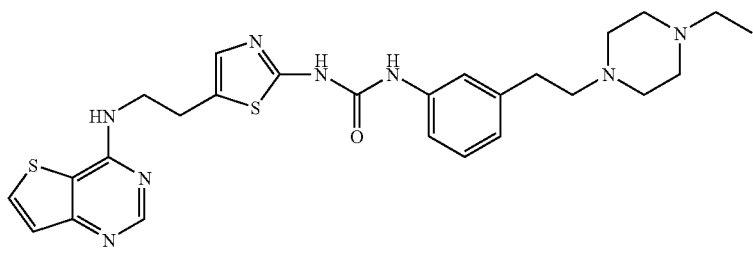 |

TABLE 6-continued
| H$_2$NR | 1. Final Compound |
|---|---|
| 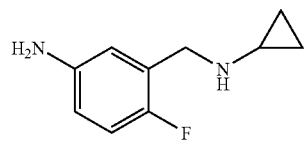 | 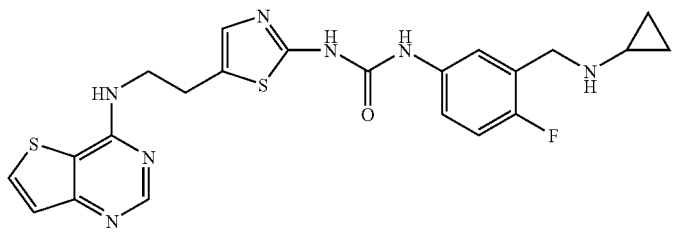 |
| 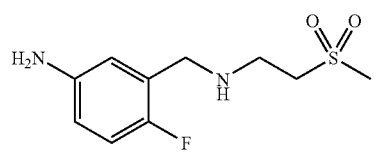 | 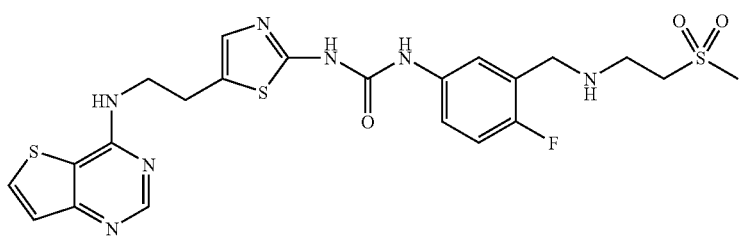 |
| 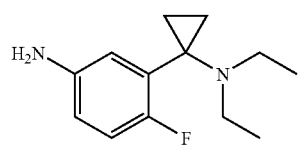 | 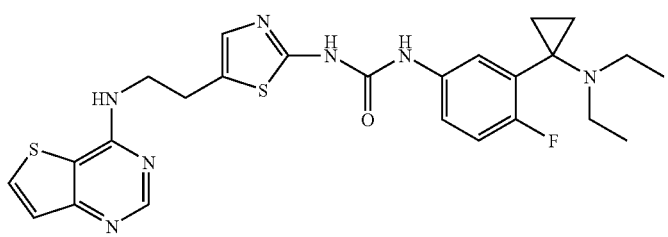 |
| 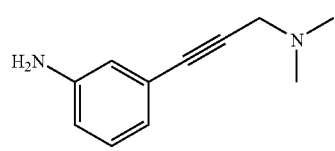 | 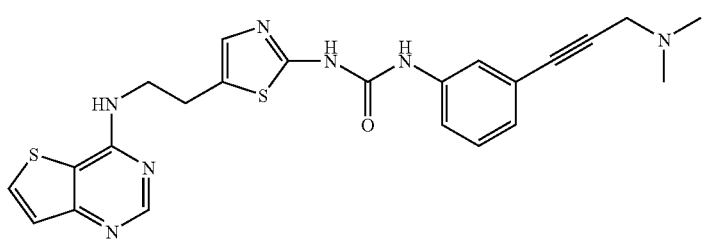 |
| 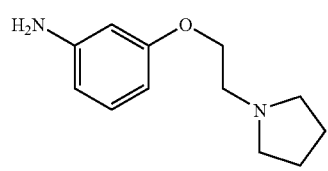 | 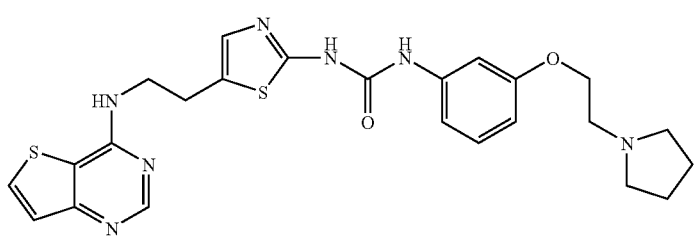 |
| 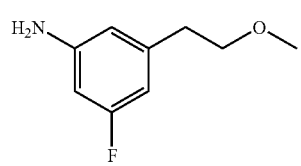 | 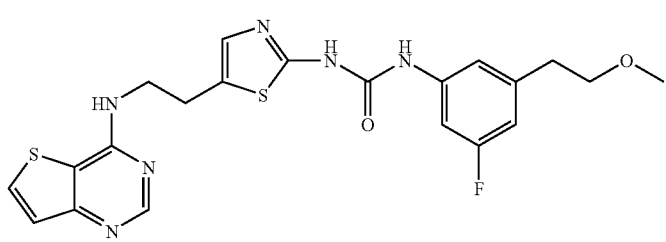 |

TABLE 6-continued
| H₂NR | 1. Final Compound |
|---|---|
| 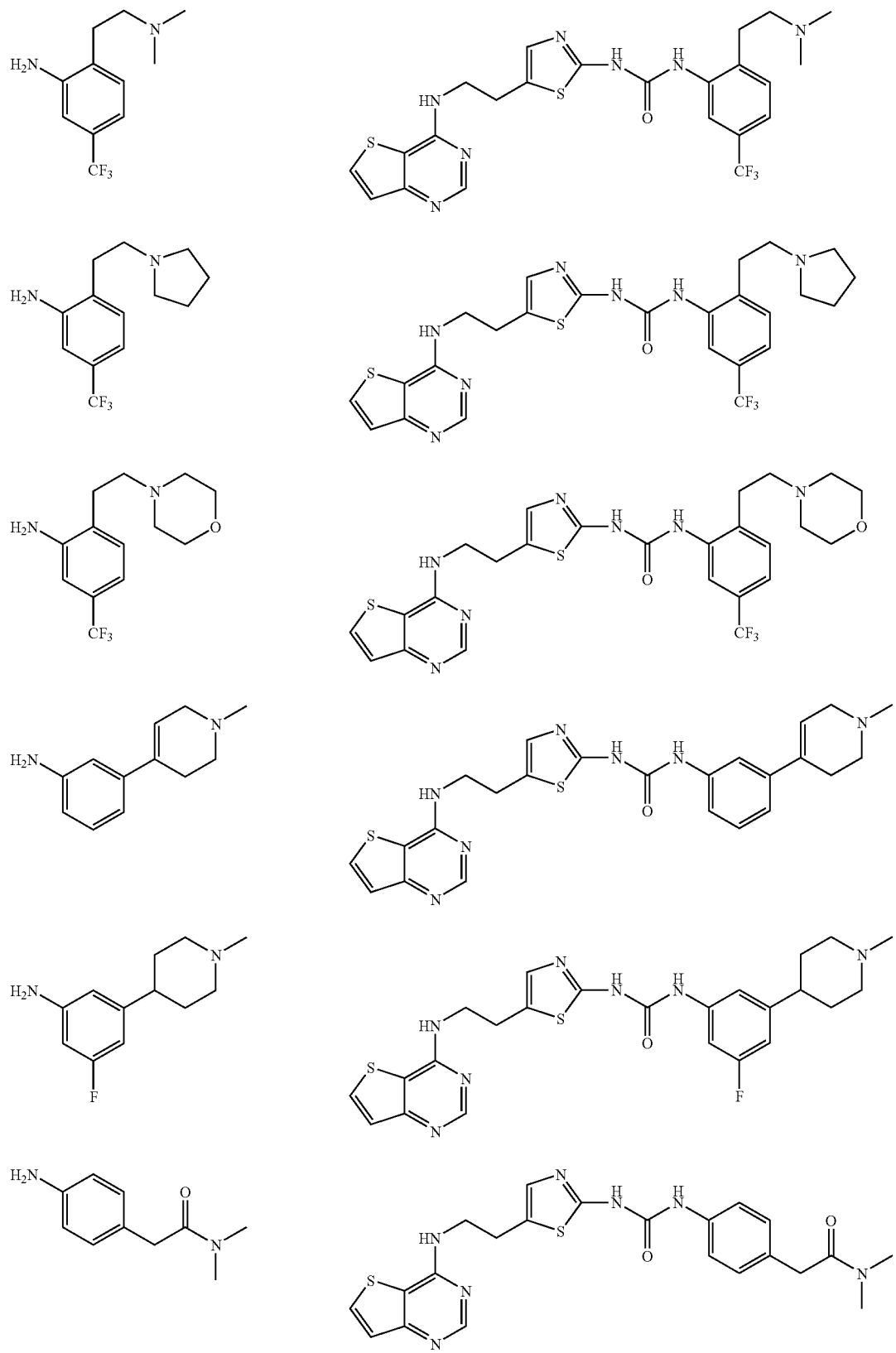 | |

TABLE 6-continued
| H$_2$NR | 1. Final Compound |
|---|---|
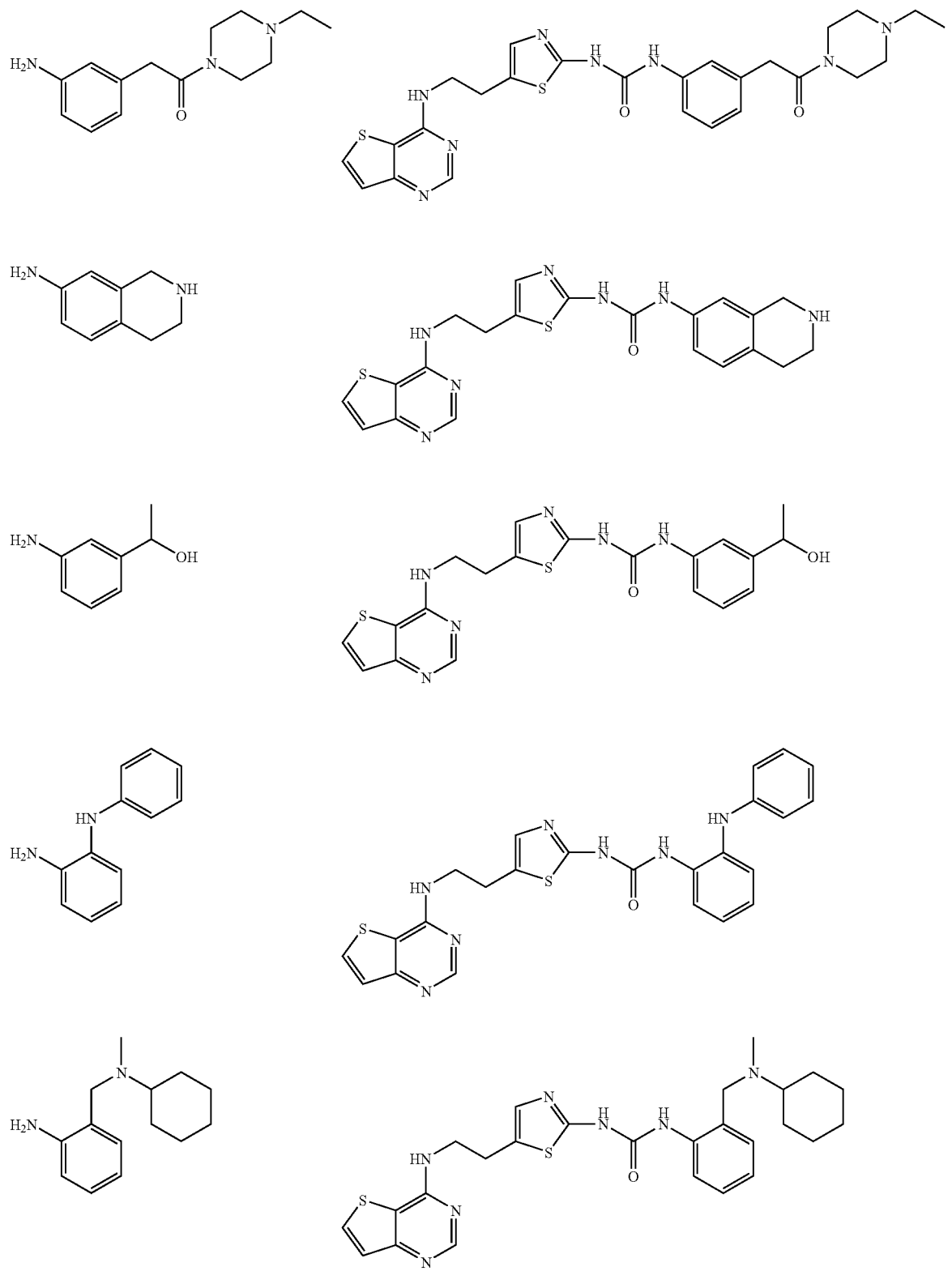

TABLE 6-continued
| H$_2$NR | 1. Final Compound |
|---|---|
| 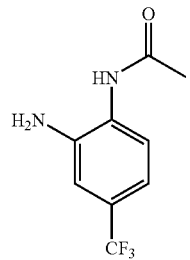 | 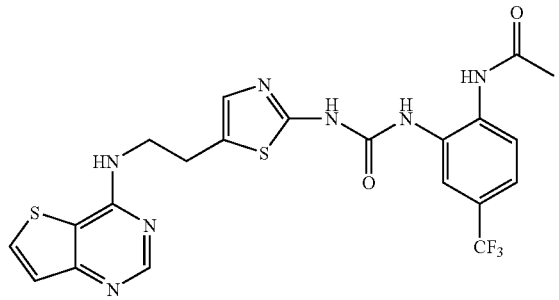 |
| 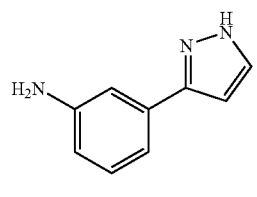 | 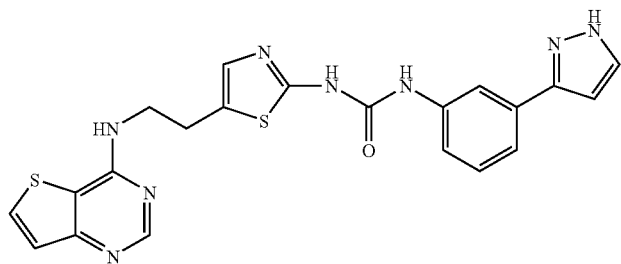 |
| 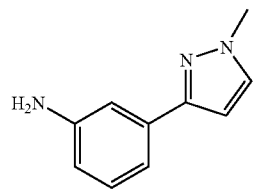 | 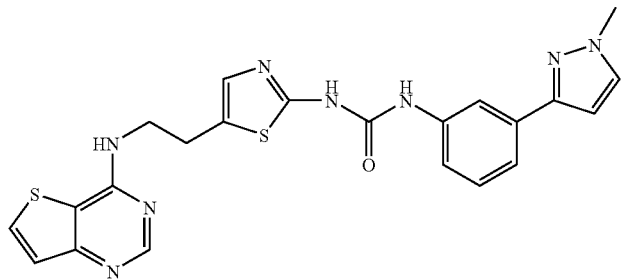 |
| 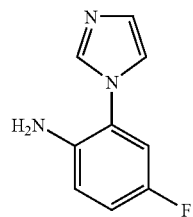 | 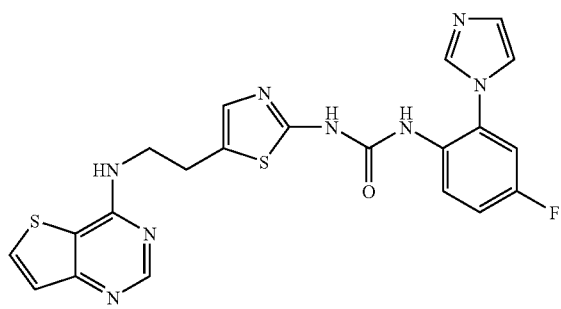 |
| 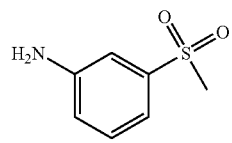 | 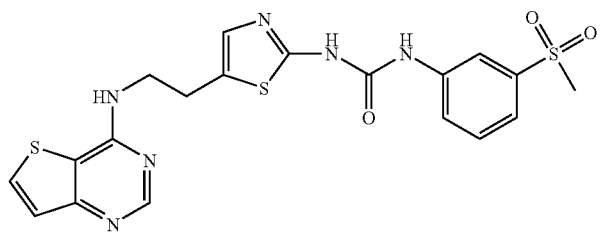 |

TABLE 6-continued
| H₂NR | 1. Final Compound |
|---|---|
| 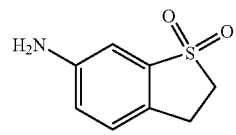 | 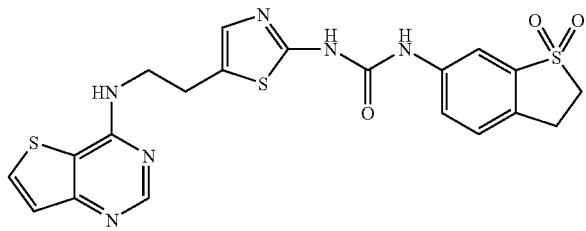 |
| 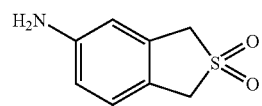 | 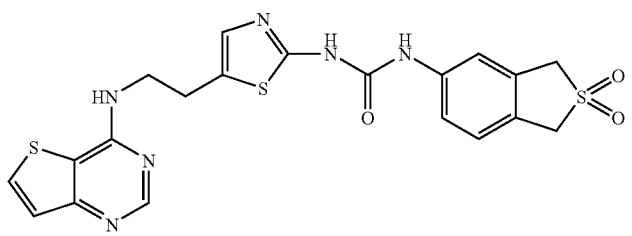 |
| 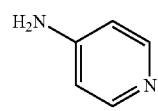 | 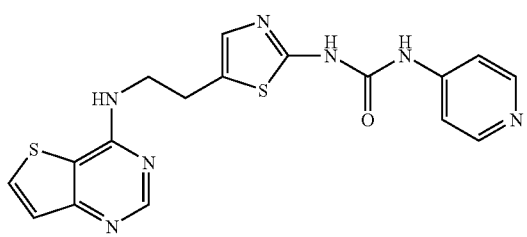 |
| 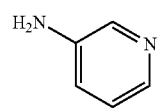 | 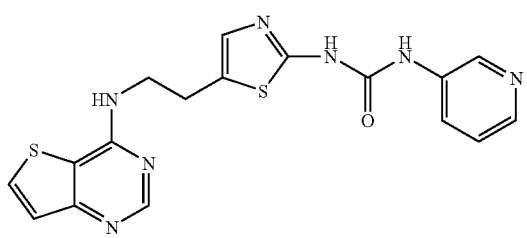 |
| 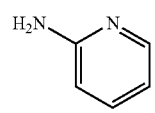 | 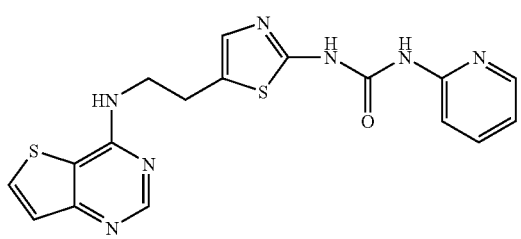 |
| 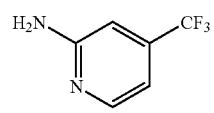 | 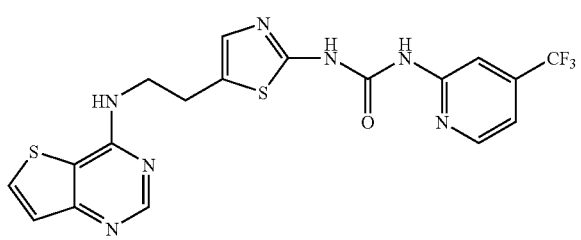 |

TABLE 6-continued
| H₂NR | 1. Final Compound |
|---|---|
| 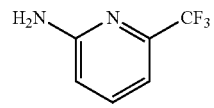 | 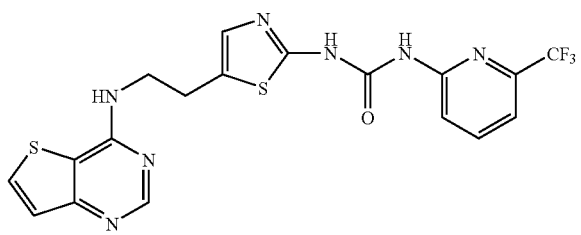 |
| 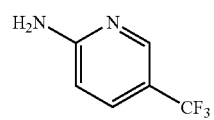 | 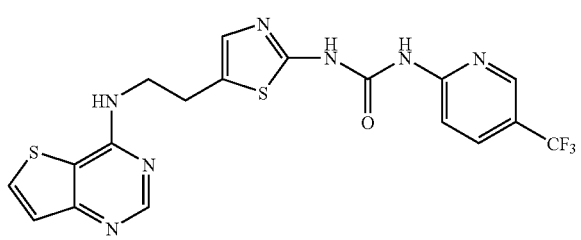 |
| 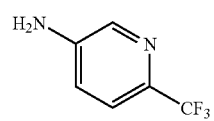 | 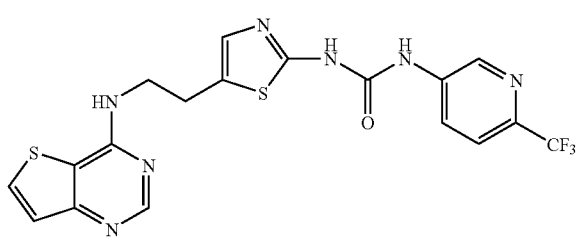 |
| 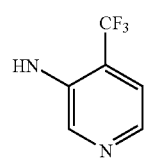 | 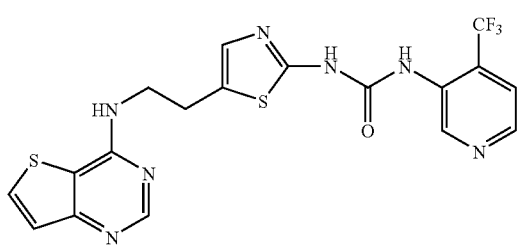 |
| 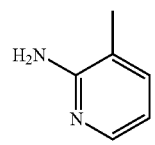 | 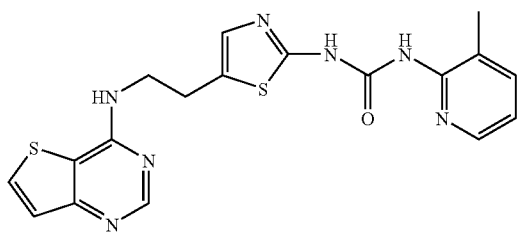 |
| 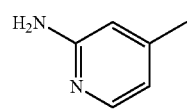 | 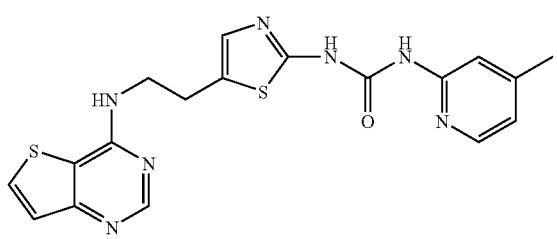 |

TABLE 6-continued
| H₂NR | 1. Final Compound |
|---|---|
| 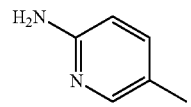 | 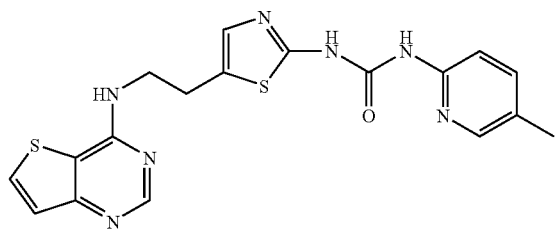 |
| 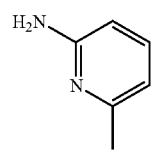 | 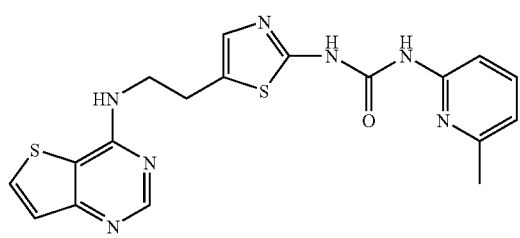 |
| 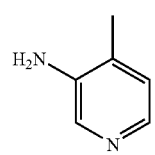 | 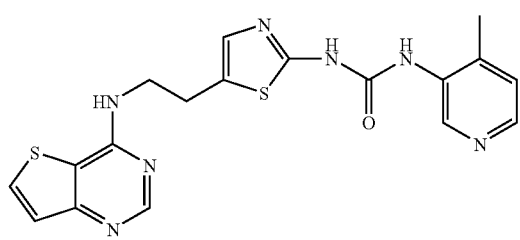 |
| 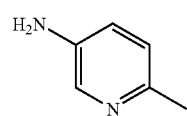 | 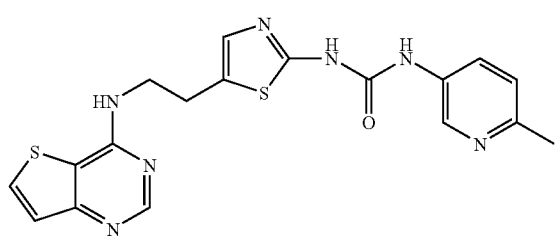 |
| 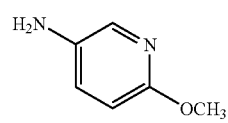 | 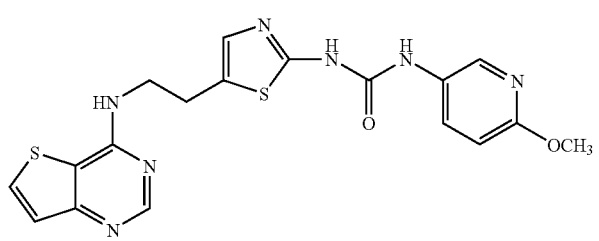 |
| 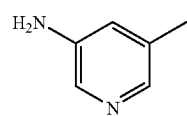 | 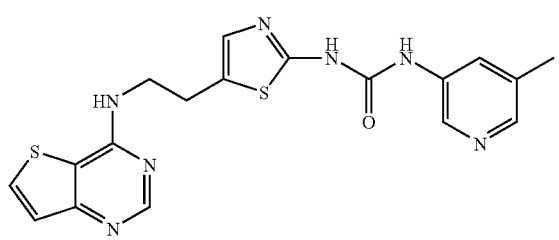 |

TABLE 6-continued
| H₂NR | 1. Final Compound |
|---|---|
| 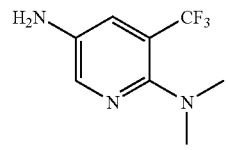 | 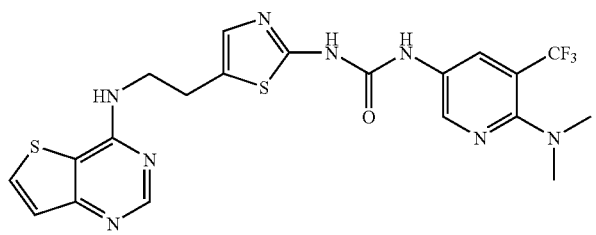 |
| 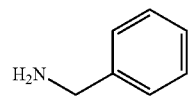 | 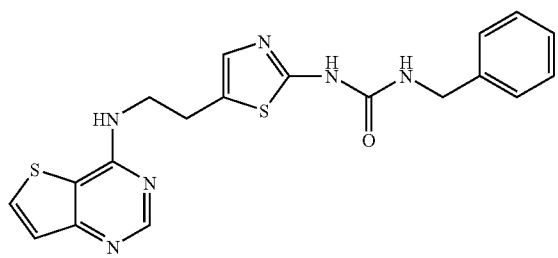 |
| 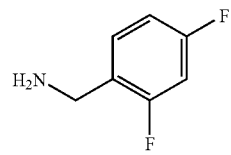 | 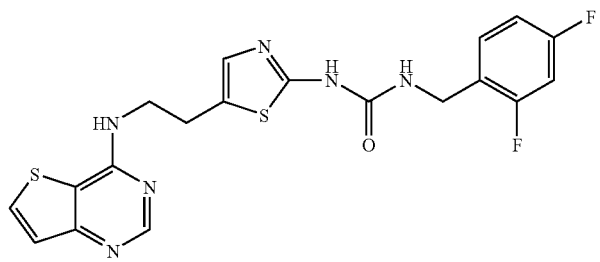 |
| 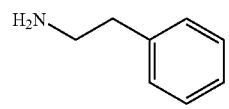 | 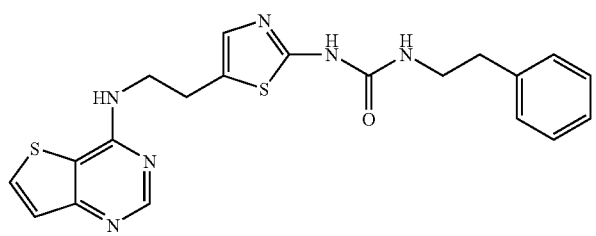 |
| 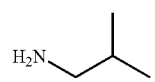 | 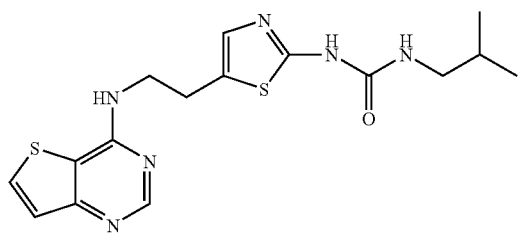 |
| 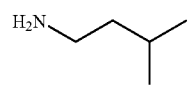 | 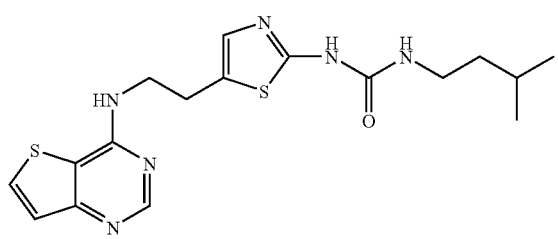 |

TABLE 6-continued
| H$_2$NR | 1. Final Compound |
|---|---|
| 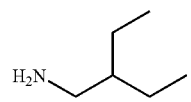 | 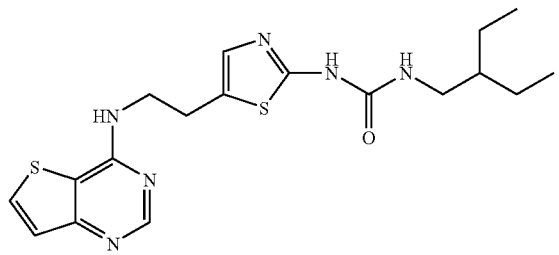 |
| 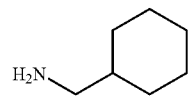 | 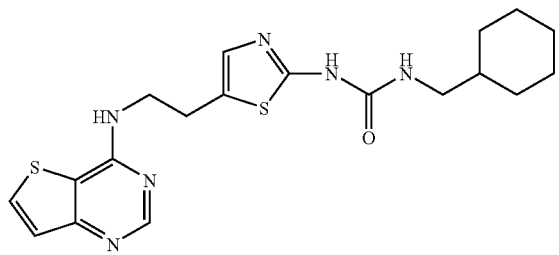 |
| 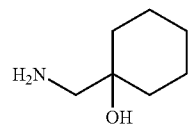 | 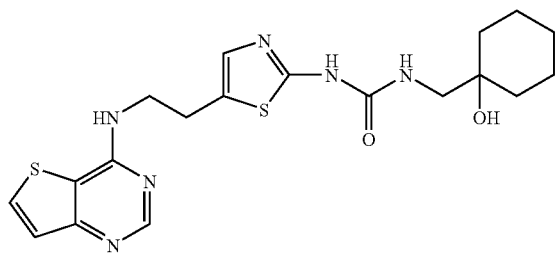 |
| 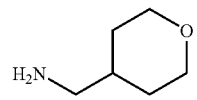 | 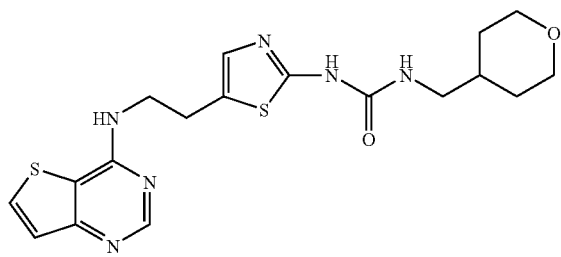 |
|  | 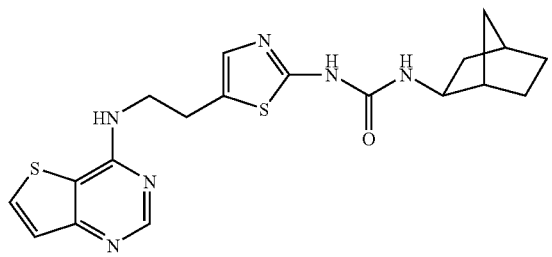 |
| 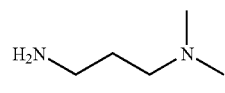 | 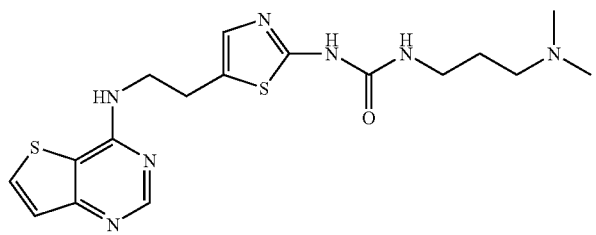 |

TABLE 6-continued

| H₂NR | 1. Final Compound |
|---|---|
| cyclopropylamine | thieno[3,2-d]pyrimidin-4-yl-aminoethyl-thiazolyl urea with cyclopropyl |
| cyclopentylamine | thieno[3,2-d]pyrimidin-4-yl-aminoethyl-thiazolyl urea with cyclopentyl |
| cyclohexylamine | thieno[3,2-d]pyrimidin-4-yl-aminoethyl-thiazolyl urea with cyclohexyl |
| cycloheptylamine | thieno[3,2-d]pyrimidin-4-yl-aminoethyl-thiazolyl urea with cycloheptyl |
| 7-amino-1H-indole-2-carboxylic acid | thieno[3,2-d]pyrimidin-4-yl-aminoethyl-thiazolyl urea with 7-(1H-indole-2-carboxylic acid) |
| (7-amino-1H-indol-3-yl)methanol | thieno[3,2-d]pyrimidin-4-yl-aminoethyl-thiazolyl urea with 7-(1H-indol-3-yl)methanol |

TABLE 6-continued
| H$_2$NR | 1. Final Compound |
|---|---|
| 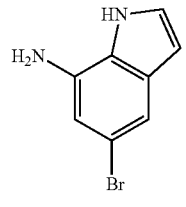 | 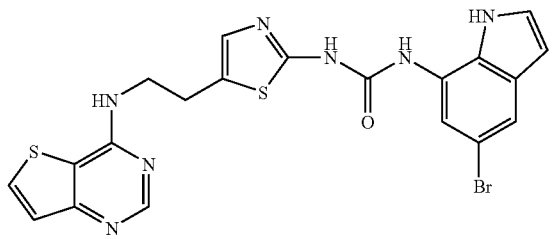 |
| 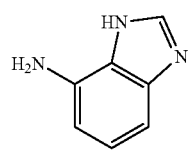 | 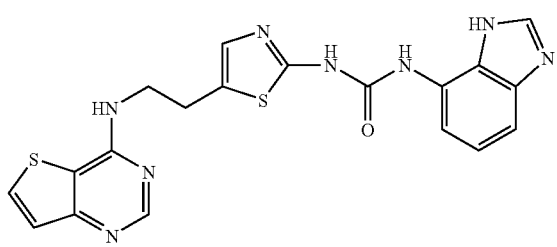 |
| 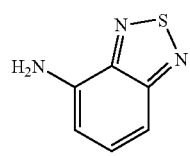 | 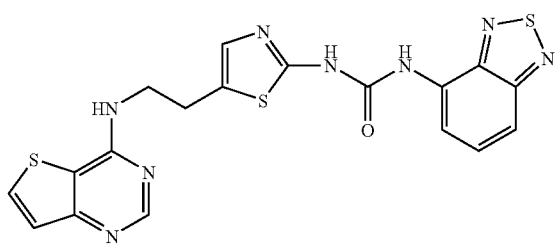 |
|  | 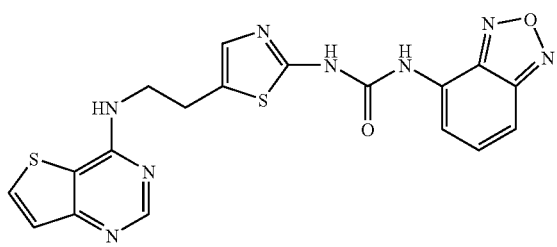 |
| 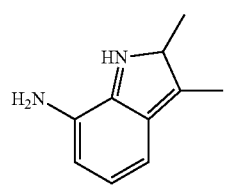 | 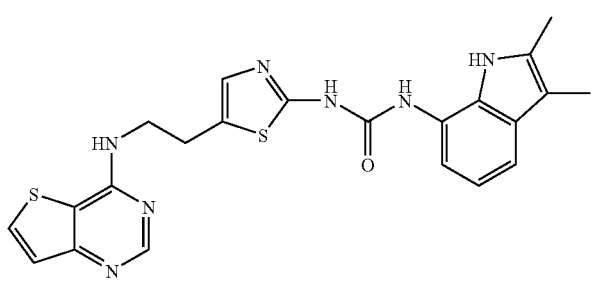 |
| 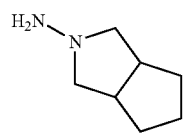 | 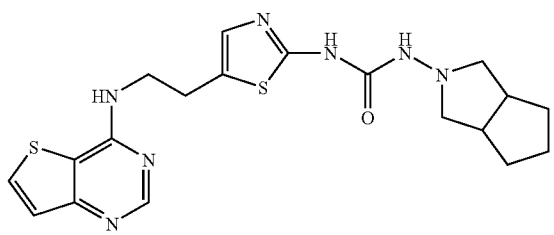 |

TABLE 6-continued
| H₂NR | 1. Final Compound |
|---|---|
| 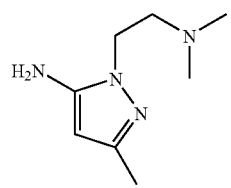 | 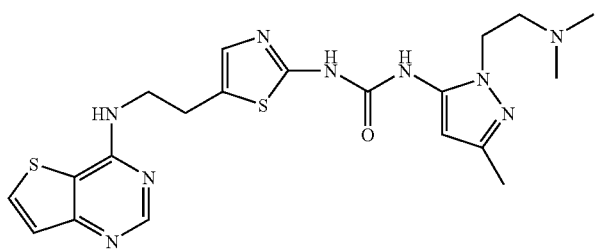 |
| 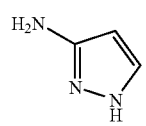 | 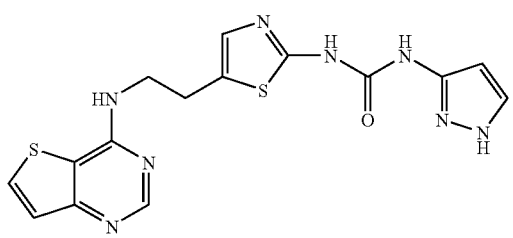 |
| 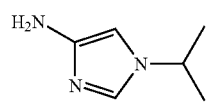 | 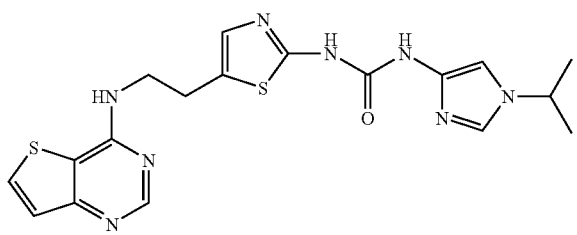 |
| 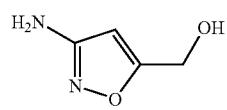 | 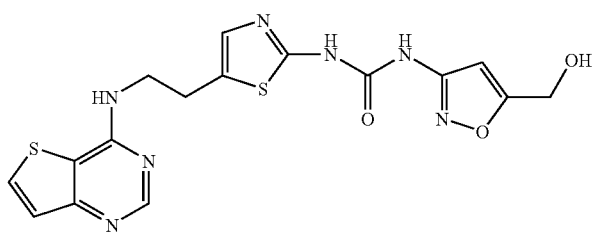 |
| 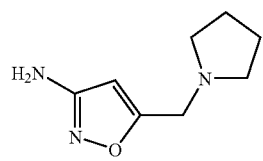 | 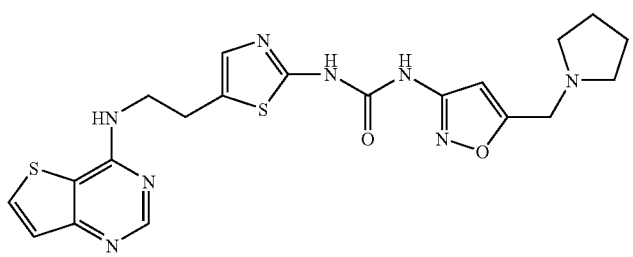 |
| 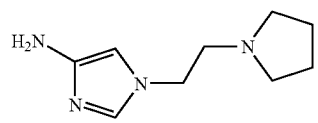 | 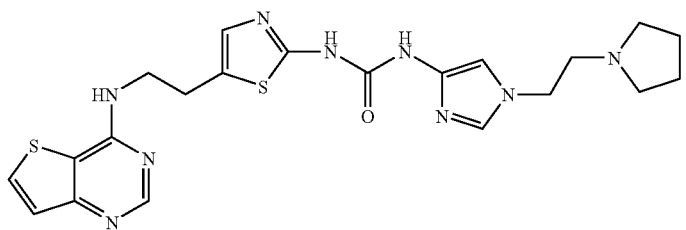 |

TABLE 6-continued

| H₂NR | 1. Final Compound |
|---|---|
| 2-pyridylmethylamine | thieno[3,2-d]pyrimidin-4-yl-aminoethyl-thiazolyl urea with 2-pyridylmethyl |
| 3-pyridylmethylamine | thieno[3,2-d]pyrimidin-4-yl-aminoethyl-thiazolyl urea with 3-pyridylmethyl |
| 4-pyridylmethylamine | thieno[3,2-d]pyrimidin-4-yl-aminoethyl-thiazolyl urea with 4-pyridylmethyl |
| 1-phenylethylamine | thieno[3,2-d]pyrimidin-4-yl-aminoethyl-thiazolyl urea with 1-phenylethyl |
| 1-phenyl-2-(dimethylamino)ethylamine | thieno[3,2-d]pyrimidin-4-yl-aminoethyl-thiazolyl urea with 1-phenyl-2-(dimethylamino)ethyl |
| 1-phenyl-3-(dimethylamino)propylamine | thieno[3,2-d]pyrimidin-4-yl-aminoethyl-thiazolyl urea with 1-phenyl-3-(dimethylamino)propyl |

TABLE 6-continued
| H₂NR | 1. Final Compound |
|---|---|
| 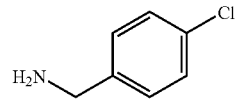 | 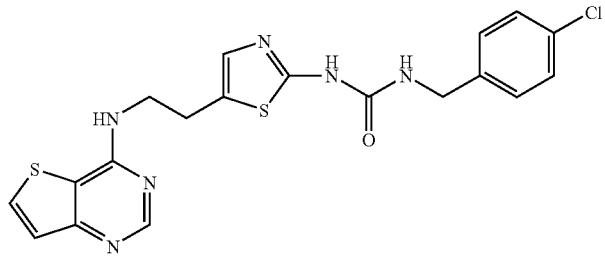 |
| 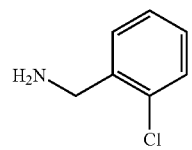 | 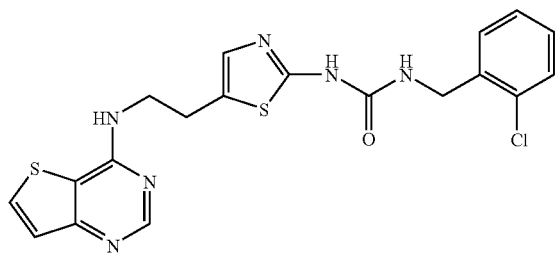 |
| 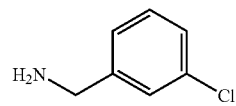 | 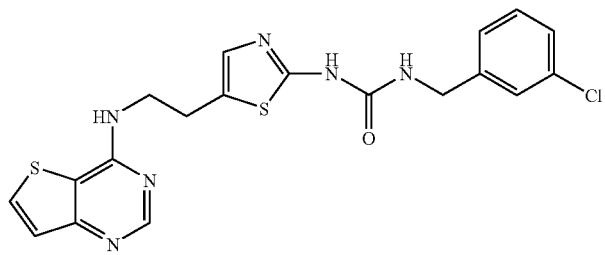 |
| 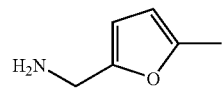 | 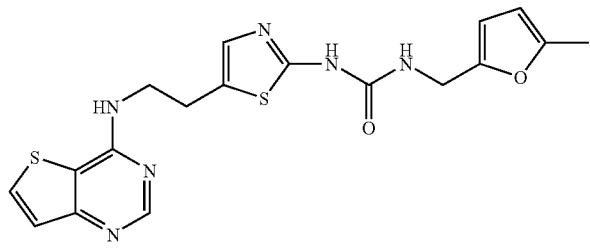 |
| 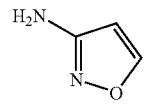 | 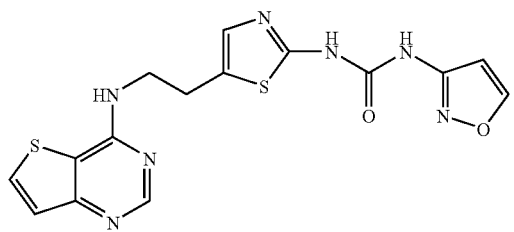 |
| 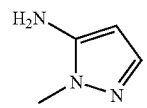 | 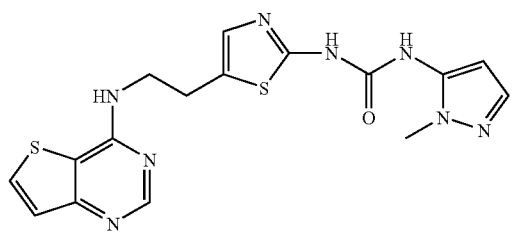 |

TABLE 6-continued
| H$_2$NR | 1. Final Compound |
|---|---|
| 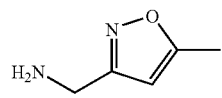 | 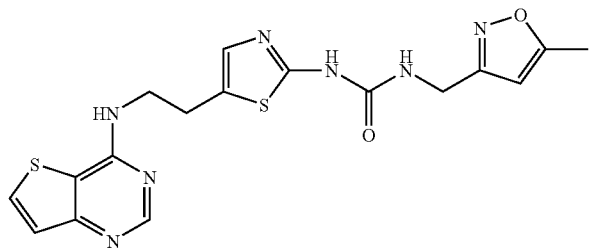 |
| 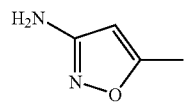 | 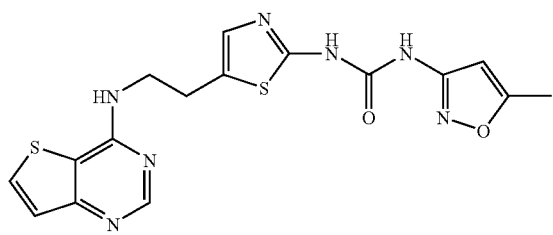 |
| 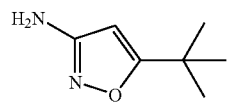 | 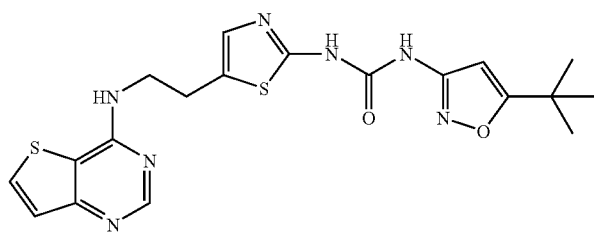 |
| 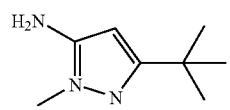 | 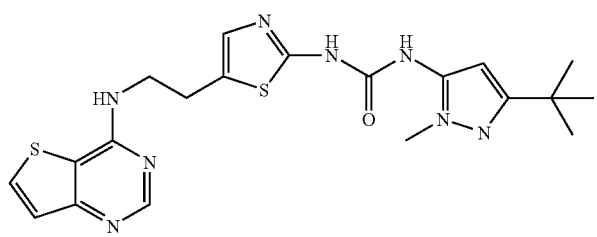 |
| 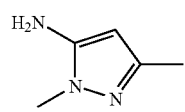 | 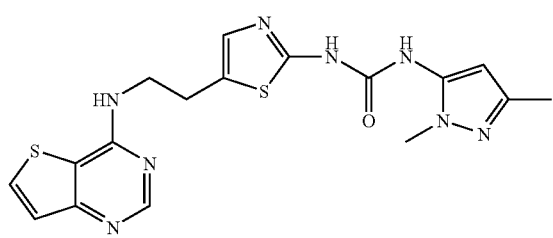 |
| 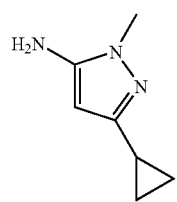 | 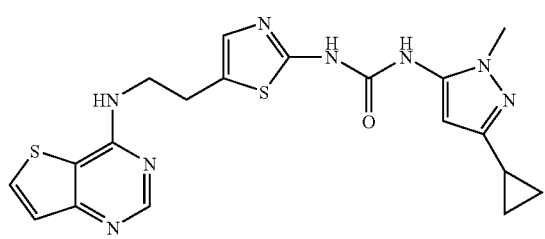 |

TABLE 6-continued
| H₂NR | 1. Final Compound |
|---|---|
| 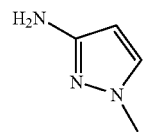 | 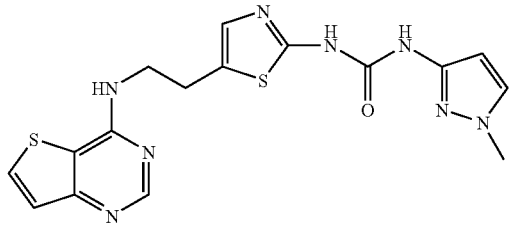 |
|  | 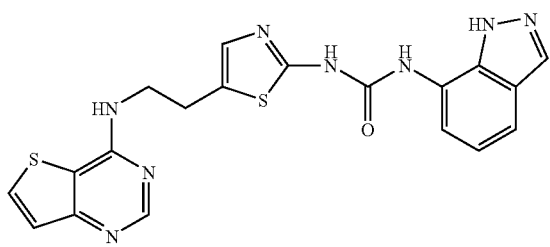 |
| 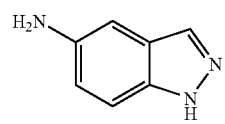 | 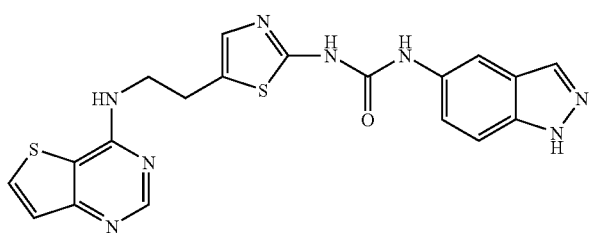 |
| 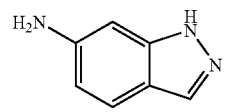 | 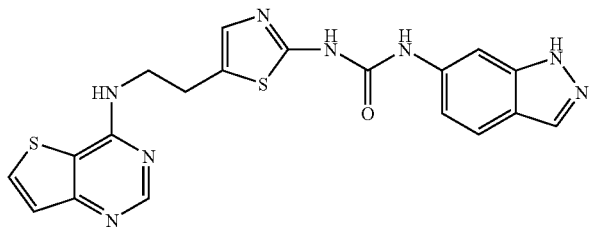 |
| 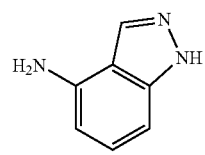 | 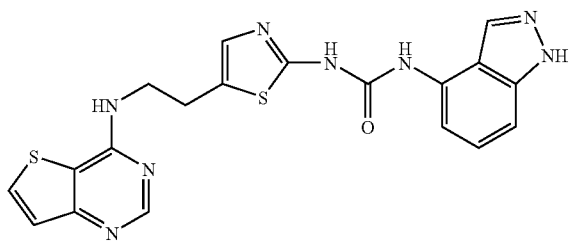 |
| 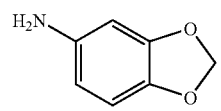 | 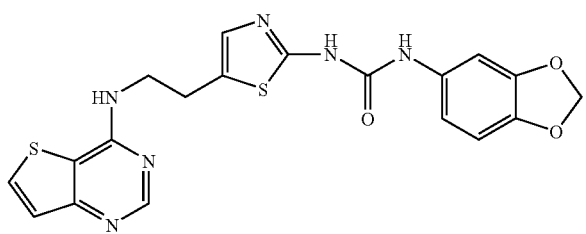 |

TABLE 6-continued

| H$_2$NR | 1. Final Compound |
|---|---|

TABLE 6-continued
| H₂NR | 1. Final Compound |
|---|---|
| 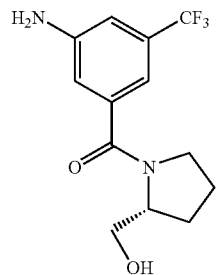 | 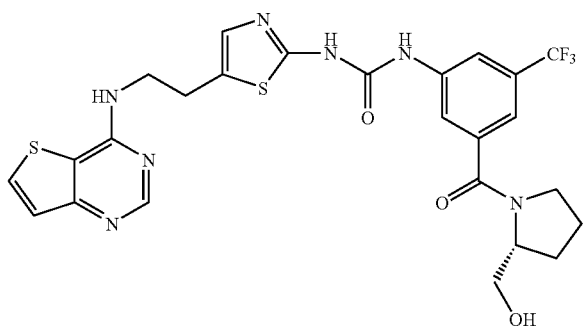 |
| 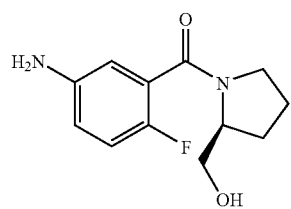 | 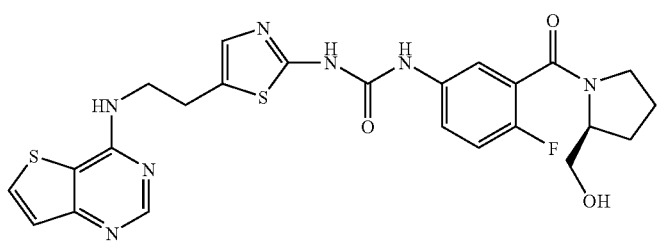 |
| 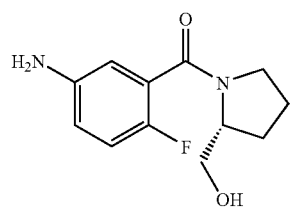 | 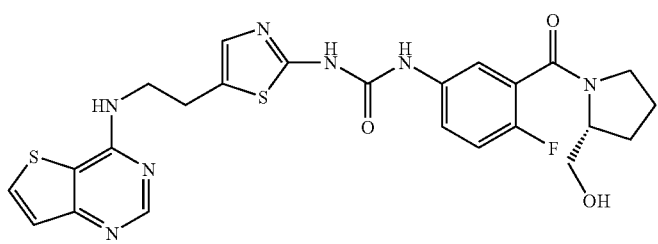 |
| 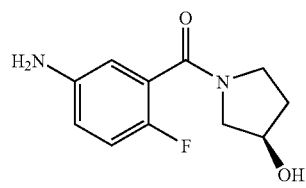 | 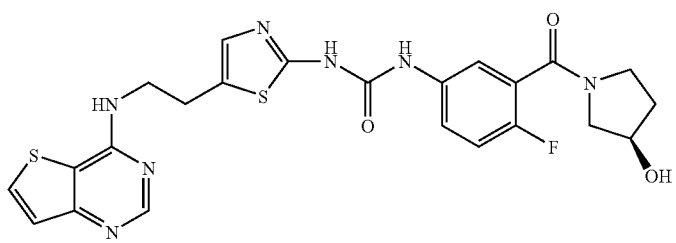 |
| 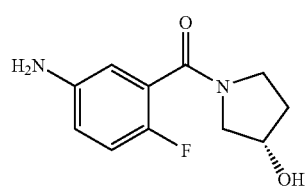 | 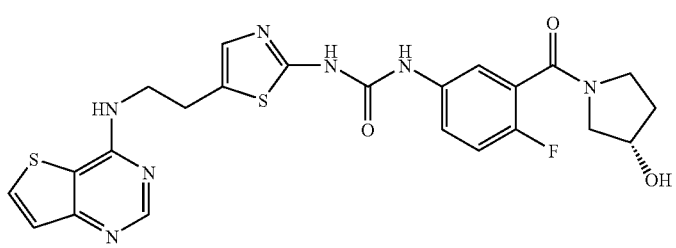 |

TABLE 6-continued

| H₂NR | 1. Final Compound |
|---|---|

TABLE 6-continued
| H₂NR | 1. Final Compound |
|---|---|
Example 18
This example describes the synthesis of
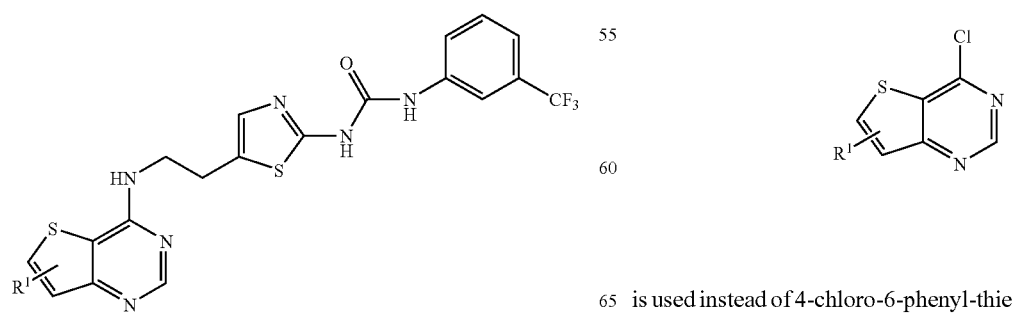
where R¹ is as described previously. These compounds are made according to the procedures of Example 18 except that
is used instead of 4-chloro-6-phenyl-thieno[3,2-d]pyrimidine in step 1. Illustrative examples of R¹'s are found throughout this disclosure as well as in Table 1.

Example 19

This example describes the synthesis of

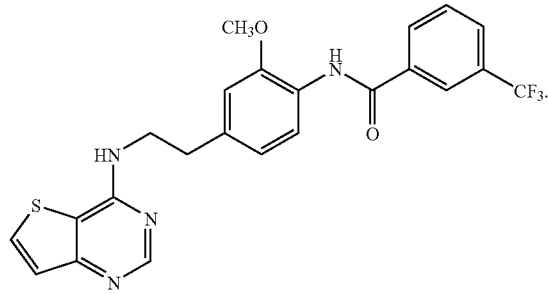

Step 1: (3-Methoxy-4-nitro-phenyl)-methanol (compound 19.1; 2.78 mmol), THF (14.0 mL), PPh$_3$ (1.5 equivalents), and carbon tetrabromide (1.5 equivalents) are combined and stirred at room temperature for 2 hours. The reaction mixture was partitioned between EtOAc and water. The organic layer was separated, washed with brine, dried, filtered and concentrated under reduced pressure. Purification by flash column chromatography on silica gel using a gradient of EtOAc/hexanes provided the corresponding bromide as a solid (87%). The resulting bromide (2.06 mmol) was added to DMSO (10 mL) and potassium cyanide (2.27 mmol), stirred at room temperature for 2.5 hours, hydrolyzed by the addition of 1.0 M HCl and then partitioned between EtOAc and water. The organic layer was separated, washed with brine, dried, filtered and concentrated under reduced pressure. Purification by flash column chromatography on silica gel using a gradient of EtOAc/hexanes provided (3-methoxy-4-nitro-phenyl)-acetonitrile (compound 19.2) in 8%.

Step 2: Compound 19.2 (0.096 mmol), and catalytic Pd/C in EtOAc (2 mL) were placed under an atmosphere of hydrogen for 3 hours. The reaction mixture was filtered, concentrated and taken on crude to the next reaction. The crude compound (0.096 mmol), dichloromethane (0.5 mL), 3-(trifluoromethyl)benzoyl chloride (1.05 mmol) and DIEA (1.10 mmol) was stirred at room temperature for 10 minutes. Water was added after which the mixture partitioned between EtOAc and water. The organic layer was separated, washed with brine, dried, filtered and concentrated under reduced pressure. Purification by flash column chromatography on silica gel using a gradient of EtOAc/hexanes provided N-(4-cyanomethyl-2-methoxy-phenyl)-3-trifluoromethyl-benzamide (compound 19.3) in 71%.

Step 3: Compound 19.3 (0.062 mmol), ethanol (1.5 mL), 4.0 M HCl/dioxane (1 equivalent) and catalytic Pd/C are placed under an atmosphere of hydrogen for 20 hours. The reaction mixture was filtered, concentrated and taken on crude to the next reaction. The crude compound (0.062 mmol), compound 6.2 (1.02 equiv), and DIEA (3.4 equiv.) was heated in n-butanol (0.52 mL) at 135° C. for 2 hours. The reaction mixture was cooled and then partitioned between dichlomethane and water. The organic layer was separated, washed with brine, dried, filtered and concentrated under reduced pressure. Purification by flash column chromatography on silica gel using a gradient of EtOAc/hexanes provided the titled compound as a pale yellow solid in 54%.

Example 20

This example describes the synthesis of

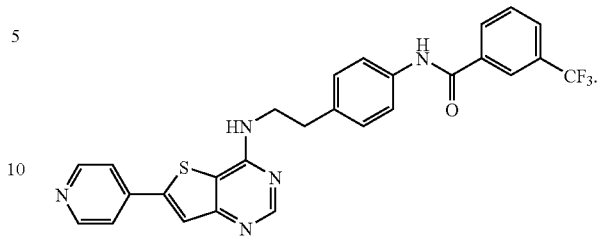

Step 1: A solution of compound 1.1 (1.0 mmol) and TEA (3.0 equiv.) in anhydrous THF (5.0 mL) was treated with the dropwise addition of 3-trifluoromethyl-benzoyl chloride (1.1 equivalents) at 0° C. After completion of the reaction, the mixture was partitioned between water and diethyl ether. The organic layer was separated, washed with 1N HCl, saturated sodium bicarbonate, brine and dried. Purification by flash column chromatography on silica gel provided {2-[4-(3-trifluoromethyl-benzoylamino)-phenyl]-ethyl}-carbamic acid tert-butyl ester (compound 20.1).

Step 2: Compound 20.1 (1.0 mmol) was treated with anhydrous 4.0 N HCl in dioxane (25 mL) at 0° C., stirred at room temperature for 2 hours and concentrated to dryness under reduced pressure. The crude amine salt, 4-chloro-6-bromo thieno[3,2-d]pyrimidine (1.0 equivalent) and N,N-diisopropylethylamine (2.5 equivalents) was then heated in n-butanol (10 mL) at 135° C. for 2 hours. The reaction mixture was cooled and then partitioned between dichloromethane and water. The organic layer was separated, washed with brine, dried and concentrated under reduced pressure. The desired product, N-{4-[2-(6-bromo-thieno[3,2-d]pyrimidin-4-ylamino)-ethyl]-phenyl}-3-trifluoromethyl-benzamide (compound 20.2), was then precipitated from EtOAc and hexanes to give a tan powder.

Step 3: Compound 20.2 (0.1 mmol), 4-pyridineboronic acid (3.0 equivalents), Pd$_2$(dba)$_3$ (16 mol %), AsPh$_3$ (30 mol %) and K$_2$HPO$_4$ (3.0 equivalents) in DMF (3.0 mL) and water (0.75 mL) was heated at 90° C. for 3 hours. The reaction was cooled and after aqueous work-up and purification by flash column chromatography on silica gel, the titled compound is obtained.

Example 21

This example describes the synthesis of

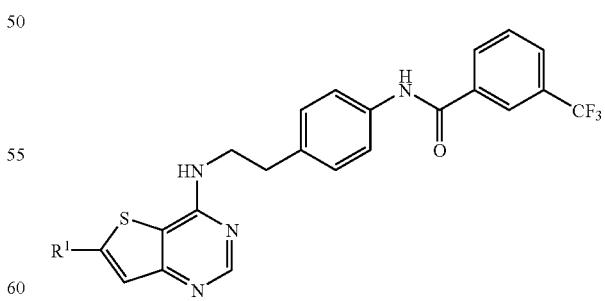

where R$^1$ is as described previously. These compounds are made according to Example 20 except that R$^1$B(OH)$_2$ is used instead of 4-chloro-6-bromo thieno[3,2-d]pyrimidine in step 2. Illustrative examples of suitable R$^1$'s are found throughout this disclosure as well as in Table 7.

TABLE 7

| R¹B(OH)₂ | Final Compound |
|---|---|
| [4-(dimethylcarbamoyl)phenyl]boronic acid | 6-[4-(dimethylcarbamoyl)phenyl]-thieno[3,2-d]pyrimidin-4-yl derivative with N-{4-[2-(aminoethyl)]phenyl}-3-(trifluoromethyl)benzamide |
| (4-carbamoylphenyl)boronic acid | corresponding 4-carbamoylphenyl analog |
| [4-(aminomethyl)phenyl]boronic acid | corresponding 4-(aminomethyl)phenyl analog |
| (4-formylphenyl)boronic acid | corresponding 4-formylphenyl analog |
| (2-chloropyridin-4-yl)boronic acid | corresponding 2-chloropyridin-4-yl analog |

Example 22

This example describes the synthesis of

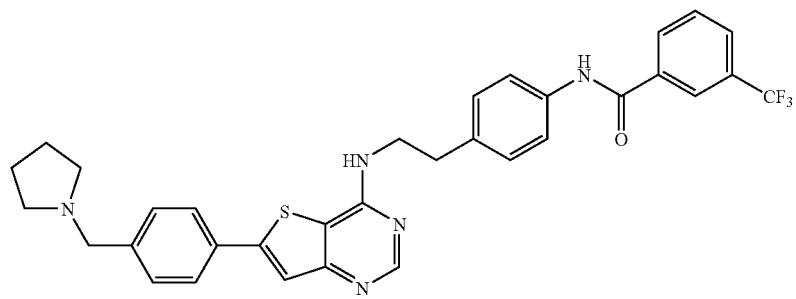

Step 1: N-(4-{2-[6-(4-Formyl-phenyl)-thieno[3,2-d]pyrimidin-4-ylamino]-ethyl}-phenyl)-3-trifluoromethyl-benzamide (compound 22.1) was prepared as described in Example 21 using 4-formylphenylboronic acid.

Step 2: To a suspension of compound 22.1 (0.07 mmol) and pyrrolidine (5.0 equivalents) in ethanol (3.0 ml) and AcOH (0.5 mL) was added NaCNBH$_3$ (1.4 equiv.) at room temperature. After 2 hours the reaction mixture was partitioned between EtOAc and saturated sodium bicarbonate. The organic layer was separated, dried and concentrated under reduced pressure. Purification by preparative TLC provided the titled compound.

Example 23

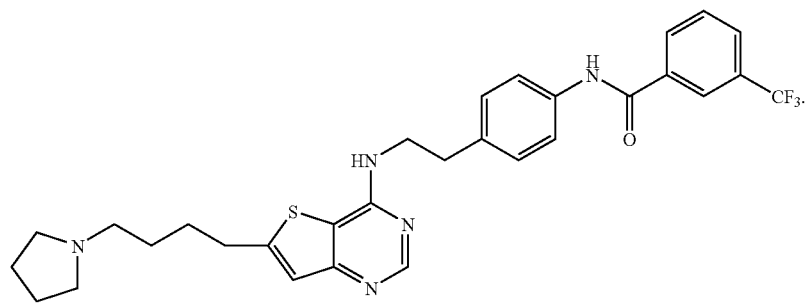

Step 1: To a nitrogen purged solution of compound 20.2 (0.79 mmol), 3-butyn-1-ol (2.5 equivalents), Pd(PhCN)$_2$Cl$_2$ (0.2 equivalent) in piperidine was added CuI (0.5 equivalent) followed by stirring at room temperature for 3 hours. The reaction mixture was then subjected to an aqueous work-up and purified by flash column chromatography on silica gel to provide N-(4-{2-[6-(4-hydroxy-but-1-ynyl)-thieno[3,2-d]pyrimidin-4-ylamino]-ethyl}-phenyl)-3-trifluoromethyl-benzamide (compound 23.1).

Step 2: To a solution of compound 23.1 (0.27 mmol) in dichloromethane was added sequentially TEA (3.0 equiv.) and methanesulfonyl chloride (2.5 equivalents). After stirring at room temperature for 2 hours, excess pyrrolidine (~5.0 equivalent) was added and the reaction was heated at 40° C. until starting material is consumed. The reaction was cooled, concentrated to dryness and purified by flash column chromatography on silica gel to provide N-(4-{2-[6-(4-pyrrolidin-1-yl-but-1-ynyl)-thieno[3,2-d]pyrimidin-4-ylamino]-ethyl}-phenyl)-3-trifluoromethyl-benzamide (compound 23.2).

Step 3: A solution of compound 23.2 (0.06 mmol) and 10% palladium on carbon (0.11 equivalent) in MeOH was stirred under an atmosphere of hydrogen (via a balloon) until all starting material was consumed. The reaction mixture was filtered, concentrated to dryness and purified by flash column chromatography on silica gel to provide the titled compound.

Example 24

This example describes the synthesis of

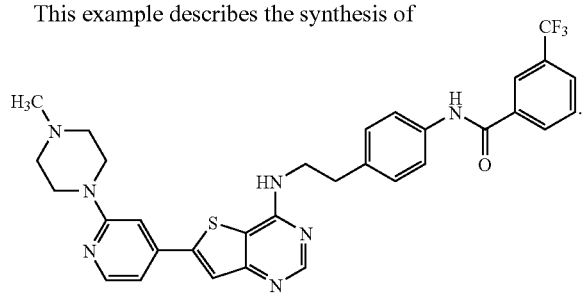

Step 1: N-(4-{2-[6-(2-Chloro-pyridin-4-yl)-thieno[3,2-d]pyrimidin-4-ylamino]-ethyl}-phenyl)-3-trifluoromethyl-benzamide (compound 21.1) was prepared as described in Example 21 using 2-chloropyridine-4-boronic acid.

Step 2: A solution of compound 21.1 (0.036 mmol) and 1-methylpiperazine (10 equiv.) in 1-methyl-2-pyrrolidinone (2.0 mL) was heated overnight at 200° C. in a screw-top reaction vial. The reaction was cooled, concentrated and purified by preparative TLC to give the titled compound.

Example 25

This example describes the synthesis of

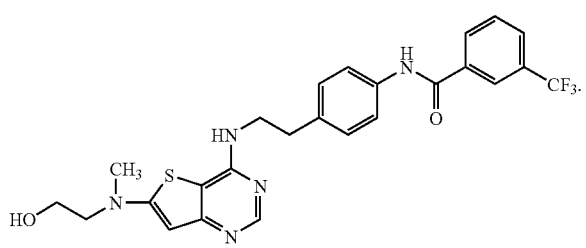

To a flame-dried round-bottom flask containing compound 20.2 (0.19 mmol) was added DMSO (1.0 mL) followed by 2-(methylamino)-ethanol (0.96 mmol). The reaction was stirred under nitrogen at 150° C. overnight and then cooled to room temperature. Purification by reverse-phase HPLC (aqueous 0.1% TFA/CH$_3$CN) provided the titled compound as an off-white powder (20 mg, 17%).

Example 26

This example describes the synthesis of

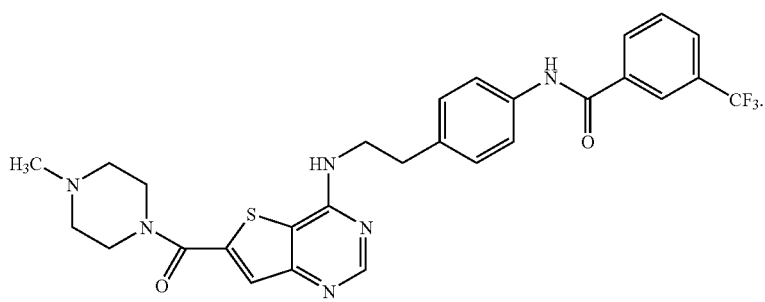

Step 1: To a nitrogen purged solution of compound 20.2 (0.42 mmol), Pd(AcO)$_2$ (0.2 equivalent) and 1,3-bis(diphenylphosphino)propane ("Dppp"; 0.2 equivalent) in DMF (10.0 mL) and MeOH (2.0 mL) was added DIEA (4.1 equivalents). CO gas was bubbled through the reaction mixture for 20 minutes and the reaction was then stirred for 3.5 hours under a CO atmosphere (via a balloon) at 80° C. After aqueous work-up and purification by flash column chromatography on silica gel, 4-{2-[4-(3-trifluoromethyl-benzoylamino)-phenyl]-ethylamino}-thieno[3,2-d]pyrimidine-6-carboxylic acid methyl ester (compound 26.1) was obtained.

Step 2: To a solution of compound 26.1 (0.72 mmol) in THF (5.0 mL) was added aqueous 1.0 M LiOH (6.0 equivalents). The reaction mixture was stirred at 70° C. until all of the starting material was consumed. The reaction was cooled, neutralized with 10% HCl and concentrated to dryness under reduced pressure to provide 4-{2-[4-(3-trifluoromethyl-benzoylamino)-phenyl]-ethylamino}-thieno[3,2-d]pyrimidine-6-carboxylic acid (compound 26.2).

Step 3: To a solution of compound 26.2 (0.08 mmol) in DMF (1.0 mL) was added 1-methylpiperazine (2.1 equivalents), DIEA (3.5 equivalents), DMAP (0.5 equivalent) and HATU (1.2 equivalents) at room temperature. After overnight stirring followed by aqueous work-up, the titled compound was isolated after preparative TLC purification.

Example 27

This example describes the synthesis of

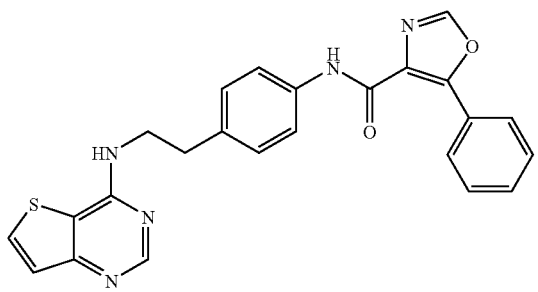

To a solution of compound 12.2 (0.37 mmol) in DMF (3.0 mL) was added 5-phenyl-oxazole-4-carboxylic acid (1.0 equivalent), DIEA (3.4 equivalents), and HATU (1.1 equivalents). After overnight heating at 50° C. the reaction was directly subjected to purification by reverse-phase HPLC (aqueous 0.1% TFA/CH$_3$CN) to provide the titled compound after lyophilization.

Example 28

This example describes the synthesis of

![structure]

where Z is as previously described. These compounds are made according to Example 27 except that ZCOOH is used instead of 5-phenyl-oxazole-4-carboxylic acid. Illustrative examples of suitable Z's are found throughout this disclosure as well as in Table 8.

Example 29

This example describes the synthesis of

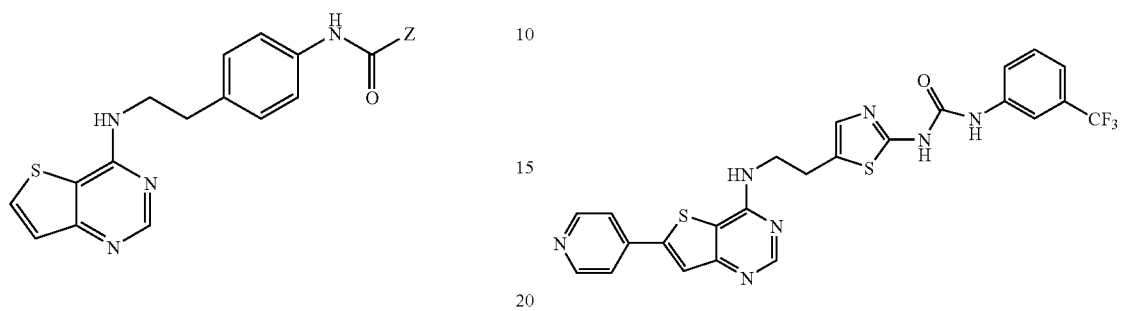

Step 1: A sealed Pyrex tube was charged, under nitrogen, with {5-[2-(6-bromo-thieno[3,2-d]pyrimidin-4-ylamino)-ethyl]-thiazol-2-yl}-carbamic acid tert-butyl ester (com

TABLE 8

| ZCOOH | Final Compound |
|---|---|
| ![structure] | ![structure] |
| ![structure] | ![structure] | pound 29.1; 0.2 mmol), 4-pyridineboronic acid (0.25 mmol), PdCl$_2$(PPh$_3$)$_2$ (0.04 mmol), 2M Na$_2$CO$_3$ (0.06 mmol), water (0.5 mL), and DMF (1.5 mL). The reaction mixture was heated subjected to microwave irradiation at 50 watts for 5 minutes at 100° C. and then at 300 watts for 20 minutes at 120° C. After cooling, the reaction mixture was filtered and concentrated to provide crude [2-(2-amino-thiazol-S-yl)-ethyl]-(6-pyridin-4-yl-thieno[3,2-d]pyrimidin-4-yl)-amine (compound 29.2) which was used in the next step without further purification.

Step 2: Compound 29.2 (0.15 mmol) and 3-trifluoromethylphenyl isocyanate (0.2 mmol) was heated in acetonitrile (2 mL) at 70° C. for 4 hours. The reaction mixture was cooled, concentrated and purified by preparative TLC chromatography (5% MeOH in dichloromethane) to provide the titled compound.

Example 30

This example describes the synthesis of

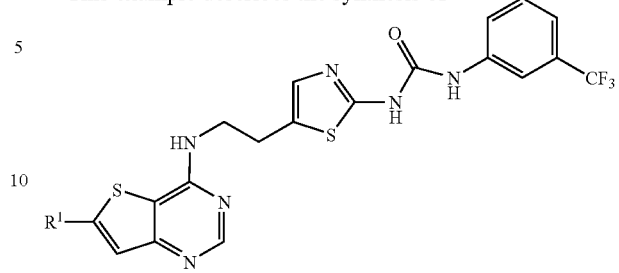

where R$^1$ is as described previously. These compounds are made according to Example 29 except that R$^1$B(OH)$_2$ is used instead of 4-pyridineboronic acid in step 1. Illustrative examples of suitable R$^1$'s are found throughout this disclosure as well as in Table 9.

TABLE 9

| R$^1$B(OH)$_2$ | Final Compound |
|---|---|

TABLE 9-continued

| R¹B(OH)₂ | Final Compound |
|---|---|

TABLE 9-continued

| R¹B(OH)₂ | Final Compound |
|---|---|
| H₃CO-pyridine-B(OH)₂ | H₃CO-pyridine-thienopyrimidine-thiazole-urea-Ph-CF₃ structure |
| morpholine-pyridine-B(OH)₂ | morpholine-pyridine-thienopyrimidine-thiazole-urea-Ph-CF₃ structure |

Example 31

This example describes the synthesis of

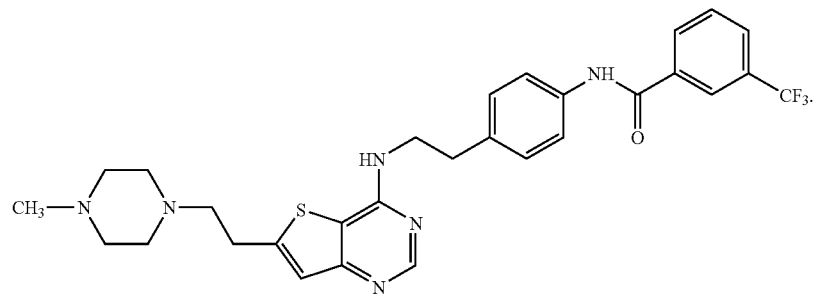

Step 1: Compound 26.1 is converted to the corresponding aldehyde via a two step reaction sequence. First, compound 26.1 is reduced to the alcohol with diisobutylaluminum hydride ("DIBAL") at −78° C. Second, after standard work-up and purification, the resulting alcohol is oxidized to N-{4-[2-(6-formyl-thieno[3,2-d]pyrimidin-4-ylamino)-ethyl]-phenyl}-3-trifluoromethyl-benzamide (compound 31.1) using pyridinium dichromate ("PDC") under standard conditions. Such transformations are found, for example, in Handbook of Reagents for Organic Synthesis: Oxidizing and Reducing Agents, Burke, S. D.; Danheiser, R. L., Ed.; John Wiley and Sons Inc: New York.

Step 2: Compound 31.1 is reacted with the ylide generated from (methoxymethyl)triphenylphosphonium chloride. The resulting product is then hydrolyzed with aqueous HCl to yield N-(4-{2-[6-(2-oxo-ethyl)-thieno[3,2-d]pyrimidin-4-ylamino]-ethyl}-phenyl)-3-trifluoromethyl-benzamide (compound 31.2). Such a transformation is found, for example, in Stork, G. et. al. *J. Am. Chem. Soc.* 2001, 123, 3239.

Step 3: The titled compound is prepared according to Step 2 of Example 22 except for using compound 31.2 instead of compound 22.1 and for using 1-methylpiperazine instead of pyrrolidine.

Example 32

This example describes the synthesis of

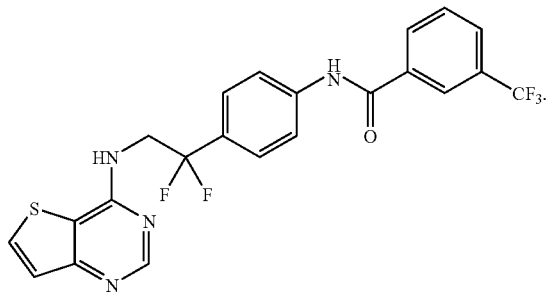

Step 1: Difluoro-(4-nitro-phenyl)-acetic acid ethyl ester (compound 32.1) is reacted according to Sato, K. et. al. *Chem. Pharm. Bull.* 1999, 47, 1013). Briefly, compound 32.1 and catalytic Pd/C in EtOAc are placed under an atmosphere of hydrogen for 3 hours. The reaction mixture is filtered, concentrated and taken on crude to the next reaction. The crude compound, dichloromethane, 3-(trifluoromethyl)benzoyl chloride and DIEA are stirred at room temperature for 10 minutes. Water is added after which the mixture partitioned between EtOAc and water. The organic layer is separated, washed with brine, dried, filtered and concentrated under reduced pressure. Purification by flash column chromatography on silica gel using a gradient of EtOAc/hexanes provides difluoro-[4-(3-trifluoromethyl-benzoylamino)-phenyl]-acetic acid ethyl ester (compound 32.2).

Step 2: Compound 32.2 is reduced with DIBAL at −78° C. to the corresponding aldehyde according to a procedure found in Ishikawa, T. et. al. *J. Am. Chem. Soc.* 2000, 122, 7633. The resulting aldehyde is then converted into N-[4-(2-amino-1,1-difluoro-ethyl)-phenyl]-3-trifluoromethyl-benzamide (compound 32.3) via reductive amination using NH₄OAc and NaCNBH₃ according to a procedure found in Aurelin, L. et. al. *J. Org. Chem.* 2003, 68, 2652.

Step 3: Compound 32.3, compound 6.2 and DIEA are heated in n-butanol at 135° C. for 2 hours. The reaction mixture is cooled and then partitioned between dichloromethane and water. The organic layer is separated, washed with brine, dried, filtered and concentrated under reduced pressure. Purification by flash column chromatography on silica gel using a gradient of EtOAc/hexanes provides the titled compound.

Example 33

This example describes the synthesis of

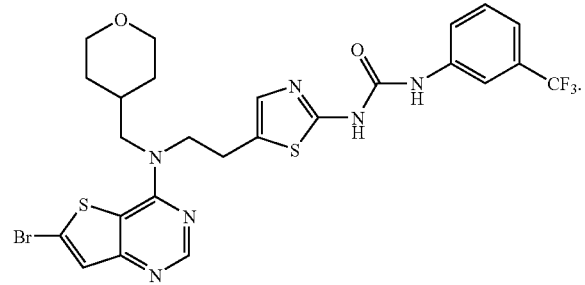

Step 1: A flask was charged with compound 14.1 (200 mg, 100 mol %), tetrahydro-pyran-4-carbaldehyde (100 mol %), and dichloroethane. To this was added NaBH(OAc)₃ (150 mol %) and the resulting slurry was stirred at room temperature for 2 hours. The solvents were removed in vacuo and the residue was re-suspended in EtOAc and H₂O. The organic layer was washed sequentially with saturated sodium bicarbonate, H₂O, and brine. The organic layers were combined, dried over Na₂SO₄, and concentrated to give (5-{2-[(tetrahydro-pyran-4-ylmethyl)-amino]-ethyl}-thiazol-2-yl)-carbamic acid tert-butyl ester (compound 33.1) as an oil which was used in the next step without further purification.

Step 2: Compound 33.1, n-butanol (2 mL), 6-bromo-4-chloro-[3,2-d]thienopyrimidine (100 mol %), and DIEA (500 mol %) was stirred for 2 hours at 100° C. and then concentrated in vacuo. The resulting oil was treated with 4N HCl in dioxane (10 mL) at room temperature for 1 hour. The reaction was concentrated to a solid and lixiviated three times with cold ether to provide [2-(2-amino-thiazol-5-yl)-ethyl]-(6-bromo-thieno[3,2-d]pyrimidin-4-yl)-(tetrahydro-pyran-4-ylmethyl)-amine (compound 33.2) as a HCl salt which was used in the next step without further purification.

Step 3: Crude 33.2 was suspended in DMF (2 mL) and DIEA (1 mL). To this solution was added trifluoromethylphenyl isocyanate (120 mol %). The solution was stirred at room temperature for 5 minutes and then purified by reverse phase HPLC providing the titled compound. LCMS [M+H]⁺ m/z 643.1

Example 34

This example describes the synthesis of

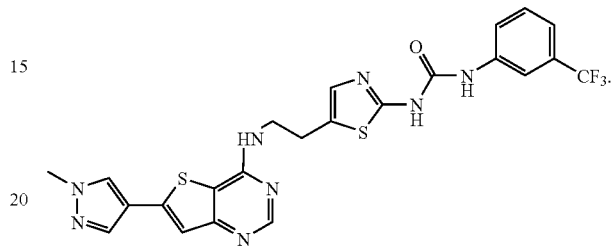

Step 1: 1-{5-[2-(6-Bromo-thieno[3,2-d]pyrimidin-4-ylamino)-ethyl]-thiazol-2-yl}-3-(3-trifluoromethyl-phenyl)-urea (compound 34.1) was prepared according to Example 18 except that 6-bromo-4-chloro-[3,2-d]thienopyrimidine was used instead of 4-chloro-6-phenyl-thieno[3,2-d]pyrimidine in step 1.

Step 2: Compound 32.1 (100 mg, 100 mol %), 1-methyl-4-(4,4,5,5-tetramethyl-[1,3,2]dioxaborolan-2-yl)-1H-pyrazole (46 mg, 120 mole %) and PdCl₂(PPh₃)₂ (20 mol %) was placed in a 100 mL reaction vial and to this was added DMF/H₂O (4:1, 4 mL) along with 2N Na₂CO₃ (1 mL). The vial was flushed with nitrogen, sealed and subjected to microwave irradiation (10 minutes, 300 W, 100° C.). The contents were cooled, the solid precipitate was filtered and washed with cold ether and recrystallized from MeOH/ether to provide the titled compound. LCMS [M+H]⁺ m/z 545.1

Example 35

This example describes the synthesis of

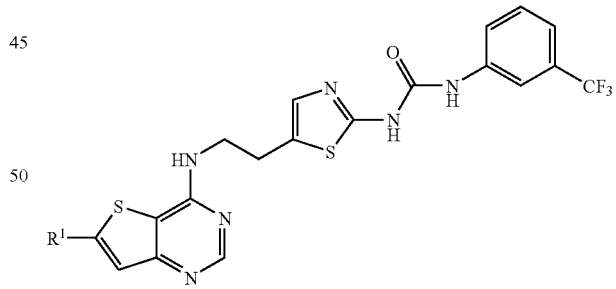

where R¹ is as previously described. These compounds are made according to Example 34 except that

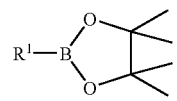

is used instead of 1-methyl-4-(4,4,5,5-tetramethyl-[1,3,2]dioxaborolan-2-yl)-1H-pyrazole in step 2. Illustrative examples of suitable R¹'s are found throughout this disclosure as well as in Table 10.

TABLE 10
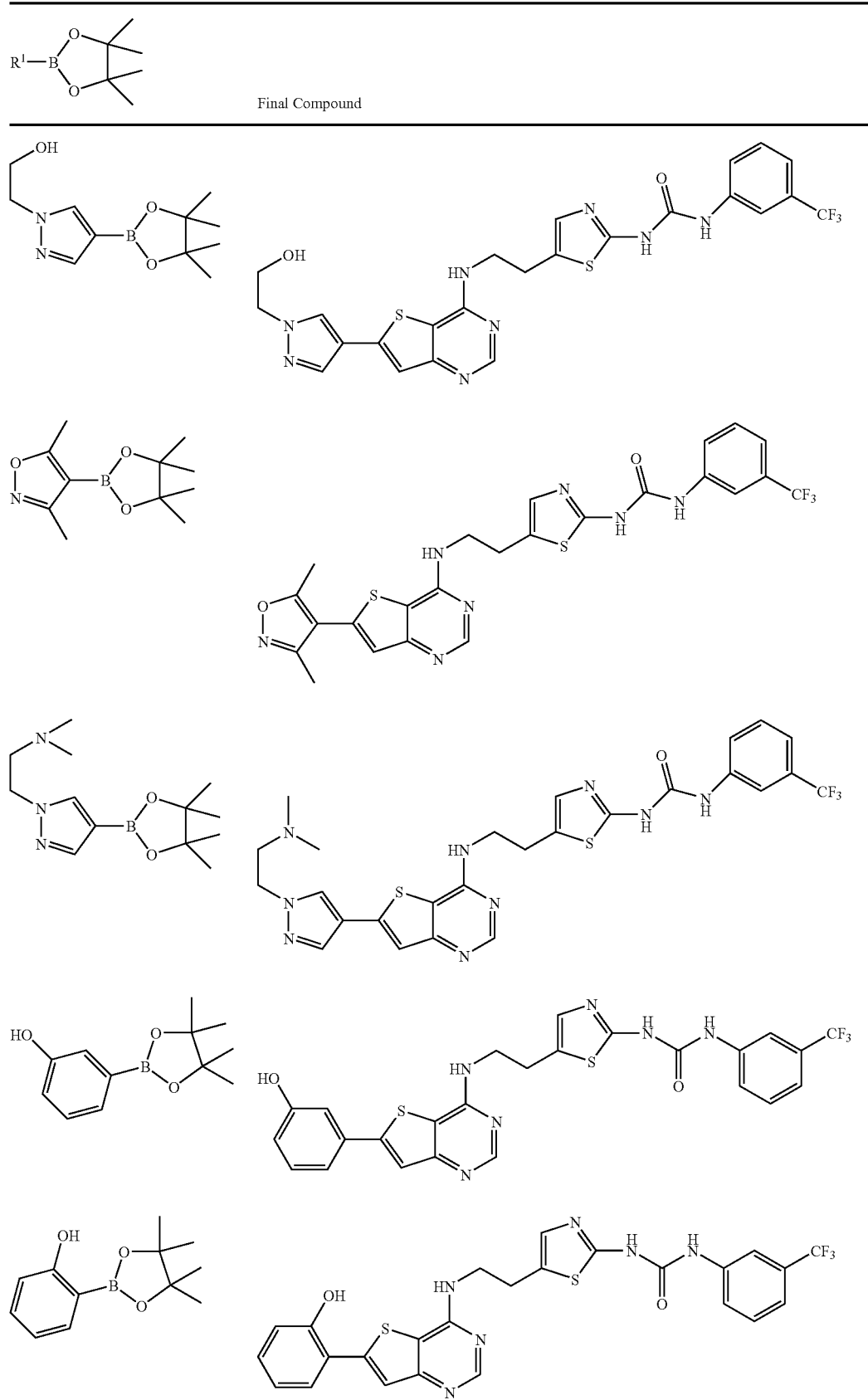

TABLE 10-continued

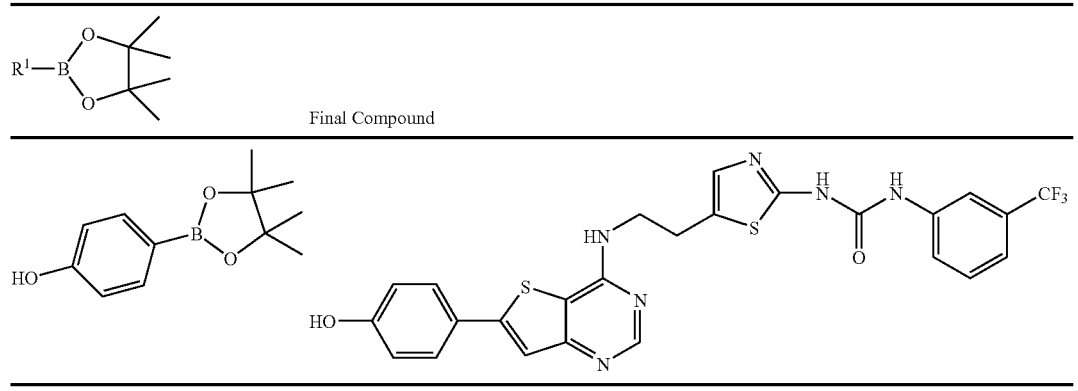

| | Final Compound |
|---|---|

Example 36

This example describes an alternate synthesis of

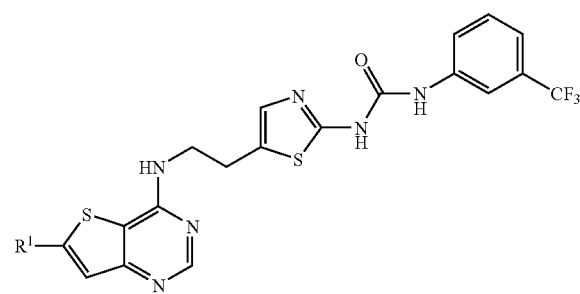

where R¹ is as previously described. Illustrative examples of suitable R¹'s are found throughout this disclosure as well as in Table 10. These compounds are made according to Example 15 except that compound 34.1 and

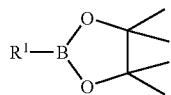

are used instead of compound 20.2 and 4-pyridineboronic acid in step 3.

Example 37

This example describes the synthesis of

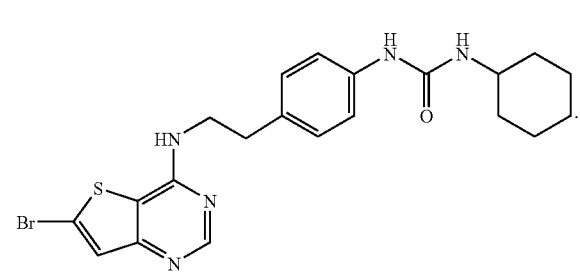

[2-(4-Amino-phenyl)-ethyl]-(6-bromo-thieno[3,2-d]pyrimidin-4-yl)-amine (compound 37.1; 75 mg, 100 mol %) was suspended in N-methyl-2-pyrrolidone (0.5 mL) and DIEA (150 uL, 400 mol %). To this solution was added cyclohexyl isocyanate (110 mol %). The reaction was heated at 95° C. for 1 hour, cooled and purified by reverse phase HPLC to provide the titled compound. LCMS [M+H]+ m/z 474.2

Example 38

This example describes the synthesis of

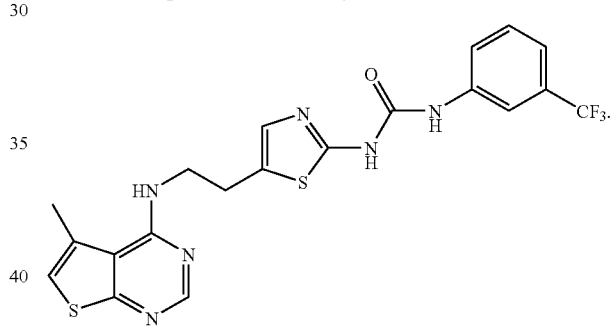

1-[5-(2-Amino-ethyl)-thiazol-2-yl]-3-(3-trifluoromethyl-phenyl)-urea (compound 38.1; 200 mg, 100 mol %), 5-methyl-4-chloro-[2,3-d]thienopyrimidine (112 mg, 100 mol %) and DIEA (500 mol %) in DMF (2 mL) was heated at 100° C. for 15 min, cooled and purified by reverse phase HPLC to provide the titled compound. LCMS [M+H]+ m/z 479.1

Example 39

This example describes the synthesis of

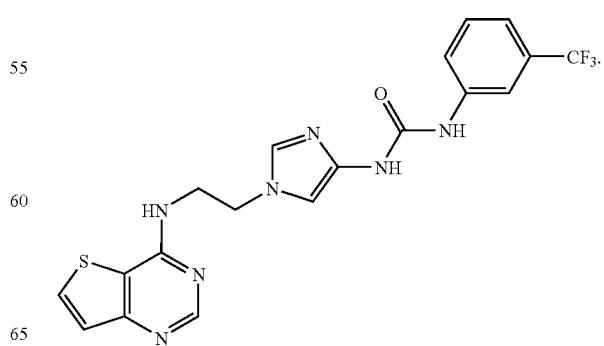

Step 1: A mixture of methanesulfonic acid 2-tert-butoxycarbonylamino-ethyl ester (compound 39.1; 2.04 g, 8.53 mmol, prepared according to the procedure of Hey, M. P. et. al J. Med. Chem 37, 1994, 381), 4-nitroimidazole (876 mg, 7.75 mmol), $K_2CO_3$ (1.18 g, 8.53 mmol), in DMF is stirred at 110° C. for 2 hours. After cooling to room temperature, the mixture is diluted with EtOAc and washed with water. The aqueous layer was extracted three times with EtOAc and the combined organic phases were dried ($Na_2SO_4$) and concentrated. The crude residue was purified by flash column chromatography ($SiO_2$, 45 to 100% EtOAc in hexanes) to yield 634 mg (32%) of [2-(4-nitro-imidazol-1-yl)-ethyl]-carbamic acid tert-butyl ester (compound 39.2) as a solid, ES (+) MS m/e=257 (M+H$^+$).

Step 2: A flask containing compound 39.2 (400 mg, 1.56 mmol) and 10% (dry basis) palladium on activated carbon (~50% wet, Deguessa, 664 mg, ~0.312 mmol) in MeOH (6.0 mL) was sealed with a septum and purged with nitrogen followed by hydrogen. The mixture was stirred under hydrogen (balloon pressure) at ambient temperature for 3 hours. After completion of the reaction, the mixture was filtered through a plug of celite and concentrated. The residue was dried under high-vacuum to yield 353 mg (quantitative) of [2-(4-amino-imidazol-1-yl)-ethyl]-carbamic acid tert-butyl ester (compound 39.3) as a solid, ES (+) MS m/e=227 (M+H$^+$).

Step 3: To a solution of compound 39.3 in dichloromethane under nitrogen was added 3-trifluoromethylphenyl isocyanate dropwise. After about 0.1 hour, a white precipitate formed. The precipitate was filtered off, washed with dichloromethane and dried under high-vacuum to yield 485 mg (75%) of (2-{4-[3-(3-trifluoromethyl-phenyl)-ureido]-imidazol-1-yl}ethyl)-carbamic acid tert-butyl ester (compound 39.4) as a white solid, ES (+) MS m/e=414 (M+H$^+$).

Step 4: A mixture of compound 39.4 (485 mg, 1.17 mmol) and 4.0 N HCl in dioxane (10.0 mL) was stirred at room temperature for 0.25 hour. The solvent was then removed under reduced pressure and the residue was dried under high-vacuum to yield 410 mg (91%) of a HCl salt of 1-[1-(2-amino-ethyl)-1H-imidazol-4-yl]-3-(3-trifluoromethyl-phenyl)-urea (compound 39.5) as a white solid, ES (+) MS m/e=314 (M+H$^+$).

Step 5: A mixture of compound 39.5 (309 mg, 0.800 mmol) and compound 6.2 (137 mg, 0.800 mmol) in DIEA/n-BuOH (1:1, 4.0 mL) was heated at 100° C. in a sealed tube behind a blast shield for 2 hours. After cooling to room temperature the mixture was concentrated under reduced pressure. The residue thus obtained was dried under high-vacuum and then purified by flash column chromatography on silica gel (0 to 10% MeOH in dichloromethane) to yield 222 mg (62%) of a solid, $R_f$ 0.32 (10% MeOH in dichloromethane). ES (+) MS m/e=448 (M+H$^+$). This material was further purified on a C-18 column (10 g, 0 to 100% MeCN in aq. 0.01 N HCl). The fractions containing pure compound were pooled and lyophilized to yield 157 mg (38%) of the titled compound as a white solid. ES (+) MS m/e=448 (M+H$^+$).

Example 40

This example describes the synthesis of

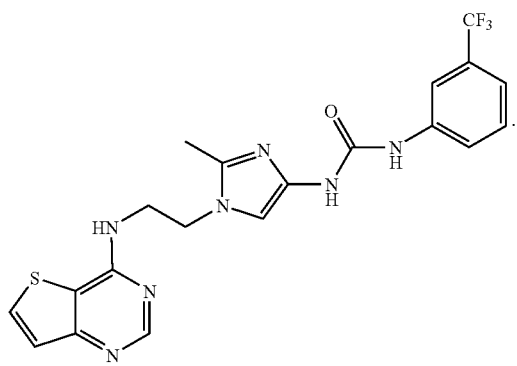

Step 1: Compound 39.1 (2.0 g, 8.4 mmol) and 2-methyl-5-nitroimidazole (1.0 g, 8.4 mmol) in DMF (50 mL) were heated to 110° C. for 2 hours. The resulting reaction mixture was cooled to room temperature and diluted with water and EtOAc. The organic layer was separated and the aqueous layer extracted with EtOAc. The combined organic layers were washed with brine, dried over $MgSO_4$, filtered, concentrated and purified by flash column chromatography on silica gel using 40% EtOAc in hexanes to afford [2-(2-methyl-4-nitro-imidazol-1-yl)-ethyl]-carbamic acid tert-butyl ester (compound 40.1; 0.44 g, 19%). ES (+) MS m/e=271(M+1).

Step 2: 10% wt Pd/C (0.17 g 0.16 mmol) was added to a solution of compound 40.1 (0.44 g, 1.6 mmol) in MeOH (10 mL). The resulting reaction mixture was stirred under a hydrogen atmosphere (1 atm via a balloon). After 2 hours, the reaction mixture was filtered thru a plug of Celite and the resulting filtrate concentrated to provide [2-(4-amino-2-methyl-imidazol-1-yl)-ethyl]-carbamic acid tert-butyl ester (compound 40.2; 0.3 g, 77%). ES (+) MS m/e=241(M+1).

Step 3: 3-Trifluoromethylphenyl isocyanate (0.23 g, 1.2 mmol) was added to a solution of compound 40.2 (0.30 g, 1.2 mmol) in dichloromethane (5 mL). The reaction mixture was stirred for 15 minutes, concentrated and purified by flash column chromatography on silica gel using EtOAc to provide (2-{2-methyl-4-[3-(3-trifluoromethyl-phenyl)-ureido]-imidazol-1-yl}-ethyl)-carbamic acid tert-butyl ester (compound 40.3; 0.11 g, 21%). ES (+) MS m/e=428(M+1).

Step 4: 4 N HCl in dioxanes (3 mL) was added to a solution of compound 40.3 (0.11 g, 0.26 mmol) in dichloromethane (3 mL). The reaction mixture stirred for 2 hours and concentrated to provide 1-[1-(2-amino-ethyl)-2-methyl-1H-imidazol-4-yl]-3-(3-trifluoromethyl-phenyl)-urea (compound 40.4; 0.10 g, 100%) as a HCl salt. ES (+) MS m/e=328(M+1).

Step 5: 4-chloro-thieno[3,2-d]pyrimidine (0.040 g, 0.25 mmol) was added to a solution of compound 40.4 (0.094 g, 0.25 mmol) and DIEA (0.13 mL, 0.94 mmol) in n-butanol (3 mL). The resulting reaction mixture was heated at 100° C. for 2 hours, cooled and concentrated to dryness. The resulting residue was purified by reverse phase HPLC to provide the titled compound (0.011 g, 10%). ES (+) MS m/e=462(M+1).

Example 41

This example describes the synthesis of

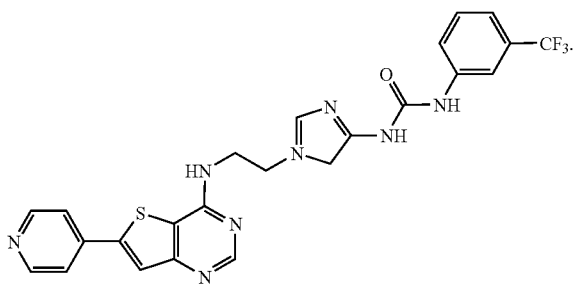

Step 1: A mixture of compound 39.5 (102 mg, 0.292 mmol) and 2-bromo-4-chloro-thieno[3,2-d]pyrimidine (73 mg, 0.292 mmol) in DIEA/n-butanol (1:1, 1.0 mL) was heated at 100° C. in a sealed tube behind a blast shield for 2 hours. After cooling to room temperature the mixture was concentrated under reduced pressure. The residue thus obtained was dried under high-vacuum and then purified by preparative TLC (SiO$_2$, 10% MeOH in dichloromethane) to yield 80 mg (52%) of 1-{1-[2-(6-bromo-thieno[3,2-d]pyrimidin-4-ylamino)-ethyl]-1H-imidazol-4-yl}-3-(3-trifluoromethyl-phenyl)-urea (compound 41.1) as a solid, R$_f$ 0.34 (10% MeOH in dichloromethane). ES (+) MS m/e=528 (M+H$^+$).

Step 2: To a degassed mixture of compound 41.1 (119 mg, 0.226 mmol), 4-pyridine boronic acid 83 mg, 0.677 mmol), 0.8 mL aq. KH$_2$PO$_4$ (1.0 M, 0.8 mmol), in DMF at 100° C. was added Pd$_2$ (dba) 3 (21 mg, 0.0226 mmol) and triphenylarsine (17 mg, 0.0542 mmol). The resulting mixture was stirred at 100° C. under nitrogen for 6 hours. After cooling to room temperature, the mixture was partitioned between water and EtOAc and filtered through a plug of celite. The aqueous layer was extracted twice with EtOAc. The combined organic layers were dried (Na$_2$SO$_4$) and concentrated. The crude residue was purified preparative TLC (SiO$_2$, 10% MeOH in dichloromethane) to yield a solid, R$_f$ 0.27 (10% MeOH in dichloromethane). The solid was taken up in MeOH/dichloromethane and treated with 2.0 M HCl in ether. The resulting mixture was concentrated and the residue was lyophilized under high-vacuum to yield 15.3 mg of the titled compound as a white solid. ES (+) MS m/e=525 (M+H$^+$).

Example 42

This example describes the synthesis of

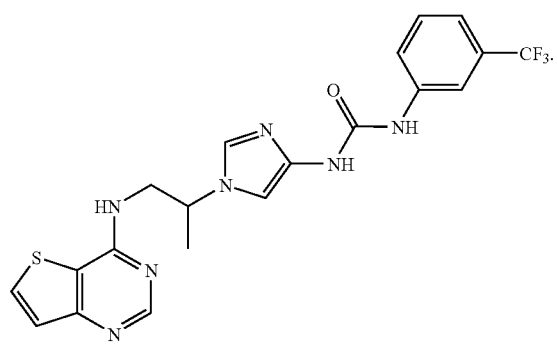

Step 1: To a mixture of 1-amino-propan-2-ol (compound 42.1; 3.53 g, 47.0 mmol) and TEA (25 mL) in MeOH (35 mL) was slowly added a solution of di-tert-butyl dicarbonate (10.3 g, 47.0 mmol) in MeOH (15 mL). The resulting solution was stirred at room temperature over night. The mixture was then concentrated and the residue was dried under high-vacuum to yield 8.23 g (quantitative) of a clear oil. The oil thus obtained was dissolved in THF (100 mL) and treated with TEA (13.1 mL, 94.0 mmol). To the resulting solution was added methansulfonyl chloride (0.3.82 mL, 49.3 mmol) dropwise at 0° C. under nitrogen. After 1 hour, the mixture was diluted with EtOAc and washed with aqueous 1 M HCl, aq sodium bicarbonate, and brine. The organic phase was dried (Na$_2$SO$_4$) and concentrated to yield 10.5 g (88%) of (compound 42.2) as a clear oil which solidified upon standing, ES (+) MS m/e=254 (M+H$^+$).

Step 2: The titled compound was prepared according to Example 39 except that compound 42.2 was used instead of compound 39.1 in step 1.

Example 43

This example describes the synthesis of

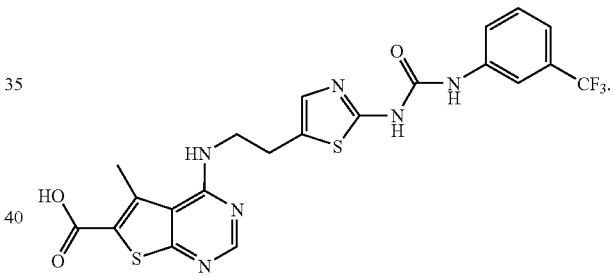

Step 1: A 20 mL vial was charged with 4-chloro-5-methyl-thieno[2,3-d]pyrimidine-6-carboxylic acid methyl ester (250 mg, 100 mol %), compound 38.1 (341 mg, 100 mole %), DIEA (1 mL) and DMF (2 mL). The resulting suspension was heated at 110° C. for 2 hours and cooled to room temperature. Concentration in vacuo provided 5-methyl-4-(2-{2-[3-(3-trifluoromethyl-phenyl)-ureido]-thiazol-5-yl}-ethylamino)-thieno[2,3-d]pyrimidine-6-carboxylic acid methyl ester; compound with methane (compound 43.1) as a solid that was used in the next reaction without further purification. LCMS [M+H]$^+$ m/z 537.2

Step 2: A 20 mL vial was charged with compound 43.1 (100 mg), DMF (1 mL), and 2N NaOH (2 mL). The reaction was stirred at room temperature for 10 minutes and then purified by reverse phase HPLC (aqueous 0.1% CF$_3$COOH/MeCN gradient). The appropriate fractions were pooled, concentrated in vacuo to ~5 mL and lyophilized to dryness to provide the titled compound. LCMS [M+H]$^+$ m/z 523.1

Example 44

This example describes the synthesis of

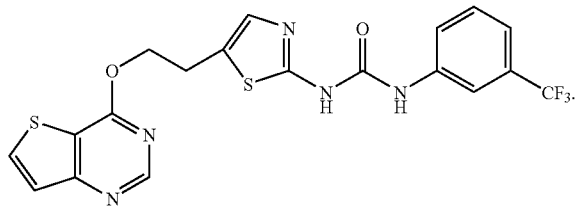

Step 1: To a solution of the HBr salt of (2-amino-thiazol-5-yl)-acetic acid methyl ester (compound 44.1; 20 mmol) in DIEA (40 mmol) and DMF (100 mL) was added 3-trifluoromethylphenyl isocyanate (20 mmol) at room temperature. After overnight stirring, the reaction mixture was concentrated and purified by flash column chromatography on silica gel to provide {2-[3-(3-trifluoromethyl-phenyl)-ureido]-thiazol-5-yl}-acetic acid methyl ester (compound 44.2) in 60% yield. EIMS (m/z): calcd. for $C_{14}H_{12}F_3N_3O_3S$ ($M^+$)+H 360.06. found 360.10.

Step 2: To a solution of compound 44.2 (10 mmol) in dry THF (50 mL) was added lithium aluminum hydride ("LAH"; 30 mmol; 1.0 M in THF) at room temperature. After stirring for 30 minutes, the reaction mixture was cooled and treated with the cautious addition of ice water. The solvent was removed, diluted with saturated sodium bicarbonate and extracted with EtOAc. The organic layers were combined, dried, concentrated and purified by flash column chromatography on silica gel to provide 1-[5-(2-hydroxy-ethyl)-thiazol-2-yl]-3-(3-trifluoromethyl-phenyl)-urea (compound 44.3) in 95% yield. EIMS (m/z): calcd. for $C_{13}H_{12}F_3N_3O_2S$ ($M^+$)+H 332.06. found 332.10.

Step 3: To a solution of compound 44.3 (0.15 mmol) in dry DMF (2 mL) was added NaH (0.45 mmol, 60% oil dispersion) at room temperature and stirred for 30 minutes. Subsequently, 4-chlorothieno[3,-d]pyrimidine (0.15 mmol) was added and the resulting mixture was stirred at 60° C. for 1 hour and quenched by the addition of several drops of saturated ammonium chloride. The solvent was removed and the residue was purified by flash column chromatography on silica gel to provide the titled compound in 30% yield. EIMS (m/z): calcd. for $C_{19}H_{14}F_3N_5O_2S_2$ ($M^+$)+H 466.05. found 466.90.

Example 45

This example describes the synthesis of

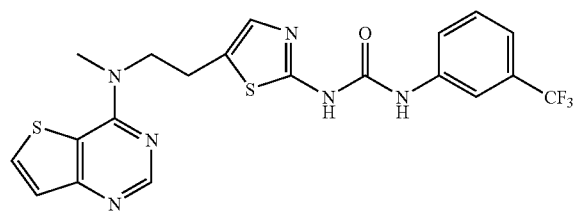

Step 1: A mixture of compound 44.2 (2.0 mmol) and anhydrous $MgCl_2$ (2.0 mmol) in methylamine (10 mL of a 2.0 M solution in THF) was stirred at room temperature for several hours. The mixture was concentrated, diluted with EtOAC and filtered. The filtrate was washed with brine, dried, concentrated and purified by flash column chromatography on silica gel to provide the intermediate amide in 90% yield. EIMS (m/z): calcd. for $C_{14}H_{13}F_3N_4O_2S$ ($M^+$)+H 359.07. found 359.10. To a solution of the intermediate amide (1.0 mmol) in dry THF (5.0 mL) was added LAH (3.0 mmol, 1.0 M in THF) at room temperature. The resulting mixture was stirred at 60° C. for several hours, cooled to 0° C. and hydrolyzed with the addition of ice water. The mixture was concentrated, diluted with saturated sodium bicarbonate and extracted with EtOAc. The organic layer was then dried, concentrated and purified by flash column chromatography on silica gel to provide 1-[5-(2-methylamino-ethyl)-thiazol-2-yl]-3-(3-trifluoromethyl-phenyl)-urea (compound 45.1) in 85% yield. EIMS (m/z): calcd. for $C_{14}H_{15}F_3N_4OS$ ($M^+$)+H 345.09. found 344.90.

Step 2: A mixture of compound 45.1 (0.15 mmol), compound 6.2 (0.15 mmol) and DIEA (0.15 mmol) in DMF (2.0 mL) was stirred at 100° C. for 2 hours. The solvent was removed and the residue purified by flash column chromatography on silica gel to provide the titled compound in 20% yield. EIMS (m/z): calcd. for $C_{20}H_{17}F_3N_6OS_2$ ($M^+$)+H 479.09. found 479.10.

Example 46

This example describes the synthesis of

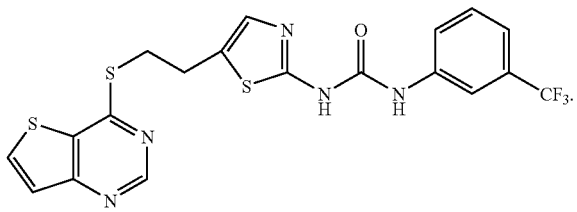

Step 1: To a solution of compound 44.3 (2.0 mmol) in dry dichloromethane (10 mL) was added TEA (2.0 mmol) and tosyl chloride (2.2 mmol) at room temperature. The resulting mixture was stirred at room temperature for several hours, concentrated and purified by flash column chromatography on silica gel to provide the intermediate tosylate in 32% yield. EIMS (m/z): calcd. for $C_{20}H_{18}F_3N_3O_4S_2$ ($M^+$)+H 486.07. found 466.10. To a solution of the intermediate tosylate (0.5 mmol) in DMF (2.0 mL) was added potassium thioacetate (1.0 mmol) and the mixture was stirred at 90° C. for 2 hours. The solvent was removed and the residue was purified by flash column chromatography on silica gel to provide thioacetic acid S-(2-{2-[3-(3-trifluoromethyl-phenyl)-ureido]-thiazol-5-yl}-ethyl) ester (compound 46.1) in 90% yield. EIMS (m/z): calcd. for $C_{15}H_{14}F_3N_3O_{282}$ ($M^+$)+H 390.05. found 390.00.

Step 2: A mixture of compound 46.1 (0.15 mmol), compound 6.2 (0.15 mmol), and $K_2CO_3$ (0.16 mmol) in DMF (2.0 mL) was stirred at 90° C. for 1 hour. The solvent was removed and the residue purified by flash column chromatography on silica gel to provide the titled compound in 42% yield. EIMS (m/z): calcd. for $C_{19}H_{14}F_3N_5O_2S_3$ ($M^+$)+H 482.03. found 482.00.

Example 47

This example describes the synthesis of

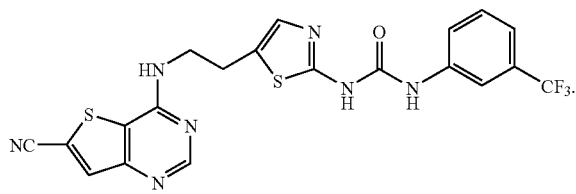

Step 1: To a suspension of compound 6.2 (5.0 mmol) in dry THF (25.0 mL) was added lithium diisopropylamide ("LDA"; 6.0 mmol; 2.0 M in heptane/THF/ethylbenzene) at −78° C. under an atmosphere of $N_2$. After stirring at −78° C. for 30 minutes, the mixture was transferred to a pre-cooled solution of TsCN (8.0 mmol) in dry THF (10 mL) at −78° C. The resulting mixture was slowly warmed to room temperature and stirred for several hours. The reaction was quenched by the addition of several drops of saturated ammonium chloride and then concentrated. The residue was diluted with saturated sodium bicarbonate and extracted with EtOAc. The organic layers was dried, concentrated and purified by flash column chromatography on silica gel to provide 4-chloro-thieno[3,2-d]pyrimidine-6-carbonitrile c (compound 47.1) in 20% yield. EIMS (m/z): calcd. for $C_7H_2CN_3S$ ($M^+$)+H 195.97. found 196.00.

Step 2: A mixture 47.1 (0.15 mmol), compound 38.1 (0.15 mmol) and DIEA (0.15 mmol) in DMF (2.0 mL) was stirred at 100° C. for 2 h. The solvent was removed and the residue purified by reverse phase HPLC (aqueous 0.1% $CF_3COOH$/MeCN gradient) to provide the titled compound in 40% yield. EIMS (m/z): calcd. for $C_{20}H_{14}F_3N_7OS_2$ ($M^+$)+H 490.07. found 490.90.

Example 48

This example describes the synthesis of

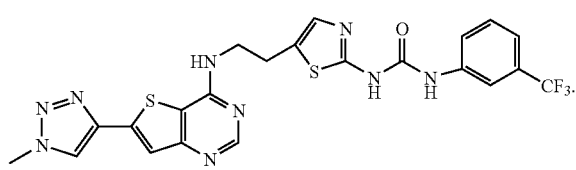

Step 1: A mixture of 6-bromo-4-chloro-thieno[3,2-d]pyrimidine (10.0 mmol), (trimethylsilyl)acetylene (12.0 mmol), $Pd(PhCN)_2Cl_2$, (1.0 mmol), CuI (1.0 mmol) and TEA (2.0 mmol) in dry THF (60.0 mL) was flushed with dry $N_2$ for several minutes and stirred at 60° C. for 30 minutes under an atmosphere of $N_2$. The solvent was removed and the residue purified by flash column chromatography on silica gel to provide 4-chloro-6-trimethylsilanylethynyl-thieno[3,2-d]pyrimidine (compound 48.1) in 65% yield. EIMS (m/z): calcd. for $C_{11}H_{11}ClN_2SSi$ ($M^+$)+H 266.01. found 266.00.

Step 2: To a solution of compound 48.1 (5.0 mmol) in THF (50 mL) was tetrabutylammonium fluoride ("TBAF"; 5.0 mmol; 1.0 M in THF) at 0° C. After stirring at 0° C. for 5 minutes, the reaction mixture was concentrated, diluted with EtOAc, washed with saturated sodium bicarbonate, brine and dried. The solvent was removed and the residue purified by flash column chromatography on silica gel to provide 4-chloro-6-ethynyl-thieno[3,2-d]pyrimidine (compound 48.2) in 92% yield. EIMS (m/z): calcd. for $C_8H_3ClN_2S$ ($M^+$)+H 194.97. found 195.00.

Step 3: A mixture of compound 48.2 (1.0 mmol), trimethylsilylmethyl azide (5.0 mmol), CuI (0.2 mmol), and DIEA (1.0 mmol) in DMF (10 mL) was stirred at room temperature for 24 hours. The solvent was removed and the residue was diluted with water and extracted with EtOAc. The organic layer was washed with dilute aqueous ammonium hydroxide, brine, dried, concentrated and purified by flash column chromatography to provide 4-chloro-6-(1-trimethylsilanylmethyl-1H-[1,2,3]triazol-4-yl)-thieno[3,2-d]pyrimidine (compound 48.3) in 80% yield. EIMS (m/z): calcd. for $C_{12}H_{14}ClN_5SSi$ ($M^+$)+H 324.04. found 324.00.

Step 4: To a solution of compound 48.3 (0.5 mmol) in THF (10.0 mL) was added several drops of water and TBAF (0.55 mmol; 1.0 M in THF) at 0° C. The resulting mixture was stirred at 0° C. for 15 minutes, concentrated and washed with hexanes. The white solid that formed was suspended in ice water (10 mL), filtered, washed with ice water and dried in vacuo to provide 4-chloro-6-(1-methyl-1H-[1,2,3]triazol-4-yl)-thieno[3,2-d]pyrimidine (compound 48.4) in 95% yield. EIMS (m/z): calcd. for $C_9H_6ClN_5S$ ($M^+$)+H 252.00. found 252.00.

Step 5: A mixture of compound 48.4 (0.15 mmol), compound 38.1 (0.15 mmol) and DIEA (0.15 mmol) in DMF (2.0 mL) was stirred at 100° C. for 8 hours. The solvent was removed and the residue was purified by flash column chromatography on silica gel to provide the titled compound in 10% yield. EIMS (m/z): calcd. for $C_{22}H_{18}F_3N_9OS_2$ ($M^+$)+H 546.10. found 545.85.

Example 49

This example describes the synthesis of

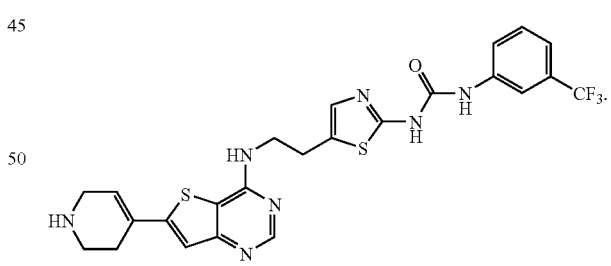

A 100 mL vial was charged with compound 34.1 (125 mg, 100 mol %), 4-(4,4,5,5-tetramethyl-[1,3,2]dioxaborolan-2-yl)-3,6-dihydro-2H-pyridine-1-carboxylic acid tert-butyl ester (86 mg, 120 mole %), and $PdCl_2(PPh_3)_2$ (33 mg, 20 mol %). To this was added DMF/$H_2O$ (4:1, 1 mL) along with 2N $Na_2CO_3$ (0.3 mL). The vial was flushed with nitrogen, sealed, and subjected to microwave irradiation (10 minutes, 300 W, 100° C.). The contents were cooled and concentrated in vacuo. The resulting residue was purified by reverse phase HPLC (aqueous 0.1% $CF_3COOH$/MeCN gradient) resulting in a 1:1 mixture of 1-{5-[2-(thieno[3,2-d]pyrimidin-4- ylamino)-ethyl]-thiazol-2-yl}-3-(3-trifluoromethyl-phenyl)-urea; compound with 3,6-dihydro-2H-pyridine-1-carboxylic acid tert-butyl ester (compound 50.1) and the titled compound. This mixture was dissolved in 4N HCl/dioxane (2 mL), stirred at room temperature for 15 minutes, and concentrated in vacuo to provide exclusively the HCl salt of the titled compound as a yellow powder LCMS [M+H]$^+$ m/z 546.1.

Example 52

This example describes the synthesis of

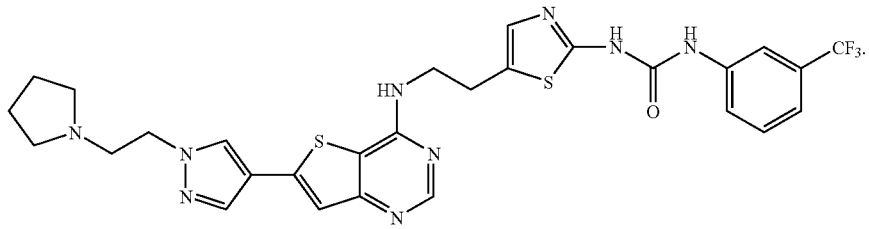

Step 1: To a flame dried flask was placed a suspension of compound 6.2 (5.92 mmol) in THF (50 mL). The reaction was cooled to −78° C. and a solution of LDA (3.25 mL of a 2.0 M solution in heptane/THF/ethyl benzene) was slowly added. After stirring for 30 minutes, a −78° C., a solution of (n-Bu)$_3$SnCl (1.9 mL) in THF (50 mL) was added via cannula over a 20 minute period at −78° C. and stirred for 2 hours. The reaction was warmed to room temperature, hydrolyzed with saturated NH$_4$Cl, extracted with EtOAc, dried and concentrated. The crude product was purified by flash column chromatography on silica gel (1:1 hexanes/dichloromethane then 10% EtOAc/dichloromethane) to provide 4-chloro-6-tributylstannanyl-thieno[3,2-d]pyrimidine (compound 52.1) in 92% yield.

Step 2: Compound 52.1 (22.58 mmol) and 4-iodo-1-(2-pyrrolidin-1-yl-ethyl)-1H-pyrazole (22.32 mmol) was dissolved in DMF and degassed with nitrogen. To this was added Pd$_2$(dba)$_3$ (0.23 mmol), Ph$_3$As (0.46 mmol) and CuI (1.16 mmol). The reaction mixture was heated at 80° C. for 6 hours, concentrated to dryness and purified by flash column chromatography on silica gel (10% MeOH in dichloromethane) to provide 4-chloro-6-[1-(2-pyrrolidin-1-yl-ethyl)-1H-pyrazol-4-yl]-thieno[3,2-d]pyrimidine (compound 52.2).

Step 3: Compound 52.2 (3.04 mmol), compound 38.1 (3.03 mmol) and DIEA (6.88 mmol) in DMF (10 mL) was heated at 100° C. for 2 hours. The reaction mixture was concentrated to dryness and purified by column chromatography on C$_{18}$ silica gel to provide the titled compound.

Example 50

This example describes the synthesis of

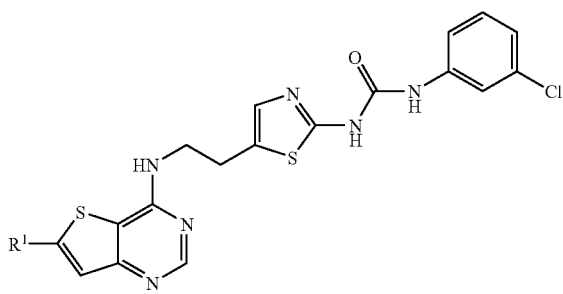

where R$^1$ is as described previously. These compounds are made according to Example 29 except that R$^1$B(OH)$_2$ is used instead of 4-pyridineboronic acid in step 1 and 3-chlorophenyl isocyanate is used instead of 3-trifluoromethylphenyl isocyanate in step 2. Illustrative examples of suitable R$^1$'s are found throughout this disclosure as well as in Table 9.

Example 51

This example describes the synthesis of

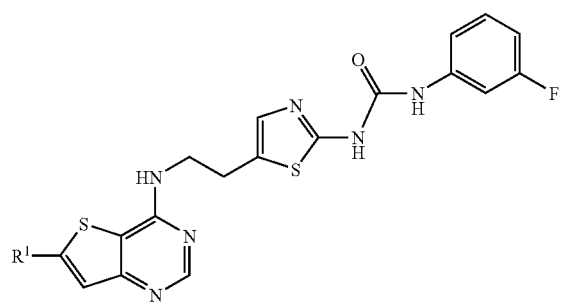

where R$^1$ is as described previously. These compounds are made according to Example 29 except that R$^1$B(OH)$_2$ is used instead of 4-pyridineboronic acid in step 1 and 3-fluorophenyl isocyanate is used instead of 3-trifluoromethylphenyl isocyanate in step 2. Illustrative examples of suitable R$^1$'s are found throughout this disclosure as well as in Table 9.

Example 53

This example describes the synthesis of

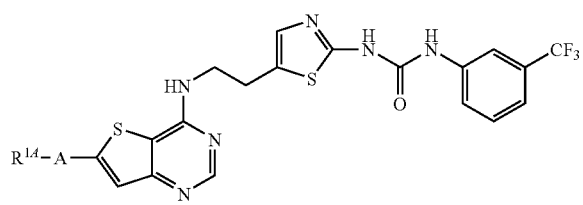

where A and $R^{1A}$ are as previously described. These compounds are made according to Example 52 except that $R^{1A}$-A-I is used instead of 4-iodo-1-(2-pyrrolidin-1-yl-ethyl)-1H-pyrazole in step 2. Illustrative examples of suitable $R^{1A}$'s and A's are found throughout this disclosure as well as in Table 11.

TABLE 11

| $R^{IA}$-A-I | Final Compound |
|---|---|

Example 54

This example describes the synthesis of

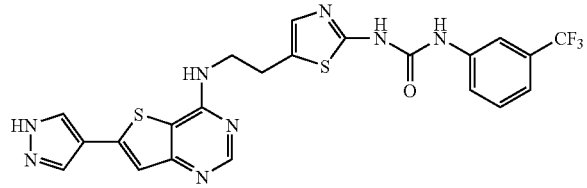

Step 1: 1-[5-(2-{6-[1-(4-Methoxy-benzyl)-1H-pyrazol-4-yl]-thieno[3,2-d]pyrimidin-4-ylamino}-ethyl)-thiazol-2-yl]-3-(3-trifluoromethyl-phenyl)-urea (compound 54.1) is synthesized according to Example 53.

Step 2: Compound 54.1 (0.19 mmol) is heated at 60° C. in neat TFA for 8 hours. The reaction was evaporated to dryness and purified by column chromatography on $C_{18}$ silica gel to provide the titled compound.

Example 55

This example describes the synthesis of

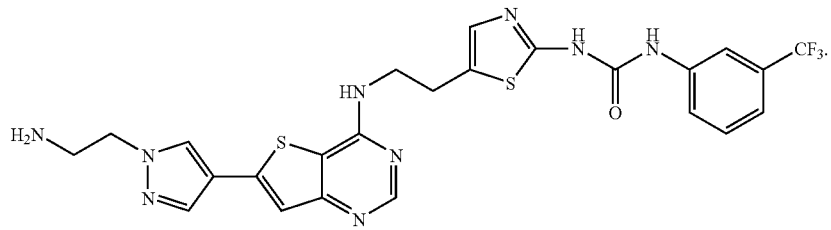

Step 1: 1-{5-[2-(6-{1-[2-(1,3-Dioxo-1,3-dihydro-isoindol-2-yl)-ethyl]-1H-pyrazol-4-yl}-thieno[3,2-d]pyrimidin-4-ylamino)-ethyl]-thiazol-2-yl}-3-(3-trifluoromethyl-phenyl)-urea (compound 55.1) is synthesized according to Example 53.

Step 2: To a solution of compound 55.1 in ethanol was added hydrazine (22 equivalents) and the reaction mixture was heated at 60° C. for 2.5 hours. The reaction is concentrated to dryness and the residue purified by preparative TLC (10% 7.0 M $NH_3$/MeOH in dichloromethane) to provide the titled compound.

Example 56

This example describes the synthesis of

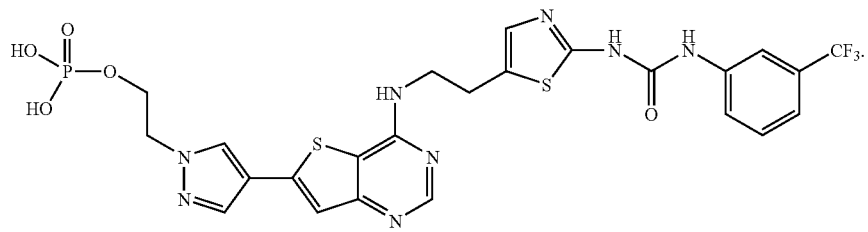

Step 1: 1-[5-(2-{6-[1-(2-Hydroxy-ethyl)-1H-pyrazol-4-yl]-thieno[3,2-d]pyrimidin-4-ylamino}-ethyl)-thiazol-2-yl]-3-(3-trifluoromethyl-phenyl)-urea (compound 56.1) is synthesized according to Example 33 or Example 53.

Step 2: To a solution of compound 56.1 (0.17 mmol) in THF was added $POCl_3$ (10.9 mmol) at room temperature. After 2 hours, an additional equivalent of $POCl_3$ was added and the reaction was stirred for 4 hours. Water was added and the reaction mixture was stirred for an additional 1 hour. Volatiles were removed under reduced pressure and the residue purified by reverse phase HPLC to provide the titled compound along with recovered compound 56.1.

Example 57

This example describes the synthesis of

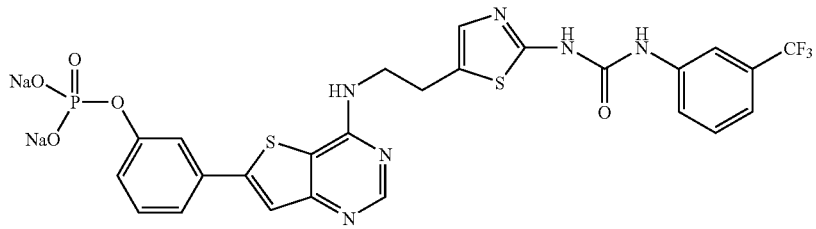

Step 1: 1-(5-{2-[6-(3-Hydroxy-phenyl)-thieno[3,2-d]pyrimidin-4-ylamino]-ethyl}-thiazol-2-yl)-3-(3-trifluoromethyl-phenyl)-urea (compound 57.1) was synthesized according to Example 35.

Step 2: To a solution of compound 57.1 (0.20 mmol) in THF (20 mL) was added 1-H-tetrazole (6.0 mL of a 3% w/w in CH$_3$CN). The reaction was purged with nitrogen and di-tert-butyl diethylphosphoramidite (1.06 mmol) was added. After stirring at room temperature for 3.5 hours, tert-butyl hydroperoxide (5 mL of 70% aqueous solution) was added. After stirring for 1 hour, the reaction was cooled to 0° C. followed by the addition of NaHSO$_3$ (15 mL of a 5% aqueous solution). After an additional 1 hour, the reaction mixture was extracted with dichloromethane, washed with brine, dried and concentrated to give phosphoric acid di-tert-butyl ester 3-[4-(2-{2-[3-(3-trifluoromethyl-penta-2,4-dienyl)-ureido]-thiazol-5-yl}-ethylamino)-thieno[3,2-d]pyrimidin-6-yl]-phenyl ester (compound 57.2)

Step 3: Crude compound 57.2 from the previous reaction was dissolved in dichloromethane and TFA (0.1 mL) was added. The reaction was stirred at room temperature overnight, concentrated to dryness and purified by reverse phase HPLC. The lyophilized product was washed with EtOAc to give a beige precipitate. The precipitate was stirred at room temperature with a suspension of ~2 g of Dowex cation exchange resin (Na$^+$ form) in water and CH$_3$CN for 2 hours. The resin was filtered and the filtrate lyophilized to give the titled compound.

Example 58

This example describes the synthesis of

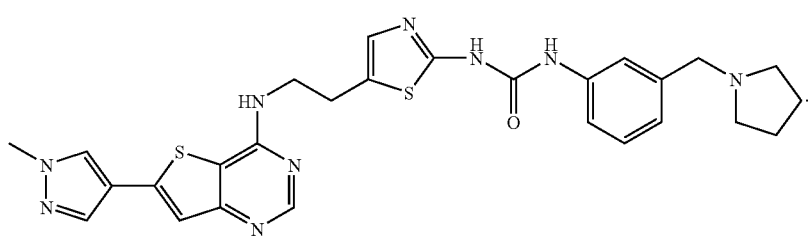

Step 1: To a suspension of a HBr salt of 2-[2-(2-amino-thiazol-5-yl)-ethyl]-isoindole-1,3-dione (compound 58.1; 1.42 mmol) in dichloromethane was added TEA (4.30 mmol) followed by the addition of phenyl chloroformate (1.43 mmol) at room temperature. After 2 hours, the reaction was concentrated to dryness to give a solid that was suspended in EtOAc, filtered, washed with additional EtOAc and dried under vacuum to provide {5-[2-(1,3-dioxo-1,3-dihydro-isoindol-2-yl)-ethyl]-thiazol-2-yl}-carbamic acid phenyl ester (compound 58.2, which is contaminated with triethyl amine salts) which was used in the next reaction without further purification.

Step 2: Compound 58.2 (0.64 mmol), 3-pyrrolidin-1-ylm-ethyl-phenylamine (0.64 mmol) and TEA (2.15 mmol) are dissolved in DMF and heated at 75° C. for 30 minutes. The reaction is concentrated to dryness and purified by flash column chromatography on silica gel (10% 7.0 M NH$_3$/MeOH in dichloromethane) to provide the desired urea. The urea was dissolved in ethanol and treated with hydrazine (0.06 mL) at 70° C. for 3 hours and concentrated. The residue is suspended and sonicated in dichloromethane, filtered and co-evaporated from MeOH/toluene four times to provide 1-[5-(2-amino-ethyl)-thiazol-2-yl]-3-(3-pyrrolidin-1-ylmethyl-phenyl)-urea (compound 58.3).

Step 3: A mixture of 6-bromo-4-chloro-thieno[3,2-d]pyrimidine (4.0 mmol), 1-methyl-4-(4,4,5,5-tetramethyl-[1,3,2]dioxaborolan-2-yl)-1H-pyrazole (4.4 mmol), Pd$_2$(dba)$_3$ (0.8 mmol), Ph$_3$As (0.8 mmol) and K$_2$HPO$_4$ (8.0 mmol) in a DMF (40 mL) and water (10 mL) are stirred at room temperature until the reaction was complete. The reaction is partitioned between EtOAc and water, washed with brine, dried, concentrated and purified by flash column chromatography on silica gel to give 4-chloro-6-(1-methyl-1H-pyrazol-4-yl)-thieno[3,2-d]pyrimidine (compound 58.4).

Step 4: Compound 58.3 (0.23 mmol), compound 58.4 (0.47 mmol) and DIEA (0.2 mL) in N,N-dimethylacetamide ("DMA") are heated at 110° C. for 5 hours. The reaction is concentrated to dryness and purified by flash column chromatography on silica gel (10% 7.0 M NH$_3$/MeOH in dichloromethane), and then is purified a second time by preparative TLC to afford the titled compound.

Example 59

This example describes the synthesis of

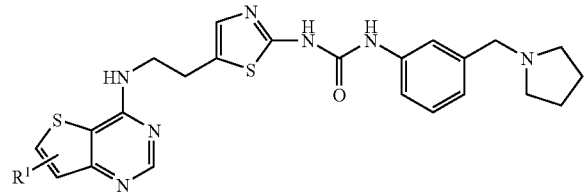

where $R^1$ is as described previously. These compounds are made according to the procedures of Example 58 except that

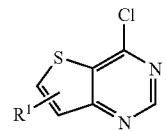

is used instead of compound 58.4 in step 4. Illustrative examples of $R^1$'s are found throughout this disclosure as well as in Table 1.

Example 60

This example describes the synthesis of

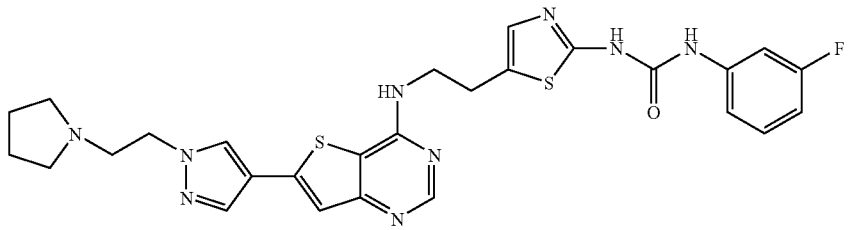

Step 1: A mixture of compound 58.1 (21.2 g) in dichloromethane (1.0 L), saturated $NaHCO_3$ (300 mL) and water (100 mL) was rapidly stirred until the organic layer became clear. The organic layer was separated and the aqueous layer was extracted with dichloromethane several times. The organic layers were combined, dried and concentrated to give the amine as a yellow solid. A portion of the amine (5.3 g) was dissolved in dichloromethane (80 mL) and treated with 3-fluorophenyl isocyanate (2.5 mL) at room temperature with overnight stirring. The solid that formed was filtered, washed with dichloromethane and dried under vacuum to provide 1-{5-[2-(1,3-dioxo-1,3-dihydro-isoindol-2-yl)-ethyl]-thiazol-2-yl}-3-(3-fluoro-phenyl)-urea (compound 60.1; 2.6 g) as a colorless solid.

Step 2: To a suspension of compound 60.1 (2.6 g) in ethanol (64 mL) was added hydrazine (2.0 mL) and the reaction stirred at 65° C. for 4 hours. The solid that formed was filtered off and the filtrate was concentrated to give 1-[5-(2-aminoethyl)-thiazol-2-yl]-3-(3-fluoro-phenyl)-urea (compound 60.2; 1.6 g) as a yellow solid.

Step 3: A solution of compound 60.2 (1.48 mmol), compound 52.2 (1.67 mmol) and DIEA (3.44 mmol) in 1-methyl-2-pyrrolidinone ("NMP") was heated at 90° C. overnight. The reaction was cooled, diluted with EtOAc, washed with water, brine, dried and concentrated. The residue was purified by column chromatography to give the titled compound.

Example 61

This example describes the synthesis of

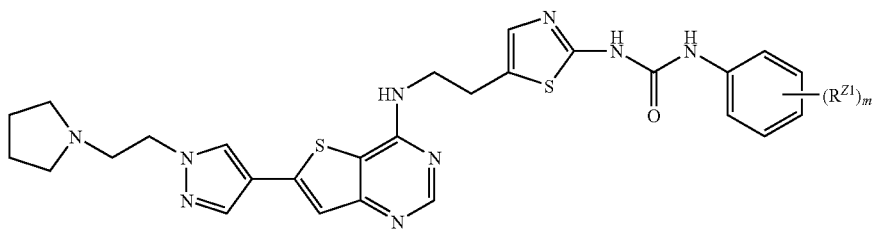

where $R^{Z1}$ and m are as described previously. These compounds are made according to the procedures of Example 60 except that

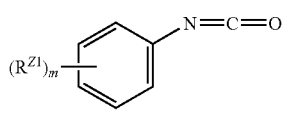

is used instead of 3-fluorophenyl isocyanate in step 1. Illustrative examples of suitable $R^{Z1}$'s are found throughout this disclosure as well as in Table 5.

Example 62

This example describes the synthesis of

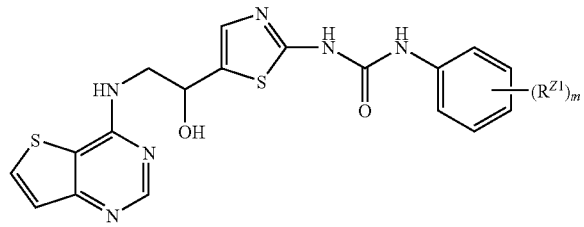

where $R^{Z1}$ and m are as described previously.

Step 1: To a suspension of 2-tert-butoxycarbonylamino-thiazole-5-carboxylic acid methyl ester (compound 62.1; 21.7 mmol) in THF was slowly added LAH (25 mL of a 1.0 M solution in THF). After stirring for 1 hour at room temperature the reaction is cautiously hydrolyzed with the sequential addition of water (0.95 mL), 15% aqueous NaOH (0.95 mL) and additional water (2.85 mL). After stirring for 30 minutes the reaction is filtered through a pad of Celite and the filtrate is dried and concentrated to give (5-hydroxymethyl-thiazol-2-yl)-carbamic acid tert-butyl ester (compound 62.2).

Step 2: To a solution of compound 62.2 (18.5 mmol) in dichloromethane is added molecular sieves (4.0 g) and PDC (39.0 mmol) at room temperature (THF is added to help dissolve the starting material). After 1.5 hours, an additional equivalent of PDC is added and the reaction is stirred for 5.5 hours. The reaction mixture is poured directly onto a silica gel column and is eluted with a gradient of 100% dichloromethane to 100% EtOAc. Fractions containing the desired product are pooled and concentrated to afford (5-formyl-thiazol-2-yl)-carbamic acid tert-butyl ester (compound 62.3).

Step 3: To a solution of compound 62.3 (4.5 mmol) in dichloromethane is added trimethylsilyl cyanide ("TMSCN"; 2.1 equivalents) and $ZnI_2$ (10% mol). After stirring at room temperature overnight, the reaction is concentrated under vacuum. The crude cyanohydrin is dissolved in THF and treated with $AlH_3$ (2.2 equivalents of a 0.5 M solution in THF). After stirring for 15 minutes, the reaction is quenched with the addition of saturated aqueous $Na_2SO_4$, is filtered through a pad of Celite, is dried and concentrated. Purification by flash column chromatography on silica gel (10% 7.0 M $NH_3$/MeOH in dichloromethane) provides [5-(2-amino-1-hydroxy-ethyl)-thiazol-2-yl]-carbamic acid tert-butyl ester (compound 62.4).

Step 4: Compound 62.4 (0.16 mmol), 4-chloro-thieno[3,2-d]pyrimidine (0.16 mmol.) and DIEA (0.28 mmol) is heated in DMA at 90° C. for 5 hours. The reaction mixture is cooled, concentrated and purified by preparative TLC (10% MeOH in EtOAc) to afford {5-[1-hydroxy-2-(thieno[3,2-d]pyrimidin-4-ylamino)-ethyl]-thiazol-2-yl}-carbamic acid tert-butyl ester (compound 62.5).

Step 5: To a solution of compound 62.5 (0.06 mmol) in dichloromethane is added anhydrous HCl (31 equivalents of a 4.0 M solution in 1,4-dioxane). After stirring for 1.5 hours at room temperature the reaction is concentrated to dryness to give a residue that is suspended in THF. To this suspension is added TEA (5.6 equivalents) and

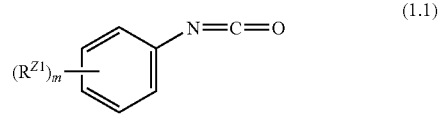

(1.1)

equivalents) and after stirring at room temperature for 1.5 hours, the reaction is concentrated and purified by preparative TLC (10% MeOH in EtOAc) to give titled compound. Illustrative examples of suitable $R^{Z1}$'s are found throughout this disclosure as well as in Table 5.

Example 63

This example describes the synthesis of

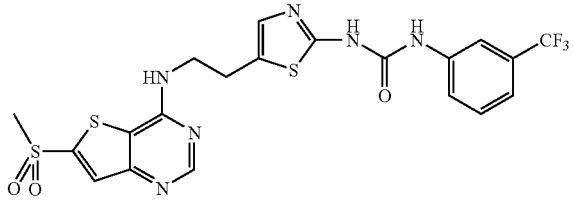

Step 1: To a suspension of compound 6.2 (5 mmol) in dry THF (25 mL) was added LDA (6 mmol, 2.0 M in heptane/THF/ethylbenzene) at −78° C. under an atmosphere of $N_2$. After stirring at −78° C. for 30 minutes, the mixture was transferred to a pre-cooled solution of methyl methanethiosulfonate (8 mmol) in of dry THF (10 mL) at −78° C. The resulting mixture was slowly warmed to room temperature and stirred for 2 hours. The reaction was quenched by the addition of several portions of sat. aq. $NH_4Cl$, concentrated and partitioned between EtOAc and saturated aqueous $NaHCO_3$. The organic layer was separated, dried and concentrated to give a residue that was purified by flash column chromatography on silica gel to give 4-chloro-6-methylsulfanyl-thieno[3,2-d]pyrimidine (compound 63.1).

Step 2: A mixture of compound 63.1 (1 mmol) and 3-chloroperoxybenzoic acid ("m-CPBA"; 2 mmol) in dichloromethane (10 mL) was stirred at room temperature for 2 hours. The reaction mixture was then diluted with dichloromethane, washed with saturated aqueous $NaHCO_3$ several times, dried and concentrated to give a residue that was purified by flash column chromatography on silica gel to give 4-chloro-6-methanesulfonyl-thieno[3,2-d]pyrimidine (compound 63.2).

Step 3: A mixture of compound 63.2 (0.2 mmol), compound 38.1 (0.2 mmol) and DIEA in DMF (2 mL) was heated at 100° C. for 2 hours. The reaction was concentrated to dryness and purified by reverse phase HPLC to provide the titled compound.

Example 64

This example describes the synthesis of

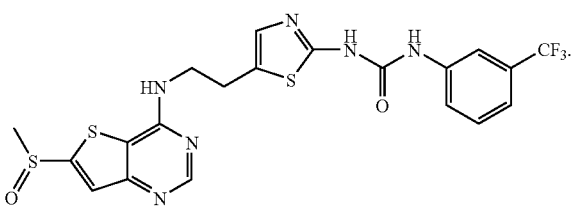

This compound is made according to Example 63 except that only one equivalent of m-CPBA is used in step 2.

Example 65

This example describes the synthesis of

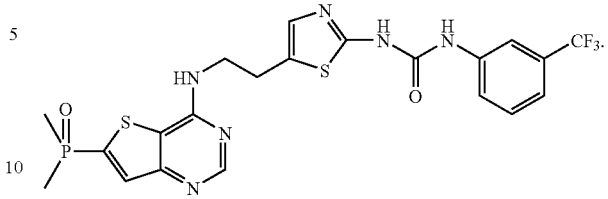

This compound is made according to Example 63 except that dimethylphosphine chloride is used instead of methyl methanethiosulfonate in step 1.

Example 66

This example describes the synthesis of

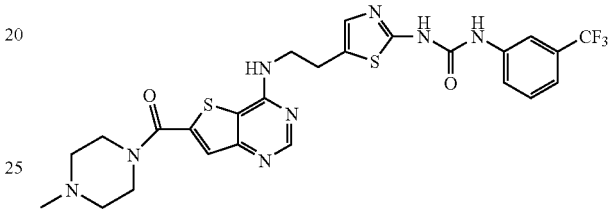

Step 1: 4-(2-{2-[3-(3-Trifluoromethyl-phenyl)-ureido]-thiazol-5-yl}-ethylamino)-thieno[3,2-d]pyrimidine-6-carboxylic acid ethyl ester (compound 66.1) is prepared according to Example 38 except that 4-chloro-thieno[3,2-d]pyrimidine-6-carboxylic acid ethyl ester is used instead of 5-methyl-4-chloro-[2,3-d]thienopyrimidine.

Step 2: A mixture of compound 66.1 (2 mmol) and $LiOH·H_2O$ (4 mmol) in THF (20 mL) and $H_2O$ (5 mL) was stirred at room temperature for 2 hours and then neutralized with 1.0 N HCl (4 mL). The reaction was concentrated to dryness to give 4-(2-{2-[3-(3-trifluoromethyl-phenyl)-ureido]-thiazol-5-yl}-ethylamino)-thieno[3,2-d]pyrimidine-6-carboxylic acid (compound 66.2) which is used without further purification in the next step.

Step 3: A mixture of compound 66.2 (0.05 mmol), 1-methylpiperazine (0.05 mmol), HATU (0.05 mmol) and DIEA (0.10 mmol) in DMF (1.0 mL) was stirred at room temperature overnight. The reaction was concentrated to dryness and purified by reverse phase HPLC to afford the titled compound.

Example 67

This example describes the synthesis of

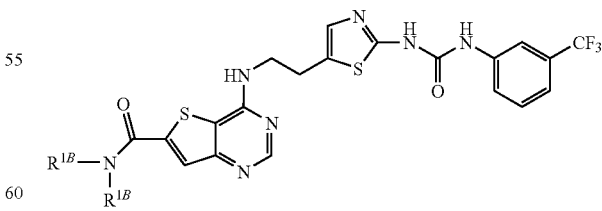

where $R^{1B}$'s are as described previously. These compounds are made according to Example 66 except that $(R^{1B})_2N$ is used instead of 1-methylpiperazine in step 3. Illustrative examples of suitable $(R^{1B})_2N$'s are found throughout this disclosure as well as in Table 12.

TABLE 12
| $(R^{1B})_2N$ | 2. Final Compound |
|---|---|
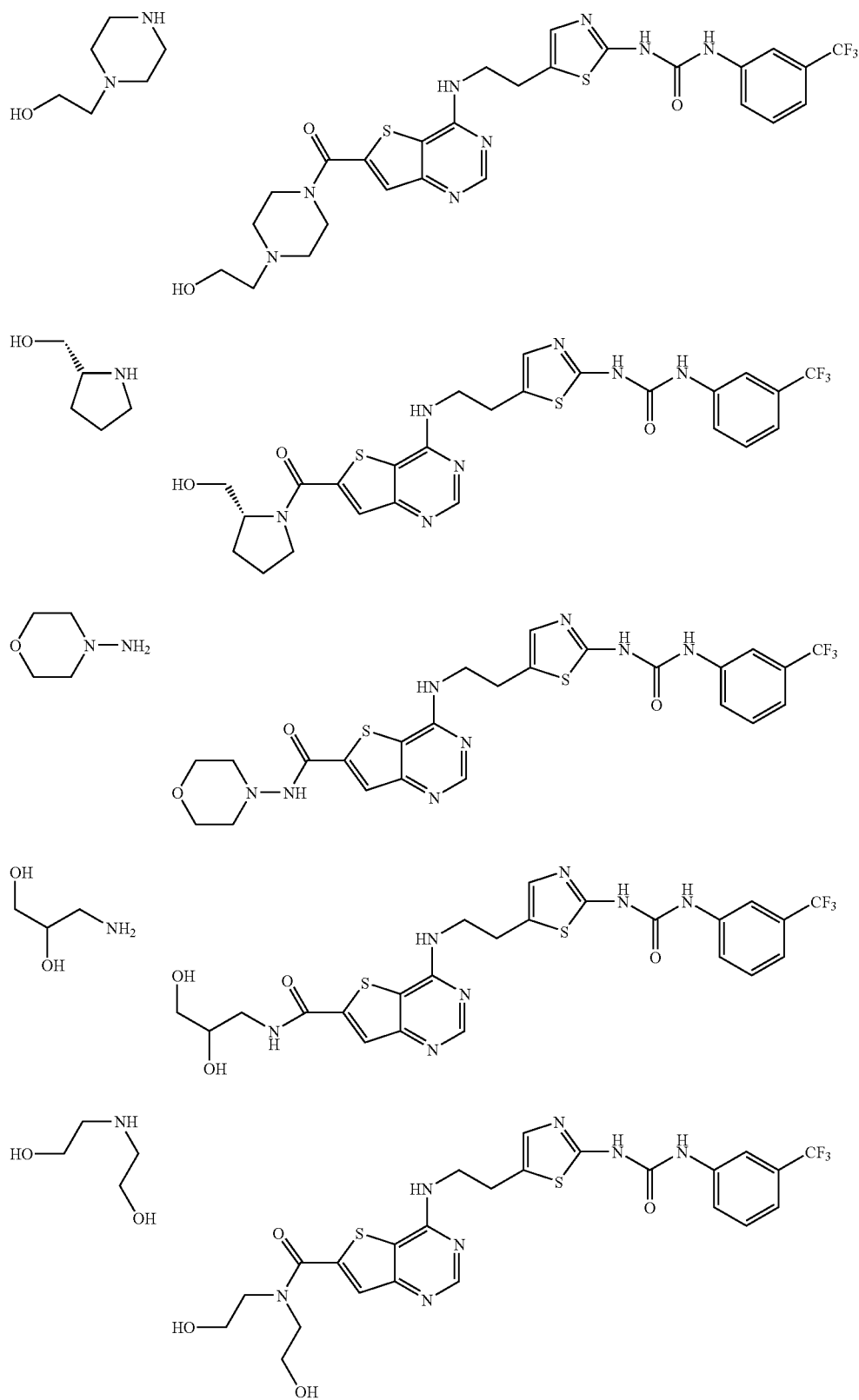

TABLE 12-continued
| (R$^{1B}$)$_2$N | 2. Final Compound |
|---|---|
| 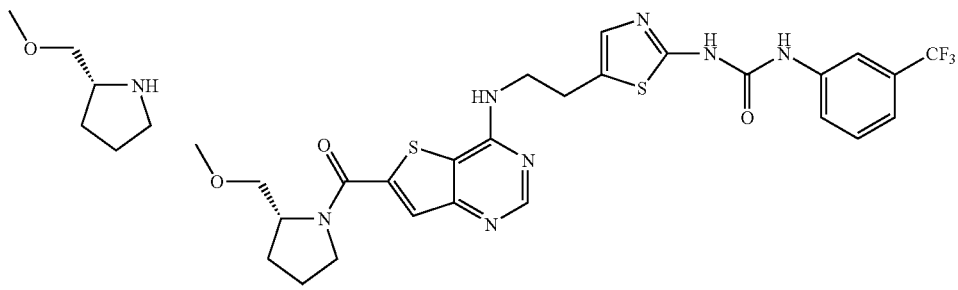 | |
| 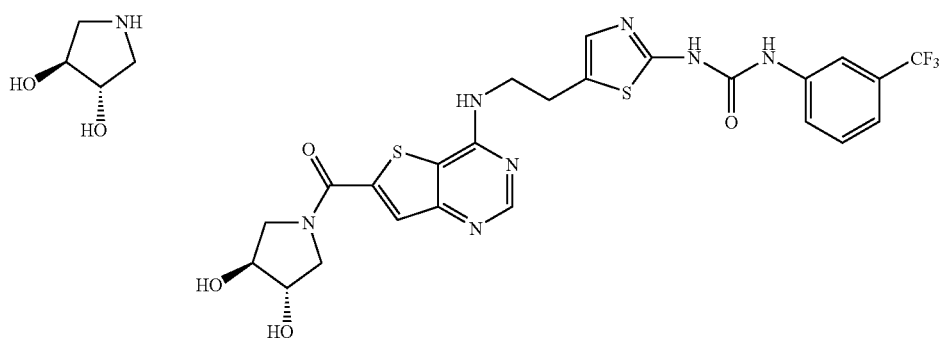 | |
| 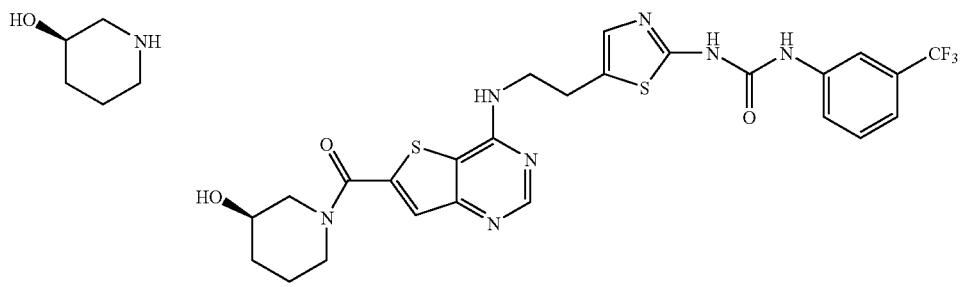 | |
Example 68
This example describes the synthesis of
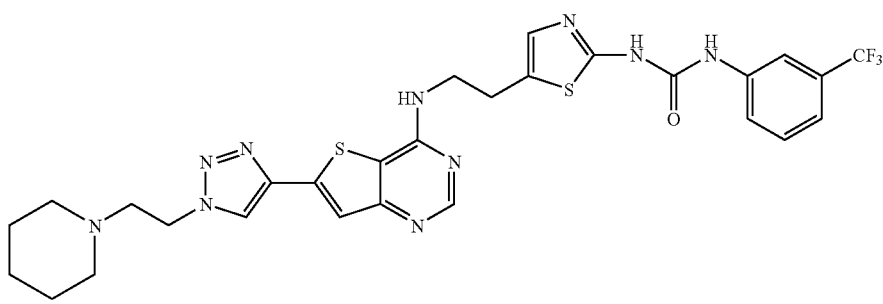
A mixture of compound 48.2 (1.0 mmol), 1-(2-azido-ethyl)-piperidine (1.0 mmol), CuI (1.0 mmol) and DEA (2.0 mmol) in DMF (10 mL) was stirred at room temperature for 2 h. Subsequently, compound 38.1 (1.0 mmol.) was added and the reaction was heated at 100° C. for 2 hours. The reaction was concentrated and the residue diluted with aqueous NH₄OH. The resulting suspension was filtered and washed with water and EtOAc. The solid was collected and dried under vacuum to provide the titled compound.

Example 69

This example describes the synthesis of

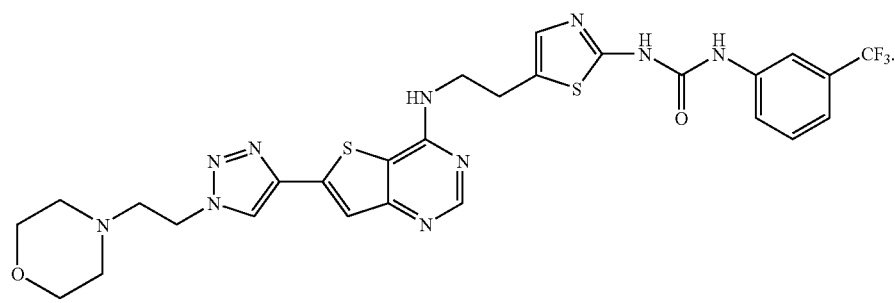

This compound is made according to Example 68 except that 4-(2-azido-ethyl)-morpholine is used instead of 1-(2-azido-ethyl)-piperidine.

Example 70

This example describes the synthesis of

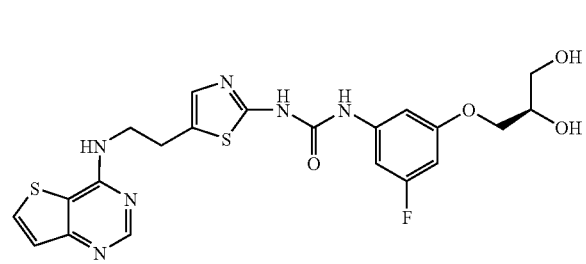

Step 1: To a solution of 3,5-difluoronitrobenzene (6.0 mmol) and (S)-(+)-2,2-dimethyl-1,3-dioxolan-4-methanol (7.5 mmol) in DMF (10 mL) is added NaH (2.3 equiv.) at room temperature. After stirring for 2 hours, saturated NH₄Cl is added and the reaction is extracted with EtOAc. The organic layer is separated, washed with brine, dried and concentrated to give a residue that was purified by preparative TLC (30% EtOAC in hexanes). The corresponding nitro compound thus obtained (1.0 mmol) is stirred at room temperature for 12 hours under a hydrogen atmosphere over 10% Pd/C (30 mg) in MeOH/EtOAc (15 mL). The reaction is filtered through a Celite pad and concentrated to dryness to provide 3-(2,2-dimethyl-[1,3]dioxolan-4-ylmethoxy)-5-fluoro-phenylamine (compound 70.1) of sufficient purity to be used in the next step.

Step 2: A solution of compound 70.1 (1.0 mmol), compound 16.1 (1.0 mmol) and DMAP (1.0 mmol) in DMSO (10 mL) is heated at 90° C. for 30 minutes. The reaction is cooled, and partitioned between EtOAC and 1.0 N NaOH. The organic layer is separated, washed with brine, dried and concentrated to give a residue that was purified by preparative TLC (6% MeOH in dichloromethane) to provide 1-[3-(2,2-dimethyl-[1,3]dioxolan-4-ylmethoxy)-5-fluoro-phenyl]-3-{5-[2-(thieno[3,2-d]pyrimidin-4-ylamino)-ethyl]-thiazol-2-yl}-urea (compound 70.2).

Step 3: To a solution of compound 70.2 (0.2 mmol) in MeOH (1.0 mL) and dichloromethane (1.0 mL) is added trifluoroacetic acid (5 equivalents). The reaction is stirred at room temperature for 12 hours and then directly purified by reverse phase HPLC to provide the titled compound.

Example 71

This example describes the synthesis of

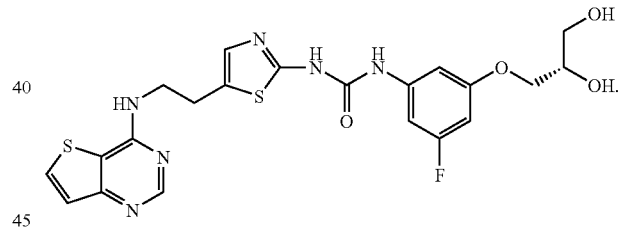

This compound is made according to Example 70 except that from (R)-(−)-2,2-dimethyl-1,3-dioxolan-4-methanol is used instead of (S)-(+)-2,2-dimethyl-1,3-dioxolan-4-methanol in step 1.

Example 72

This example describes the synthesis of

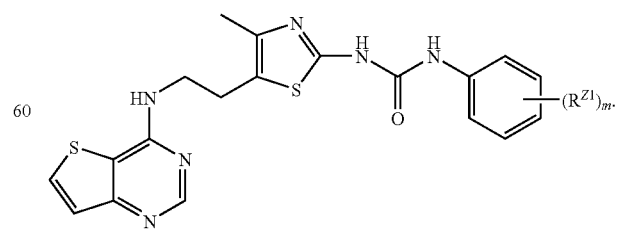

where $R^{Z1}$ and m are as described previously.

Step 1: 2-[2-(2-Amino-4-methyl-thiazol-5-yl)-ethyl]-isoindole-1,3-dione is (compound 72.1; 1.0 mmol) is prepared according to the procedure of Ericks, J. C. et al; *J. Med. Chem.* 1992, 35, 3239. Compound 72.1 is refluxed with

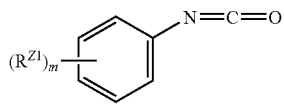

(1 equivalent) in acetone (10 mL) for 30 minutes. The reaction is cooled to room temperature and the solvent is removed under reduced pressure. Trituration from dichloromethane and hexanes gives urea product (compound 72.2).

Step 2: Compound 72.2 (0.7 mmol) is refluxed in EtOH (10 mL) with hydrazine (3 equivalents) for 2 hours. The reaction mixture is cooled to room temperature and the precipitate is filtered off and the filtrate concentrated to dryness to give the corresponding amine (compound 72.3).

Step 3: To a solution of compound 72.3 (0.35 mmol) in DMF (1.0 mL) was added compound 6.2 (1 equivalent) and triethylamine (5 equivalents). The reaction is stirred at 90° C. for 1 hour, cooled, diluted with EtOAc, washed with water, brine, dried and concentrated to provide the titled compound.

Example 73

This example describes the synthesis of

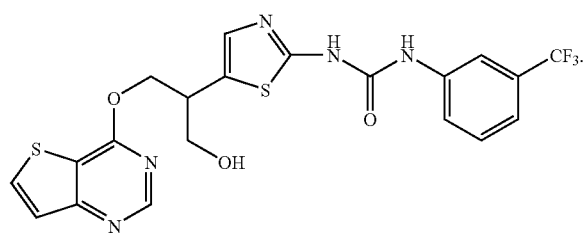

Step 1: A mixture of {2-[3-(3-trifluoromethyl-phenyl)-ureido]-thiazol-5-yl}-acetic acid methyl ester (4.17 mmol), paraformaldehyde (0.95 equiv.) and K$_2$CO$_3$ (0.95 equiv.) in DMSO (10.0 mL) was heated at 50° C. for 1.5 hours. The reaction was cooled, diluted with EtOAc, washed with water, dried and concentrated to give a residue that was purified by flash column chromatography on silica gel (0 to 6% MeOH in EtOAc) to provide 3-hydroxy-2-{2-[3-(3-trifluoromethyl-phenyl)-ureido]-thiazol-5-yl}-propionic acid methyl ester (compound 73.1).

Step 2: To a mixture of compound 73.1 (1.67 mmol) and triethylamine (2.2 equivalent) in 1:1 dichloromethane/THF (12.0 mL) was added triisopropylsilyl trifluoromethanesulfonate (2.2 equivalents) dropwise at 0° C. After complete consumption of the starting material (TLC 30% EtOAc in hexanes) the reaction mixture is diluted with EtOAc and washed with 0.5 N HCl, saturated sodium bicarbonate, dried and concentrated to give a residue that was purified by flash column chromatography on silica gel (0 to 60% EtOAc in hexanes) to provide 2-{2-[3-(3-trifluoromethyl-phenyl)-ureido]-thiazol-5-yl}-3-triisopropylsilanyloxy-propionic acid methyl ester (compound 73.2) as a foam.

Step 3: To a solution of compound 73.2 (0.275 mmol) in THF (2.5 mL) was added LAH (0.275 mL of a 1.0 M solution in THF) dropwise at 0° C. The reaction is allowed to warmed to room temperature and stirred until the starting material was consumed. The reaction is quenched by the dropwise addition of water and the reaction mixture was extracted with EtOAc. The combined organic layers were combined, dried and concentrated to give a residue that was purified by flash column chromatography (20 to 100% EtOAc in hexanes) to provide 1-[5-(2-hydroxy-1-triisopropylsilanyloxymethyl-ethyl)-thiazol-2-yl]-3-(3-trifluoromethyl-phenyl)-urea (compound 73.3).

Step 4: To a suspension of NaH (0.12 mmol as a 60% oil dispersion) in THF (0.20 mL) was added a solution of compound 73.3 (0.04 mmol) in THF (1.0 mL) at room temperature. After stirring for 1 hour, 4-chlorothieno[3,2-d]pyrimidine (0.04 mmol) was added and the reaction mixture was heated at 60° C. for 1 hour. The reaction was cooled and quenched with the addition of saturated NH$_4$Cl. The reaction mixture was extracted with EtOAc, dried and concentrated to give a residue that was purified by preparative TLC (20% hexanes in EtOAc) to afford 1-{5-[2-(thieno[3,2-d]pyrimidin-4-yloxy)-1-triisopropylsilanyloxymethyl-ethyl]-thiazol-2-yl}-3-(3-trifluoromethyl-phenyl)-urea (compound 73.4).

Step 5: To a solution of compound 73.4 (70 mg) in ethanol (4.0 mL) was added concentrated aqueous HCl (1.0 mL) and the reaction was stirred at room temperature overnight. The reaction is then diluted with water and methanol and directly purified by reverse phase HPLC. The fractions containing the desired product were pooled and lyophilized to afford the titled compound as a colorless solid.

Example 74

This example describes the synthesis of

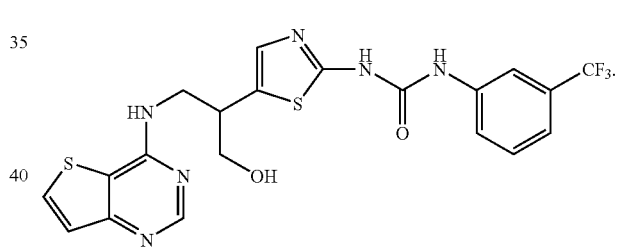

Step 1: Ammonia gas is bubbled through a solution of compound 73.1 (435 mg) in methanol (20.0 mL) for 10 minutes. The reaction vessel is then sealed and heated at 80° C. for 3 hours. The mixture is concentrated and the residue purified by preparative TLC to give 3-hydroxy-2-{2-[3-(3-trifluoromethyl-phenyl)-ureido]-thiazol-5-yl}-propionamide (compound 74.1).

Step 2: To a solution of compound 74.1 (0.08 mmol) in THF (1.0 mL) is added LAH (0.24 mL of 1.0 M solution in THF) and the reaction mixture is heated at 50° C. for 4 hours. The reaction is quenched with the dropwise addition of saturated NH$_4$Cl, the volatiles are removed under reduced pressure and then extracted with EtOAc. The combined organic layers are filtered and concentrated to provide 1-[5-(2-amino-1-hydroxymethyl-ethyl)-thiazol-2-yl]-3-(3-trifluoromethyl-phenyl)-urea (compound 74.2) of sufficient purity for use in the next step.

Step 3: A mixture of compound 74.2 (0.20 mmol), 4-chlorothieno[3,2-d]pyrimidine (0.20 mmol) and DIEA (1.0 mL) in n-butanol (1.0 mL) are heated at 110° C. for 2 hours. The reaction mixture is concentrated to dryness to give a residue that was purified by reverse phase HPLC. The product that is obtained was dissolved in methanol, treated with solid

Example 75

This example describes the synthesis of

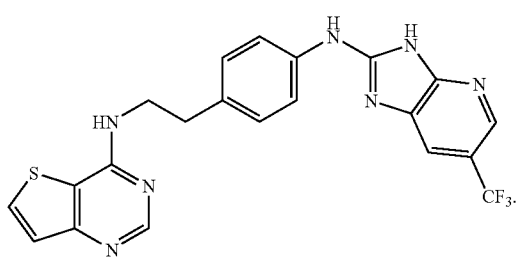

Step 1: A mixture of 4-nitrophenylethylamine (compound 75.1; 20 mmol), compound 6.2 (20 mmol) and DIEA (20 mmol) in DMF (100 mL) was stirred at 100° C. for 4 hours. The reaction mixture was concentrated to dryness and diluted with 100 mL of water. The resulting suspension was filtered and the solid collected was washed with water and dried in vacuo to give the nitro-intermediate. To the nitro-intermediate was added zinc powder (100 mmol), saturated aqueous $NH_4Cl$ (20 mL) and MeOH (100 mL) and the resulting mixture was stirred at 50° C. for 8 hours. The mixture was filtered through a short column of Celite8545 and washed with methanol. The filtrate was then concentrated and diluted with 50 mL of 0.1 N HCl. The mixture was extracted with EtOAc several times and the aqueous phase was adjusted to pH 10 by the addition of 4N NaOH. Subsequently, the aqueous layer was back extracted with EtOAc. The organic layers were combined, dried and concentrated in vacuo to give [2-(4-amino-phenyl)-ethyl]-thieno[3,2-d]pyrimidin-4-yl-amine (compound 75.2) in 80% yield. $^1$H NMR (CD$_3$OD, 400 MHz): δ 8.74 (s, 1H), 8.37 (d, J=5.4 Hz, 1H), 7.50 (d, J=5.4 Hz, 1H), 7.45 (d, J=8.3 Hz, 2H), 7.31 (d, J=7.8 Hz, 2H), 4.00 (t, J=7.1, 2H), 3.11 (t, J=7.3 Hz, 2H) ppm; EIMS (m/z): 271.1 (M$^+$+H).

Step 2: A mixture of compound 1.2 (0.2 mmol) and thiocarbonyldiimidazole (0.2 mmol) in dry THF (2.0 mL) was stirred at room temperature for 30 minutes under an atmosphere of N$_2$. 5-Trifluoromethyl-pyridine-2,3-diamine (0.2 mmol) was added and the reaction stirred at room temperature until the reaction was deemed complete. The reaction mixture was then treated with N,N'-dicyclohexylcarbodiimide (0.2 mmol) and the resulting mixture was stirred at 40-60° C. for several hours. The solvent was removed and the residue was purified by preparative HPLC to give the titled compound. $^1$H NMR (CD$_3$OD, 400 MHz): δ 8.76 (s, 1H), 8.51 (s, 1H), 8.38 (s, 1H), 7.95 (s, 1H), 7.56 (d, J=7.3 Hz, 2H), 7.48 (s, 1H), 7.38 (d, J=6.4 Hz, 2H), 4.03 (s, 2H), 3.09 (s, 2H) ppm; EIMS (m/z): 456.1 (M$^+$+H).

Example 76

This compound describes the synthesis of

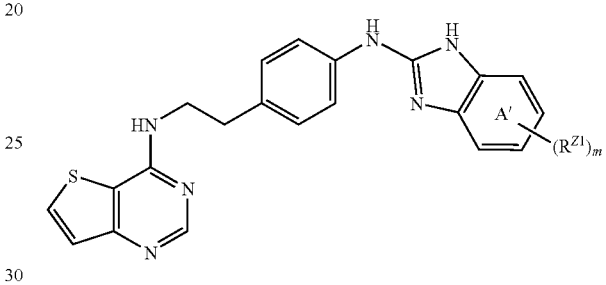

where A' is a 6-membered aryl or heteroaryl group and $R^{Z1}$ and m are as previously described. These compounds are made according to Example 75 except that

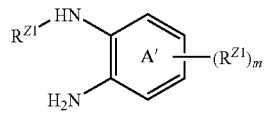

is used instead of 5-trifluoromethyl-pyridine-2,3-diamine in step 2. Illustrative examples of suitable $R^{Z1}$'s are found throughout this disclosure as well as in Table 13.

TABLE 13

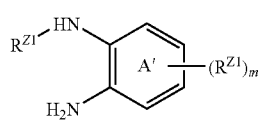

3. Final Compound

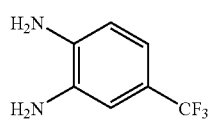

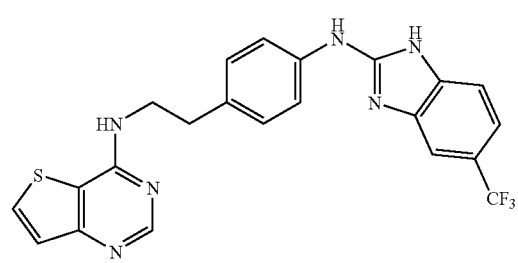

TABLE 13-continued
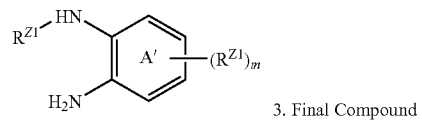
3. Final Compound
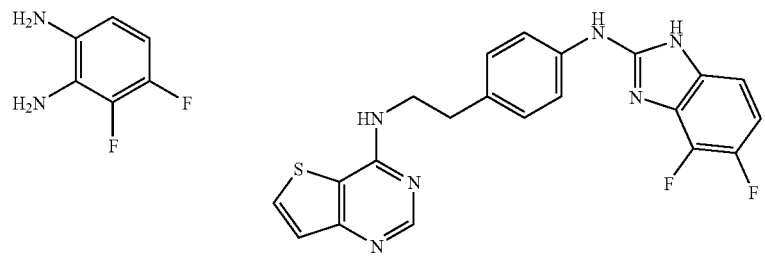
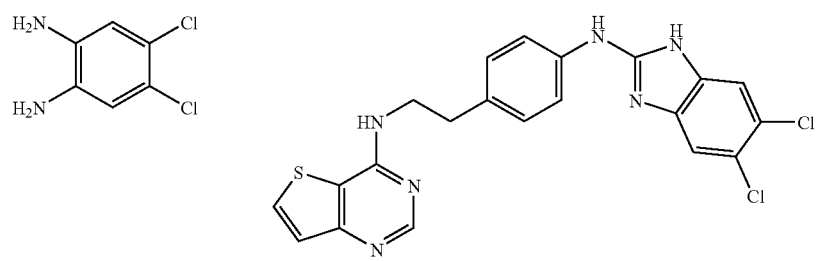
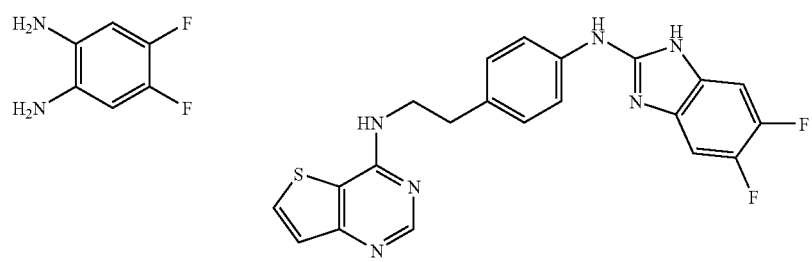
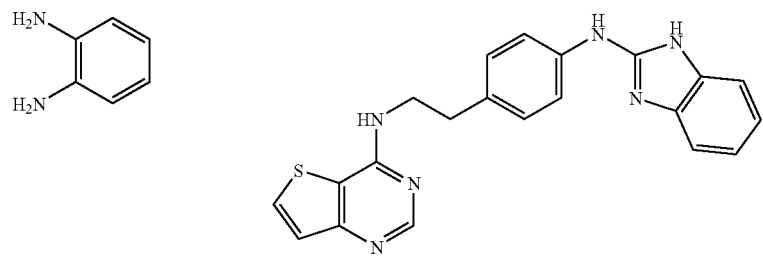
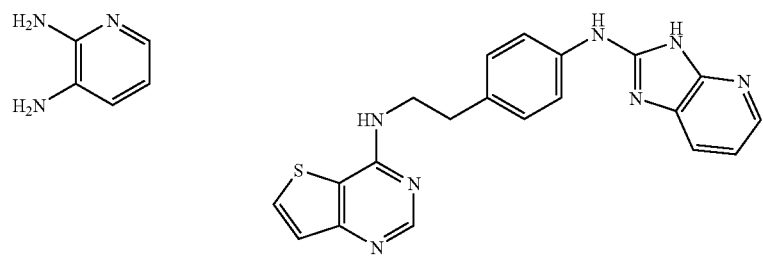

TABLE 13-continued
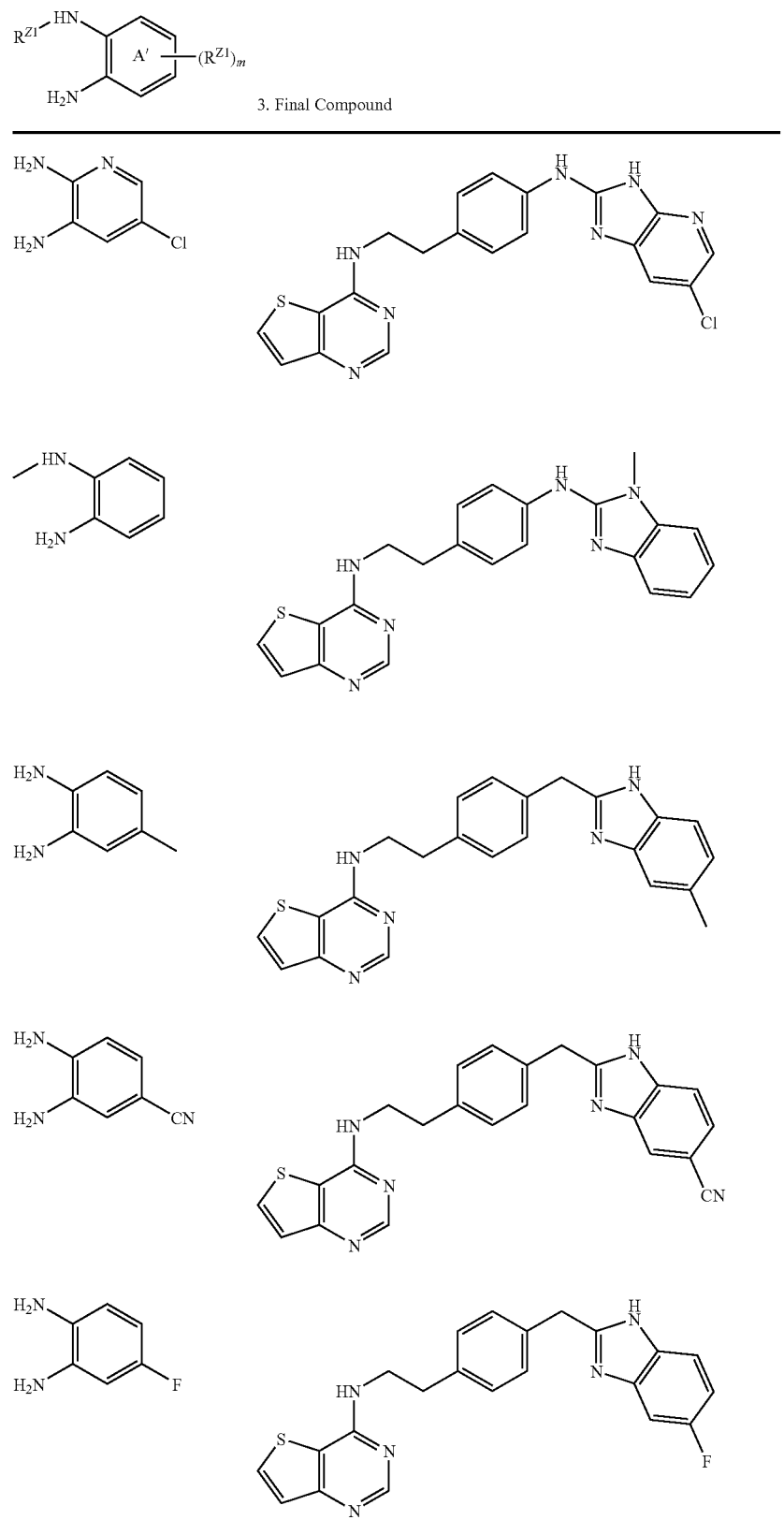

TABLE 13-continued

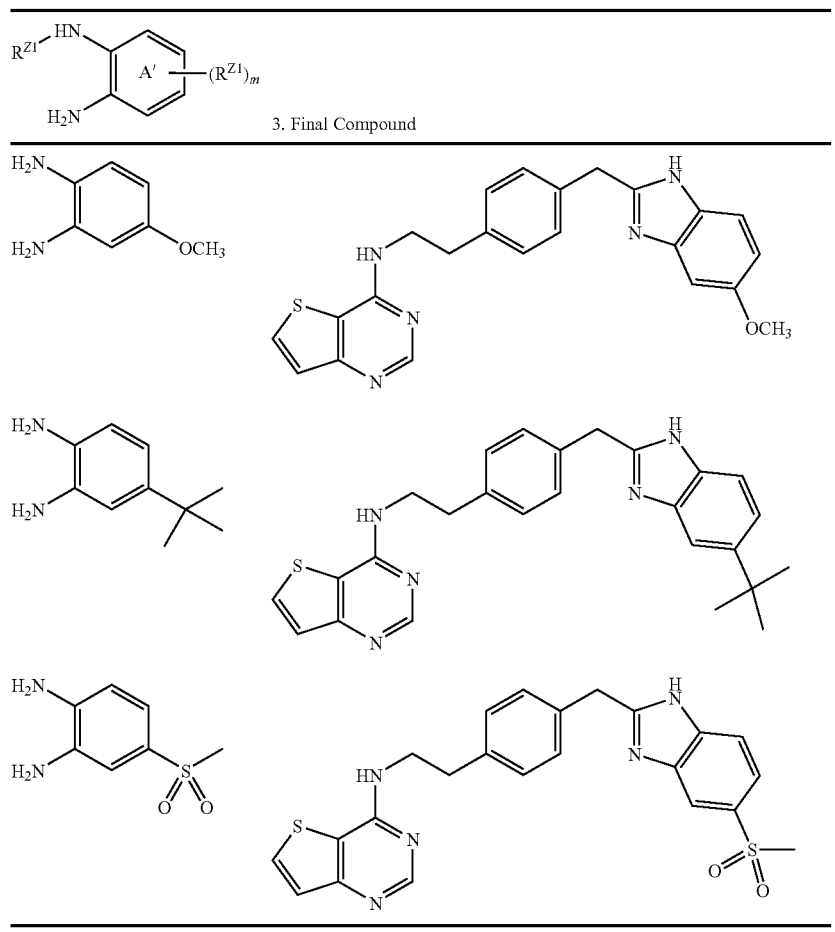

Example 77

This example describes the synthesis of

A mixture of compound 75.2 (0.2 mmol), 2-chlorobenzoxazole (0.2 mmol), DIEA (0.4 mmol) and DMAP (0.02 mmol) in DMSO (2 mL) was stirred at 110° C. for several hours. The solvent was removed and the residue was purified by preparative HPLC to give the titled compound. $^1$H NMR (CD$_3$OD, 400 MHz): δ 8.74 (s, 1H), 8.38 (d, J=5.4 Hz, 1H), 7.58 (d, J=8.3 Hz, 2H), 7.48 (d, J=5.4 Hz, 1H), 7.39 (t, J=8.1 Hz, 2H), 7.28 (d, J=8.3 Hz, 2H), 7.23 (t, J=7.6 Hz, 1H), 7.14 (t, J=7.6 Hz, 1H), 4.03 (t, J=7.1 Hz, 2H), 3.05 (t, J=7.1 Hz, 2H) ppm; EIMS (m/z): 388.1 (M$^+$+H).

Example 78

This example describes the synthesis of

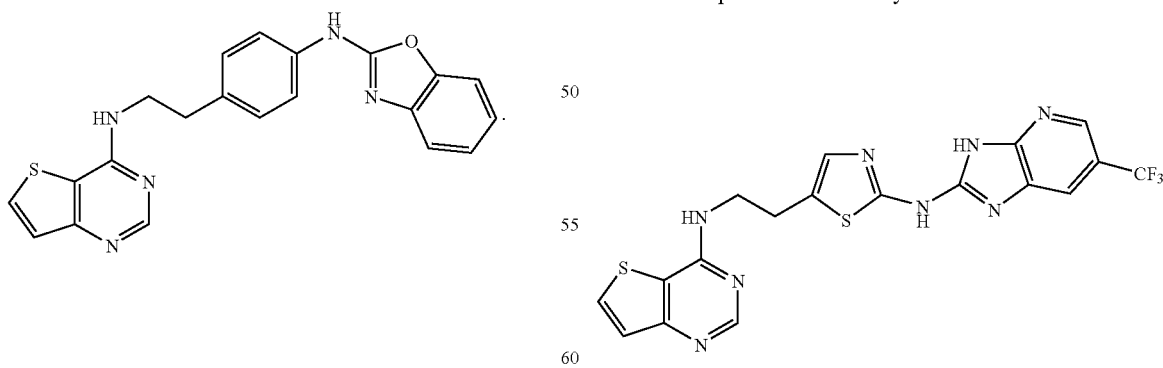

This compound is prepared according to step 2 of Example 75 except that compound 14.3 is used instead of compound 75.2. $^1$H NMR (CD$_3$OD, 400 MHz): δ 8.79 (s, 1H), 8.46 (s, 1H), 8.41 (d, J=5.9 Hz, 1H), 7.98 (s, 1H), 7.50 (d, J=5.4 Hz, 2H), 7.17 (s, 1H), 4.07 (t, J=6.8 Hz, 2H), 3.21 (t, J=6.6 Hz, 2H) ppm; EIMS (m/z): 463.1 (M++H).

Example 79

This example describes the synthesis of

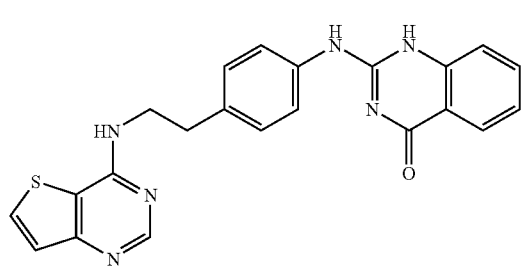

Step 1: A solution of compound 1.1 (2.0 mmol) and thiocarbonyldiimidazole (2.0 mmol) in dry THF (10.0 mL) was stirred at room temperature for 30 minutes and then saturated with NH₃ (gas). The resulting mixture was stirred at room temperature for 10 minutes and concentrated to give a residue that was purified by preparative chromatography to give [2-(4-thioureido-phenyl)-ethyl]-carbamic acid tert-butyl ester (compound 79.2) in 95% yield. $^1$H NMR (CD$_3$OD, 400 MHz): δ 7.25 (m, 4H), 3.26 (t, J=7.1 Hz, 2H), 2.76 (t, J=7.1 Hz, 2H), 1.43 (s, 9H) ppm; EIMS (m/z): 296.1 (M++H).

Step 2: A solution of compound 79.2 (1.5 mmol) and methyl iodide (6.0 mmol) in acetone (15.0 mL) was stirred at 40° C. overnight. The solvent was removed and the residue was dried in vacuo to give {2-[4-(2-methyl-isothioureido)-phenyl]-ethyl}-carbamic acid tert-butyl ester (compound 79.3) in quantitative yield. $^1$H NMR (CD$_3$OD, 400 MHz): δ 7.40 (d, J=7.8 Hz, 2H), 7.28 (d, J=8.3 Hz, 2H), 3.30 (t, J=7.1 Hz, 2H), 2.82 (t, J=7.1 Hz, 2H), 2.73 (s, 3H) ppm; EIMS (m/z): 310.1 (M++H).

Step 3: A mixture of compound 79.3 (1.5 mmol), isatoic anhydride (1.5 mmol), and Na₂CO₃ (3.0 mmol) in dioxane (15 mL) was stirred at 100° C. for 8 hours. The solvent was removed and the residue was diluted with 20 mL of water. Subsequently, the suspension was filtered and the white solid was washed sequentially with water and ether, and then dried in vacuo to give {2-[4-(4-oxo-1,4-dihydro-quinazolin-2-ylamino)-phenyl]-ethyl}-carbamic acid tert-butyl ester (compound 79.4) in 52% yield. $^1$H NMR (d$^6$-DMSO, 400 MHz): δ 10.77 (s, 1H), 8.60 (s, 1H), 7.92 (d, J=7.3 Hz, 1H), 7.59 (m, 3H), 7.35 (d, J=8.3 Hz, 1H), 7.12-7.20 (m, 3H), 6.86 (s, 1H), 3.09 (t, J=7.1 Hz, 2H), 2.62 (t, J=7.1 Hz, 2H), 1.34 (s, 9H) ppm; EIMS (m/z): 381.2 (M++H).

Step 4: A mixture of compound 79.4 (0.5 mmol) in anhydrous HCl in dioxane (5.0 mL of a 4.0 N solution in dioxane) was stirred at 60° C. for 1 hour. The solvent was removed and the residue dried in vacuo to give the amine intermediate. A mixture of this intermediate (0.2 mmol), compound 6.2 (0.2 mmol) and DIEA (1.0 mmol) was stirred at 100° C. for several hours. The solvent was removed and the residue was purified by preparative HPLC to give the titled compound. $^1$H NMR (CD$_3$OD, 400 MHz): δ 8.75 (s, 1H), 8.39 (d, J=4.9 Hz, 1H), 8.12 (d, J=8.3 Hz, 1H), 7.75 (t, J=7.8 Hz, 1H), 7.45-7.52 (m, 4H), 7.37-7.41 (m, 3H), 4.05 (t, J=7.1 Hz, 2H), 3.11 (t, J=7.1 Hz, 2H) ppm; EIMS (m/z): 415.1 (M++H).

Example 80

This example describes the synthesis of

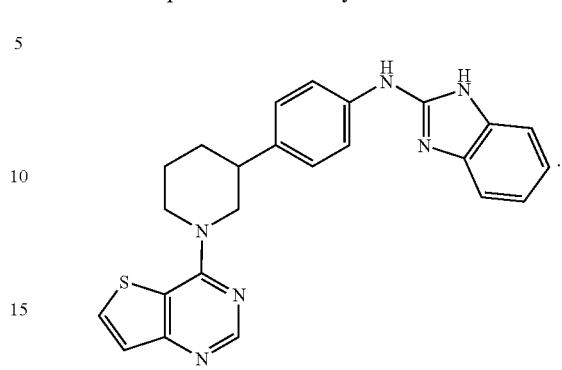

Step 1:
A mixture of 1.0 mmol of 3-(4-amino-phenyl)-piperidine-1-carboxylic acid tert-butyl ester and 1.0 mmol of thiocarbonyldiimidazole in 10 mL of dry THF was stirred at room temperature for 30 minutes under an atmosphere of N₂. After stirring with 1.0 mmol of diaminobenzene at room temperature for 30 minutes under an atmosphere of N₂, the reaction mixture was treated with 1.0 mmol of DCC and the resulting mixture was stirred at 60° C. for several hours. The solvent was removed and the residue was purified by preparative TLC to give 3-(4-amino-phenyl)-piperidine-1-carboxylic acid tert-butyl ester (compound 80.1) in 55% yield. EIMS (m/z): 393.2 (M++H).

Step 2:
A mixture of 0.5 mmol of compound 80.1 in 10 mL of 4.0N HCl in dioxane was stirred at 60° C. for 1 h. The solvent was removed and the residue was dried in vacuo to give the free amine, (1H-benzoimidazol-2-yl)-(4-piperidin-3-yl-phenyl)-amine (compound 80.2) in quantitative yield. EIMS (m/z): 293.1 (M++H).

Step 3:
A mixture of 0.2 mmol of compound 6.2, 0.2 mmol of compound 80.2, and 1 mmol of DIEA was stirred at 100° C. for several hours. The solvent was removed and the residue was purified by preparative HPLC to give the titled compound. $^1$H NMR (CD$_3$OD, 400 MHz): δ 8.72 (s, 1H), 8.46 (d, J=5.4 Hz, 1H), 7.57 (m, 3H), 7.49 (d, J=8.3 Hz, 2H), 7.43 (m, 2H), 7.34 (m, 2H), 5.16 (d, J=11.3 Hz, 2H), 3.58 (m, 2H), 3.10 (t, J=10.0 Hz, 1H), 2.04-2.17 (m, 3H), 1.92 (m, 1H) ppm; EIMS (m/z): 427.2 (M++H).

Formulation of Compounds

The solubility of poorly soluble compounds are improved by making them as acid salts. Illustrative examples of such acids include methane sulfonic acid and citric acid. Solubility of these compounds can be additionally improved by the addition of solubility enhancing agents such as Tween-80 and PEG-400. Illustrative formulations of poorly soluble compounds of the present invention include 10%/30%/60%, 5%/30%/65%, and 2.5%/30%/67.5% respectively of Tween-80, PEG-400 and water. The pH of these formulations can also be varied to identify a range for optimal solubility.

Target Modulation Studies.

Nu/nu mice were subcutaneously injected into their hind flank with human HCT-116 cells and 50% Matrigel (Becton-Dickinson). Human HCT-116 tumors were then allowed to grow to 400 mm³. The tumor bearing mice were then either given an administration of SPD or vehicle (Sigma-Aldrich) (orally, intravenously or intraperitoneally). At prescribed time points post dose, mice were anesthetized and blood taken via terminal cardiac puncture, and sacrificed. The HCT-116 tumors were excised from the mice, pulverized using liquid nitrogen-cooled mortar and pestle, and flash-frozen in liquid nitrogen. Tumor lysates were made from the pulverized samples by addition of lysis buffer.

For detection of response markers by Western blotting, the protein concentration of the lysates was determined by calorimetric detection. Twenty-five micrograms of protein was loaded per lane on an SDS-PAGE gel. Proteins were separated by gel electrophoresis, blotted onto nitrocellulose membranes, and probed using anti-Histone H3 and anti-phosphorylated Histone H3 antibodies, (both from Cell Signaling Technology)

Maximum Tolerated Dose Studies.

Maximum Tolerated Dose (MTD) is defined as the dose at which the mouse is no longer able to function normally and is determined by either significant toxicity (eg. body weight loss) or mortality. Mice (nu/nu) were sorted according to weight and randomized into groups prior to being dosed with a test compound, by oral, intravenous or intraperitoneal routes. Escalating doses of a test compound were used. Animal weights were measured daily for 5 days and about every 3 days after that until the animal was removed from the study due to body weight loss of >20% or any alterations in physiological function that would affect normal function. Clinical observations were performed throughout the study to note any toxicity and mice were monitored until the end of the study.

Efficacy Studies.

Nu/nu mice were subcutaneously injected into their hind flank with human HCT-116 cells and 50% Matrigel (Becton-Dickinson). Human HCT-116 tumors were allowed to grow to 150-200 mm³. The tumor bearing mice were then either given an administration of a test compound or a vehicle control. The tumor dimensions (length [1 mm] and width [w mm]) were measured by electronic calipers and the tumor volume (mm³) determined from the equation ([w²×1]÷2). Weights of the mice and their respective tumor volumes were measured twice weekly until the animal was removed from the study, either because there was a body weight loss of greater than 20% or a tumor volume greater than 2000 mm³. Clinical observations were performed throughout the study, which usually lasted for up to 70 days after the initial implantation of the tumor cells. Tumor volume increases were compared to negative (vehicle) and positive controls. Percentage tumor growth inhibition (TGI) was calculated from the equation [(tumor volume T−tumor volume)÷tumor volume C]×100, where T=treatment group and C=control or vehicle group. The tumor volume for both groups was usually determined at defined times after the administration of the last dose of compound. Survival plots (Kaplan-Maier) were also performed to examine the pattern of survival.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A compound of the formula:

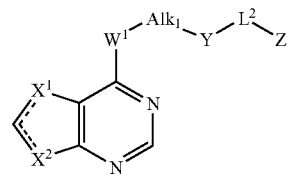

or pharmaceutically acceptable salt thereof;

wherein one of - - - - - is a double bond, as valency permits;

$X^1$ is S, $X^2$ is —CH—;

$W^1$ is $NR^{W1}$, where $R^{W1}$ is hydrogen, lower alkyl, $C_{3-6}$cycloalkyl, lower heteroalkyl, aryl, -(alkyl)aryl, or acyl;

$Alk_1$ is a $C_2$ alkylene chain wherein up to two non-adjacent methylene units are independently optionally replaced by —C(=O) or —C(=O)C(=O);

$L^2$ is —$NR^{W2}$, —$N(R^{W2})C(=O)G_2$, —$N(R^{W2})C(=O)N(R^{W2})CR^{W3}R^{W4}$— or —$CR^{W3}R^{W4}C(=O)N(R^{W2})$—; wherein $G_2$ is absent, O or $NR^{W2}$; and $R^{W2}$, $R^{W3}$, $R^{W4}$ and $R^{G2}$ are independently hydrogen, lower alkyl, lower heteroalkyl, aryl, -(alkyl)aryl, or acyl;

Y is a thiazolyl ring; and

Z is an aliphatic, heteroaliphatic, alicyclic, aromatic, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, pyridyl, quinolinyl, dihydroquinolinyl, isoquinolinyl, quinazolinyl, dihydroquinazolinyl, tetrahydroquinazolinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, or furanyl moiety, or Z has one of the following structures:

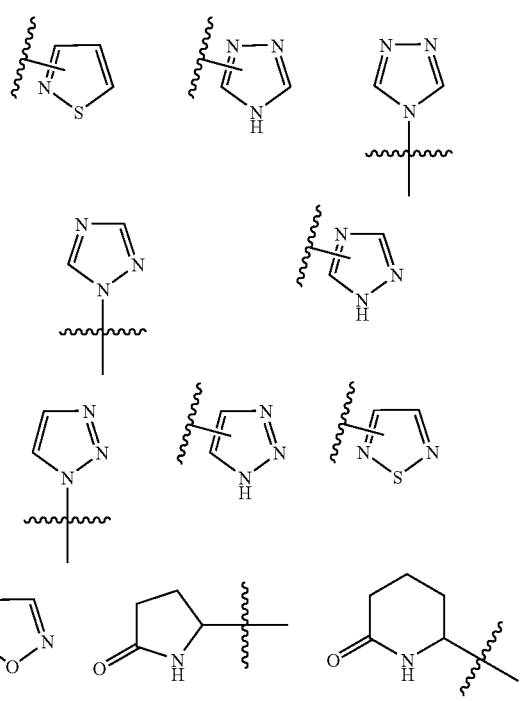

-continued

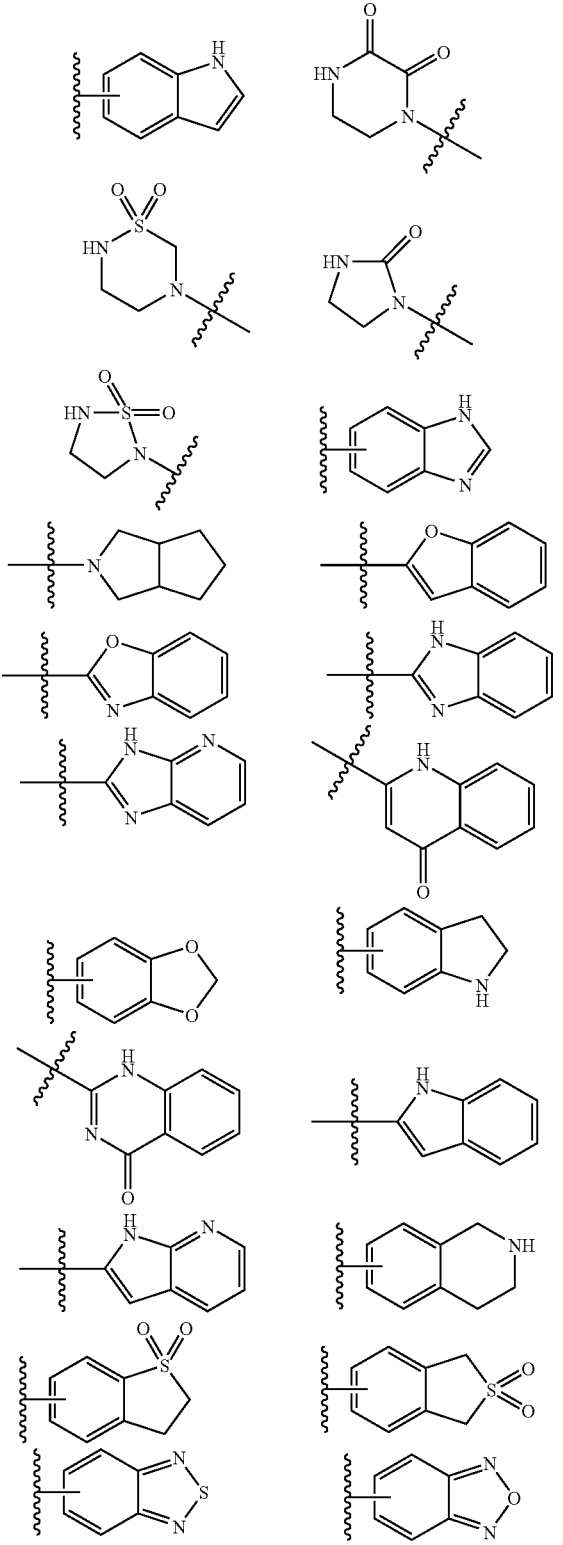

wherein Z is optionally substituted with aliphatic; heteroaliphatic; alicyclic; heteroalicyclic; aromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN;

—CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or —GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O) O—, —NR$^{G2}$C(=O)NR$^{G2}$—, —C(=S)—, —C(=S) S—, —SC(=S)—, —SC(=S)S—, —C(=NR$^{G2}$)—, —C(=NR$^{G2}$)O—, —C(=NR$^{G2}$)NR$^{G3}$—, —OC (=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ is independently hydrogen, halogen, aliphatic, heteroaliphatic, alicyclic, heteroalicyclic, aromatic, aryl, heteroaryl, alkylaryl, or alkylheteroaryl, wherein each heteroalicyclic group is selected from pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, dihydropyrrolyl, dihydropyridyl, or azetidinyl, and wherein each heteroaryl group is selected from pyridyl, quinolinyl, dihydroquinolinyl, isoquinolinyl, quinazolinyl, dihydroquinazolinyl, tetrahydroquinazolinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, or furanyl.

2. The compound of claim 1 wherein L$^2$ is NH, —NHC(=O)—, —NHC(=O)O—, —NHC(=O)NH—, —NHC(=O)NHCH$_2$—, or —CH$_2$C(=O)NH—.

3. The compound of claim 1 having the structure:

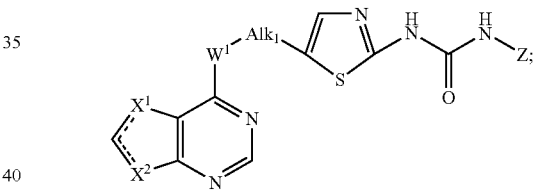

wherein Z is an aromatic, heteroaromatic, or heteroalicyclic moiety;

W$^1$ is NR$^{W1}$, where R$^{W1}$ is hydrogen, lower alkyl, lower heteroalkyl, aryl, -(alkyl)aryl, or acyl; and Alk$_1$ is a C$_2$ alkylene chain wherein up to two non-adjacent methylene units are independently optionally replaced by —C(=O)—.

4. A composition comprising the compound of claim 1, and a pharmaceutically acceptable carrier, adjuvant, or vehicle.

5. A compound of the formula:

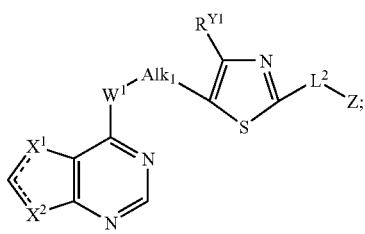

or pharmaceutically acceptable salt thereof;

wherein one of - - - - - is a double bond, as valency permits;

X$^1$ is S and X$^2$ is —CH—;

W¹ is NR^{W1}, where R^{W1} is hydrogen, lower alkyl, C$_{3-6}$cycloalkyl, lower heteroalkyl, aryl, -(alkyl)aryl, or acyl;

Alk$_1$ is a C$_2$ alkylene chain wherein up to two non-adjacent methylene units are independently optionally replaced by —C(=O)—;

L² is —NR^{W2}—, —N(R^{w2})C(=O)G$_2$—, —N(R^{W2})C(=O)N(R^{W2})CR^{W3}R^{W4}— or —CR^{W3}R^{W4}C(=O)N(R^{W2})—; wherein G$_2$ is absent, O or NR^{W2}; and R^{W2}, R^{W3}, R^{W4} and R^{G2} are independently hydrogen, lower alkyl, lower heteroalkyl, aryl, -(alkyl)aryl, or acyl;

Z is an aliphatic, heteroaliphatic, alicyclic, aromatic, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, pyridyl, quinolinyl, dihydroquinolinyl, isoquinolinyl, quinazolinyl, dihydroquinazolinyl, tetrahydroquinazolinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, or furanyl moiety, or Z has one of the following structures:

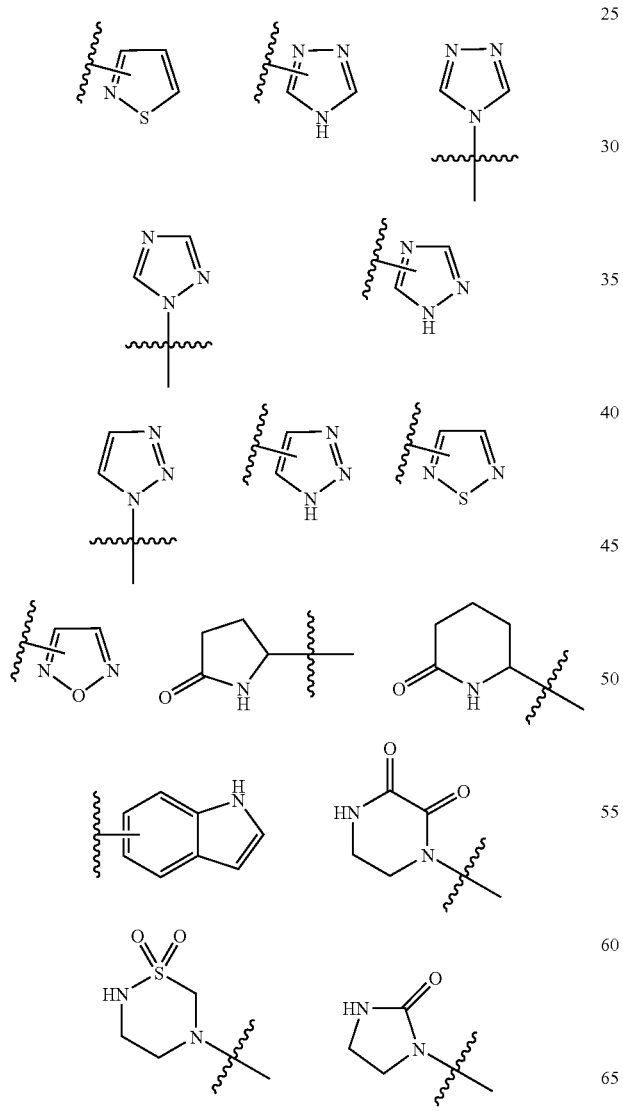
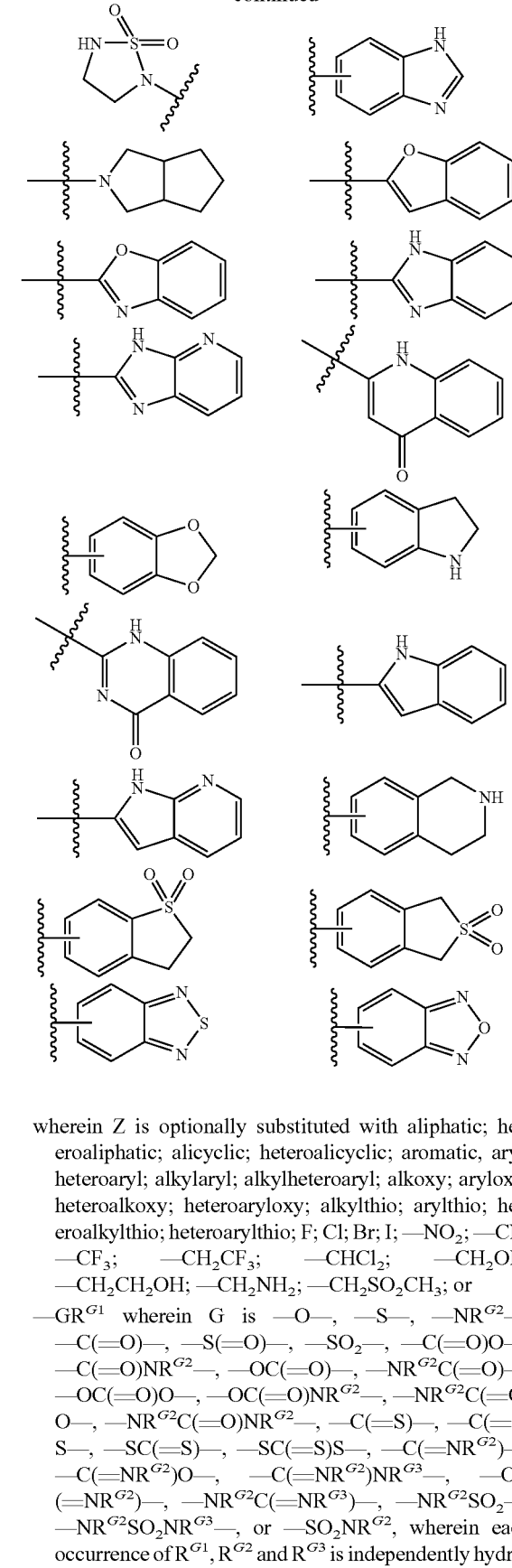

wherein Z is optionally substituted with aliphatic; heteroaliphatic; alicyclic; heteroalicyclic; aromatic, aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or —GR^{G1} wherein G is —O—, —S—, —NR^{G2}—, —C(=O)—, —S(=O)—, —SO$_2$—, —C(=O)O—, —C(=O)NR^{G2}—, —OC(=O)—, —NR^{G2}C(=O)—, —OC(=O)O—, —OC(=O)NR^{G2}—, —NR^{G2}C(=O)O—, —NR^{G2}C(=O)NR^{G2}—, —C(=S)—, —C(=S)S—, —SC(=S)—, —SC(=S)S—, —C(=NR^{G2})—, —C(=NR^{G2})O—, —C(=NR^{G2})NR^{G3}—, —OC(=NR^{G2})—, —NR^{G2}C(=NR^{G3})—, —NR^{G2}SO$_2$—, —NR^{G2}SO$_2$NR^{G3}—, or —SO$_2$NR^{G2}, wherein each occurrence of R^{G1}, R^{G2} and R^{G3} is independently hydrogen, halogen, aliphatic, heteroaliphatic, alicyclic, heteroalicyclic, aromatic, aryl, heteroaryl, alkylaryl, or alkylheteroaryl, wherein each heteroalicyclic group is selected from pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, dihydropyrrolyl, dihydropyridyl, or azetidinyl, and wherein each heteroaryl group is selected from pyridyl, quinolinyl, dihydroquinolinyl, isoquinolinyl, quinazolinyl, dihydroquinazolinyl, tetrahydroquinazolinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, or furanyl;

and $R^{Y1}$ is independently hydrogen, alkyl, heteroalkyl, aryl, -(alkyl)aryl or —$OR^{Y3}$, —$SR^{Y3}$, —$NR^{Y2}R^{Y3}$, —$SO_2NR^{Y2}R^{Y3}$, —$C(=O)NR^{Y2}R^{Y3}$, halogen, —CN, —$NO_2$, —$C(=O)OR^{Y3}$, —$N(R^{Y2})C(=O)R^{Y3}$, wherein each occurrence of $R^{Y2}$ and $R^{Y3}$ is independently hydrogen, lower alkyl, lower heteroalkyl, aryl, -(alkyl)aryl, or acyl.

6. The compound of claim 5 having the structure:

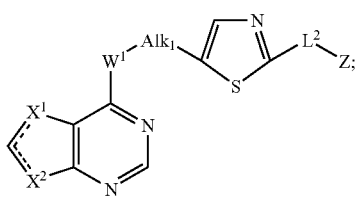

wherein:

$Alk_1$ is a $CH_2$—$CH_2$ group.

7. The compound of claim 6 wherein $L^2$ is NH, —NHC(=O)—, —NHC(=O)O—, —NHC(=O)NH—, —NHC(=O)NHCH_2—, or —$CH_2C(=O)NH$—.

8. The compound of claim 7 wherein Z is a branched alkyl, alkenyl, alkynyl, heteroalkyl or heteroalkenyl moiety.

9. The compound of claim 7 wherein Z is one of:

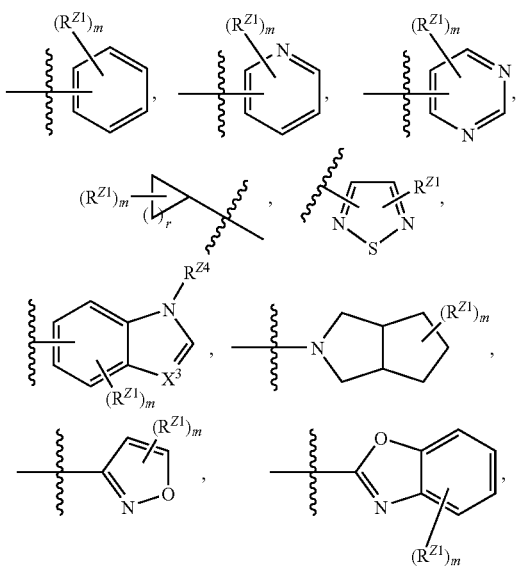

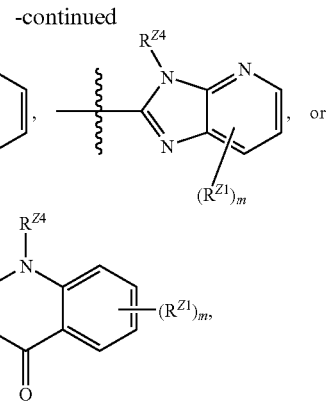

wherein:

m is an integer from 0 to 3;

r is an integer from 1 to 4;

$X^3$ is N or $CR^{Z1}$;

each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, —$SO_2NR^{Z2}R^{Z3}$, —$SO_2R^{Z1}$, —$C(=O)NR^{Z2}R^{Z3}$, halogen, —CN, —$NO_2$, —$C(=O)OR^{Z3}$, —$N(R^{Z2})C(=O)R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, wherein the heteroaryl group is selected from pyridyl, quinolinyl, dihydroquinolinyl, isoquinolinyl, quinazolinyl, dihydroquinazolinyl, tetrahydroquinazolinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, or furanyl; or $R^{Z2}$ and $R^{Z3}$ taken together with the nitrogen or carbon atom to which they are attached form a 5-6 membered ring selected from aryl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, pyridyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, or furanyl; and $R^{Z4}$ is hydrogen, lower alkyl, lower heteroalkyl, aryl, heteroaryl, -(alkyl)aryl, -(alkyl)heteroaryl or acyl, wherein the heteroaryl group is selected from pyridyl, quinolinyl, dihydroquinolinyl, isoquinolinyl, quinazolinyl, dihydroquinazolinyl, tetrahydroquinazolinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, or furanyl.

10. The compound of claim 9 wherein Z is one of:

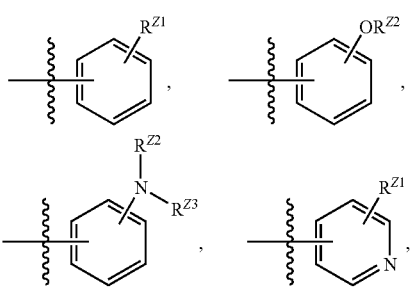

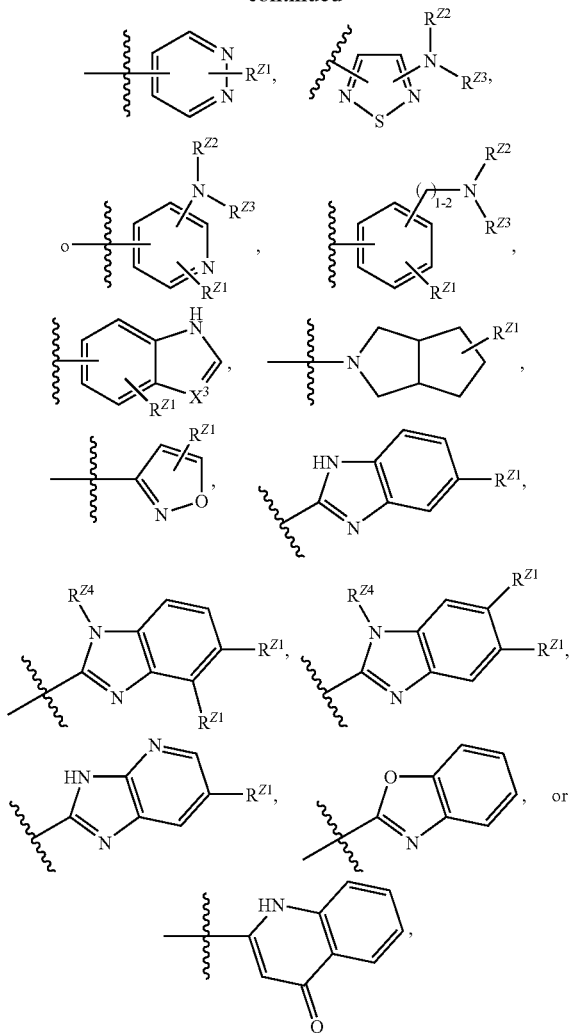

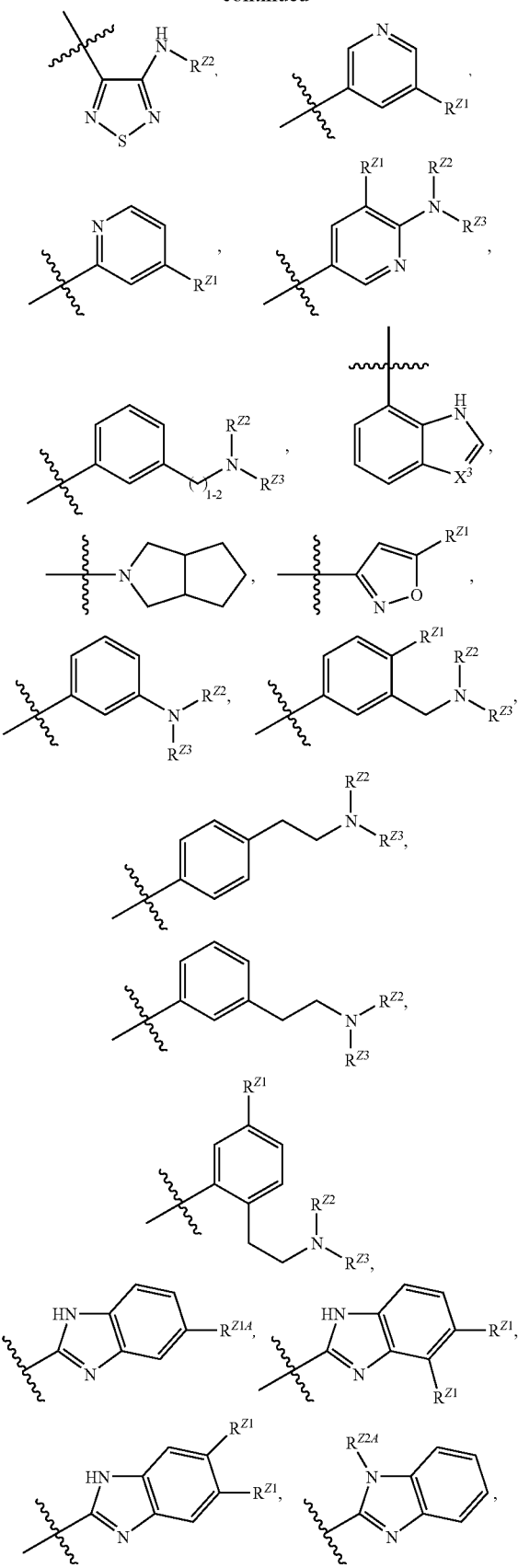

wherein:

$X^3$ is N or $CR^{Z1}$;

$R^{Z1}$ is hydrogen, halogen, lower alkyl, lower hydroxyalkyl or lower haloalkyl;

$R^{Z2}$ and $R^{Z3}$ are independently hydrogen, lower alkyl, lower heteroalkyl, acyl, or $R^{Z2}$ and $R^{Z3}$ together atom to which are attached a R taken with the nitrogen they form 5-6 membered ring selected from pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, or isothiazolidinyl; and $R^{Z4}$ is hydrogen or lower alkyl.

11. The compound of claim 9 wherein Z is one of:

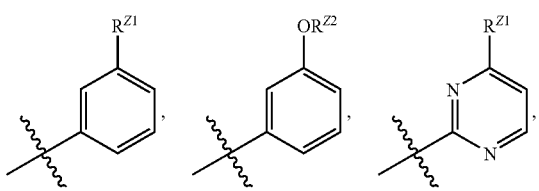

-continued

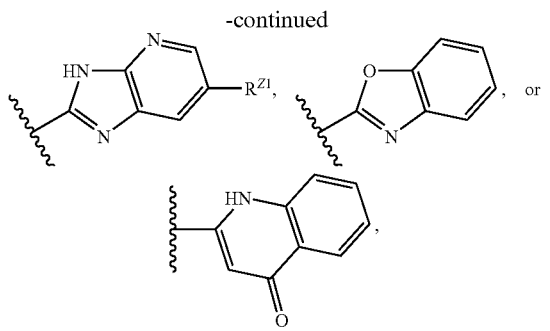

wherein:

$X^3$ is N or $CR^{Z1}$;

$R^{Z1}$ is hydrogen, halogen, lower alkyl or lower haloalkyl;

$R^{Z2}$ and $R^{Z3}$ are independently hydrogen, lower alkyl, lower heteroalkyl, acyl, or $R^{Z2}$ and $R^{Z3}$ taken together with the nitrogen atom to which they are attached form a 5-6 membered ring selected from pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, or isothiazolidinyl;

X is halogen;

$R^{Z1A}$ is hydrogen, halogen, —CN, lower alkyl, lower alkoxy, lower haloalkyl or —$SO_2R^{Z4}$; wherein $R^{Z4}$ is lower alkyl; and $R^{Z2A}$ is hydrogen or lower alkyl.

12. The compound of claim 9 wherein Z is one of:

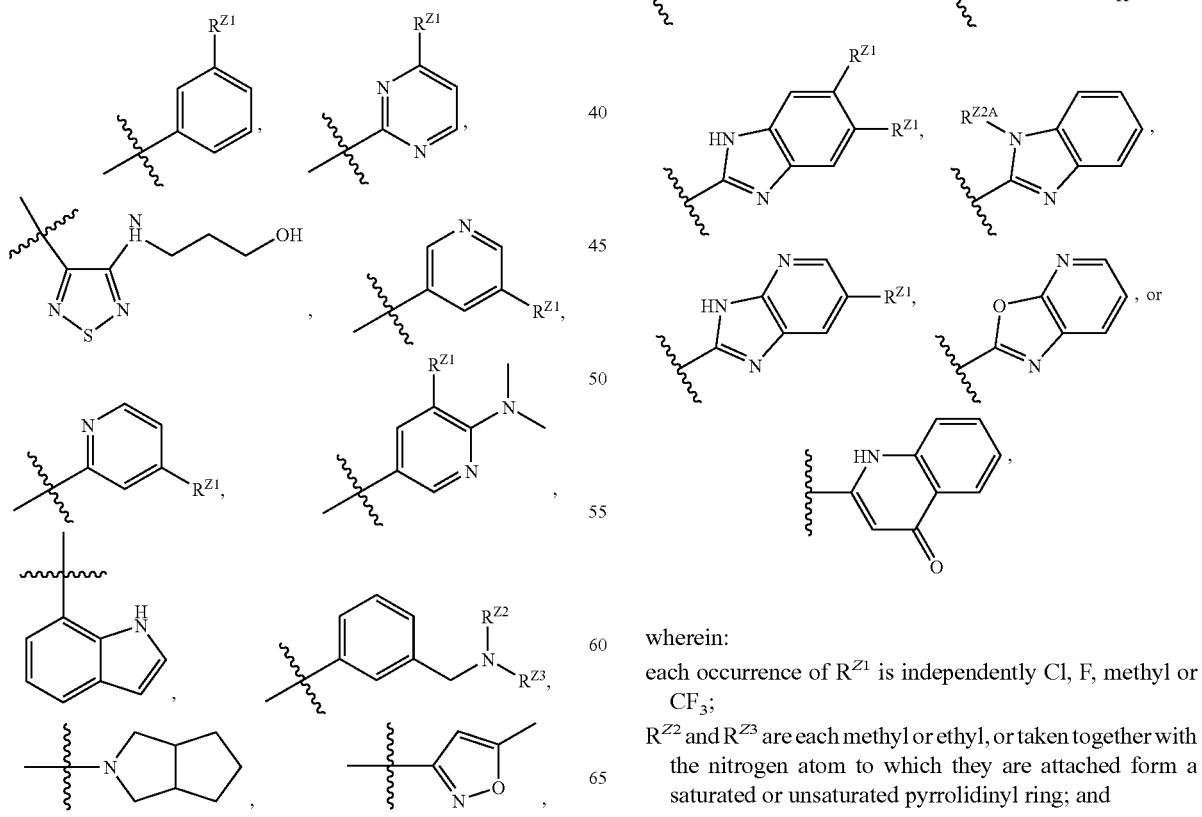

wherein:

each occurrence of $R^{Z1}$ is independently Cl, F, methyl or $CF_3$;

$R^{Z2}$ and $R^{Z3}$ are each methyl or ethyl, or taken together with the nitrogen atom to which they are attached form a saturated or unsaturated pyrrolidinyl ring; and $R^{Z2A}$ is hydrogen or methyl.

13. The compound of claim 12 wherein Z is one of:

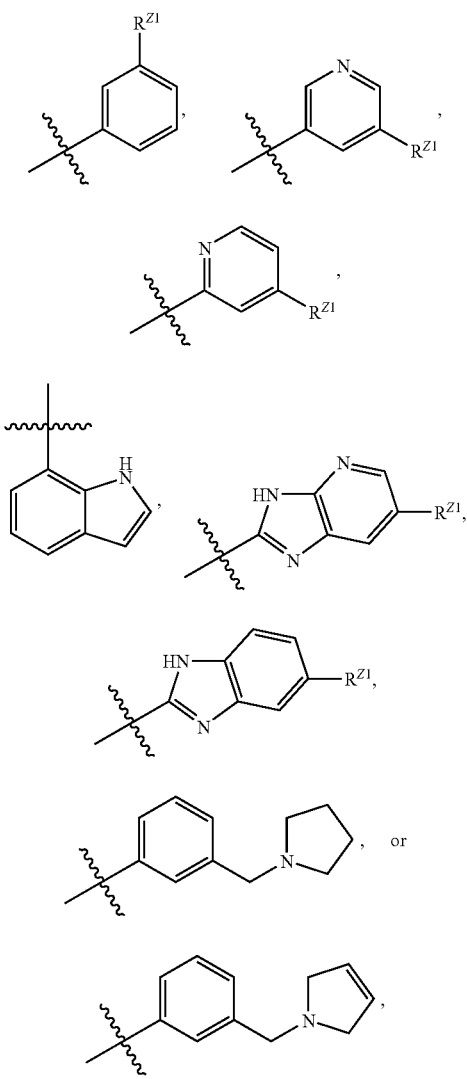

wherein $R^{Z1}$ is Cl, F, methyl or $CF_3$.

14. A compound of the formula:

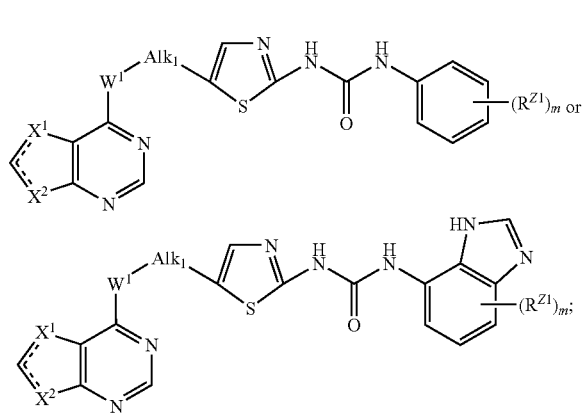

or pharmaceutically acceptable salt thereof;

wherein one of - - - - - is a double bond, as valency permits;

$X^1$ is S, $X^2$ is —CH—;

$W^1$ is $NR^{W1}$, where $R^{W1}$ is hydrogen, lower alkyl, lower heteroalkyl, aryl, -(alkyl)aryl, or acyl;

$Alk_1$ is a $C_2$ alkylene chain wherein up to two non-adjacent methylene units are independently optionally replaced by —C(=O)—;

m is an integer from 0 to 3; and each occurrence of $R^{Z1}$ is independently hydrogen, alkyl, heteroalkyl, aryl, heteroaryl, -(alkyl)aryl or -(alkyl)heteroaryl, —$OR^{Z2}$, —$SR^{Z2}$, —$NR^{Z2}R^{Z3}$, —$SO_2NR^{Z2}R^{Z3}$, —$SO_2R^{Z1}$, —C(=O)$NR^{Z2}R^{Z3}$, halogen, —CN, —$NO_2$, —C(=O)$OR^{Z3}$, —N($R^{Z2}$)C(=O)$R^{Z3}$, wherein each occurrence of $R^{Z2}$ and $R^{Z3}$ is independently hydrogen, lower alkyl, lower heteroalkyl, aryl, heteroaryl, -(alkyl)aryl, -(alkyl)heteroaryl or acyl, wherein each heteroaryl group is selected from pyridyl, quinolinyl, dihydroquinolinyl, isoquinolinyl, quinazolinyl, dihydroquinazolinyl, tetrahydroquinazolinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, or furanyl; or $R^{Z2}$ and $R^{Z3}$ taken together with the nitrogen or carbon atom to which they are attached form a 5-6 membered ring selected from aryl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, pyridyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, or furanyl.

15. A compound having the structure:

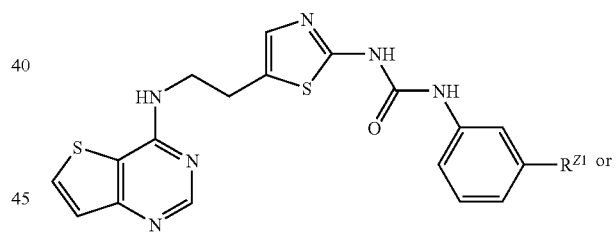

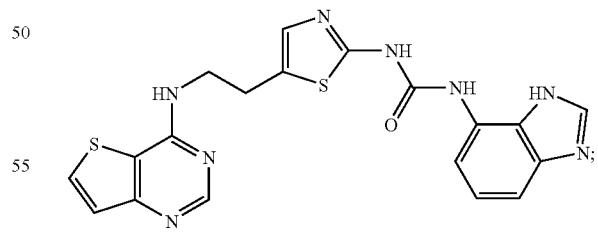

wherein $R^{Z1}$ is halogen, lower alkyl or lower haloalkyl.

16. The compound of claim 15 wherein $R^{Z1}$ is Cl, F, methyl or —$CF_3$.

17. The compound of claim 5, 6, 3 or 14 wherein —$W^1$-$Alk_1$-$W^1$-$Alk_1$ is —NH—$CH_2$—$CH_2$ group.

18. A compound of the structure:
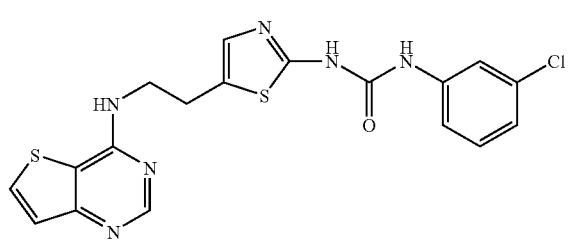
or a pharmaceutically acceptable salt thereof.
19. A compound of the structure:
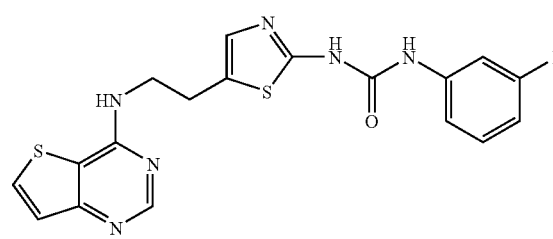
or a pharmaceutically acceptable salt thereof.
20. A compound of the structure:
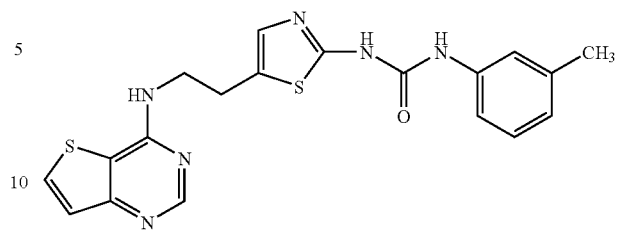
or a pharmaceutically acceptable salt thereof.
21. A compound of the structure:
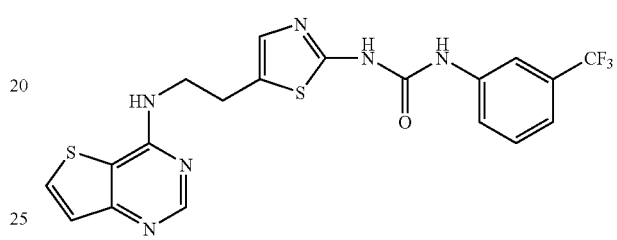
or a pharmaceutically acceptable salt thereof.
* * * * *

UNITED STATES PATENT AND TRADEMARK OFFICE
CERTIFICATE OF CORRECTION

| | |
|---|---|
| PATENT NO. | : 7,601,725 B2 |
| APPLICATION NO. | : 11/182215 |
| DATED | : October 13, 2009 |
| INVENTOR(S) | : Lew et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 679 days.

Signed and Sealed this

Fifth Day of October, 2010

David J. Kappos
*Director of the United States Patent and Trademark Office*